US012275963B2

(12) United States Patent
Kim et al.

(10) Patent No.: US 12,275,963 B2
(45) Date of Patent: Apr. 15, 2025

(54) ARTIFICIALLY MANIPULATED IMMUNE CELL

(71) Applicant: TOOLGEN INCORPORATED, Seoul (KR)

(72) Inventors: Seok Joong Kim, Seoul (KR); Yoon-Young Kim, Seoul (KR); Ho-Sung Yu, Gyeonggi-do (KR); In-Young Jung, Gyeonggi-do (KR); Jung Min Lee, Gyeongsangbuk-do (KR)

(73) Assignee: TOOLGEN INCORPORATED, Seoul (KR)

(*) Notice: Subject to any disclaimer, the term of this patent is extended or adjusted under 35 U.S.C. 154(b) by 1075 days.

(21) Appl. No.: 16/611,383

(22) PCT Filed: May 8, 2018

(86) PCT No.: PCT/KR2018/005284
§ 371 (c)(1),
(2) Date: Nov. 6, 2019

(87) PCT Pub. No.: WO2018/208067
PCT Pub. Date: Nov. 15, 2018

(65) Prior Publication Data

US 2021/0147798 A1 May 20, 2021

Related U.S. Application Data

(60) Provisional application No. 62/595,159, filed on Dec. 6, 2017, provisional application No. 62/502,822, filed on May 8, 2017.

(30) Foreign Application Priority Data

Aug. 14, 2017 (WO) ................ PCT/KR2017/008835

(51) Int. Cl.

| | |
|---|---|
| ***A61K 39/00*** | (2006.01) |
| ***C07K 14/705*** | (2006.01) |
| ***C07K 16/28*** | (2006.01) |
| ***C12N 5/078*** | (2010.01) |
| ***C12N 5/0783*** | (2010.01) |
| ***C12N 9/22*** | (2006.01) |
| ***C12N 15/10*** | (2006.01) |
| ***C12N 15/113*** | (2010.01) |
| ***C12N 15/115*** | (2010.01) |
| ***C12N 15/117*** | (2010.01) |
| ***C12N 15/87*** | (2006.01) |
| *C07K 14/725* | (2006.01) |

(52) U.S. Cl.

CPC ............ *C12N 9/22* (2013.01); *A61K 39/4611* (2023.05); *A61K 39/4631* (2023.05); *A61K 39/4644* (2023.05); *C07K 14/705* (2013.01); *C07K 16/2863* (2013.01); *C12N 5/0634* (2013.01); *C12N 5/0636* (2013.01); *C12N 15/102* (2013.01); *C12N 15/113* (2013.01); *C12N 15/115* (2013.01); *C12N 15/117* (2013.01); *C12N 15/87* (2013.01); *C12Y 207/01107* (2013.01); *A61K 2239/31* (2023.05); *A61K 2239/38* (2023.05); *C07K 14/7051* (2013.01); *C07K 2317/622* (2013.01); *C07K 2319/03* (2013.01); *C12N 2501/515* (2013.01)

(58) Field of Classification Search

None
See application file for complete search history.

(56) References Cited

U.S. PATENT DOCUMENTS

| | | | | |
|---|---|---|---|---|
| 8,207,316 B1 * | 6/2012 | Bentwich | C12N 15/1131 | 435/375 |
| 8,865,406 B2 * | 10/2014 | Zhang | C12N 15/63 | 435/320.1 |
| 10,876,120 B2 * | 12/2020 | Wucherpfennig | A61K 35/17 | |
| 11,041,173 B2 | 6/2021 | Zhang et al. | | |
| 2005/0112568 A1 * | 5/2005 | Friedman | G01N 33/5011 | 435/6.16 |
| 2005/0221354 A1 | 10/2005 | Mounts | | |
| 2005/0244851 A1 | 11/2005 | Blume et al. | | |
| 2011/0166037 A1 | 7/2011 | Cao et al. | | |

(Continued)

FOREIGN PATENT DOCUMENTS

| | | |
|---|---|---|
| AU | 2014 366047 A1 | 6/2016 |
| AU | 2013/359123 B2 | 7/2016 |

(Continued)

OTHER PUBLICATIONS

Prinz, P. U., "High DGK-¤ and Disabled MAPK Pathways Cause Dysfunction of Human Tumor-Infiltrating CD8+ T Cells That Is Reversible by Pharmacologic Intervention", *J Immunol* 2012; 188:5990-6000.

Riese, M. J., et al.; "Enhanced Effector Responses in Activated CD8+ T Cells Deficient in Diacylglycerol Kinases", Cancer Res; 73(12) Jun. 15, 2013, pp. 3566-3577.

Cencic, R. et al.; "Protospacer Adjacent Motif (PAM)-Distal Sequences Engage CRISPR Cas9 DNA Target Cleavage", PLOS One, Oct. 2014, vol. 9, Issue 10, pp. 1-13.

Riese, M. J., et al.; "Diacylglycerol Kinases (DGKs): Novel Targets for Improving T Cell Activity in Cancer", Frontiers in Cell and Developmental Biology, Oct. 2016, vol. 4, Article 108, pp. 1-7.

(Continued)

*Primary Examiner* — Michail A Belyavskyi

(74) *Attorney, Agent, or Firm* — Harness, Dickey & Pierce, P.L.C.

(57) ABSTRACT

The presents invention relates to a composition for manipulating an immune cell which is used for artificially manipulating an immune cell. More particularly, the present invention relates to a composition for manipulating an immune cell which is used for artificially manipulating an immune cell and a manipulated immune cell comprising an artificially modified immunity regulating gene and an artificial receptor which is produced using the composition, and use thereof.

13 Claims, 48 Drawing Sheets

Specification includes a Sequence Listing.

(56) References Cited

U.S. PATENT DOCUMENTS

| | | | | |
|---|---|---|---|---|
| 2013/0129668 | A1 | 5/2013 | Firestein et al. | |
| 2014/0120622 | A1 | 5/2014 | Gregory et al. | |
| 2015/0224142 | A1 | 8/2015 | Albelda et al. | |
| 2016/0120906 | A1 | 5/2016 | Galetto et al. | |
| 2016/0184362 | A1 | 6/2016 | Duchateau et al. | |
| 2016/0272999 | A1 | 9/2016 | Duchateau et al. | |
| 2017/0204372 | A1 | 7/2017 | Mohler et al. | |
| 2017/0335281 | A1 | 11/2017 | Loew et al. | |
| 2018/0119140 | A1 | 5/2018 | Porteus et al. | |
| 2019/0185860 | A1 | 6/2019 | Kim et al. | |
| 2019/0388468 | A1* | 12/2019 | Lock | C07K 14/705 |
| 2020/0299686 | A1* | 9/2020 | Kwong | C12N 15/11 |
| 2021/0128616 | A1* | 5/2021 | Dave | C12N 5/0636 |
| 2021/0147798 | A1 | 5/2021 | Kim et al. | |
| 2021/0317406 | A1* | 10/2021 | Marson | C12N 15/113 |

FOREIGN PATENT DOCUMENTS

| | | | |
|---|---|---|---|
| CN | 105121648 | A | 12/2015 |
| CN | 105164264 | A | 12/2015 |
| EP | 3498846 | A1 | 6/2019 |
| JP | 2017-500869 | A | 1/2017 |
| JP | 2019-524140 | A | 9/2019 |
| KR | 10-2015-0016588 | A | 2/2015 |
| KR | 10-2015-0105635 | A | 9/2015 |
| KR | 10-2016-0018425 | A | 2/2016 |
| KR | 10-2016-0138404 | A | 12/2016 |
| KR | 10-2017-0032406 | A | 3/2017 |
| WO | WO-2013/176772 | A1 | 11/2013 |
| WO | WO-2014/039513 | A2 | 3/2014 |
| WO | WO-2014/186585 | A2 | 11/2014 |
| WO | WO-2015/090230 | A1 | 6/2015 |
| WO | WO-2015/121454 | A1 | 8/2015 |
| WO | WO-2016/021972 | A1 | 2/2016 |
| WO | WO-2016/069283 | A1 | 5/2016 |
| WO | WO-2016/080097 | A1 | 5/2016 |
| WO | WO-2016/123578 | A1 | 8/2016 |
| WO | WO-2018/030874 | A1 | 2/2018 |

OTHER PUBLICATIONS

Jung, I. Y., et al.; "CRISPR/Cas9-Medicated Knockout of DGK Improves Antitumor Activities of Human T Cells", Cancer Res., 78(16), Aug. 15, 2018, pp. 4692-4703.

Extended European Search Report from corresponding European Patent Application No. 17839891.3, dated Feb. 11, 2020.

Search Report and Written Opinion from corresponding Singapore Patent Application No. 11201901184Q, dated Jun. 1, 2020.

Su S., et al.; "CRISPR-Cas9 mediated efficient PD-1 disruption on human primary T cells from cancer patients", Sci Rep., Jan. 28, 2016, vol. 6:20070, pp. 1-13.

1st Office Action from corresponding Australian Patent Application No. 2017308473, dated Aug. 14, 2020.

2nd Office Action from corresponding Australian Patent Application No. 2017308473, dated Sep. 11, 2020.

Examination Report from corresponding Russian Patent Application No. 2019106669, dated Sep. 23, 2020.

Office Action from corresponding European Patent Application No. 17839891.3, dated Oct. 23, 2020.

Office Action from corresponding Korean Patent Application No. 10-2019-0068999, dated Sep. 17, 2020.

Prinz et al., "NK?cell dysfunction in human renal carcinoma reveals diacylglycerol kinase as key regulator and target for therapeutic intervention" International Jornal of Cancer, vol. 135, No. 8, pp. 1832-1841, 2014.

Yang et al, "Diacylglycerol Kinase z Is a Target To Enhance NK Cell Function", The Juornal of Immunology, vol. 197, No. 3, pp. 934-941, 2016.

Office Action from corresponding U.S. Appl. No. 16/324,955, issued on Apr. 1, 2022.

Office Action from corresponding Canadian Patent Application No. 3,033,736, dated Aug. 26, 2022.

PCT Application No. PCT/KR2017/008835_International Search Report Written Opinion with its translation, Dec. 20, 2017.

PCT Application No. PCT/KR2018/005284_International Search Report with its translation, Aug. 24, 2018.

PCT Application No. PCT/KR2018/005284_International Search Report Written Opinion with its translation, Aug. 24, 2018.

JP Patent Application No. 2019-561310_Office Action with its translation, Jan. 26, 2021.

Australian Patent Application No. 2017308473_Office Action, Jan. 20, 2021.

Australian Patent Application No. 2018264636_Office Action, Feb. 25, 2021.

RU Patent Application No. 2019106669_Office Action with its translation, Feb. 18, 2021.

RU Patent Application No. 2019106669_Search Report with its translation, Feb. 18, 2021.

Kuklina E.M., Molecular Mechanisms of T Cell Anergy, Biokhimiya (Biochemistry), vol. 78, 144-156, 2013.

Su, S., et al.; "CRISPR-Cas9 mediated efficient PD-1 disruption on human primary T cells from cancer patients", Scientific Reports, 2016,6: 20070, pp. 1-14.

The Journal of Immunology, vol. 196, Issue 1, Supplement, Immunology.

NCBI, GenBank: EF064716.1, Nov. 13, 2006.

KR Patent Application No. 10-2017-0103009_Office Action with its translation, Apr. 9, 2018.

KR Patent Application No. 10-2017-0103009_Final rejection with its translation, Aug. 2, 2018.

KR Patent Application No. 10-2017-0103009_Office Action after Re-examination with its translation, Oct. 8, 2018.

KR Patent Application No. 10-2017-0103009_Final rejection after Re-examination with its translation, Apr. 11, 2019.

Korean Patent Application No. 10-2019-0068999_Final rejection with its translation, Mar. 10, 2021.

Korean Patent Application No. 10-2019-7036278_Office Action with its translation, Apr. 23, 2021.

Fagerlund et al. (2015) "The Cpf1 CRISPR-Cas protein expands genome-editing tools.", *Genome Biology*, 16:251, pp. 1-3.

International Search Report (ISR) dated Aug. 24, 2018 issued in International Patent Application No. PCT/KR2018/005284, with English Translation.

International Search Report (ISR) dated Dec. 20, 2017 issued in International Patent Application No. PCT/KR2017/008835, with English Translation.

Office Action from corresponding Japanese Patent Application No. 2019-561310, issued Dec. 17, 2021.

Park, J., et al.; "Cas-Designer: a web-based tool for choice of CRISPR-Cas9 target sites", Bioinformatics, 31(24), 2015, 4014-4016.

Notice of Allowance from corresponding Korean Patent Application No. 10-2019-0068999, issued Apr. 21, 2021.

Pennisi, E., "The CRISPR Craze", *Science*, 341 (6148), pp. 833-836, 2013.

Chinese Office Action for Application No. 201880045774.2, dated Nov. 24, 2022.

Office Action from corresponding Chinese Patent Application No. 201780063250.1, dated Mar. 31, 2023.

Office Action from corresponding U.S. Appl. No. 16/324,955, dated May 25, 2023.

Office Action from corresponding U.S. Appl. No. 16/324,955, dated Nov. 28, 2023.

Mout et al. In vivo delivery of CRISPR/Cas9 for therapeutic gene editing: Progress and Challenges. Bioconjugate Chem. 28:880-884, (Year: 2017).

Notice of Allowance from corresponding Chinese Application No. 201780063250.1, dated Jun. 17, 2024.

* cited by examiner (A)

(B)

ARTIFICIALLY MANIPULATED IMMUNE CELL

CROSS-REFERENCE TO RELATED APPLICATIONS

This application is a national phase application of PCT Application No. PCT/KR2018/005284, filed on May 8, 2018, which claims the benefit and priority to U.S. Provisional Patent Application No. 62/502,822, filed May 8, 2017, PCT Application No. PCT/KR2017/008835, filed Aug. 14, 2017 and U.S. Provisional Patent Application No. 62/595,159, filed Dec. 6, 2017. The entire disclosures of the applications identified in this paragraph are incorporated herein by references.

FIELD

The presents invention relates to artificial manipulation or modification of an immunity regulating gene. More particularly, the present invention relates to a composition for gene manipulation which is used for artificially manipulating an immunity regulating gene and an immune cell comprising the artificially manipulated immunity regulating gene.

BACKGROUND

Cell therapeutic agents are pharmaceutical drugs that induce regeneration using live cells to restore damaged or diseased cells/tissues/entity and they are pharmaceutical drugs that are produced by physical, chemical, or biological manipulation, e.g., ex vivo cultivation, proliferation, selection, or the like of autologous, allogeneic, or heterologous cells.

Among them, immune regulatory cell therapeutic agents are pharmaceutical drugs that are used for the purpose of treating diseases by regulating immune responses in the body using immune cells (e.g., dendritic cells, natural killer cells, T cells, etc.).

Currently, immune regulatory cell therapeutic agents are being developed mainly targeting cancer treatment as an indication. Unlike the surgery therapy, anticancer agents, and radiation therapy which are conventionally used for cancer treatment, the immune regulatory cell therapeutic agents have therapeutic mechanisms and efficacies that acquire therapeutic effects by activating immune functions via direct administration of immune cells to patients; they are expected to occupy a major part of future new biologics.

The physical and chemical characteristics of the antigens introduced into cells vary with each other depending on the type of the immune regulatory cell therapeutic agents. When an exogenous gene is introduced into immune cells in the form of a viral vector, etc., these cells will be able to have both the characteristics of a cell therapeutic agent and a gene therapeutic agent.

The administration of immune regulatory cell therapeutic agents may be performed by activating various immune cells (e.g., peripheral blood mononuclear cells (PBMCs), T cells, NK cells, etc. isolated from patients through apheresis) with various antibodies and cytokines, then proliferating ex vivo, and injecting again into a patient; or injecting again into the patient immune cells, into which a gene (e.g., T-cell receptors (TCRs) or chimeric antigen receptors (CARs)) is introduced.

Adoptive immunotherapy, which involves the delivery of autologous antigen-specific immune cells (e.g., T cells)

produced ex vivo, may become a promising strategy for treating various immune diseases as well as cancer.

Recently, it was reported that immune cell therapeutic agents can be used variously, for example, as an autoimmune inhibitor, etc. as well as exhibiting an anticancer function. Therefore, immune cell therapeutic agents can be used in various indications by modulating the immune responses. Accordingly, there is a great demand for improvement and development of therapeutic efficacy of manipulated immune cells used for adoptive immunotherapy.

DISCLOSURE

Technical Problem

As an exemplary embodiment, the present invention provides a composition for manipulating an immune cell, which is used for artificially manipulating an immune cell.

As an exemplary embodiment, the present invention provides a manipulated immune cell comprising at least one artificially modified immunity regulating gene and at least one artificial receptor.

As an exemplary embodiment, the present invention provides a method for producing an artificial immune cell comprising at least one artificially modified immunity regulating gene and at least one artificial receptor.

As an exemplary embodiment, the present invention provides a method for treating an immune disease including an artificial immune cell comprising at least one artificially modified immunity regulating gene and at least one artificial receptor as an active ingredient.

Technical Solution

To solve these problems, the present invention relates to a composition for manipulating an immune cell. More specifically, the present invention relates to a composition for manipulating an immune cell which is used for artificially manipulating an immune cell and a manipulated immune cell comprising an artificially modified immunity regulating gene and an artificial receptor which is produced using the composition, and use thereof.

The present invention provides a composition for manipulating an immune cell for a particular purpose.

The term "composition for manipulating an immune cell" refers to one or more substances selected from DNA, RNA, nucleic acid, protein, virus, chemical compound, etc. which is used for artificially manipulating or modifying an immune cell.

In certain embodiments, the composition for manipulating an immune cell may comprise:

a guide nucleic acid capable of forming a complementary bond to a target sequence in the nucleic acid sequences of at least one immunity regulating gene selected from the group consisting PD-1 gene, CTLA-4 gene, Dgkα gene, Dgkζ gene, Fas gene, EGR2 gene, PPP2R2D gene, Tet2 gene, PSGL-1 gene, A20 gene, and KDM6A gene; and an artificial receptor which is artificially prepared and is not a wild type receptor.

The term "immunity regulating gene" is intended to include any genes that directly anticipates to or indirectly effects the formation and performance of an immune function or response. In the present invention, the immunity regulating gene includes any genes that directly anticipates to or indirectly effects functional regulation of not only an immune cell, but also cells that can interact with an immune cell, such as a phagocyte. Here, the immunity regulating gene may perform functions related to the formation and performance of an immune function or response, in the form of the immunity regulating gene itself or a protein expressed from the immunity regulating gene.

The term "artificial receptor" refers to a functional entity which is artificially prepared, not a wild-type receptor and which has specific ability to recognize antigens and performs a specific function.

The composition for manipulating an immune cell may selectively further comprise at least one editor protein which is selected from the group consisting of *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and Cpf1 protein.

The target sequence may be a nucleotide sequence of a continuous 10 bp to 25 bp located at a promoter region of the immunity regulating gene The target sequence may be a nucleotide sequence of a continuous 10 bp to 25 bp located at an intron region of the immunity regulating gene.

The target sequence may be a nucleotide sequence of a continuous 10 bp to 25 bp located at an exon region of the immunity regulating gene.

The target sequence may be a nucleotide sequence of a continuous 10 bp to 25 bp located at an enhancer region of the immunity regulating gene.

The target sequence may be a nucleotide sequence of a continuous 10 bp to 25 bp located at a 3'-UTR (Untranslated Region) or a 5'-UTR of the immunity regulating gene.

The target sequence may be a nucleotide sequence of a continuous 10 bp to 25 bp adjacent to the 5' end and/or 3' end of a PAM (proto-spacer-adjacent Motif) sequence in a nucleic acid sequence of the immunity regulating gene.

Here, the PAM sequence may be at least one selected from the following sequences:

5'-NGG-3'(N is A, T, C or G);

5'-NNNNRYAC-3' (each of N is independently A, T, C or G, R is A or G, and Y is C or T);

5'-NNAGAAW-3' (each of N is independently A, T, C or G, and W is A or T);

5'-NNNNGATT-3' (each of N is independently A, T, C or G);

5'-NNGRR(T)-3' (each of N is independently A, T, C or G, R is A or G, and Y is C or T); and 5'-TTN-3' (N is A, T, C or G).

In certain embodiments, the target sequence may be one or more selected from SEQ ID NO:1 to 289.

The guide nucleic acid may comprise a guide domain which is able to form a complementary bond with the target sequence on the immunity regulating gene, wherein the complementary bond may comprise 0 to 5 mismatches Here, the guide domain may comprise a nucleotide sequence complementary to the target sequence on the immunity regulating gene, wherein the complementary nucleotide sequence may comprise 0 to 5 mismatches.

The guide nucleic acid may comprise at least one domain selected from the group consisting of a first complementary domain, a linker domain, a second complementary domain, a proximal domain, and a tail domain.

The artificial receptor may have a binding specificity for at least one antigen.

Here, the at least one antigen may be an antigen expressed specifically expressed by a cancer cell or/and a virus.

Here, the at least one antigen may be tumor associated antigen.

Here, the at least one antigen may be one or more selected from the group consisting of A33, ALK, alpha-fetoprotein (AFP), adrenoreceptor beta 3 (ADRB3), alpha-folate receptor, AD034, AKT1, BCMA, beta-human chorionic gonadotropin, B7H3 (CD276), BST2, BRAP, CD5, CD13, CD19, CD20, CD22, CD24, CD30, CD33, CD38, CD40, CD44v6, CD52, CD72, CD79a, CD79b, CD89, CD97, CD123, CD138, CD160, CD171, CD179a, carbonic anhydrase IX (CAIX), CA-125, carcinoembryonic antigen (CEA), CCR4, C-type lectin-like molecules (CLL-1 or CLECL1), claudin6 (CLDN6), CXORF61, CAGE, CDX2, CLP, CT-7, CT8/HOM-TES-85, cTAGE-1, ERBB2, epidermal growth factor receptor (EGFR), EGFR variants III (EGFRvIII), epithelial cell adhesion molecule (EPCAM), E74-like factor 2 mutation (ELF2M), Ephrin type-A receptor 2 (EphA2), EMR2, Fms-like tyrosine kinase 3 (FLT3), FCRL5, fibulin-1, G250, GD2, glycoprotein 36 (gp36), glycoprotein 100 (gp100), glucocorticoid-induced tumor necrosis factor receptor (GITR), GPRC5D, GloboH, G protein-coupled receptor 20 (GPR20), GPC3, hsp70-2, human high molecular weight-melanoma-associated antigen (HMWMAA), hepatitis A virus cellular receptor 1 (HAVCR1), human papillomavirus E6 (HPV E6), human papillomavirus E7 (HPV E7), HAGE, HCA587/MAGE-C2, hCAP-G, HCE661, HER2/neu, HLA-Cw, HOM-HD-21/galectin9, HOM-MEEL-40/SSX2, HOM-RCC-3.1.3/CAXII, HOXA7, HOXB6, Hu, HUB 1, insulin growth factor (IGF1)-I, IGF-II, IGFI receptor, interleukin-13 receptor subunit alpha-2 (IL-13Ra2 or CD213A2), interleukin 11 receptor alpha (IL-11Ra), IGLL1, KIT (CD117), KM-HN-3, KM-KN-1, KOC1, KOC2, KOC3, KOC3, LAGA-1a, LAGE-1, LAIR1, LILRA2, LY75, Lewis Y antigen, MUC1, MN-CA IX, M-CSF, MAGE-1, MAGE-4a, mesothelin, MAGE-A1, MAD-CT-1, MAD-CT-2, MART1, MPP11, MSLN, neural cell adhesion molecule (NCAM), NY-ESO-1, NY-ESO-5, Nkp30, NKG2D, NY-BR-1, NY-BR-62, NY-BR-85, NY-CO-37, NY-CO-38, NNP-1, NY-LU-12, NY-REN-10, NY-REN-19/LKB/STK11, NY-REN-21, NY-REN-26/BCR, NY-REN-3/NY-CO-38, NY-REN-33/SNC6, NY-REN-43, NY-REN-65, NY-REN-9, NY-SAR-35, o-acetyl-GD2 ganglioside (OAcGD2), OGFr, PSMA, prostatic acid phosphatase (PAP), p53, prostate carcinoma tumor antigen-1 (PCTA-1), prostate stem cell antigen (PSCA), serine protease 21 (testisin or PRSS21), platelet-derived growth factor receptor-beta (PDGFR-beta), PLAC1, pannexin 3 (PANX3), PLU-1, ROR-1, RAGE-1, RU1, RU2, Rab38, RBPJ kappa, RHAMM, stage-specific embryonic antigen-4 (SSEA-4), SCP1, SSX3, SSX4, SSX5, Tyrp-1, TAG72, thyroglobulin, human telomerase reverse transcriptase (hTERT), 5T4, tumor-associated glycoprotein (TAG72), tyrosinase, transglutaminase 5 (TGS5), TEM1, TEM7R, thyroid-stimulating hormone receptor (TSHR), Tie 2, TRP-2, TOP2A, TOP2B, uroplakin 2 (UPK2), vimentin, vascular endothelial growth factor receptor 2 (VEGFR2), Wilms tumor protein 1 (WT1), and lewis (Y) antigen.

The artificial receptor may be a chimeric antigen receptor (CAR).

The artificial receptor may be an artificially manipulated or modified T-cell receptor (TCR).

The guide nucleic acid, the artificial receptor and the editor protein may be in the form of a nucleic acid sequence encoding each of them.

The nucleic acid sequence may be included in a plasmid or a viral vector.

Here, the virus vector may be one or more selected from the group consisting of a retrovirus, a lentivirus, an adenovirus, an adeno-associated virus (AAV), a vaccinia virus, a poxvirus or a herpes simplex virus.

The artificial receptor and the editor protein may be in the form of mRNA encoding each of them.

The artificial receptor and the editor protein may be in the form of polypeptide or protein.

When the composition for manipulating an immune cell selectively further comprises an editor protein, the composition may be in the form of a guide nucleic acid-editor protein complex.

The present invention provides a manipulated immune cell for a particular purpose.

"Manipulated immune cell" refers to an immune cell which is artificially manipulated, not a wild-type.

In certain embodiments, the manipulated immune cell may comprise at least one artificially engineered immunity regulating gene selected from the group consisting PD-1 gene, CTLA-4 gene, DGKA gene, DGKZ gene, FAS gene, EGR2 gene, PPP2r2d gene, TET2 gene, PSGL-1 gene, A20 gene, and KDM6A gene, and/or product expressed from the artificially engineered immunity regulating gene; and at least one artificial receptor protein and/or nucleic acid encoding the artificial receptor protein.

The at least one artificially engineered immunity regulating gene may comprise an artificial modification within a nucleotide sequence of the immunity regulating gene.

The at least one artificially engineered immunity regulating gene may comprise deletion and/or insertion of at least one nucleotide in a nucleotide sequence region of 1 bp to 50 bp within a target sequence in the immunity regulating gene, or adjacent to the 5' end and/or 3' end of the target sequence.

The at least one artificially engineered immunity regulating gene may comprise deletion and/or insertion of at least one nucleotides in a nucleotide sequence region of a continuous 1 bp to 50 bp adjacent to the 5' end and/or 3' end of a PAM sequence in a nucleic acid sequence of the immunity regulating gene.

Here, the deletion of at least nucleotide may be a deletion of a continuous 1 bp to 50 bp, a discontinuous 1 bp to 50 bp, or a deletion of 1 bp to 50 bp in which continuous form and discontinuous form are mixed.

Here, the deletion of at least one nucleotide may be a deletion of a continuous 2 bp to 50 bp.

Here, The insertion of at least one nucleotide may be an insertion of a continuous 1 bp to 50 bp, a discontinuous 1 bp to 50 bp, or an insertion of 1 bp to 50 bp in which continuous form and discontinuous form are mixed.

Here, the insertion of at least one nucleotide may be an insertion of a nucleotide fragment of a continuous 5 bp to 1000 bp.

Here, the insertion of at least one nucleotide may be an insertion of a portion or the entire nucleotide sequence of a specific gene.

The specific gene may be an exogenous gene which is introduced from an external region and which is not included in an immune cell including the immunity regulating gene.

The specific gene may be an endogenous gene existing in a genome of an immune cell comprising the immunity regulating gene.

Here, the deletion and insertion of at least one nucleotide may occur in a same nucleotide sequence region.

Here, the deletion and insertion of at least one nucleotide may occur in a different nucleotide sequence region.

The at least one product expressed from the artificially engineered immunity regulating gene may be in the form of mRNA and/or protein.

The product expressed from the artificially engineered immunity regulating gene may have reduced or inhibited quantity of expression thereof compared with the quantity of a product expressed from an immunity regulating gene by a wild type immune cell which is not artificially manipulated.

Here, the wild type immune cell which is not artificially manipulated may be an immune cell separated from human.

Here, the wild type immune cell which is not artificially manipulated may be an immune cell prior to an artificial manipulation.

The nucleic acid encoding the artificial receptor protein exists in the cell, but may not be inserted into a genome of the manipulated immune cell.

The nucleic acid encoding the artificial receptor protein may be inserted into a 3'-UTR, 5'-UTR, intron, exon, promoter, and/or enhancer region of the immunity regulating gene in a genome of the manipulated immune cell.

The nucleic acid encoding the artificial receptor protein may be inserted into at least one intron selected from introns existing in a genome of the manipulated immune cell.

The nucleic acid encoding the artificial receptor protein may be inserted into at least one exon selected from exons existing in a genome of the manipulated immune cell.

The nucleic acid encoding the artificial receptor protein may be inserted into at least one promoter selected from promoters existing in a genome of the manipulated immune cell.

The nucleic acid encoding the artificial receptor protein may be inserted into at least one enhancer selected from enhancers existing in a genome of the manipulated immune cell The nucleic acid encoding the artificial receptor protein may be inserted into one or more regions other than introns, exons, promoters, and enhancers existing in a genome of the manipulated immune cell.

The manipulated immune cell may be an immune cell selected and artificially manipulated from the group consisting of a dendritic cell, a T cell, an NK cell, an NKT cell, and a CIK cell.

The present invention provides a manipulated immune cell for a particular purpose, showing at least one feature.

In certain embodiments, the at least one feature may be one or more selected from the group consisting of:

an increase of production and/or secretion of a cytokine;

a cell proliferation, and increase of cytotoxicity.

Here, the cytokine may be one or more selected from the group consisting of IL-2, TNFα, and IFN-γ.

Explanations related to the manipulate immune cell are as described above.

The present invention provide a method for producing a manipulated immune cell for a particular purpose.

In certain embodiments, the method for producing a manipulated immune cell may comprises:

contacting (a) an immune cell;

(b) an artificial receptor protein or a composition for expressing the artificial receptor protein; and (c) a composition for gene manipulation capable of artificially manipulating at least one immunity regulating gene selected from the group consisting of PD-1 gene, CTLA-4 gene, DGKA gene, DGKZ gene, FAS gene, EGR2 gene, PPP2r2d gene, TET2 gene, PSGL-1 gene, A20 gene, and KDM6A gene.

(a) The immune cell may be an immune cell isolated from a human body or an immune cell differentiated from a stem cell.

(b) The composition for expressing the artificial receptor protein may comprise a nucleic acid sequence encoding the artificial receptor protein.

(c) The composition for gene manipulation may comprise:

a guide nucleic acid that is homologous or capable of forming a complementary bond to a target sequence of SEQ ID NOS: 1 to 289 in a nucleic acid sequences of at least one immunity regulating gene selected from the group consisting PD-1 gene, CTLA-4 gene, DGKA gene, DGKZ gene, FAS gene, EGR2 gene, PPP2r2d gene, TET2 gene, PSGL-1 gene, A20 gene, and KDM6A gene, or a nucleic acid encoding the guide nucleic acid; and at least one editor protein selected from the group consisting of *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and Cpf1 protein, or a nucleic acid encoding the editor protein.

Here, the guide nucleic acid and the editor protein may be each in the form of a nucleotide sequence in the form of at least one vector, or may be in the form of a guide nucleic acid-editor protein complex in which the guide nucleic acid and the editor protein are bound.

The contacting may be performed ex vivo.

The contacting may be sequentially or simultaneously contacting (a) the immune cell with (b) the composition for expressing the artificial receptor protein, and (c) the composition for gene manipulation The contacting may be performed by at least one method selected from electroporation, liposome, plasmid, viral vector, nanoparticles, and protein translocation domain (PTD) fusion protein method.

The present invention provides a method for treating an immune disease using a manipulated immune cell for a particular purpose.

In certain embodiments, the method for treating an immune disease comprising administering a pharmaceutical composition to a subject, which comprises a manipulated immune cell as an active ingredient.

Explanations related to the manipulate immune cell are as described above.

The pharmaceutical composition may further comprise additional component.

Here, the additional component may be immune checkpoint inhibitor.

The immune checkpoint inhibitor may be an inhibitor of PD-1, PD-L1, LAG-3, TIM-3, CTLA-4, TIGIT, BTLA, IDO, VISTA, ICOS, KIRs, CD160, CD244, or CD39.

Here, the additional component may be an antigen binding agent, a cytokine, a secretagogue of cytokine, or an inhibitor of cytokine.

Here, the additional component may be a suitable carrier for delivering the manipulated immune cell into the body.

The manipulated immune cell included in the pharmaceutical composition may be an autologous cell of the subject, or an allogeneic cell The immune disease may be an autoimmune disease.

Here, the autoimmune disease may be graft versus host disease (GVHD), systemic lupus erythematosus, celiac disease, diabetes mellitus type 1, graves disease, inflammatory bowel disease, psoriasis, rheumatoid arthritis, or multiple sclerosis.

The disease may be an intractable disease in which pathogens are known but the treatment is unknown.

Here, the intractable disease may be a viral infection disease, a disease caused by a prion pathogen, or a cancer.

The administering of the pharmaceutical composition to the subject with an immune disease may be performed by a method selected from injection, transfusion, implantation, or transplantation.

The subject is a mammal including humans, monkeys, mice, and rats.

BRIEF DESCRIPTIONS OF DRAWINGS

Figure 43:
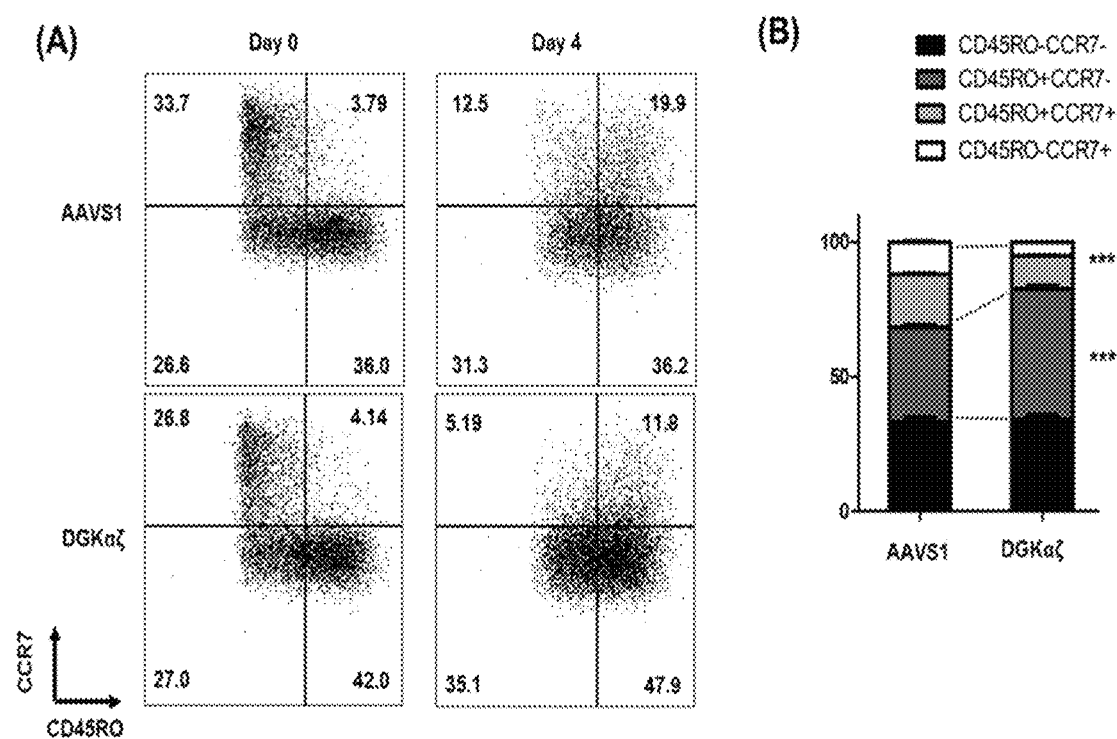
Figure 44:
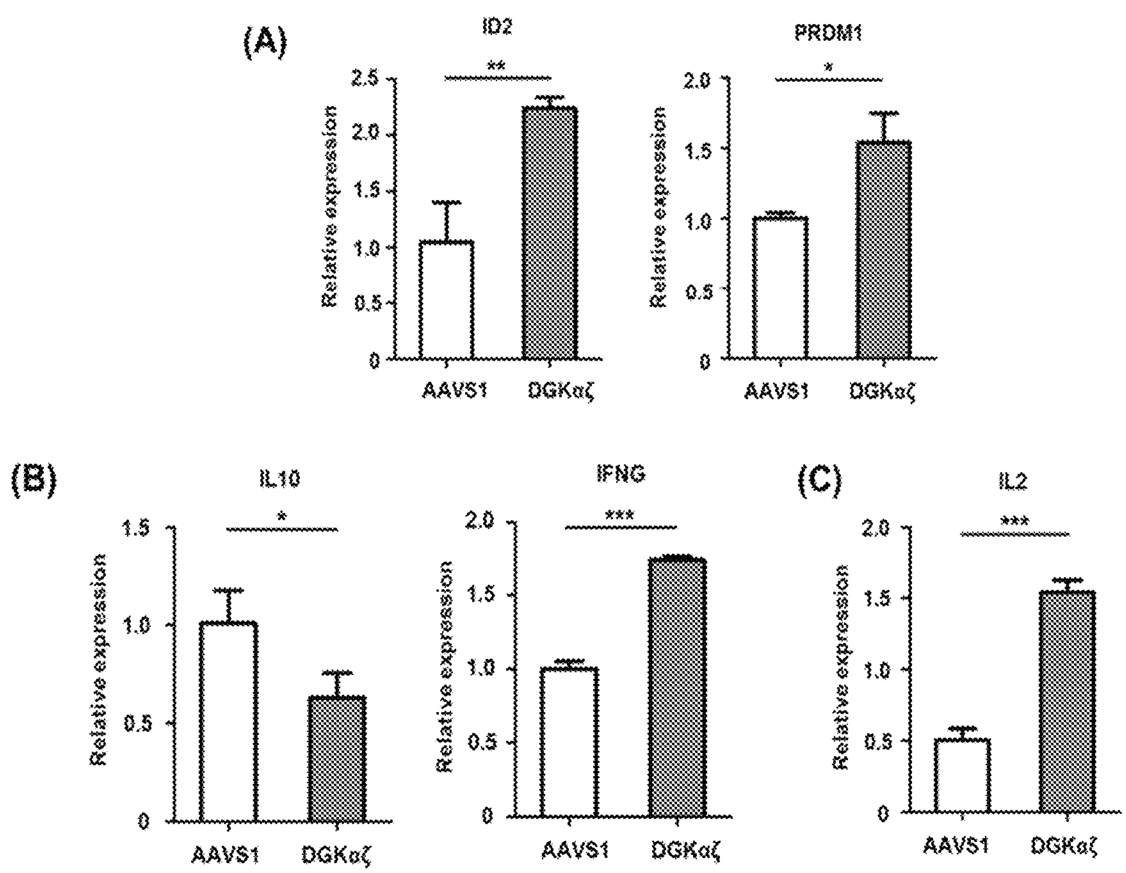
Figure 45:
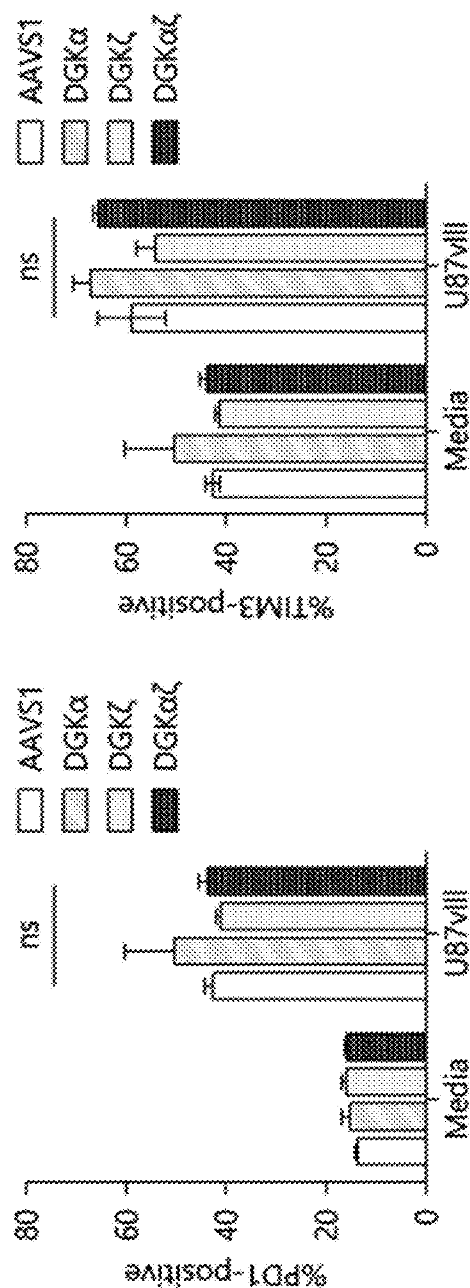
Figure 46:
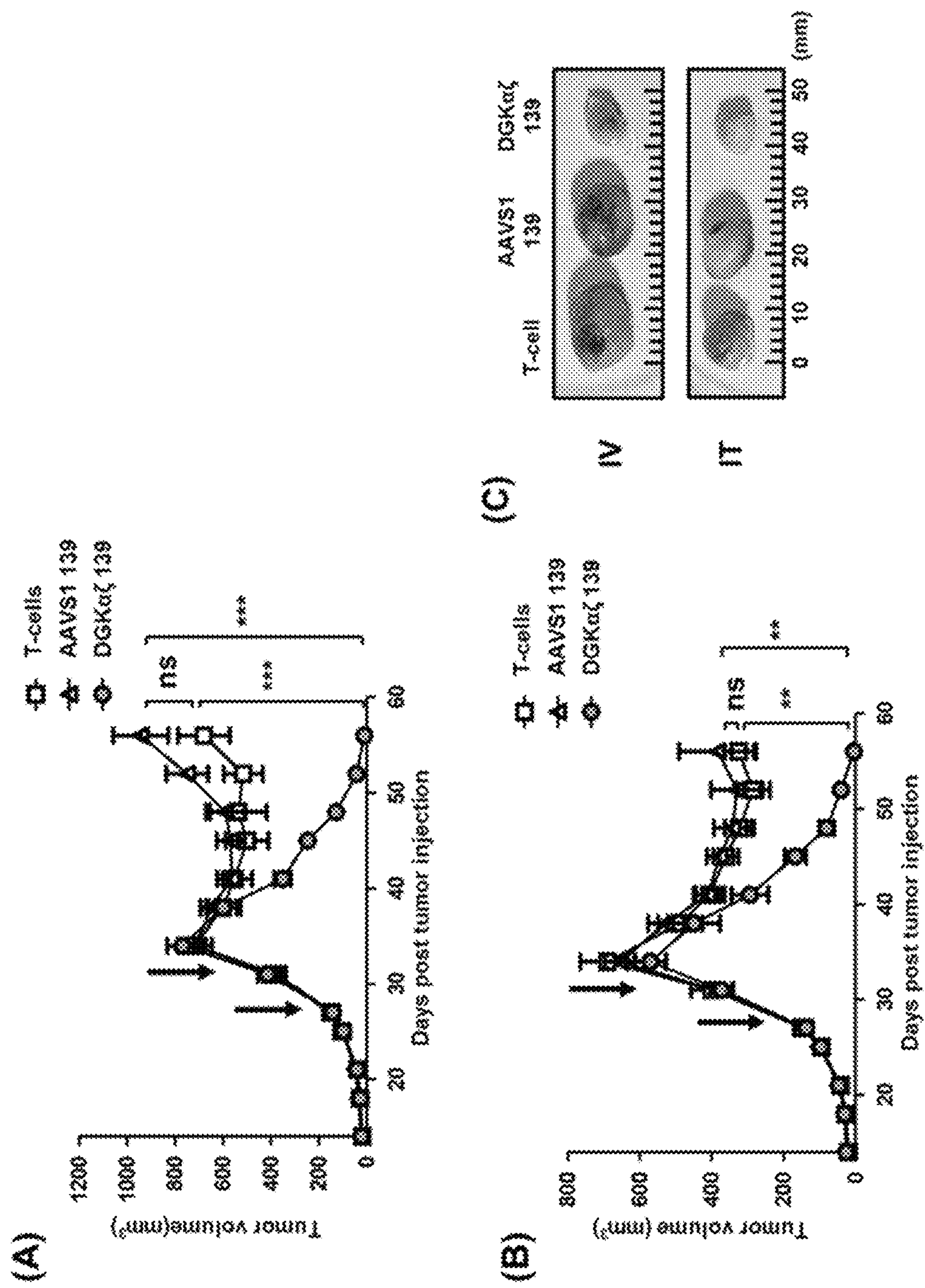

FIG. 43 is a graph showing (A) collective quantity of naïve T cells and (B) collective quantity of effector memory T cells of AAVS1-knockout or DGK-knockout 139 CAR-T cells FIG. 44 is a graph showing (A) expression level of effector memory regulatory factor, (B) expression level of type 1 cytokine and (C) expression level of type 2 cytokine of AAVS1-knockout or DGK-knockout 139 CAR-T cells FIG. 45 is a graph showing the expression level of a marker related with T cell exhaustion in AAVS1-knockout or DGK-knockout 139 CAR-T cells FIG. 46 illustrates an anti-tumor effect of AAVS1-knockout or DGK-knockout 139 CAR-T cells, in which a graph shows (A) an anti-tumor effect when intravenously injected and (B) an anti-tumor effect when intratumorally injected, and an image compares (C) size of tumors in each condition.

Figure 47:
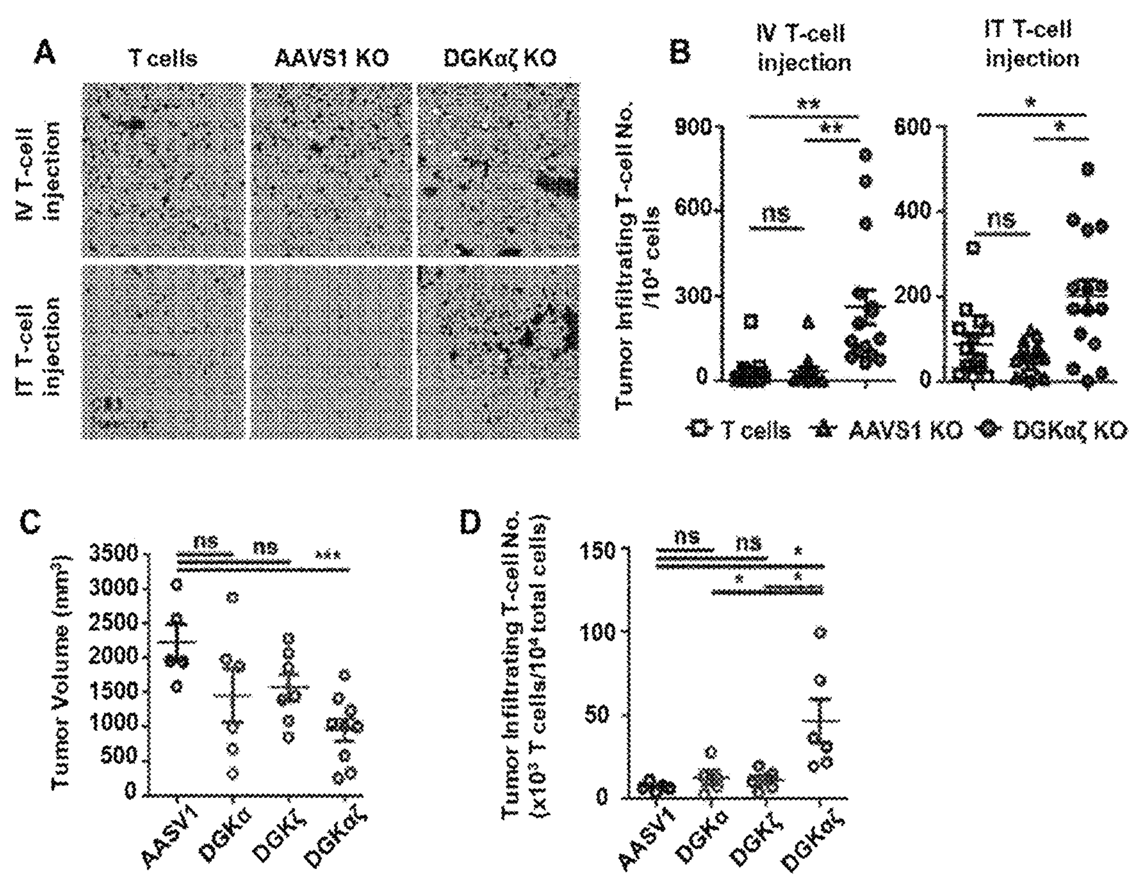

FIG. 47 shows a graph comparing (A), (B) remain status of in vivo-injected AAVS1, αKO, ζKO, and dKO 139 CAR-T cells and (C) size of tumors in each condition, and a graph illustrating (D) number of tumor infiltrating T cells in each condition.

Figure 48:
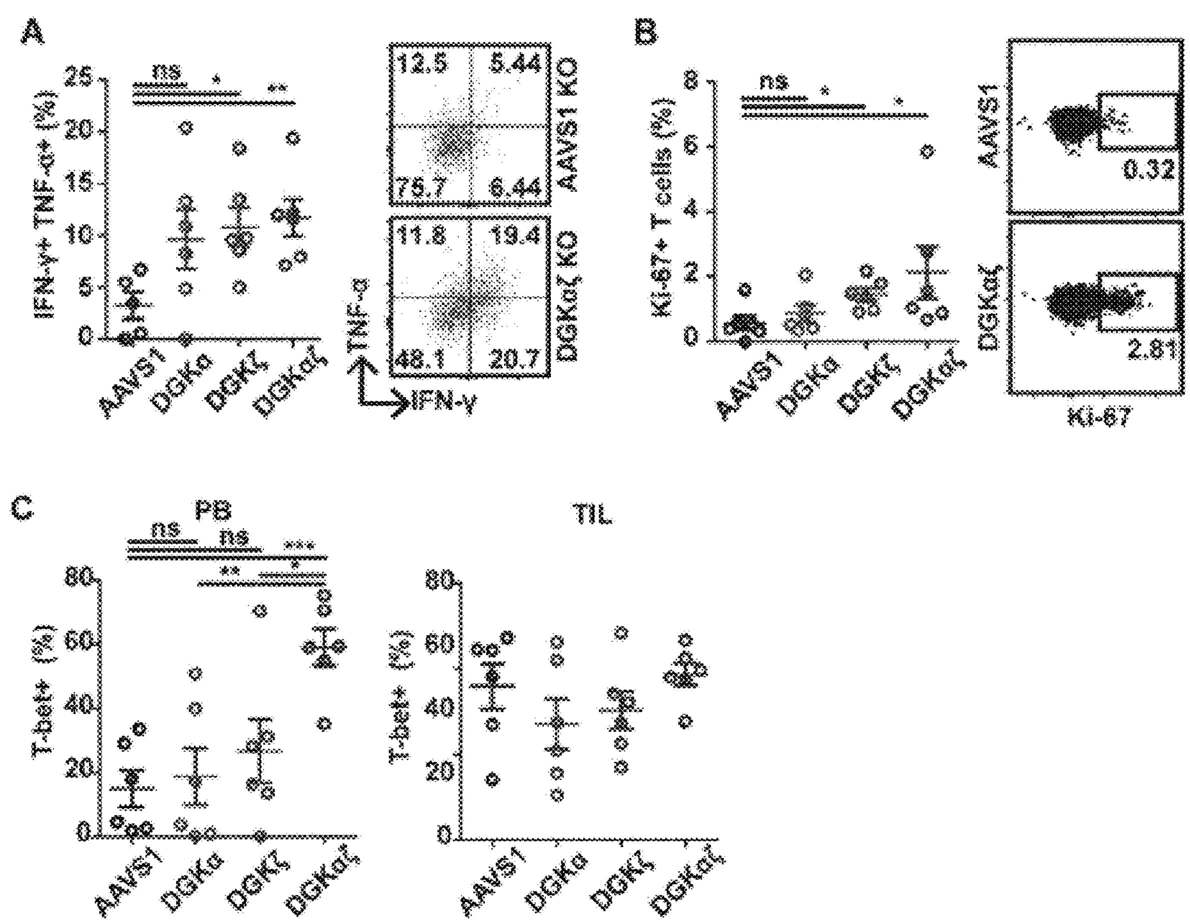

FIG. 48 is a graph comparing (A) IFN-γ, TNFα positive cells (%), (B) Ki-67 positive cells (%), and (C) T-bet positive cells (%) of in vivo-injected AAVS1, αKO, ζKO, and dKO 139 CAR-T cells.

DETAILED DESCRIPTION

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limited.

An aspect disclosed in the present invention relates to a guide nucleic acid.

The term "guide nucleic acid" refers to a nucleotide sequence that can recognize target nucleic acids, genes or chromosomes, and interact with editor proteins. The guide nucleic acids can complementarily bind with a portion of nucleotide sequences in target nucleic acids, genes or chromosomes. Also, a portion of nucleotide sequences in the guide nucleic acid can interact with a portion of amino acids in editor proteins and form a guide nucleic acid-editor protein complex.

The guide nucleic acid can function to induce the guide nucleic acid-editor protein complex to be located at a target region of target nucleic acids, genes or chromosomes.

The guide nucleic acid may be present in the form of DNA, RNA or a DNA/RNA mixture, and have a 5 to 150-nucleic acid sequence.

The guide nucleic acid may be one continuous nucleic acid sequence.

For example, the one continuous nucleic acid sequence may be (N)m, where N is A, T, C or G, or A, U, C or G, and m is an integer of 1 to 150.

The guide nucleic acid may be two or more continuous nucleic acid sequences.

For example, the two or more continuous nucleic acid sequences may be (N)m and (N)o, where N represents A, T, C or G, or A, U, C or G, m and o are an integer of 1 to 150, and may be the same as or different from each other.

The guide nucleic acid includes one or more domains.

The domains may be functional domains such as, but are not limited to, a guide domain, a first complementary domain, a linker domain, a second complementary domain, a proximal domain, or a tail domain.

Here, one guide nucleic acid may have two or more functional domains. Furthermore, the two or more functional domains may be different from one another. Alternatively, two or more functional domains included in a guide nucleic acid may be identical to one another. For example, one guide nucleic acid may have two or more proximal domains, and in another example, one guide nucleic acid may have two or more tail domains. However, functional domains included in a guide nucleic acid being two identical domains does not represent that the two functional domains have identical sequences; domains can be considered identical even when their sequences differ, as long as they perform functionally identical.

Details about the functional domains are elaborated below.

i) Guide Domain

The term "guide domain" is a domain having a complementary guide sequence which is able to form a complementary bond with a portion of sequences in a target gene or nucleic acid, and serves to specifically interact with the target gene or nucleic acid. For example, a guide domain can serve to induce a guide nucleic acid-editor protein complex to a location having a specific nucleotide sequence of a target gene or nucleic acids.

The guide domain may be a 10 bp to 35 bp nucleotide sequence.

In one example, the guide domain may be a 10 bp to 35 bp, 15 bp to 35 bp, 20 bp to 35 bp, 25 bp to 35 bp, or 30 bp to 35 bp nucleotide sequence.

In another example, the guide domain may be a 10 bp to 15 bp, 15 bp to 20 bp, 20 bp to 25 bp, 25 bp to 30 bp, or 30 bp to 35 bp nucleotide sequence.

The guide domain may include a guide sequence.

The term "guide sequence" is a nucleotide sequence complementary to a portion of sequences in one strand of a double strand of a target gene or nucleic acid, wherein the guide sequence may be a nucleotide sequence having at least 50%, 55%, 60%, 65%, 70%, 75%, 80%, 85%, 90%, or 95% or more complementarity or complete complementarity.

The guide sequence may be a 10 bp to 25 bp nucleotide sequence.

In one example, the guide sequence may be a 10 bp to 25 bp, 15 bp to 25 bp, or 20 bp to 25 bp nucleotide sequence.

In another example, the guide sequence may be a 10 bp to 15 bp, 15 bp to 20 bp, or 20 bp to 25 bp nucleotide sequence.

Additionally, the guide domain may have an additional nucleotide sequence.

The additional nucleotide sequence may be one which promotes or inhibits function of the guide domain.

The additional nucleotide sequence may be one which promotes or inhibits function of the guide sequence.

The additional nucleotide sequence may be a 1 bp to 10 bp nucleotide sequence.

In one example, the additional nucleotide sequence may be a 2 bp to 10 bp, 4 bp to 10 bp, 6 bp to 10 bp, or 8 bp to 10 bp nucleotide sequence.

In another example, the additional nucleotide sequence may be a 1 bp to 3 bp, 3 bp to 6 bp, or 7 bp to 10 bp nucleotide sequence.

In an embodiment, the additional nucleotide sequence may be a 1 bp, 2 bp, 3 bp, 4 bp, 5 bp, 6 bp, 7 bp, 8 bp, 9 bp, or 10 bp nucleotide sequence.

For example, the additional nucleotide sequence may be 1-base nucleotide sequence G (guanine), or a 2-base nucleotide sequence GG.

The additional nucleotide sequence may be located at the 5' end of the guide sequence.

The additional nucleotide sequence may be located at the 3' end of the guide sequence.

ii) First Complementary Domain

The term "first complementary domain" is a domain including a nucleotide sequence complementary to a second complementary domain explained hereafter, and has enough complementarity so as to form a double strand with the second complementary domain. For example, the first complementary domain may be a nucleotide sequence having at least 50%, 55%, 60%, 65%, 70%, 75%, 80%, 85%, 90%, or 95% or more complementarity or complete complementarity to the second complementary domain.

The first complementary domain may form a double strand with the secondary complementary domain by complementary bonding. The double strand may serve to interact with a portion of amino acids in editor proteins and thereby form a guide nucleic acid-editor protein complex.

The first complementary domain may be a 5 to 35-nucleotide sequence.

In one example, the first complementary domain may be a 5 to 35, 10 to 35, 15 to 35, 20 to 35, 25 to 35, or 30 to 35-nucleotide sequence.

In another example, the first complementary domain may be a 1 to 5, 5 to 10, 10 to 15, 15 to 20, 20 to 25, 25 to 30 or 30 to 35-nucleotide sequence.

iii) Linker Domain

The term "linker domain" is a nucleic acid sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a 1 to 30-nucleotide sequence.

In one example, the linker domain may be a 1 to 5, 5 to 10, 10 to 15, 15 to 20, 20 to 25, or 25 to 30-nucleotide sequence.

In another example, the linker domain may be a 1 to 30, 5 to 30, 10 to 30, 15 to 30, 20 to 30, or 25 to 30-nucleotide sequence.

iv) Second Complementary Domain

The term "second complementary domain" is a domain including a nucleotide sequence containing a nucleic acid sequence complementary to the first complementary domain described above, and has enough complementarity so as to form a double strand with the first complementary domain. For example, the second complementary domain may be a nucleotide sequence having at least 50%, 55%, 60%, 65%, 70%, 75%, 80%, 85%, 90%, or 95% or more complementarity or complete complementarity to the first complementary domain.

The second complementary domain may form a double strand with the first complementary domain by complementary bonding. The formed double strand may serve to interact with a portion of amino acids in editor proteins and thereby form a guide nucleic acid-editor protein complex.

The second complementary domain may have a nucleotide sequence complementary to the first complementary domain, and a nucleotide sequence having no complementarity to the first complementary domain, for example, a nucleotide sequence not forming a double strand with the first complementary domain, and may have a longer nucleotide sequence than the first complementary domain.

The second complementary domain may have a 5 to 35-nucleotide sequence.

In an example, the second complementary domain may be a 1 to 35, 5 to 35, 10 to 35, 15 to 35, 20 to 35, 25 to 35, or 30 to 35-nucleotide sequence.

In another example, the second complementary domain may be a 1 to 5, 5 to 10, 10 to 15, 15 to 20, 20 to 25, 25 to 30, or 30 to 35-nucleotide sequence.

v) Proximal Domain

The term "proximal domain" is a nucleotide sequence located adjacent to the second complementary domain.

The proximal domain may have a complementary nucleotide sequence therein, and may be formed in a double strand due to a complementary nucleotide sequence.

The proximal domain may be a 1 to 20-nucleotide sequence.

In one example, the proximal domain may be a 1 to 20, 5 to 20, 10 to 20 or 15 to 20-nucleotide sequence.

In another example, the proximal domain may the proximal domain may be a 1 to 20, 5 to 20, 10 to 20 or 15 to 20-base sequence be a 1 to 5, 5 to 10, 10 to 15 or 15 to 20-nucleotide sequence.

vi) Tail Domain

The term "tail domain" is a nucleotide sequence located at one or more ends of the both ends of the guide nucleic acid.

The tail domain may have a complementary nucleotide sequence therein, and may be formed in a double strand due to a complementary nucleotide sequence.

The tail domain may be a 1 to 50-nucleotide sequence.

In an example, the tail domain may be a 5 to 50, 10 to 50, 15 to 50, 20 to 50, 25 to 50, 30 to 50, 35 to 50, 40 to 50, or 45 to 50-nucleotide sequence.

In another example, the tail domain may be a 1 to 5, 5 to 10, 10 to 15, 15 to 20, 20 to 25, 25 to 30, 30 to 35, 35 to 40, 40 to 45, or 45 to 50-nucleotide sequence.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

As an embodiment of the contents disclosed by the present specification, the guide nucleic acid may be a gRNA.

gRNA

The term "gRNA" refers to a nucleic acid capable of specifically targeting a gRNA-CRISPR enzyme complex, that is, a CRISPR complex, with respect to a target gene or nucleic acid. In addition, the gRNA is a nucleic acid-specific RNA which may bind to a CRISPR enzyme and guide the CRISPR enzyme to the target gene or nucleic acid.

The gRNA may include multiple domains. Due to each domain, interactions may occur in a three-dimensional structure or active form of a gRNA strand, or between these strands.

The gRNA may be called single-stranded gRNA (single RNA molecule); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain, a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid and a first complementary domain; and a second strand which includes a second complementary domain, a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; a second complementary domain, and a domain having a sequence complementary to the first complementary domain sequence, thereby forming a double-stranded nucleic acid with the first complementary domain in the 3' to 5' direction.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus* pyogenes, *Campylobacter jejuni, Streptococcus* thermophilus, *Streptococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' or a base sequence having partial, that is, at least 50% or more, or complete homology with 5'-GUUUUAGAGCUA-3'. Here, the first complementary domain may further include $(X)_n$, resulting in 5'-GUUUUAGAGCUA(X)n-3'. The X may be selected from the group consisting of bases A, T, U and G, and the n may represent the number of bases, which is an integer of 5 to 15. Here, the $(X)_n$ may be n repeats of the same base, or a mixture of n bases of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3', or a base sequence having partial, that is, at least 50% or more, or complete homology with 5'-GUUUUAGUCCCUUUUUAAAUUUCUU-3'. Here, the first complementary domain may further include (X)n, resulting in 5'-GUUUUAGUCCCUUUUUAAAUUUCUU(X)n-3'. The X may be selected from the group consisting of bases A, T, U and G, and the n may represent the number of bases, which is an integer of 5 to 15. Here, the $(X)_n$ may represent n repeats of the same base, or a mixture of n bases of A, T, U and G.

In another embodiment, the first complementary domain may have partial, that is, at least 50% or more, or complete homology with a first complementary domain of *Parcubacteria bacterium* (GWC2011_GWC2_44_17), *Lachnospiraceae bacterium* (MC2017), *Butyrivibrio proteoclasiicus, Peregrinibacteria bacterium* (GW2011_GWA_33_10), *Acidaminococcus* sp. (BV3L6), *Porphyromonas macacae, Lachnospiraceae bacterium* (ND2006), *Porphyromonas crevioricanis, Prevotella disiens, Moraxella bovoculi* (237), *Smiihella* sp. (SC_KO8D17), *Leptospira inadai, Lachnospiraceae bacterium* (MA2020), *Francisella novicida* (U112), *Candidatus Methanoplasma termitum* or *Eubacterium eligens*, or a first complementary domain derived therefrom.

For example, when the first complementary domain is the first complementary domain of *Parcubacteria bacterium* or a first complementary domain derived therefrom, the first complementary domain may be 5'-UUUGUAGAU-3', or a base sequence having partial, that is, at least 50% or more homology with 5'-UUUGUAGAU-3'. Here, the first complementary domain may further include $(X)_n$, resulting in 5'-(X)nUUUGUAGAU-3'. The X may be selected from the group consisting of bases A, T, U and G, and the n may represent the number of bases, which is an integer of 1 to 5. Here, the $(X)_n$ may represent n repeats of the same base, or a mixture of n bases of A, T, U and G.

Here, the linker domain may be a nucleotide sequence connecting a first complementary domain with a second complementary domain.

The linker domain may be connected with the first complementary domain and the second complementary domain by covalent or non-covalent bonding, respectedly.

The linker domain may connect the first complementary domain with the second complementary domain by covalent or non-covalent bonding.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding.

The linker domain may be used to produce single-stranded gRNA by being connected with crRNA and tracrRNA of double-stranded gRNA or connecting the crRNA with the tracrRNA by covalent or non-covalent bonding.

Here, the second complementary domain may have homology with a natural second complementary domain, or may be derived from the natural second complementary domain. In addition, the second complementary domain may have a difference in base sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus* pyogenes, *Campylobacter jejuni, Streptococcus* thermophilus, *Streptococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3', or a base sequence having partial, that is, at least 50% or more homology with 5'-UAGCAAGUUAAAAU-3' (a base sequence forming a double strand with the first complementary domain is underlined). Here, the second complementary domain may further include (X)n and/or (X)m, resulting in 5'-(X)n UAGCAAGUUAAAAU(X)m-3'. The X may be selected from the group consisting of bases A, T, U and G, and each of the n and m may represent the number of bases, in which the n may be an integer of 1 to 15, and the m may be an integer of 1 to 6. Here, the (X)n may represent n repeats of the same base, or a mixture of n bases of A, T, U and G. In addition, (X)m may represent m repeats of the same base, or a mixture of m bases of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3', or a base sequence having partial, that is, at least 50% or more homology with 5'-AAGAAAUUUAAAAAGGGACUAAAAU-3' (a base sequence forming a double strand with the first complementary domain is underlined). Here, the second complementary domain may further include (X)n and/or (X)m, resulting in 5'-(X)nAAGAAAUUUAAAAAGGGACUAAAAU(X)m-3'. The X may be selected from the group consisting of bases A, T, U and G, and each of the n and m may represent the number of bases, in which the n may be an integer of 1 to 15, and the m may be an integer of 1 to 6. Here, (X)n may represent n repeats of the same base, or a mixture of n bases of A, T, U and G. In addition, (X)m may represent m repeats of the same base, or a mixture of m bases of A, T, U and G.

In another embodiment, the second complementary domain may have partial, that is, at least 50% or more, or complete homology with a first complementary domain of *Parcubacteria bacterium* (GWC2011_GWC2_44_17), *Lachnospiraceae bacterium* (MC2017), *Butyrivibrio proteoclasiicus, Peregrinibacteria bacterium* (GW2011_GWA_33_10), *Acidaminococcus* sp. (BV3L6), *Porphyromonas macacae, Lachnospiraceae bacterium* (ND2006), *Porphyromonas crevioricanis, Prevotella disiens, Moraxella bovoculi* (237), *Smiihella* sp. (SC_KO8D17), *Leptospira inadai, Lachnospiraceae bacterium* (MA2020), *Francisella novicida* (U112), *Candidatus Methanoplasma termitum* or *Eubacterium eligens*, or a second complementary domain derived therefrom.

For example, when the second complementary domain is a second complementary domain of *Parcubacteria bacterium* or a second complementary domain derived therefrom, the second complementary domain may be 5'-AAAUUUCUACU-3', or a base sequence having partial, that is, at least 50% or more homology with 5'-AAAUUUCUACU-3' (a base sequence forming a double strand with the first complementary domain is underlined). Here, the second complementary domain may further include (X)n and/or (X)m, resulting in 5'-(X)nAAAUUUCUACU(X)m-3'. The X may be selected from the group consisting of bases A, T, U and G, and each of the n and m may represent the number of bases, in which the n may be an integer of 1 to 10, and the m may be an integer of 1 to 6. Here, the (X)n may represent n repeats of the same base, or a mixture of n bases of A, T, U and G. In addition, the (X)m may represent m repeats of the same base, or a mixture of m bases of A, T, U and G.

Here, the first complementary domain and the second complementary domain may form a complementary bond.

The first complementary domain and the second complementary domain may form a double strand through the complementary bond.

The formed double strand may interact with a CRISPR enzyme.

Selectively, the first complementary domain may include an additional nucleotide sequence that does not form a complementary bond with the second complementary domain of the second strand.

Here, the additional nucleotide sequence may be a 1 bp to 15 bp nucleotide sequence. For example, the additional nucleotide sequencey may be a 1 bp to 5 bp, 5 bp to 10 bp, or 10 bp to 15 bp nucleotide sequence.

Here, the proximal domain may be a domain in the 5' to 3' direction of the second complementary domain.

The proximal domain may have homology with a natural proximal domain, or may be derived from the natural proximal domain. In addition, the proximal domain may have a difference in base sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes, Campylobacter jejuni, Streptococcus thermophilus, Streptococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGCUAGUCCG-3', or a base sequence having partial, that is, at least 50% or more homology with 5'-AAGGCUAGUCCG-3'. Here, the proximal domain may further include $(X)_n$, resulting in 5'-AAGGCUAGUCCG$(X)_n$-3'. The X may be selected from the group consisting of bases A, T, U and G, and the n may represent the number of bases, which is an integer of 1 to 15. Here, the $(X)_n$ may represent n repeats of the same base, or a mixture of n bases of A, T, U and G.

In yet another example, when the proximal domain is a proximal domain of *Campylobacter jejuni* or a proximal domain derived therefrom, the proximal domain may be 5'-AAAGAGUUUGC-3', or a base sequence having at least 50% or more homology with 5'-AAAGAGUUUGC-3'. Here, the proximal domain may further include $(X)_n$, resulting in 5'-AAAGAGUUUGC$(X)_n$-3'. The X may be selected from the group consisting of bases A, T, U and G, and the n may represent the number of bases, which is an integer of 1 to 40. Here, the $(X)_n$ may represent n repeats of the same base, or a mixture of n bases of A, T, U and G.

Here, the tail domain may be selectively added to the 3' end of a first strand or a second strand of single-stranded gRNA or double-stranded gRNA.

In addition, the tail domain may have homology with a natural tail domain, or may be derived from the natural tail domain. In addition, the tail domain may have a difference in base sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes, Campylobacter jejuni, Streptococcus thermophilus, Streptococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAACUUGAAAAAGUGGCACCGAGUCGGUGC-3', or a base sequence having partial, that is, at least 50% or more homology with 5'-UUAUCAACUUGAAAAAGUGGCACCGAGUCGGUGC-3'.

Here, the tail domain may further include (X), resulting in 5'-UUAUCAACUUGAAAAAGUGGCACCGAGUCGGUGC$(X)_n$-3'. The X may be selected from the group consisting of bases A, T, U and G, and the n may represent the number of bases, which is an integer of 1 to 15. Here, the $(X)_n$ may represent n repeats of the same base, or a mixture of n bases such as A, T, U and G.

In another example, when the tail domain is a tail domain of *Campylobacter jejuni* or a tail domain derived therefrom, the tail domain may be 5'-GGGACUCUGCGGGGUUACAAUCCCCUAAAACCGCUUUU-3', or a base sequence having partial, that is, at least 50% or more homology with 5'-GGGACUCUGCGGGGUUACAAUCCCCUAAAACCGCUUUU-3'. Here, the tail domain may further include (X), resulting in 5'-GGGACUCUGCGGGGUUACAAUCCCCUAAAACCGCUUUU$(X)_n$-3'. The X may be selected from the group consisting of bases A, T, U and G, and the n may represent the number of bases, which is an integer of 1 to 15. Here, the $(X)_n$ may represent n repeats of the same base, or a mixture of n bases of A, T, U and G.

In another embodiment, the tail domain may include a 1 to 10-base sequence at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of

5'-[guide domain]-[first complementary domain]-3', and the second strand may consist of 5'-[second complementary domain]-[proximal domain]-3' or 5'-[second complementary domain]-[proximal domain]-[tail domain]-3'.

Here, the first strand may be referred to as crRNA, and the second strand may be referred to as tracrRNA.

Here, the first strand and the second strand may optionally include an additional nucleotide sequence.

In one example, the first strand may be

5'-(Ntarget)-(Q)m-3'; or

5'-(X)a-(Ntarget)-(X)b-(Q)m-(X)c-3'.

Here, the $N_{target}$ is a nucleotide sequence complementary to a portion of sequences in one strand of a double strand of a target gene or nucleic acid, and a nucleotide sequence region which may be changed according to a target sequence on a target gene or nucleic acid.

Here, the $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a *Streptococcus pyogenes*-derived first complementary domain, the $(Q)_m$ may be 5'-GUUUUAGAGCUA-3', or a base sequence having at least 50% or more homology with 5'-GUUUUAGAGCUA-3'.

In another example, when the first complementary domain has partial or complete homology with a first complementary domain of *Campylobacter jejuni* or a *Campylobacter jejuni*-derived first complementary domain, the $(Q)_m$ may be 5'-GUUUUAGUCCCUUUUUAAAUUUCUU-3', or a base sequence having at least 50% or more homology with 5'-GUUUUAGUCCCUUUUUAAAUUUCUU-3'.

In still another example, when the first complementary domain has partial or complete homology with a first complementary domain of *Streptococcus thermophilus* or a *Streptococcus thermophilus*-derived first complementary domain, the $(Q)_m$ may be 5'-GUUUUAGAGCUGUGUUGUUUCG-3', or a base sequence having at least 50% or more homology with 5'-GUUUUAGAGCUGUGUUGUUUCG-3'.

In addition, each of the $(X)_a$, $(X)_b$ and $(X)_c$ is selectively an additional base sequence, where the X may be each independently selected from the group consisting of A, U, C and G, and each of the a, b and c may be the number of bases, which is 0 or an integer of 1 to 20.

In one exemplary embodiment, the second strand may be

5'-$(Z)_h$—$(P)_k$-3'; or

5'-$(X)_d$—$(Z)_h$—$(X)_e$—$(P)_k$—$(X)_f$-3'.

In another embodiment, the second strand may be

5'-$(Z)_h$—$(P)_k$—$(F)_i$-3'; or

5'-$(X)_d$—$(Z)_h$—$(X)_e$—$(P)_k$—$(X)_f$—$(F)_i$-3'.

Here, the $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3', or a base sequence having at least 50% or more homology with 5'-UAGCAAGUUAAAAU-3'.

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3', or a base sequence having at least 50% or more homology with 5'-AAGAAAUUUAAAAAGGGACUAAAAU-3'.

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3', or a base sequence having at least 50% or more homology with 5'-CGAAACAACACAGCGAGUUAAAAU-3'.

The $(P)_k$ is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3', or a base sequence having at least 50% or more homology with 5'-AAGGCUAGUCCG-3'.

In another example, when the proximal domain has partial or complete homology with a proximal domain of *Campylobacter jejuni* or a proximal domain derived therefrom, the $(P)_k$ may be 5'-AAAGAGUUUGC-3', or a base sequence having at least 50% or more homology with 5'-AAAGAGUUUGC-3'.

In still another example, when the proximal domain has partial or complete homology with a proximal domain of *Streptococcus thermophilus* or a proximal domain derived therefrom, the $(P)_k$ may be 5'-AAGGCUUAGUCCG-3', or a base sequence having at least 50% or more homology with 5'-AAGGCUUAGUCCG-3'.

The $(F)_i$ may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F) may be 5'-UUAUCAACUUGAAAAAGUGGCACCGAGUCGGUGC-3', or a base sequence having at least 50% or more homology with 5'-UUAUCAACUUGAAAAAGUGGCACCGAGUCGGUGC-3'.

In another example, when the tail domain has partial or complete homology with a tail domain of *Campylobacter jejuni* or a tail domain derived therefrom, the $(F)_i$ may be 5'-GGGACUCUGCGGGGUUACAAUCCCCUAAAACCGCUUUU-3', or a base sequence having at least 50% or more homology with 5'-GGGACUCUGCGGGGUUACAAUCCCCUAAAACCGCUUUU-3'.

In still another example, when the tail domain has partial or complete homology with a tail domain of *Streptococcus thermophilus* or a tail domain derived therefrom, the (F) may be 5'-UACUCAACUUGAAAAGGUGGCACCGAUUCG- GUGUUUUU-3', or a base sequence having at least 50% or more homology with 5'-UACUCAACUUGAAAAG-GUGGCACCGAUUCGGUGUUUUU-3'.

In addition, the $(F)_i$ may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the $(X)_d$, $(X)_e$ and $(X)_f$ may be base sequences selectively added, where the X may be each independently selected from the group consisting of A, U, C and G, and each of the d, e and f may be the number of bases, which is 0 or an integer of 1 to 20.

Single-Stranded gRNA

Single-stranded gRNA may be classified into a first single-stranded gRNA and a second single-stranded gRNA.

First Single-Stranded gRNA

A first single-stranded gRNA is a single-stranded gRNA wherein a first strand and a second strand of the double-stranded gRNA is linked by a linker domain Specifically, the single-stranded gRNA may consist of 5'-[guide domain]-[first complementary domain]-[linker domain]-[second complementary domain]-3', 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3'.

The first single-stranded gRNA may optionally include an additional nucleotide sequence.

In one exemplary embodiment, the first single-stranded gRNA may be

5'-$(N_{target})$-$(Q)_m$-$(L)_j$-$(Z)_h$-3';

5'-$(N_{target})$-$(Q)_m$-$(L)_j$-$(Z)_h$—$(P)_k$-3'; or

5'-$(N_{target})$-$(Q)_m$-$(L)_j$-$(Z)_h$—$(P)_k$—$(F)_i$-3'.

In another exemplary embodiment, the single-stranded gRNA may be

5'-$(X)_a$—$(N_{target})$—$(X)_b$-$(Q)_m$-$(X)_c$-$(L)_j$-$(X)_d$—$(Z)_h$—$(X)_c$-3';

5'-$(X)_d$—$(N_{target})$—$(X)_b$-$(Q)_m$-$(X)_c$-$(L)_j$-$(X)_d$—$(Z)_h$—$(X)_c$—$(P)_k$—$(X)_f$-3'; or 5'-$(X)_d$—$(N_{target})$—$(X)_b$-$(Q)_m$-$(X)_c$-$(L)_j$-$(X)_d$—$(Z)_h$—$(X)_d$—$(P)_k$—$(X)_f$—$(F)_i$-3'.

Here, the $N_{target}$ is a base sequence capable of forming a complementary bond with a target sequence on a target gene or nucleic acid, and a base sequence region capable of being changed according to a target sequence on a target gene or nucleic acid.

The $(Q)_m$ includes a base sequence including the first complementary domain, which is able to form a complementary bond with a second complementary domain. The $(Q)_m$ may be a sequence having partial or complete homology with a first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a first complementary domain derived therefrom, the $(Q)_m$ may be 5'-GUUUUA-GAGCUA-3', or a base sequence having at least 50% or more homology with 5'-GUUUUAGAGCUA-3'.

In another example, when the first complementary domain has partial or complete homology with a first complementary domain of *Campylobacter jejuni* or a first complementary domain derived therefrom, the $(Q)_m$ may be 5'-GUUUUAGUCCCUUUUUAAAUUUCUU-3', or a base sequence having at least 50% or more homology with 5'-GUUUUAGUCCCUUUUUAAAUUUCUU-3'.

In still another example, when the first complementary domain has partial or complete homology with a first complementary domain of *Streptococcus thermophilus* or a first complementary domain derived therefrom, the $(Q)_m$ may be 5'-GUUUUAGAGCUGUGUUGUUUCG-3', or a base sequence having at least 50% or more homology with 5'-GUUUUAGAGCUGUGUUGUUUCG-3'.

In addition, the $(L)_j$ is a base sequence including the linker domain, and connecting the first complementary domain with the second complementary domain, thereby producing single-stranded gRNA. Here, the L may be each independently selected from the group consisting of A, U, C and G, and the j may be the number of bases, which is an integer of 1 to 30.

The $(Z)_h$ is a base sequence including the second complementary domain, which is able to have a complementary bond with the first complementary domain. The $(Z)_h$ may be a sequence having partial or complete homology with the second complementary domain of a species existing in nature, and the base sequence of the second complementary domain may be changed according to the species of origin. The Z may be each independently selected from the group consisting of A, U, C and G, and the h is the number of bases, which may be an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3', or a base sequence having at least 50% or more homology with 5'-UAGCAAGUUAAAAU-3'.

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3', or a base sequence having at least 50% or more homology with 5'-AAGAAAUUUAAAAAGGGACUAAAAU-3'.

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3', or a base sequence having at least 50% or more homology with 5'-CGAAACAACACAGCGAGUUAAAAU-3'.

The $(P)_k$ is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3', or a base sequence having at least 50% or more homology with 5'-AAGGCUAGUCCG-3'.

In another example, when the proximal domain has partial or complete homology with a proximal domain of *Campylobacter jejuni* or a proximal domain derived therefrom, the $(P)_k$ may be 5'-AAAGAGUUUGC-3', or a base sequence having at least 50% or more homology with 5'-AAAGAGUUUGC-3'.

In still another example, when the proximal domain has partial or complete homology with a proximal domain of *Streptococcus thermophilus* or a proximal domain derived therefrom, the $(P)_k$ may be 5'-AAGGCUUAGUCCG-3', or a base sequence having at least 50% or more homology with 5'-AAGGCUUAGUCCG-3'.

The $(F)_i$ may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F) may be 5'-UUAUCAACUUGAAAAAGUGGCACCGAGUCGGUGC-3', or a base sequence having at least 50% or more homology with 5'-UUAUCAACUUGAAAAAGUGGCACCGAGUCGGUGC-3'

In another example, when the tail domain has partial or complete homology with a tail domain of *Campylobacter jejuni* or a tail domain derived therefrom, the $(F)_i$ may be 5'-GGGACUCUGCGGGGUUACAAUCCCCUAAAACCGCUUUU-3', or a base sequence having at least 50% or more homology with 5'-GGGACUCUGCGGGGUUACAAUCCCCUAAAACCGCUUUU-3'.

In still another example, when the tail domain has partial or complete homology with a tail domain of *Streptococcus thermophilus* or a tail domain derived therefrom, the (F) may be 5'-UACUCAACUUGAAAAGGUGGCACCGAUUCGGUGUUUUU-3', or a base sequence having at least 50% or more homology with 5'-UACUCAACUUGAAAAGGUGGCACCGAUUCGGUGUUUUU-3'.

In addition, the $(F)_i$ may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the $(X)_a$, $(X)_b$, $(X)_c$, $(X)_d$, $(X)_e$ and $(X)_f$ may be base sequences selectively added, where the X may be each independently selected from the group consisting of A, U, C and G, and each of the a, b, c, d, e and f may be the number of bases, which is 0 or an integer of 1 to 20.

Second Single-Stranded gRNA

A second single-stranded gRNA may be a single-stranded gRNA consisting of a guide domain, a first complementary domain and a second complementary domain.

Here, the second single-stranded gRNA may consist of:

5'-[second complementary domain]-[first complementary domain]-[guide domain]-3'; or 5'-[second complementary domain]-[linker domain]-[first complementary domain]-[guide domain]-3'.

The second single-stranded gRNA may optionally include an additional nucleotide sequence.

In one exemplary embodiment, the second single-stranded gRNA may be $5'-(Z)_h-(Q)_m-(N_{target})-3'$; or $5'-(X)_a—(Z)_h—(X)_b-(Q)_m-(X)_c—(N_{target})-3'$.

In another embodiment, the single-stranded gRNA may be $5'-(Z)_h-(L)_j-(Q)_m-(N_{target})-3'$; or $5'-(X)_a—(Z)_h-(L)_j-(Q)_m-(X)_c—(N_{target})-3'$.

Here, the $N_{target}$ is a base sequence capable of forming a complementary bond with a target sequence on a target gene or nucleic acid, and a base sequence region which may be changed according to a target sequence on a target gene or nucleic acid.

The $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Parcubacteria bacterium* or a first complementary domain derived therefrom, the $(Q)_m$ may be 5'-UUUGUAGAU-3', or a base sequence having at least 50% or more homology with 5'-UUUGUAGAU-3'.

The $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of *Parcubacteria bacterium* or a *Parcubacteria bacterium*-derived second complementary domain, the $(Z)_h$ may be 5'-AAAUUUCUACU-3', or a base sequence having at least 50% or more homology with 5'-AAAUUUCUACU-3'.

In addition, the $(L)_j$ is a base sequence including the linker domain, which connects the first complementary domain with the second complementary domain. Here, the L may be each independently selected from the group consisting of A, U, C and G, and the j may be the number of bases, which is an integer of 1 to 30.

In addition, each of the $(X)_a$, $(X)_b$ and $(X)_c$ is selectively an additional base sequence, where the X may be each independently selected from the group consisting of A, U, C and G, and the a, b and c may be the number of bases, which is 0 or an integer of 1 to 20.

As an aspect disclosed in the present invention, a guide nucleic acid may be a gRNA capable of forming a complementary bond with a target sequence of an immunity regulating gene.

The term "immunity regulating gene" refers to all of the genes which are directly involved in or indirectly affecting the regulation of immune functions or the functions associated with the formation and performance of immune responses. In the present invention, the immunity regulating gene includes all of the genes which are directly involved in or indirectly affecting the regulation of the functions of immune cells as well as phagocytes, etc. that can interact with the immune cells. In particular, the immunity regulating gene can perform immune functions or functions associated with the formation and performance of immune responses due to the immunity regulating gene itself or a protein expressed by the immunomodulatory gene.

The immunity regulating gene may be categorized on the basis of functions of the proteins expressed by the immunity regulating gene. The following listed immunity regulating genes are only examples of immunity regulating genes based on function and thus do not limit the types of immunity regulating genes encompassed by the present invention. The genes listed below may not have only one type of immunu regulatory function but may have multiple types of functions. Additionally, two or more immunity regulating genes may be provided if necessary.

In one example, the immunity regulating gene may be an immune cell activity regulating gene.

The term "immune cell activity regulating gene" is a gene that functions to regulate the degree or activity of an immune response, for example, it may be a gene that stimulates or suppresses the degree or activity of an immune response. Here, the immune cell activity regulating gene may perform functions to control the degree or activity of an immune response by the immune cell activity regulating gene or by proteins expressed from the immune cell activity regulating gene.

The immune cell activation regulating gene may perform functions associated with activation or deactivation of immune cells.

The immune cell activity regulating gene may perform functions associated with activation or deactivation of immune cells.

The immune cell activity regulating gene may function to suppress the immune response.

The immune cell activity regulating gene may bind to the channel proteins of the cell membrane and the receptors and thereby perform functions associated with synthesis of proteins that regulate immune responses.

For example, the immune cell activity regulating gene may be a Programmed cell death protein (PD-1)

The PD-1 gene (also referred to as the PDCD1 gene; hereinafter, the PD-1 gene and the PDCD1 gene are used to mean the same gene) refers to a gene (full-length DNA, cDNA or mRNA) that encodes the protein PD-1 which is also referred to as cluster of differentiation 279 (CD279). In an embodiment, the PD-1 gene may be, but is not limited to, one or more selected from the group consisting of the following genes: genes encoding human PD-1 (e.g., NCBI Accession No. NP_005009.2, etc.), for example PD-1 genes expressed as NCBI Accession No. NM_005018.2, NG_012110.1, etc The immune cell activity regulating gene may be cytotoxic T-lymphocyte-associated protein 4 (CTLA-4).

CTLA-4 gene refers to a gene (full-length DNA, cDNA or mRNA) that encodes the protein CTLA-4, which is also referred to as cluster of differentiation 152 (CD152). In an embodiment, the CTLA-4 gene may be, but is not limited to, one or more selected from the group consisting of the following genes: genes encoding human CTLA-4 (e.g., NCBI Accession No. NP_001032720.1, NP_005205.2, etc.), for example CTLA-4 genes expressed as NCBI Accession No. NM_001037631.2, NM_005214.4, NG_011502.1, etc.

The immune cell activity regulating gene may be CBLB.

The immune cell activity regulating gene may be PSGL-1.

The immune cell activity regulating gene may be ILT2.

The immune cell activity regulating gene may be KIR2DL4.

The immune cell activity regulating gene may be SHP-1.

The above genes may be derived from mammals including primates (e.g. humans, monkeys, etc.), rodents (e.g. rats, mice, etc.).

Genetic information can be obtained from the known database such as GenBank of National Center for Biotechnology Information (NCBI).

In one embodiment, the immune cell activity regulating gene may function to stimulate the immune response.

The immune cell activity regulating gene may be an immune cell growth regulating gene.

The term "immune cell growth regulating gene" refers to a gene that functions to regulate the growth of immune cells by regulating protein synthesis, etc. in immune cells, for example, a gene stimulating or suppressing growth of immune cells. In this case, the immune cell growth regulating gene may perform functions to control the growth of immune cells by controlling the protein synthesis in immune cells with the immune cell growth regulating gene itself or a protein expressed from the immune cell growth regulating gene.

The immune cell growth regulating gene may function in DNA transcription, RNA translation, and cell differentiation.

Examples of the immune cell growth regulating gene may be genes involved in the expression pathways of NFAT, IκB/NF-κB, AP-1, 4E-BP1, eIF4E, and S6.

For example, the immune cell growth regulating gene may be DGK-alpha.

The DGKA (Dgk-alpha) gene refers to a gene (full-length DNA, cDNA or mRNA) that encodes the protein diacylglycerol kinase alpha (DGKA). In an embodiment, the DGKA gene may be, but is not limited to, one or more selected from the group consisting of the following genes: genes encoding human DGKA(e.g., NCBI Accession No. NP_001336.2, NP_958852.1, NP_958853.1, NP_963848.1, etc.), for example DGKA genes expressed as NCBI Accession No. NM_001345.4, NM_201444.2, NM_201445.1, NM_201554.1, NC_000012.12, etc.

The immune cell growth regulating gene may be DGK-zeta.

The DGKZ (Dgk-zeta) gene refers to a gene (full-length DNA, cDNA or mRNA) that encodes the protein diacylglycerol kinase zeta (DGKZ). In an embodiment, the DGKZ gene may be, but is not limited to, one or more selected from the group consisting of of the following genes: genes encoding human DGKZ (e.g., NCBI Accession No. NP_001099010.1, NP_001186195.1, NP_001186196.1, NP_001186197.1, NP_003637.2, NP_963290.1, NP_963291.2, etc.), for example DGKZ gene expressed as NCBI Accession No. NM_001105540.1, NM_001199266.1, NM_001199267.1, NM_001199268.1, NM_003646.3, NM_201532.2, NM_201533.3, NG_047092.1, etc.

The immune cell growth regulating gene may be EGR2.

The EGR2 gene refers to a gene (full-length DNA, cDNA or mRNA) that encodes early growth response protein 2 (EGR2). In an embodiment, the EGR2 gene, may be, but is not limited to, one or more selected from the group consisting of the followings: a gene encoding human EGR2 (e.g., NCBI Accession No. NP_000390, NP_001129649, NP_001129650, NP_001129651, NP_001307966, etc.). For example, EGR2 genes expressed as NCBI Accession No. NM_000399, NM_001136177, NM_001136178, NM_001136179, NM_001321037

The immune cell growth regulating gene may be EGR3.

The immune cell growth regulating gene may be PPP2r2d.

The immune cell growth regulating gene may be A20 (TNFAIP3).

The above genes may be derived from mammals including primates (e.g. humans, monkeys, etc.), rodents (e.g. rats, mice, etc.).

Genetic information can be obtained from the known database such as GenBank of National Center for Biotechnology Information (NCBI).

In an embodiment, the immune cell activity regulating gene may be an immune cell death regulating gene.

The term "immune cell death regulating gene" refers to a gene that functions relating to the death of immune cells, for example, stimulating or suppressing the death of immune cells. Here, the immune cell death regulating gene may perform functions to control the death of immune cells by the immune cell death regulating gene itself or a protein expressed from the immune cell death regulating gene.

The immune cell death regulating gene may perform functions associated with apoptosis or necrosis of immune cells.

For example, the immune cell death regulating gene may be a caspase cascade-associated gene.

In this case, the immune cell death regulating element may be Fas. When referring to the gene hereinafter, it is apparent to those of ordinary skill in the art that a receptor or binding portion on which the gene act can be manipulated.

The immune cell death regulating gene may be a death domain-associated gene.

Here, the immune cell death regulating gene may be Daxx.

The immune cell death regulating gene may be a Bcl-2 family gene.

The immune cell death regulating gene may be a BH3-only family gene.

The immune cell death regulating gene may be Bim.

The immune cell death regulating gene may be Bid.

The immune cell death regulating gene may be BAD.

The immune cell death regulating gene may be a gene encoding a ligand or a receptor located in the immune extracellular membrane.

Here, the immune cell death regulating gene may be PD-1.

Additionally, the immune cell death regulating gene may be CTLA-4.

The above genes may be derived from mammals including primates (e.g. humans, monkeys, etc.), rodents (e.g. rats, mice, etc.).

Genetic information can be obtained from the known database such as GenBank of National Center for Biotechnology Information (NCBI).

In an embodiment, the immune cell activity regulating gene may be an immune cell exhaustion regulating gene.

The term "immune cell exhaustion regulating gene" is a gene performing functions associated with the progressive loss of functions of immune cells, and here, the immune cell exhaustion regulating gene may perform functions to control the progressive loss of functions of immune cells by the immune cell exhaustion regulating gene itself or a protein expressed from the immune cell exhaustion regulating gene.

The immune cell exhaustion regulating gene may function to help transcription or translation of genes involved in inactivation of immune cells.

Here, the function of assisting transcription may be a function of demethylating the corresponding genes.

Additionally, the genes involved in inactivation of immune cells include the immune cell activity regulating genes.

For example, the immune cell exhaustion regulating gene may be TET2.

The TET2 gene refers to a gene (full-length DNA, cDNA or mRNA) that encodes TET2 (Tet methylcytosine dioxygenase 2). In an embodiment, the TET2 gene may be, but is not limited to, one or more selected from the group consisting of a gene encoding human TET2 (e.g., NCBI Accession No. NP_001120680.1, NP_060098.3) (e.g. TET2 gene expressed as NCBI Accession NM_001127208.2, No. NM_017628.4, NG_028191.1 etc.).

The immune cell exhaustion regulating gene may function to participate in the excessive growth of immune cells. Here, immune cells that undergo excessive growth and do not regenerate will lose their functions.

Here, the immune cell exhaustion regulating gene may be Wnt.

Additionally, the immune cell exhaustion regulating gene may be Akt.

The above genes may be derived from mammals including primates (e.g. humans, monkeys, etc.), rodents (e.g. rats, mice, etc.).

Genetic information can be obtained from the known database such as GenBank of National Center for Biotechnology Information (NCBI).

In another embodiment, the immune cell activity regulating element may be a cytokine production regulating gene.

The term "cytokine production regulating gene" is an element involved in the secretion of cytokines of immune cells, that is expressed from the immune cells performing such a function, and here, the cytokine production regulating gene may perform functions to control the production of cytokine of immune cells by the cytokine production regulating gene itself or a protein expressed from the cytokine production regulating gene.

Cytokine is a collective term referring to a protein which is secreted by immune cells, and is a signal protein that plays an important role in vivo. Cytokines are involved in infection, immunity, inflammation, trauma, corruption, cancer, etc. Cytokines can be secreted from cells and then affect other cells or the cells which secreted themselves. For example, they can induce the proliferation of macrophages or promote the differentiation of the secretory cells themselves. However, when cytokines are secreted in an excessive amount, they may cause problems such as attacking normal cells, and thus proper secretion of cytokines is also important in immune responses.

The cytokine production regulating gene may be, for example, preferably a gene in the pathways of TTNFα, IFN-γ, TGF-β, IL-2, IL-4, IL-10, IL-13, IL-1, IL-6, IL-12, and IFN-α secretion.

Alternatively, the cytokines may function to deliver a signal to other immune cells to induce the immune cells to kill the recognized antigen-bearing cells or to assist in differentiation. In this case, the cytokine production regulating gene may be, preferably, a gene in the gene pathway relating to IL-2 secretion.

The above genes may be derived from mammals including primates (e.g. humans, monkeys, etc.), rodents (e.g. rats, mice, etc.).

Genetic information can be obtained from the known database such as GenBank of National Center for Biotechnology Information (NCBI).

In an embodiment, the immunity regulating gene disclosed by the present specification may be an immune cell activity regulating gene.

The immunity regulating gene may be PD-1 gene, CTLA-4 gene, DGKA gene, DGKZ gene, FAS gene, EGR2 gene, PPP2r2d gene, TET2 gene, PSGL-1 gene, A20 gene and/or KDM6A gene.

In one embodiment of the contents disclosed by the present specification, the guide nucleic acid may be a gRNA that complementarily binds to a target sequence of PD-1 gene, CTLA-4 gene, DGKA gene, DGKZ gene, FAS gene, EGR2 gene, PPP2r2d gene, TET2 gene, PSGL-1 gene, A20 gene and/or KDM6A gene.

The term "target sequence" refers to a nucleotide sequence in the target gene or nucleic acid, specifically a portion of nucleotide sequences of a target region in the target gene or nucleic acid, wherein the "target region" is a region in the target gene or nucleic acid which can be modified by the guide nucleic acid-editor protein.

The target gene disclosed by the present specification may be an immunity regulating gene.

The target gene disclosed by the present specification may be PD-1 gene, CTLA-4 gene, DGKA gene, DGKZ gene, FAS gene, EGR2 gene, PPP2r2d gene, TET2 gene, PSGL-1 gene, A20 gene and/or KDM6A gene.

Hereinafter, the term "target sequence" may refer to both nucleotide sequence information. For example, for the target gene, the target sequence may refer to the transcribed strand sequence information of the target gene DNA, or the nucleotide sequence information of the non-transcribed strand.

For example, the target sequence may refer to a portion of nucleotide sequence (transcribed strand) in the target region of the target gene A, 5'-ATCATTGGCAGACTAGTTCG-3', or the nucleotide sequence complementary thereto (non-transcribed strand), 5'-CGAACTAGTCTGCCAATGAT-3'.

The target sequence may be a 5 to 50-nucleotide sequence.

In an embodiment, the target sequence may be a 16 bp, 17 bp, 18 bp, 19 bp, 20 bp, 21 bp, 22 bp, 23 bp, 24 bp, or 25 bp nucleotide sequence.

The target sequence includes a guide nucleic acid binding sequence or a guide nucleic acid non-binding sequence.

The term "guide nucleic acid binding sequence" refers to the nucleotide sequence having a partial or complete complementarity with the guide sequence included in the guide domain of the guide nucleic acid, which may form a complementary bond with the guide sequence included in the guide domain of the guide nucleic acid. The target sequence and the guide nucleic acid binding sequence are the nucleotide sequences that may vary depending on the target gene or nucleic acid, that is, a subject for gene manipulation or correction, and may be designed in various forms according to the target gene or nucleic acid.

The term "guide nucleic acid non-binding sequence" refers to the nucleotide sequence having a partial or complete homology with the guide sequence included in the guide domain of the guide nucleic acid, which cannot form a complementary bond with the guide sequence included in the guide domain of the guide nucleic acid. Additionally, the guide nucleic acid non-binding sequence is a nucleotide sequence complementary to the guide nucleic acid binding sequence, and may form a complementary bond with the guide nucleic acid binding sequence.

The guide nucleic acid binding sequence is a portion of nucleotide sequence in the target sequence, and may be either one of the two nucleotide sequences having different sequence order of the target sequence, that is, the two nucleotide sequences that may form a complementary bond. Here, the guide nucleic acid non-binding sequence may be the nucleotide sequence of the target sequence other than the guide nucleic acid binding sequence.

For example, when a portion of nucleotide sequence in the target region of the target gene A, 5'-ATCATTGGCAGACTAGTTCG-3', and the nucleotide sequence complementary thereto, 5'-CGAACTAGTCTGCCAATGAT-3', are the target sequences, the guide nucleic acid binding sequence may be either one of the two target sequences, that is, 5'-ATCATTGGCAGACTAGTTCG-3' or 5'-CGAACTAGTCTGCCAATGAT-3'. Here, the guide nucleic acid non-binding sequence may be 5'-CGAACTAGTCTGCCAATGAT-3' when the guide nucleic acid binding sequence is 5'-ATCATTGGCAGACTAGTTCG-3', or when the guide nucleic acid binding sequence is 5'-CGAACTAGTCTGCCAATGAT-3', the guide nucleic acid non-binding sequence may be 5'-ATCATTGGCAGACTAGTTCG-3'.

The guide nucleic acid binding sequence may be the nucleotide sequence selected from the nucleotide sequence homologous to the target sequence, that is, the transcribed strand, and the nucleotide sequence homologous to the non-transcribed strand. Here, the guide nucleic acid non-binding sequence may be the nucleotide sequence other than the nucleotide sequence selected from between the nucleotide sequence homologous to the guide nucleic acid binding sequence in the target sequence, that is, the transcribed strand, and the nucleotide sequence homologous to the non-transcribed strand.

The guide nucleic acid binding sequence may have the same length as the target sequence.

The guide nucleic acid non-binding sequence may have the same length as the target sequence or the guide nucleic acid binding sequence.

The guide nucleic acid binding sequence may be a 5 to 50-nucleotide sequence.

In an embodiment, the guide nucleic acid binding sequence may be a 16 bp, 17 bp, 18 bp, 19 bp, 20 bp, 21 bp, 22 bp, 23 bp, 24 bp, or 25 bp nucleotide sequence.

The guide nucleic acid non-binding sequence may be a 5 bp to 50 bp nucleotide sequence.

In an embodiment, the guide nucleic acid non-binding sequence may be a 16 bp, 17 bp, 18 bp, 19 bp, 20 bp, 21 bp, 22 bp, 23 bp, 24 bp, or 25 bp nucleotide sequence.

The guide nucleic acid binding sequence may form a partially or a completely complementary bond with the guide sequence included in the guide domain of the guide nucleic acid, and the length of the guide nucleic acid binding sequence may be the same as that of the guide sequence.

The guide nucleic acid binding sequence may be a nucleotide sequence complementary to the guide sequence included in the guide domain of the guide nucleic acid, which has, for example, at least 70%, 75%, 80%, 85%, 90%, or 95% or more complementarity or complete complementarity.

In one example, the guide nucleic acid binding sequence may have or include a 1 bp to 8 bp nucleotide sequence not complementary to the guide sequence included in the guide domain of the guide nucleic acid.

The guide nucleic acid non-binding sequence may have a partial or a complete homology with the guide sequence included in the guide domain of the guide nucleic acid, and the length of the guide nucleic acid non-binding sequence may be the same as that of the guide sequence.

The guide nucleic acid non-binding sequence may be a nucleotide sequence having homology with the guide sequence included in the guide domain of the guide nucleic acid, which has, for example, at least 70%, 75%, 80%, 85%, 90%, or 95% or more homology or complete homology.

In one example, the guide nucleic acid non-binding sequence may have or include 1 bp to 8 bp nucleotide sequence not complementary to the guide sequence included in the guide domain of the guide nucleic acid.

The guide nucleic acid non-binding sequence may form a complementary bond with the guide nucleic acid binding sequence, and the length of the guide nucleic acid non-binding sequence may be the same as that of the the guide nucleic acid binding sequence.

The guide nucleic acid non-binding sequence may be a nucleotide sequence complementary to the guide nucleic acid binding sequence, which has, for example, at least 90%, or 95% or more complementarity or complete complementarity.

In one example, the guide nucleic acid non-binding sequence may have or include 1 bp to 2 bp nucleotide sequence not complementary to the guide nucleic acid binding sequence.

Additionally, the guide nucleic acid binding sequence may be a nucleotide sequence located close to the nucleotide sequence that is able to be recognized by the editor protein.

In one example, the guide nucleic acid binding sequence may be a continuous 5 bp to 50 bp nucleotide sequence adjacent to the 5' end and/or 3' end of the nucleotide sequence that is able to be recognized by the editor protein.

In an embodiment, the target sequence disclosed by the present specification may be a continuous 10 bp to 35 bp-nucleotide sequence located in the promoter region of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence located in the promoter region of PD-1 gene.

In another example, the target sequence may be a continuous 10 bp to 25 bp nucleotide sequence located in the promoter region of CTLA-4 gene.

In one example, the target sequence may be a continuous 10 bp to 25 bp nucleotide sequence located in the promoter region of A20 gene.

In another example, the target sequence may be a continuous 10 bp to 25 bp nucleotide sequence located in the promoter region of DGKA gene.

In one example, the target sequence may be a continuous 10 bp to 25 bp nucleotide sequence located in the promoter region of DGKZ gene.

In another example, the target sequence may be a continuous 10 bp to 25 bp nucleotide sequence located in the promoter region of FAS gene.

In one example, the target sequence may be a continuous 10 bp to 25 bp nucleotide sequence located in the promoter region of EGR2 gene.

In another example, the target sequence may be a continuous 10 bp to 25 bp nucleotide sequence located in the promoter region of PPP2r2d gene.

In one example, the target sequence may be a continuous 10 bp to 25 bp nucleotide sequence located in the promoter region of TET2 gene.

In another example, the target sequence may be a continuous 10 bp to 25 bp nucleotide sequence located in the promoter region of PSGL-1 gene.

In still another example, the target sequence may be a continuous 10 bp to 25 bp nucleotide sequence located in the promoter region of KDM6A gene.

The target sequence disclosed by the present specification may be a continuous 10 bp to 35 bp nucleotide sequence located in the intron region of the immunity regulating gene.

Here, the target sequence may be a 10 bp to 35 bp, 15 bp to 35 bp, 20 bp to 35 bp, 25 bp to 35 bp or 30 bp to 35 bp nucleotide sequence.

Alternatively, the target sequence may be a 10 bp to 15 bp, 15 bp to 20 bp, 20 bp to 25 bp, 25 bp to 30 bp or 30 bp to 35 bp nucleotide sequence.

In one example, the target sequence may be a continuous 10 bp to 25 bp nucleotide sequence located in the intron region of PD-1 gene.

In another example, the target sequence may be a continuous 10 bp to 25 bp nucleotide sequence located in the intron region of CTLA-4 gene.

In one example, the target sequence may be a continuous 10 bp to 25 bp nucleotide sequence located in the intron region of A20 gene.

In another example, the target sequence may be a continuous 10 bp to 25 bp nucleotide sequence located in the intron region of DGKA gene.

In one example, the target sequence may be a continuous 10 bp to 25 bp nucleotide sequence located in the intron region of DGKZ gene.

In another example, the target sequence may be a continuous 10 bp to 25 bp nucleotide sequence located in the intron region of FAS gene.

In one example, the target sequence may be a continuous 10 bp to 25 bp nucleotide sequence located in the intron region of EGR2 gene.

In another example, the target sequence may be a continuous 10 bp to 25 bp nucleotide sequence located in the intron region of PPP2r2d gene.

In one example, the target sequence may be a continuous 10 bp to 25 bp nucleotide sequence located in the intron region of TET2 gene.

In another example, the target sequence may be a continuous 10 bp to 25 bp nucleotide sequence located in the intron region of PSGL-1 gene.

In still another example, the target sequence may be a continuous 10 bp to 25 bp nucleotide sequence located in the intron region of KDM6A gene.

The target sequence disclosed by the present specification may be a continuous 10 bp to 35 bp nucleotide sequence located in the exon region of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence located in the exon region of PD-1 gene.

In another example, the target sequence may be a continuous 10 bp to 25 bp nucleotide sequence located in the exon region of CTLA-4 gene.

In one example, the target sequence may be a continuous 10 bp to 25 bp nucleotide sequence located in the exon region of A20 gene.

In another example, the target sequence may be a continuous 10 bp to 25 bp nucleotide sequence located in the exon region of DGKA gene.

In one example, the target sequence may be a continuous 10 bp to 25 bp nucleotide sequence located in the exon region of DGKZ gene.

In another example, the target sequence may be a continuous 10 bp to 25 bp nucleotide sequence located in the exon region of FAS gene.

In one example, the target sequence may be a continuous 10 bp to 25 bp nucleotide sequence located in the exon region of EGR2 gene.

In another example, the target sequence may be a continuous 10 bp to 25 bp nucleotide sequence located in the exon region of PPP2r2d gene.

In one example, the target sequence may be a continuous 10 bp to 25 bp nucleotide sequence located in the exon region of TET2 gene.

In another example, the target sequence may be a continuous 10 bp to 25 bp nucleotide sequence located in the exon region of PSGL-1 gene.

In still another example, the target sequence may be a continuous 10 bp to 25 bp nucleotide sequence located in the exon region of KDM6A gene.

The target sequence disclosed by the present specification may be a continuous 10 bp to 35 bp nucleotide sequence located in the enhancer region of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence located in the enhancer region of PD-1 gene.

In another example, the target sequence may be a continuous 10 bp to 25 bp nucleotide sequence located in the enhancer region of CTLA-4 gene.

In one example, the target sequence may be a continuous 10 bp to 25 bp nucleotide sequence located in the enhancer region of A20 gene.

In another example, the target sequence may be a continuous 10 bp to 25 bp nucleotide sequence located in the enhancer region of DGKA gene.

In one example, the target sequence may be a continuous 10 bp to 25 bp nucleotide sequence located in the enhancer region of DGKZ gene.

In another example, the target sequence may be a continuous 10 bp to 25 bp nucleotide sequence located in the enhancer region of FAS gene.

In one example, the target sequence may be a continuous 10 bp to 25 bp nucleotide sequence located in the enhancer region of EGR2 gene.

In another example, the target sequence may be a continuous 10 bp to 25 bp nucleotide sequence located in the enhancer region of PPP2r2d gene.

In one example, the target sequence may be a continuous 10 bp to 25 bp nucleotide sequence located in the enhancer region of TET2 gene.

In another example, the target sequence may be a continuous 10 bp to 25 bp nucleotide sequence located in the enhancer region of PSGL-1 gene.

In still another example, the target sequence may be a continuous 10 bp to 25 bp nucleotide sequence located in the enhancer region of KDM6A gene.

The target sequence disclosed by the present specification may be a continuous 10 bp to 35 bp nucleotide sequence located in the coding, noncoding or their combined region of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence located in the coding, noncoding, or their combined region of PD-1 gene.

In another example, the target sequence may be a continuous 10 bp to 25 bp nucleotide sequence located in the coding, noncoding, or their combined region of CTLA-4 gene.

In one example, the target sequence may be a continuous 10 bp to 25 bp nucleotide sequence located in the coding, noncoding, or their combined region of A20 gene.

In another example, the target sequence may be a continuous 10 bp to 25 bp nucleotide sequence located in the coding, noncoding, or their combined region of DGKA gene.

In one example, the target sequence may be a continuous 10 bp to 25 bp nucleotide sequence located in the coding, noncoding, or their combined region of DGKZ gene.

In another example, the target sequence may be a continuous 10 bp to 25 bp nucleotide sequence located in the coding, noncoding, or their combined region of FAS gene.

In one example, the target sequence may be a continuous 10 bp to 25 bp nucleotide sequence located in the coding, noncoding, or their combined region of EGR2 gene.

In another example, the target sequence may be a continuous 10 bp to 25 bp nucleotide sequence located in the coding, noncoding, or their combined region of PPP2r2d gene.

In one example, the target sequence may be a continuous 10 bp to 25 bp nucleotide sequence located in the coding, noncoding, or their combined region of TET2 gene.

In another example, the target sequence may be a continuous 10 bp to 25 bp nucleotide sequence located in the coding, noncoding, or their combined region of PSGL-1 gene.

In still another example, the target sequence may be a continuous 10 bp to 25 bp nucleotide sequence located in the coding, noncoding, or their combined region of KDM6A gene.

The target sequence disclosed by the present specification may be a continuous 10 bp to 35 bp nucleotide sequence located in the promoter, enhancer, 3'-UTR, 5'-UTR, polyA, or their combined region of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence located in the promoter, enhancer, 3'-UTR, 5'-UTR, polyA, or their combined region of PD-1 gene.

In another example, the target sequence may be a continuous 10 bp to 25 bp nucleotide sequence located in the promoter, enhancer, 3'-UTR, 5'-UTR, polyA, or their combined region of CTLA-4 gene.

In one example, the target sequence may be a continuous 10 bp to 25 bp nucleotide sequence located in the promoter, enhancer, 3'-UTR, 5'-UTR, polyA, or their combined region of A20 gene.

In another example, the target sequence may be a continuous 10 bp to 25 bp nucleotide sequence located in the promoter, enhancer, 3'-UTR, 5'-UTR, polyA, or their combined region of DGKA gene.

In one example, the target sequence may be a continuous 10 bp to 25 bp nucleotide sequence located in the promoter, enhancer, 3'-UTR, 5'-UTR, polyA, or their combined region of DGKZ gene.

In another example, the target sequence may be a continuous 10 bp to 25 bp nucleotide sequence located in the promoter, enhancer, 3'-UTR, 5'-UTR, polyA, or their combined region of FAS gene.

In one example, the target sequence may be a continuous 10 bp to 25 bp nucleotide sequence located in the promoter, enhancer, 3'-UTR, 5'-UTR, polyA, or their combined region of EGR2 gene.

In another example, the target sequence may be a continuous 10 bp to 25 bp nucleotide sequence located in the promoter, enhancer, 3'-UTR, 5'-UTR, polyA, or their combined region of PPP2r2d gene.

In one example, the target sequence may be a continuous 10 bp to 25 bp nucleotide sequence located in the promoter, enhancer, 3'-UTR, 5'-UTR, polyA, or their combined region of TET2 gene.

In another example, the target sequence may be a continuous 10 bp to 25 bp nucleotide sequence located in the promoter, enhancer, 3'-UTR, 5'-UTR, polyA, or their combined region of PSGL-1 gene.

In still another example, the target sequence may be a continuous 10 bp to 25 bp nucleotide sequence located in the promoter, enhancer, 3'-UTR, 5'-UTR, polyA, or their combined region of KDM6A gene.

The target sequence disclosed by the present specification may be a continuous 10 bp to 35 bp nucleotide sequence located in the exon, intron, or their combined region of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence located in the exon, intron, or their combined region of PD-1 gene.

In another example, the target sequence may be a continuous 10 bp to 25 bp nucleotide sequence located in the exon, intron, or their combined region of CTLA-4 gene.

In one example, the target sequence may be a continuous 10 bp to 25 bp nucleotide sequence located in the exon, intron, or their combined region of A20 gene.

In another example, the target sequence may be a continuous 10 bp to 25 bp nucleotide sequence located in the exon, intron, or their combined region of DGKA gene.

In one example, the target sequence may be a continuous 10 bp to 25 bp nucleotide sequence located in the exon, intron, or their combined region of DGKZ gene.

In another example, the target sequence may be a continuous 10 bp to 25 bp nucleotide sequence located in the exon, intron, or their combined region of FAS gene.

In one example, the target sequence may be a continuous 10 bp to 25 bp nucleotide sequence located in the exon, intron, or their combined region of EGR2 gene.

In another example, the target sequence may be a continuous 10 bp to 25 bp nucleotide sequence located in the exon, intron, or their combined region of PPP2r2d gene.

In one example, the target sequence may be a continuous 10 bp to 25 bp nucleotide sequence located in the exon, intron, or their combined region of TET2 gene.

In another example, the target sequence may be a continuous 10 bp to 25 bp nucleotide sequence located in the exon, intron, or their combined region of PSGL-1 gene.

In still another example, the target sequence may be a continuous 10 bp to 25 bp nucleotide sequence located in the exon, intron, or their combined region of KDM6A gene.

The target sequence disclosed by the present specification may be a continuous 10 bp to 35 bp nucleotide sequence including, or adjacent to, the mutant region (for example, a region different from the wild type gene) of the immunity regulating gene.

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence including, or adjacent to, the mutant region (for example, a region different from the wild type gene) of PD-1 gene.

In another example, the target sequence may be a continuous 10 bp to 25 bp nucleotide sequence including, or adjacent to, the mutant region (for example, a region different from the wild type gene) of CTLA-4 gene.

In one example, the target sequence may be a continuous 10 bp to 25 bp nucleotide sequence including, or adjacent to, the mutant region (for example, a region different from the wild type gene) of A20 gene.

In another example, the target sequence may be a continuous 10 bp to 25 bp nucleotide sequence including, or adjacent to, the mutant region (for example, a region different from the wild type gene) of DGKA gene.

In one example, the target sequence may be a continuous 10 bp to 25 bp nucleotide sequence including, or adjacent to, the mutant region (for example, a region different from the wild type gene) of DGKZ gene.

In another example, the target sequence may be a continuous 10 bp to 25 bp nucleotide sequence including, or adjacent to, the mutant region (for example, a region different from the wild type gene) of FAS gene.

In one example, the target sequence may be a continuous 10 bp to 25 bp nucleotide sequence including, or adjacent to, the mutant region (for example, a region different from the wild type gene) of EGR2 gene.

In another example, the target sequence may be a continuous 10 bp to 25 bp nucleotide sequence including, or adjacent to, the mutant region (for example, a region different from the wild type gene) of PPP2r2d gene.

In one example, the target sequence may be a continuous 10 bp to 25 bp nucleotide sequence including, or adjacent to, the mutant region (for example, a region different from the wild type gene) of TET2 gene.

In another example, the target sequence may be a continuous 10 bp to 25 bp nucleotide sequence including, or adjacent to, the mutant region (for example, a region different from the wild type gene) of PSGL-1 gene.

In still another example, the target sequence may be a continuous 10 bp to 25 bp nucleotide sequence including, or adjacent to, the mutant region (for example, a region different from the wild type gene) of KDM6A gene.

The target sequence disclosed by the present specification may be a continuous 10 bp to 35 bp nucleotide sequence adjacent to the 5' end and/or 3' end of a proto-spacer-adjacent motif (PAM) sequence in the nucleic acid sequence of the immunity regulating gene.

The term "proto-spacer-adjacent motif (PAM) sequence" is a nucleotide sequence that can be recognized by the editor protein. Here, the PAM sequence may have a nucleotide sequence varying according to the type of the editor proteins and the species of origin.

Here, the PAM sequence may be, for example, one or more of the following sequences (described in the 5' to 3' direction)

NGG (N is A, T, C or G);

NNNNRYAC (N is each independently A, T, C or G, R is A or G, Y is C or T);

NNAGAAW (N is each independently A, T, C or G, W is A or T);

NNNNGATT (N is each independently A, T, C or G);

NNGRR(T) (N is each independently A, T, C or G, R is A or G, Y is C or T); and

TTN (N is A, T, C or G).

Here, the target sequence may be a 10 bp to 35 bp, 15 bp to 35 bp, 20 bp to 35 bp, 25 bp to 35 bp, or 30 bp to 35 bp nucleotide sequence.

Alternatively, the target sequence may be a 10 bp to 15 bp, 15 bp to 20 bp, 20 bp to 25 bp, 25 bp to 30 bp, or 30 bp to 35 bp nucleotide sequence.

In one example, the target sequence may be a continuous 10 bp to 25 bp nucleotide sequence adjacent to the 5' end or/and 3' end of a PAM sequence in the nucleic acid sequence of PD-1 gene.

In an embodiment, when the PAM sequence recognized by the editor protein is 5'-NGG-3', 5'-NAG-3' or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3' or/and 5'-NGA-3' (N=A, T, G or C; or A, U, G or C) in the nucleic acid sequence of PD-1 gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of PD-1 gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of PD-1 gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of PD-1 gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of PD-1 gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of PD-1 gene.

In an embodiment, when the PAM sequence recognized by the editor protein is 5'-TTN-3' (N=A, T, G or C; or A, U, G or C), the target sequence may be a continuous 10 to 25-nucleotide sequence adjacent to the 5' end or/and 3' end of 5'-TTN-3' (N=A, T, G or C; or A, U, G or C) in the nucleic acid sequence of PD-1 gene.

In another example, the target sequence may be a continuous 10 bp to 25 bp nucleotide sequence adjacent to the 5' end and/or 3' end of a PAM sequence in the nucleic acid sequence of CTLA-4 gene In an embodiment, when the PAM sequence recognized by the editor protein is 5'-NGG-3', 5'-NAG-3' or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3' or/and 5'-NGA-3' (N=A, T, G or C; or A, U, G or C) in the nucleic acid sequence of CTLA-4 gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of CTLA-4 gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of CTLA-4 gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of CTLA-4 gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of CTLA-4 gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of CTLA-4 gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of CTLA-4 gene.

In one example, the target sequence may be a continuous 10 bp to 25 bp nucleotide sequence adjacent to the 5' end or/and 3' end of a PAM sequence in the nucleic acid sequence of A20 gene In an embodiment, when the PAM sequence recognized by the editor protein is 5'-NGG-3', 5'-NAG-3' or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3' or/and 5'-NGA-3' (N=A, T, G or C; or A, U, G or C) in the nucleic acid sequence of A20 gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of A20 gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of A20 gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of A20 gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of A20 gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of A20 gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of A20 gene.

In another example, the target sequence may be a continuous 10 bp to 25 bp nucleotide sequence adjacent to the 5' end or/and 3' end of a PAM sequence in the nucleic acid sequence of DGKA gene In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of DGKA gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of DGKA gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of DGKA gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of DGKA gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of DGKA gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of DGKA gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of DGKA gene.

In one example, the target sequence may be a continuous 10 bp to 25 bp nucleotide sequence adjacent to the 5' end or/and 3' end of a PAM sequence in the nucleotide sequence of DGKZ gene In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of DGKZ gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of DGKZ gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of DGKZ gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of DGKZ gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of DGKZ gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of DGKZ gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of DGKZ gene.

In another example, the target sequence may be a continuous 10 bp to 25 bp nucleotide sequence adjacent to the 5' end or/and 3' end of a PAM sequence in the nucleotide sequence of FAS gene.

In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of FAS gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of FAS gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of FAS gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of FAS gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of FAS gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of FAS gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of FAS gene.

In one example, the target sequence may be a continuous 10 bp to 25 bp nucleotide sequence adjacent to the 5' end or/and 3' end of a proto-spacer-adjacent motif (PAM) in the nucleic acid sequence of EGR2 gene In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of EGR2 gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of EGR2 gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of EGR2 gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of EGR2 gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of EGR2 gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of EGR2 gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of EGR2 gene.

In another example, the target sequence may be a continuous 10 bp to 25 bp nucleotide sequence adjacent to the 5' end or/and 3' end of a PAM sequence in the nucleotide sequence of PPP2r2d gene In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of PPP2r2d gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of PPP2r2d gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of PPP2r2d gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of PPP2r2d gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of PPP2r2d gene.

In yet another embodiment, when the PAM sequence recognized by the editor protein is 5'-NNGRR-3', 5'-NNGRRT-3', or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3', or/and 5'-NNGRRV-3' (R=A or G, V=G, C or A, N=A, T, G or C; or A, U, G or C) in the nucleic acid sequence of PPP2r2d gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of PPP2r2d gene.

In one example, the target sequence may be a continuous 10 bp to 25 bp nucleotide sequence adjacent to the 5' end or/and 3' end of a PAM sequence in the nucleic acid sequence of TET2 gene In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of TET2 gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of TET2 gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of TET2 gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of TET2 gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of TET2 gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of TET2 gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of TET2 gene.

In another example, the target sequence may be a continuous 10 bp to 25 bp nucleotide sequence adjacent to the 5' end or/and 3' end of a PAM sequence in the nucleic acid sequence of PSGL-1 gene In an embodiment, when the PAM sequence recognized by the editor protein is 5'-NGG-3', 5'-NAG-3', or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3', or/and 5'-NGA-3' (N=A, T, G or C; or A, U, G or C) in the nucleic acid sequence of PSGL-1 gene.

In another embodiment, when the PAM sequence recognized by the editor protein is 5'-NGGNG-3', 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', 5'-NNAGAAW-3' (W=A or T, N=A, T, G or C; or A, U, G or C) in the nucleic acid sequence of PSGL-1 gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of PSGL-1 gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of PSGL-1 gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of PSGL-1 gene.

In yet another embodiment, when the PAM sequence recognized by the editor protein is 5'-NNGRR-3', 5'-NNGRRT-3' or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3' or/and 5'-NNGRRV-3' (R=A or G, V=G, C or A, N=A, T, G or C; or A, U, G or C) in the nucleic acid sequence of PSGL-1 gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of PSGL-1 gene.

In yet another example, the target sequence may be a continuous 10 bp to 25 bp nucleotide sequence adjacent to the 5' end or/and 3' end of a proto-spacer-adjacent motif (PAM) in the nucleic acid sequence of KDM6A gene In an embodiment, when the PAM sequence recognized by the editor protein is 5'-NGG-3', 5'-NAG-3' or/and 5'-NGA-3' (N=A, T, G or C; or A, U, G or C), the target sequence may be a continuous 10 bp to 25 bp nucleotide sequence adjacent to the 5' end or/and 3' end of 5'-NGG-3', 5'-NAG-3' or/and 5'-NGA-3' (N=A, T, G or C; or A, U, G or C) in the nucleic acid sequence of KDM6A gene.

In another embodiment, when the PAM sequence recognized by the editor protein is 5'-NGGNG-3', or/and 5'-NNAGAAW-3' (W=A or T, N=A, T, G or C; or A, U, G or C), the target sequence may be a continuous 10 bp to 25 bp nucleotide sequence adjacent to the 5' end or/and 3' end of 5'-NGGNG-3', or/and 5'-NNAGAAW-3' (W=A or T, N=A, T, G or C; or A, U, G or C) in the nucleic acid sequence of KDM6A gene.

In yet another embodiment, when the PAM sequence recognized by the editor protein is 5'-NNNNGATT-3' or/and 5'-NNNGCTT-3' (N=A, T, G or C; or A, U, G or C), the target sequence may be a continuous 10 bp to 25 bp nucleotide sequence adjacent to the 5' end or/and 3' end of 5'-NNNNGATT-3' or/and 5'-NNNGCTT-3' (N=A, T, G or C; or A, U, G or C) in the nucleic acid sequence of KDM6A gene.

In an embodiment, when the PAM sequence recognized by the editor protein is 5'-NNNVRYAC-3' (V=G, C or A; R=A or G, Y=C or T, N=A, T, G or C; or A, U, G or C), the target sequence may be a continuous 10 bp to 25 bp nucleotide sequence adjacent to the 5' end or/and 3' end of 5'-NNNVRYAC-3' (V=G, C or A; R=A or G, Y=C or T, N=A, T, G or C; or A, U, G or C) in the nucleic acid sequence of KDM6A gene.

In another embodiment, when the PAM sequence recognized by the editor protein is 5'-NAAR-3' (R=A or G, N=A, T, G or C; or A, U, G or C), the target sequence may be a continuous 10 bp to 25 bp nucleotide sequence adjacent to the 5' end or/and 3' end of 5'-NAAR-3' (R=A or G, N=A, T, G or C; or A, U, G or C) in the nucleic acid sequence of KDM6A gene.

In yet another embodiment, when the PAM sequence recognized by the editor protein is 5'-NNGRR-3', 5'-NNGRRT-3', or/and 5'-NNGRRV-3' (R=A or G, V=G, C or A, N=A, T, G or C; or A, U, G or C), the target sequence may be a continuous 10 bp to 25 bp nucleotide sequence adjacent to the 5' end or/and 3' end of 5'-NNGRR-3', 5'-NNGRRT-3', or/and 5'-NNGRRV-3' (R=A or G, V=G, C or A, N=A, T, G or C; or A, U, G or C) in the nucleic acid sequence of KDM6A gene.

In an embodiment, when the PAM sequence recognized by the editor protein is 5'-TTN-3' (N=A, T, G or C; or A, U, G or C), the target sequence may be a continuous 10 bp to 25 bp nucleotide sequence adjacent to the 5' end or/and 3' end of 5'-TTN-3' (N=A, T, G or C; or A, U, G or C) in the nucleic acid sequence of KDM6A gene.

Hereinafter, examples of the target sequences that may be used in one embodiment of the present invention are tabulated, and the target sequences described in the table are guide nucleic acid non-binding sequences; the complementary sequence, that is, the guide nucleic acid binding sequence can be predicted via the described sequences.

TABLE 1

Target sequences of immunity regulating gene

| Target gene | DNA Target Sequence | ID SEQ NO |
|---|---|---|
| A20 | CTTGTGGCGCTGAAAACGAACGG | ID SEQ NO 1 |
| | ATGCCACTTCTCAGTACATGTGG | ID SEQ NO 2 |
| | GCCACTTCTCAGTACATGTGGGG | ID SEQ NO 3 |
| | GCCCCACATGTACTGAGAAGTGG | ID SEQ NO 4 |
| | TCAGTACATGTGGGGCGTTCAGG | ID SEQ NO 5 |
| | GGGCGTTCAGGACACAGACTTGG | ID SEQ NO 6 |
| | CACAGACTTGGTACTGAGGAAGG | ID SEQ NO 7 |
| | GGCGCTGTTCAGCACGCTCAAGG | ID SEQ NO 8 |
| | CACGCAACTTTAAATTCCGCTGG | ID SEQ NO 9 |
| | CGGGGCTTTGCTATGATACTCGG | ID SEQ NO 10 |
| | GGCTTCCACAGACACACCCATGG | ID SEQ NO 11 |
| | TGAAGTCCACTTCGGGCCATGGG | ID SEQ NO 12 |
| **Target gene** | **DNA Target Sequence** | **ID SEQ NO** |
| DGKα | CTGTACGACACGGACAGAAATGG | ID SEQ NO 13 |
| | TGTACGACACGGACAGAAATGGG | ID SEQ NO 14 |
| | CACGGACAGAAATGGGATCCTGG | ID SEQ NO 15 |
| | GATGCGAGTGGCTGAATACCTGG | ID SEQ NO 16 |
| | GAGTGGCTGAATACCTGGATTGG | ID SEQ NO 17 |
| | AGTGGCTGAATACCTGGATTGGG | ID SEQ NO 18 |
| | ATTGGGATGTGTCTGAGCTGAGG | ID SEQ NO 19 |
| | ATGAAAGAGATTGACTATGATGG | ID SEQ NO 20 |
| | CTCTGTCTCTCAAGCTGAGTGGG | ID SEQ NO 21 |
| | TCTCTCAAGCTGAGTGGGTCCGG | ID SEQ NO 22 |
| | CTCTCAAGCTGAGTGGGTCCGGG | ID SEQ NO 23 |
| | CAAGCTGAGTGGGTCCGGGCTGG | ID SEQ NO 24 |
| **Target gene** | **DNA Target Sequence** | **ID SEQ NO** |
| EGR2 | TTGACATGACTGGAGAGAAGAGG | ID SEQ NO 25 |
| | GACTGGAGAGAAGAGGTCGTTGG | ID SEQ NO 26 |
| | GAGACGGGAGCAAAGCTGCTGGG | ID SEQ NO 27 |
| | AGAGACGGGAGCAAAGCTGCTGG | SEQ ID NO 28 |
| | TGGTTTCTAGGTGCAGAGACGGG | SEQ ID NO 29 |
| | TAAGTGAAGGTCTGGTTTCTAGG | SEQ ID NO 30 |
| | TGCCCATGTAAGTGAAGGTCTGG | SEQ ID NO 31 |
| | GAACTTGCCCATGTAAGTGAAGG | SEQ ID NO 32 |
| | TCCATTGACCCTCAGTACCCTGG | SEQ ID NO 33 |
| | TATGCCTTCTCGGTAGCAGCTGG | SEQ ID NO 34 |
| | TGAGTGCAGGCATCTTGCAAGGG | SEQ ID NO 35 |
| | GAGTGCAGGCATCTTGCAAGGGG | SEQ ID NO 36 |
| | GATGAGGCTGTGGTTGAAGCTGG | SEQ ID NO 37 |
| | CCACTGGCCACAGGACCCCTGGG | SEQ ID NO 38 |
| | GGGACATGGTGCACACACCCAGG | SEQ ID NO 39 |
| | GAGTACAGGTGGTCCAGGTCAGG | SEQ ID NO 40 |
| | GCGGAGAGTACAGGTGGTCCAGG | SEQ ID NO 41 |
| | GCGGTGGCGGAGAGTACAGGTGG | SEQ ID NO 42 |
| | TCTCCTGCACAGCCAGAATAAGG | SEQ ID NO 43 |
| | ACGCAGAAGGGTCCTGGTAGAGG | SEQ ID NO 44 |
| | AGGTGGTGGGTAGGCCAGAGAGG | SEQ ID NO 45 |
| | CCCAAGCCAGCCACGGACCCAGG | SEQ ID NO 46 |
| | ACCTGGGTCCGTGGCTGGCTTGG | SEQ ID NO 47 |
| | AAGAGACCTGGGTCCGTGGCTGG | SEQ ID NO 48 |
| | GGATCATTGGGAAGAGACCTGGG | SEQ ID NO 49 |
| | GGGATCATTEGGAAGAGACCTGG | SEQ ID NO 50 |
| | CAGGATAGTCTGGGATCATTGGG | SEQ ID NO 51 |
| | GGAAAGAATCCAGGATAGTCTGG | SEQ ID NO 52 |
| | CAGTGCCAGAGAGACCTACATGG | SEQ ID NO 53 |
| | CTGTACCATGTAGGTCTCTCTGG | SEQ ID NO 54 |
| | AGAGACCTACATGGTACAGCTGG | SEQ ID NO 55 |
| | CTGGGCCAGCTGTACCATGTAGG | SEQ ID NO 56 |
| | AGGGAAAGGGCTTACGGTCTGGG | SEQ ID NO 57 |
| | CAGGGAAAGGGCTTACGGTCTGG | ID SEQ NO 58 |
| **Target gene** | **DNA Target Sequence** | **ID SEQ NO** |
| PPP2R2D | TCTGGAGATCTTCTTGCAACAGG | ID SEQ NO 59 |
| | CTCCGGTTCATGACTTTGAAAGG | ID SEQ NO 60 |
| | GTCTTCCATCTTCGTCTTTCAGG | ID SEQ NO 61 |
| | GAAGACTTCGAGACCCATTTAGG | ID SEQ NO 62 |
| | TCGAGACCCATTTAGGATCACGG | ID SEQ NO 63 |

TABLE 1-continued

Target sequences of immunity regulating gene

| Target gene | DNA Target Sequence | ID SEQ NO |
|---|---|---|
| | GTAGCGCCGTGATCCTAAATGGG | ID SEQ NO 64 |
| | CATTTAGGATCACGGCGCTACGG | ID SEQ NO 66 |
| | GGTCCCAATATTGAAGCCCATGG | ID SEQ NO 67 |
| | GATCCATGGGCTTCAATATTGGG | ID SEQ NO 68 |
| | AGATCCATGGGCTTCAATATTGG | ID SEQ NO 69 |
| | GCTTCTACCATAAGATCCATGGG | ID SEQ NO 70 |
| | CGCTTCTACCATAAGATCCATGG | ID SEQ NO 71 |
| | GCATTTGCAAAAATTCGCCGTGG | ID SEQ NO 72 |
| | ATGACCTGAGAATTAATTTATGG | ID SEQ NO 73 |
| | CCATGCACTCCCAGACATCGTGG | ID SEQ NO 74 |
| | GCACTGGTGCGGGTGGAACTCGG | ID SEQ NO 75 |
| | ACACGTTGCACTGGTGCGGGTGG | ID SEQ NO 76 |
| | CGAACACGTTGCACTGGTGCGGG | ID SEQ NO 77 |
| | ACGAACACGTTGCACTGGTGCGG | ID SEQ NO 78 |
| | TGTAGACGAACACGTTGCACTGG | ID SEQ NO 79 |
| | GCGCATGTCACACAGGCGGATGG | ID SEQ NO 80 |
| | AGGAGCGCATGTCACACAGGCGG | ID SEQ NO 81 |
| | CCGAGGAGCGCATGTCACACAGG | ID SEQ NO 82 |
| | CCTGTGTGACATGCGCTCCTCGG | ID SEQ NO 83 |
| **Target gene** | **DNA Target Sequence** | **ID SEQ NO** |
| PD-1 | CGACTGGCCAGGGCGCCTGTGGG | ID SEQ NO 84 |
| | ACCGCCCAGACGACTGGCCAGGG | ID SEQ NO 85 |
| | CACCGCCCAGACGACTGGCCAGG | SEQ ID NO 86 |
| | GTCTGGGCGGTGCTACAACTGGG | SEQ ID NO 87 |
| | CTACAACTGGGCTGGCGGCCAGG | SEQ ID NO 88 |
| | CACCTACCTAAGAACCATCCTGG | SEQ ID NO 89 |
| | CGGTCACCACGAGCAGGGCTGGG | SEQ ID NO 90 |
| | GCCCTGCTCGTGGTGACCGAAGG | SEQ ID NO 91 |
| | CGGAGAGCTTCGTGCTAAACTGG | SEQ ID NO 92 |
| | CAGCTTGTCCGTCTGGTTGCTGG | SEQ ID NO 93 |
| | AGGCGGCCAGCTTGTCCGTCTGG | SEQ ID NO 94 |
| | CCGGGCTGGCTGCGGTCCTCGGG | SEQ ID NO 95 |
| | CGTTGGGCAGTTGTGTGACACGG | SEQ ID NO 96 |
| **Target gene** | **DNA Target Sequence** | **SEQ ID NO** |
| CTLA-4 | CATAAAGCCATGGCTTGCCTTGG | SEQ ID NO 97 |
| | CCTTGGATTTCAGCGGCAcAAGG | SEQ ID NO 98 |
| | CCTTGTGCCGCTGAAATCCAAGG | SEQ ID NO 99 |
| | CACTCACCTTTGCAGAAGACAGG | SEQ ID NO 100 |
| | TTCCATGCTAGCAATGCACGTGG | SEQ ID NO 101 |
| | GGCCACGTGCATTGCTAGCATGG | SEQ ID NO 102 |
| | GGCCCAGCCTGCTGTGGTACTGG | SEQ ID NO 103 |
| | AGGTCCGGGTGACAGTGCTTCGG | SEQ ID NO 104 |
| | CCGGGTGACAGTGCTTCGGCAGG | SEQ ID NO 105 |
| | CTGTGCGGCAACCTACATGATGG | SEQ ID NO 106 |
| | CAACTCATTCCCCATCATGTAGG | SEQ ID NO 107 |
| | CTAGATGATTCCATCTGCACGGG | SEQ ID NO 108 |
| **Target gene** | **DNA Target Sequence** | **SEQ ID NO** |
| DGKζ | GGCTAGGAGTCAGCGACATATGG | SEQ ID NO 109 |
| | GCTAGGAGTCAGCGACATATGGG | SEQ ID NO 110 |
| | CTAGGAGTCAGCGACATATGGGG | SEQ ID NO 111 |
| | GTACTGTGTAGCCAGGATGCTGG | SEQ ID NO 112 |
| | ACGAGCACTCACCAGCATCCTGG | SEQ ID NO 113 |
| | AGGCTCCAGGAATGTCCGCGAGG | SEQ ID NO 114 |
| | ACTTACCTCGCGGACATTCCTGG | SEQ ID NO 115 |
| | CACCCTGGGCACTTACCTCGCGG | SEQ ID NO 116 |
| | GTGCCGTACAAAGGTTGGCTGGG | SEQ ID NO 117 |
| | GGTGCCGTACAAAGGTTGGCTGG | SEQ ID NO 118 |
| | CTCTCCTCAGTACCACAGCAAGG | SEQ ID NO 119 |
| | CCTGGGGCCTCCGGGCGCGGAGG | SEQ ID NO 120 |
| | AGTACTCACCTGGGGCCTCCGGG | SEQ ID NO 121 |
| | AGGGTCTCCAGCGGCCCTCCTGG | SEQ ID NO 122 |
| | GCAAGTACTTACGCCTCCTTGGG | SEQ ID NO 123 |
| | TTGCGGTACATCTCCAGCCTGGG | SEQ ID NO 124 |
| | TTTGCGGTACATCTCCAGCCTGG | SEQ ID NO 125 |

TABLE 1-continued

Target sequences of immunity regulating gene

| Target gene | DNA Target Sequence | SEQ ID NO |
|---|---|---|
| TET2 | GCAAAACCTGTCCACTCTTATGG | SEQ ID NO 126 |
| | TTGGTGCCATAAGAGTGGACAGG | SEQ ID NO 127 |
| | GGTGCAAGTTTCTTATATGTTGG | SEQ ID NO 128 |
| | ACCTGATGCATATAATAATCAGG | SEQ ID NO 129 |
| | ACCTGATTATTATATGCATCAGG | SEQ ID NO 130 |
| | CAGAGCACCAGAGTGCCGTCTGG | SEQ ID NO 131 |
| | AGAGCACCAGAGTGCCGTCTGGG | SEQ ID NO 132 |
| | AGAGTGCCGTCTGGGTCTGAAGG | SEQ ID NO 133 |
| | AGGAAGGCCGTCCATTCTCAGGG | SEQ ID NO 134 |
| | GGATAGAACCAACCATGTTGAGG | SEQ ID NO 135 |
| | TCTGTTGCCCTCAACATGGTTGG | SEQ ID NO 136 |
| | TTAGTCTGTTGCCCTCAACATGG | SEQ ID NO 137 |
| | GTCTGGCAAATGGGAGGTGATGG | SEQ ID NO 138 |
| | CAGAGGTTCTGTCTGGCAAATGG | SEQ ID NO 139 |
| | TTGTAGCCAGAGGTTCTGTCTGG | SEQ ID NO 140 |
| | ACTTCTGGATGAGCTCTCTCAGG | SEQ ID NO 141 |
| | AGAGCTCATCCAGAAGTAAATGG | SEQ ID NO 142 |
| | TTGGTGTCTCCATTTACTTCTGG | SEQ ID NO 143 |
| | TTCTGGCTTCCCTTCATACAGGG | SEQ ID NO 144 |
| | CAGGACTCACACGACTATTCTGG | SEQ ID NO 145 |
| | CTACTTTCTTGTGTAAAGTCAGG | SEQ ID No 146 |
| | GACTTTACACAAGAAAGTAGAGG | SEQ ID NO 147 |
| | GTCTTTCTCCATTAGCCTTTTGG | SEQ ID NO 148 |
| | AATGGAGAAAGACGTAACTTCGG | SEQ ID NO 149 |
| | ATGGAGAAAGACGTAACTTCGGG | SEQ ID NO 150 |
| | TGGAGAAAGACGTAACTTCGGGG | SEQ ID NO 151 |
| | TTTGGTTGACTGCTTTCACCTGG | SEQ ID NO 152 |
| | TCACTCAAATCGGAGACATTTGG | SEQ ID NO 153 |
| | ATCTGAAGCTCTGGATTTTCAGG | SEQ ID NO 154 |
| | GCTTCAGATTCTGAATGAGCAGG | SEQ ID NO 155 |
| | CAGATTCTGAATGAGCAGGAGGG | SEQ ID NO 156 |
| | AAGGCAGTGCTAATGCCTAATGG | SEQ ID NO 157 |
| | GCAGAAACTGTAGCACCATTAGG | SEQ ID NO 158 |
| | ACCGCAATGGAAACACAATCTGG | SEQ ID NO 159 |
| | TGTGGTTTTCTGCACCGCAATGG | SEQ ID NO 160 |
| | CATAAATGCCATTAACAGTCAGG | SEQ ID NO 161 |
| | ATTAGTAGCCTGACTGTTAATGG | SEQ ID NO 162 |
| | CGATGGGTGAGTGATCTCACAGG | SEQ ID NO 163 |
| | ACTCACCCATCGCATACCTCAGG | SEQ ID NO 164 |
| | CTCACCCATCGCATACCTCAGGG | SEQ ID NO 165 |

| Target gene | DNA Target Sequence | SEQ ID NO |
|---|---|---|
| PSGL-1 | AGCAACAGGAGGAGTTGCAGAGG | SEQ ID NO 166 |
| | CCAGTAGGATCAGCAACAGGAGG | SEQ ID NO 167 |
| | CTCCTGTTGCTGATCCTACTGGG | SEQ ID NO 168 |
| | GGCCCAGTAGGATCAGCAACAGG | SEQ ID NO 169 |
| | TTGCTGATCCTACTGGGCCCTGG | SEQ ID NO 170 |
| | TGGCAACAGCTTGCAGCTGTGGG | SEQ ID NO 171 |
| | CTTGGGTCCCCTGCTTGCCCGGG | SEQ ID NO 172 |
| | GTCCCCTGCTTGCCCGGGACCGG | SEQ ID NO 173 |
| | CTCCGGTCCCGGGCAAGCAGGGG | SEQ ID NO 174 |
| | TCTCCGGTCCCGGGCAAGCAGGG | SEQ ID NO 175 |
| | GTCTCCGGTCCCGGGCAAGCAGG | SEQ ID NO 176 |
| | GCTTGCCCGGGACCGGAGACAGG | SEQ ID NO 177 |
| | GGTGGCCTGTCTCCGGTCCCGGG | SEQ ID NO 178 |
| | CGGTGGCCTGTCTCCGGTCCCGG | SEQ ID NO 179 |
| | CATATTCGGTGGCCTGTCTCCGG | SEQ ID NO 180 |
| | ATCTAGGTACTCATATTCGGTGG | SEQ ID NO 181 |
| | ATAATCTAGGTACTCATATTCGG | SEQ ID NO 182 |
| | TTATGATTTCCTGCCAGAAACGG | SEQ ID NO 183 |
| | ATTTCTGGAGGCTCCGTTTCTGG | SEQ ID NO 184 |
| | ACTGACACCACTCCTCTGACTGG | SEQ ID NO 185 |
| | CTGACACCACTCCTCTGACTGGG | SEQ ID NO 186 |
| | ACCACTCCTCTGACTGGGCCTGG | SEQ ID NO 187 |
| | AACCCCTGAGTCTACCACTGTGG | SEQ ID NO 188 |
| | CTCCACAGTGGTAGACTCAGGGG | SEQ ID NO 189 |
| | GCTCCACAGTGGTAGACTCAGGG | SEQ ID NO 190 |
| | GGCTCCACAGTGGTAGACTCAGG | SEQ ID NO 191 |
| | CCTGCTGCAAGGCGTTCTACTGG | SEQ ID NO 192 |
| | CCAGTAGAACGCCTTGCAGCAGG | SEQ ID NO 193 |
| | CGTTCTACTGGCCTGGATGCAGG | SEQ ID NO 194 |
| | TCTACTGGCCTGGATGCAGGAGG | SEQ ID NO 195 |
| | CCACGGAGCTGGCCAACATGGGG | SEQ ID NO 196 |
| | CGTGGACAGGTTCCCCATGTTGG | SEQ ID NO 197 |
| | GTCCACGGATTCAGCAGCTATGG | SEQ ID NO 198 |
| | GACCACTCAACCAGTGCCCACGG | SEQ ID NO 199 |
| | GGAGTGGTCTGTGCCTCCGTGGG | SEQ ID NO 200 |
| | GGCACAGACAACTCGACTGACGG | SEQ ID NO 201 |
| | GACAACTCGACTGACGGCCACGG | SEQ ID NO 202 |
| | AACTCGACTGACGGCCACGGAGG | SEQ ID NO 203 |
| | CACAGAACCCAGTGCCACAGAGG | SEQ ID NO 204 |
| | GGTAGTAGGTTCCATGGACAGGG | SEQ ID NO 205 |
| | TGGTAGTAGGTTCCATGGACAGG | SEQ ID NO 206 |
| | TCTTTTGGTAGTAGGTTCCATGG | SEQ ID NO 207 |
| | ATGGAACCTACTACCAAAAGAGG | SEQ ID NO 208 |
| | AACAGACCTCTTTTGGTAGTAGG | SEQ ID NO 209 |
| | GGGTATGAACAGACCTCTTTTGG | SEQ ID NO 210 |
| | TGTGTCCTCTGTTACTCACAAGG | SEQ ID NO 211 |
| | GTGTCCTCTGTTACTCACAAGGG | SEQ ID NO 212 |
| | GTAGTTGACGGACAAATTGCTGG | SEQ ID NO 213 |
| | TTTGTCCGTCAACTACCCAGTGG | SEQ ID NO 214 |
| | TTGTCCGTCAACTACCCAGTGGG | SEQ ID NO 215 |
| | TGTCCGTCAACTACCCAGTGGGG | SEQ ID NO 216 |
| | GTCCGTCAACTACCCAGTGGGGG | SEQ ID NO 217 |
| | CTCTGTGAAGCAGTGCCTGCTGG | SEQ ID NO 218 |
| | CCTGCTGGCCATCCTAATCTTGG | SEQ ID NO 219 |
| | CCAAGATTAGGATGGCCAGCAGG | SEQ ID NO 220 |
| | GGCCATCCTAATCTTGGCGCTGG | SEQ ID NO 221 |
| | CACCAGCGCCAAGATTAGGATGG | SEQ ID NO 222 |
| | AGTGCACACGAAGAAGATAGTGG | SEQ ID NO 223 |
| | TATCTTCTTCGTGTGCACTGTGG | SEQ ID NO 224 |
| | CTTCGTGTGCACTGTGGTGCTGG | SEQ ID NO 225 |
| | GGCGGTCCGCCTCTCCCGCAAGG | SEQ ID NO 226 |
| | GCGGTCCGCCTCTCCCGCAAGGG | SEQ ID NO 227 |
| | AATTACGCACGGGGTACATGTGG | SEQ ID NO 228 |
| | TGGGGGAGTAATTACGCACGGGG | SEQ ID NO 229 |
| | GTGGGGGAGTAATTACGCACGGG | SEQ ID NO 230 |
| | GGTGGGGGAGTAATTACGCACGG | SEQ ID NO 231 |
| | TAATTACTCCCCCACCGAGATGG | SEQ ID NO 232 |
| | AGATGCAGACCATCTCGGTGGGG | SEQ ID NO 233 |
| | GAGATGCAGACCATCTCGGTGGG | SEQ ID NO 234 |
| | TGAGATGCAGACCATCTCGGTGG | SEQ ID NO 235 |
| | GGATGAGATGCAGACCATCTCGG | SEQ ID NO 236 |
| | ATCTCATCCCTGTTGCCTGATGG | SEQ ID NO 237 |
| | TCATCCCTGTTGCCTGATGGGGG | SEQ ID NO 238 |
| | CTCACCCCCATCAGGCAACAGGG | SEQ ID NO 239 |
| | GAGGGCCCCTCACCCCCATCAGG | SEQ ID NO 240 |
| | GGGCCCTCTGCCACAGCCAATGG | SEQ ID NO 241 |
| | CCCTCTGCCACAGCCAATGGGGG | SEQ ID NO 242 |
| | CCCCCATTGGCTGTGGCAGAGGG | SEQ ID NO 243 |
| | GCCCCCATTGGCTGTGGCAGAGG | SEQ ID NO 244 |
| | GGACAGGCCCCCATTGGCTGTGG | SEQ ID NO 245 |
| | CCGGGCTCTTGGCCTTGGACAGG | SEQ ID NO 246 |
| | CTGTCCAAGGCCAAGAGCCCGGG | SEQ ID NO 247 |
| | TGGCGTCAGGCCCGGGCTCTTGG | SEQ ID NO 248 |
| | CGGGCCTGACGCCAGAGCCCAGG | SEQ ID NO 249 |

| Target gene | DNA Target Sequence | SEQ ID NO |
|---|---|---|
| FAS | CAACAACCATGCTGGGCATCTGG | SEQ ID NO 250 |
| | GAGGGTCCAGATGCCCAGCATGG | SEQ ID NO 251 |
| | CATCTGGACCCTCCTACCTCTGG | SEQ ID NO 252 |
| | AGGGCTCACCAGAGGTAGGAGGG | SEQ ID NO 253 |
| | GGAGTTGATGTCAGTCACTTGGG | SEQ ID NO 254 |
| | TGGAGTTGATGTCAGTCACTTGG | SEQ ID NO 255 |
| | AGTGACTGACATCAACTCCAAGG | SEQ ID NO 256 |
| | GTGACTGACATCAACTCCAAGGG | SEQ ID NO 257 |
| | ACTCCAAGGGATTGGAATTGAGG | SEQ ID NO 258 |
| | CTTCCTCAATTCCAATCCCTTGG | SEQ ID NO 259 |
| | TACAGTTGAGACTCAGAACTTGG | SEQ ID NO 260 |
| | TTGGAAGGCCTGCATCATGATGG | SEQ ID NO 261 |
| | AGAATTGGCCATCATGATGCAGG | SEQ ID NO 262 |
| | GACAGGGCTTATGGCAGAATTGG | SEQ ID NO 263 |
| | TGTAACATACCTGGAGGACAGGG | SEQ ID NO 264 |
| | GTGTAACATACCTGGAGGACAGG | SEQ ID NO 265 |

TABLE 1-continued

| Target sequences of immunity regulating gene | | |
|---|---|---|
| Target gene | DNA Target Sequence | SEQ ID NO |
| KDM6A | CGTACCTGTGCAACTCCTGTTGG | SEQ ID NO 266 |
| | GATCTACTGGAATTCCTAATGGG | SEQ ID NO 267 |
| | GAGTCAGCTGTTGGCCCATTAGG | SEQ ID NO 268 |
| | CTGCCTACAAACTCAGTCTCTGG | SEQ ID NO 269 |
| | GGGCAGGCAGGACGGACTCCAGG | SEQ ID NO 270 |
| | GGAGTCCGTCCTGCCTGCCCTGG | SEQ ID NO 271 |
| | GAGTCCGTCCTGCCTGCCCTGGG | SEQ ID NO 272 |
| | GAAAAGGGTCCATTGGCCAAAGG | SEQ ID NO 273 |
| | GCCTGCAGAAAAGGGTCCATTGG | SEQ ID NO 274 |
| | TTGATGTGCTACAGGGAACATGG | SEQ ID NO 275 |
| | AGCGTTCTTGATGTGCTACAGGG | SEQ ID NO 276 |
| | CAGCGTTCTTGATGTGCTACAGG | SEQ ID NO 277 |
| | CTGTAGCACATCAAGAACGCTGG | SEQ ID NO 278 |
| | TGTAGCACATCAAGAACGCTGGG | SEQ ID NO 279 |
| | ATAGGCAATAATCATATAACAGG | SEQ ID NO 280 |
| | AGTGCGTTTCGCTGCAGGTAAGG | SEQ ID NO 281 |
| | GAGTGAGTGCGTTTCGCTGCAGG | SEQ ID NO 282 |
| | GTCAGGTTTGTGCGGTTATGAGG | SEQ ID No 283 |
| | CGCTGCTGGTCAGGTTTGTGCGG | SEQ ID NO 284 |
| | AAACCTGACCAGCAGCGCAGAGG | SEQ ID NO 285 |
| | CCAGCAGCGCAGAGGAGCCGTGG | SEQ ID NO 286 |
| | CCACGGCTCCTCTGCGCTGCTGG | SEQ ID NO 287 |
| | CCAACTATCTAACTCCACTCAGG | SEQ ID NO 288 |
| | CCTGAGTGGAGTTAGATAGTTGG | SEQ ID NO 289 |

An aspect of the contents disclosed by the present specification relates to the composition of gene manipulation for artificially manipulating immunity regulating gene.

The composition for gene manipulation may be used for producing an artificially modified immunity regulating gene. Additionally, the immunity regulating gene artificially modified by the composition of gene manipulation may regulate the immune system.

The term "artificially modified or engineered or artificially engineered" refers to a state in which an artificial modification is applied, not a state of being as it is that occurs in a natural state. Hereinafter, artificially modified or engineered non-natural immunity regulating gene may be used interchangeably with artificial immunity regulating gene.

The "immune system" of the present invention is a term including all phenomena that affects in vivo immune responses by the changes in the function of the manipulated immune regulatory factor (i.e., being involved in mechanism exhibiting new immune efficacies), and it includes all materials, compositions, methods, and uses which are directly or indirectly involved in such an immune system. For example, it includes all the genes, immune cells, and immune organs/tissues involved in innate immunity, adaptive immunity, cellular immunity, humoral immunity, active immunity, and passive immune response.

The composition for gene manipulation disclosed by the present specification may include the guide nucleic acid and the editor protein.

The composition for gene manipulation may include:

(a) the guide nucleic acid that may form a complementary bond with the target sequence of the immunity regulating gene or the nucleic acid sequence encoding thereof; and (b) one or more editor protein or the nucleic acid sequence encoding thereof.

The explanation on the above immunity regulating gene is as described above.

The explanation on the above target sequence is as described above.

The composition for gene manipulation may include the guide nucleic acid-editor protein complex.

The term "guide nucleic acid-editor protein complex" refers to a complex formed by the interaction between the guide nucleic acid and the editor protein.

The explanation on the above guide nucleic acid is as described above.

The "editor protein" refers to a peptide, polypeptide or protein that are able to directly bind to or interact with, without directly binding to, a nucleic acid.

In this case, the nucleic acid may be a nucleic acid included in a target nucleic acid, gene or chromosome. Here, the nucleic acid may be a guide nucleic acid.

The editor protein may be an enzyme.

Here, the term "enzyme" refers to a polypeptide or protein that contains a domain capable of cleaving a nucleic acid, gene, or chromosome.

The enzyme may be a nuclease or a restriction enzyme.

The editor protein may include a complete active enzyme.

Here, the "complete active enzyme" refers to an enzyme having the same function as an original function of a wild-type enzyme cleaving the nucleic acid, gene or chromosome. For example, the wild type enzyme cleaving the double strand of DNA may be a complete active enzyme that cleaves all the double strand of DNA. In another example, when a portion of amino acid sequence of the wild type enzyme cleaving the double strand of DNA is deleted or substituted by an artificial modification, the artificially modified enzyme mutant may be a complete active enzyme if the artificially modified enzyme mutant cleaves the double strand of DNA equally with the wild-type enzyme.

Additionally, the complete active enzyme may include an enzyme having an improved function compared to the function of the wild-type enzyme. For example, a specifically modified or engineered form of the wild-type enzyme cleaving the double strand of DNA may have complete enzyme activity which is improved compared to the wild type enzyme, that is, an improved activity of cleaving the double strand of DNA.

The editor protein may include an incomplete or partially active enzyme.

Here, the term "incomplete or partially active enzyme" refers to an enzyme having only some of the original function of the wild-type enzyme cleaving the nucleic acid, gene or chromosome. For example, a specifically modified or engineered form of the wild-type enzyme cleaving the double strand of DNA may be a form having a first function, or a form having a second function. Here, the first function may be a function cleaving a first strand of the double strand of DNA, and the second function may be a function cleaving a second strand of the double strand of DNA. Here, the enzyme having the first function or the enzyme having the second function may be the incomplete or partially active enzyme.

The editor protein may include an inactive enzyme.

Here, the term "inactive enzyme" refers to an enzyme in which the original function of the wild-type enzyme cleaving the nucleic acid, gene or chromosome is completely inactivated. For example, a specifically modified or engineered form of the wild type enzyme may be a form that lost both the first function and the second function, that is, both the first function cleaving the first strand of the double strand of DNA and the second function cleaving the second strand of the double strand of DNA are lost. Here, the enzyme that lost both the first function and the second function may be the inactive enzyme.

The editor protein may be a fusion protein.

Here, the "fusion protein" refers to a protein that is produced by fusing an enzyme with an additional domain, peptide, polypeptide or protein.

The additional domain, peptide, polypeptide or protein may be a functional domain, peptide, polypeptide or protein, which has a function the same as or different from the functional domain, peptide, polypeptide or protein included in the enzyme.

The fusion protein may include an additional functional domain, peptide, polypeptide or protein at one or more regions of the amino terminus of the enzyme or the vicinity thereof; the carboxyl terminus or the vicinity thereof; the middle part of the enzyme; and a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV; NLS derived from nucleoplasmin (e.g., nucleoplasmin bipartite NLS with a sequence KRPAATKKAGQAKKKK); c-myc NLS with an amino acid sequence PAAKRVKLD or RQRRNELKRSP; hRNPA1 M9 NLS with a sequence NQSSNFGPMKGGNFGGRSSGPYGGGGQYFAKPRNQGGY; an importin-α-derived IBB domain sequence RMRIZFKNKGKDTAELRRRRVEVSVELRKAKKDEQILKRRNV; myoma T protein sequences VSRKRPRP and PPKKARED; human p53 sequence POPKKKPL; a mouse c-abl IV sequence SALIKKKKKMAP; influenza virus NS1 sequences DRLRR and PKQKKRK; a hepatitis virus-δ antigen sequence RKLKKKIKKL; a mouse Mx1 protein sequence REKKKFLKRR; a human poly(ADP-ribose) polymerase sequence KRKGDEVDGVDEVAKKKSKK; or steroid hormone receptor (human) glucocorticoid sequence RKCLQAGMNLEARKTKK, but the present invention is not limited thereto.

The additional domain, peptide, polypeptide or protein may be a dysfunctional domain, peptide, polypeptide or protein that do not perform a specific function. Here, the dysfunctional domain, peptide, polypeptide or protein may be a domain, peptide, polypeptide or protein which does not affect the function of the enzyme.

The fusion protein may include an additional dysfunctional domain, peptide, polypeptide or protein at one or more regions of the amino terminus of the enzyme or the vicinity thereof, the carboxyl terminus or the vicinity thereof; the middle part of the enzyme; and a combination thereof.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

In addition, the modification may be substitution, removal, addition of some bases in the base sequence encoding the editor protein, or a combination thereof.

Additionally, the composition for gene manipulation may optionally further include a donor including a specific nucleotide sequence desired to be inserted, or a nucleic acid sequence encoding the same.

Here, the nucleotide sequence desired to be inserted may be a portion of nucleotide sequence in an immunity involving gene.

Here, the nucleotide sequence desired to be inserted may be a nucleotide sequence that is to correct or introduce the mutation of the immunity regulating gene which is subjected to manipulation.

The term "donor" refers to a nucleic acid sequence that helps to repair the damaged gene or nucleic acid via HDR The donor may be a double-stranded nucleic acid or single-stranded nucleic acid.

The donor may be linear or circular.

The donor may include a nucleotide sequence having homology to a target gene or nucleic acid.

For example, the donor may include a nucleotide sequence which has homology to a nucleotide sequence at positions in which a specific nucleic acid is to be inserted (e.g., the upstream and the downstream of a damaged nucleic acid), respectively. In particular, the specific nucleic acid to be inserted may be located between the nucleotide sequence having homology to the downstream nucleotide sequence of the damaged nucleic acid and the nucleotide sequence having homology to the upstream nucleotide sequence of the damaged nucleic acid. In particular, the nucleotide sequence having the above homology may have at least 50%, 55%, 60%, 65%, 70%, 75%, 80%, 85%, 90% or 95% or more of homology, or complete homology.

The donor may optionally include an additional nucleotide sequence. In particular, the additional nucleotide sequence may have roles in enhancing the stability, knockin efficiency, or HDR efficiency of the donor.

For example, the additional nucleotide sequence may be a nucleotide sequence rich in A and T bases (i.e., an A-T rich domain). Alternatively, the additional nucleotide sequence may be a scaffold/matrix attachment region (S/MAR).

The guide nucleic acid, editor protein or guide nucleic acid-editor protein complex disclosed by the present specification may be delivered or introduced to a subject in various forms.

The term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including the target gene or chromosome of the guide nucleic acid-editor protein complex.

The organism may be an animal, animal tissue or animal cell.

The organism may be a human, human tissue or human cell.

The tissue may be eyes, skin, liver, kidney, heart, lung, brain, muscle or blood.

The cells may be immune cells such as natural killer cells (NK cells), T cells, B cells, dendritic cells, and macrophages or stem cells.

The specimen or sample may be obtained from an organism (e.g., saliva, blood, liver tissues, brain tissues, liver cells, neuron, phagocyte, T cells, B cells, astrocytes, cancer cells or stem cells) that includes a target gene or chromosome Preferably, the subject may be an organism comprising an immunity regulating gene.

The guide nucleic acid, editor protein or guide nucleic acid-editor protein complex may be delivered or introduced into a subject by in the form of DNA, RNA or a mixed form.

Here, The form of DNA, RNA or a mixture thereof, which encodes the guide nucleic acid and/or editor protein may be delivered or introduced into a subject by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

The nucleic acid sequence encoding the guide nucleic acid and/or editor protein may be delivered or introduced into a subject by a vector.

The vector may include a nucleic acid sequence encoding a guide nucleic acid and/or editor protein.

For example, the vector may simultaneously include nucleic acid sequences, which encode the guide nucleic acid and the editor protein, respectively.

For example, the vector may include the nucleic acid sequence encoding the guide nucleic acid.

As an example, domains included in the guide nucleic acid may be contained all in one vector, or may be divided and then contained in different vectors.

For example, the vector may include the nucleic acid sequence encoding the editor protein.

In one example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

A nucleic acid sequence encoding a guide nucleic acid and/or editor protein may be delivered or introduced into a subject using a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, particle bombardment, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

As an example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nano-vesicle which transfers a protein and RNA and which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-permeable. While the liposome may be made from several different types of lipids, phospholipids are most generally used to produce the liposome as a drug carrier.

Additionally, the composition for non-vector delivery may include other additives.

An editor may be delivered or introduced into a subject in the form of a peptide, polypeptide, or protein.

An editor protein in the form of a peptide, polypeptide or protein may be delivered or introduced into a subject by a method known in the art.

The peptide, polypeptide or protein form may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

The guide nucleic acid and editor protein may be delivered or introduced into a subject in the form of nucleic acid-protein mixture.

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

The guide nucleic acid-editor protein complex disclosed by the present specification may modify the target nucleic acid, gene or chromosome.

For example, the guide nucleic acid-editor protein complex induces modification to a sequence of the target nucleic acid, gene or chromosome. As a result, the protein expressed by the target nucleic acid, gene or chromosome may have modified structure and/or function thereof, controlled expression thereof, or removed expression thereof.

The guide nucleic acid-editor protein complex may act at a DNA, RNA, gene or chromosome level.

In one example, the guide nucleic acid-editor protein complex may be used to regulate (e.g., inhibit, suppress, reduce, increase or promote) the expression of a protein encoded by the target gene, or regulate (e.g., inhibit, suppress, reduce, increase or promote) protein activity, or express a modified protein by engineering or modifying the target gene.

The guide nucleic acid-editor protein complex may act at gene transcription and translation stages.

In one example, the guide nucleic acid-editor protein complex may promote or suppress the transcription of a target gene, thereby regulating (e.g., inhibiting, suppressing, reducing, increasing or promoting) the expression of a protein encoded by the target gene.

In another example, the guide nucleic acid-editor protein complex may promote or suppress the translation of a target gene, thereby regulating (e.g., inhibiting, suppressing, reducing, increasing or promoting) the expression of a protein encoded by the target gene.

In an embodiment disclosed by the present specification, the composition for gene manipulation may include a gRNA and CRISPR enzyme.

The composition for gene manipulation may include:

(a) a gRNA capable of forming a complementary bond to the target sequence of the immunity regulating gene or a nucleic acid sequence encoding thereof; and (b) one or more CRISPR enzyme or a nucleic acid sequence encoding thereof.

The explanation on the above immunity regulating gene is as described above.

The explanation on the above target sequence is as described above.

The composition of gene manipulation may include a gRNA-CRISPR enzyme complex.

The term "gRNA-CRISPR enzyme complex" refers to a complex formed by an interaction between a gRNA and a CRISPR enzyme.

The explanation on the above gRNA is as described above.

The "CRISPR enzyme" is a major protein component of a CRISPR-Cas system, forming the CRISPR-Cas system by forming a complex with a gRNA.

The CRISPR enzyme may be a nucleic acid or a polypeptide (or a protein) having a sequence encoding the CRISPR enzyme.

The CRISPR enzyme may be a Type II CRISPR enzyme.

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, or the HNH domain is used to include HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as a RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs.

The PI domain recognizes a specific nucleotide sequence in a target gene or nucleic acid, that is, a protospacer adjacent motif (PAM) or interacts with PAM. Here, the PAM may vary according to the origin of the type II CRISPR enzyme. For example, when the CRISPR enzyme is SpCas9, PAM may be 5'-NGG-3', when the CRISPR enzyme is *Streptococcus thermophilus* Cas9 (StCas9), PAM may be 5'-NNAGAAW-3' (W=A or T), when the CRISPR enzyme is *Neisseria meningitides* Cas9 (NmCas9), PAM may be 5'-NNNNGATT-3', and when the CRISPR enzyme is *Campylobacter jejuni* Cas9 (CjCas9), PAM may be 5'-NNNVRYAC-3' (V=G or C or A, R=A or G, Y=C or T), where the N may be A, T, G or C; or A, U, G or C. However, although it is commonly understood that the PAM is determined according to the origin of the enzyme as described above, the PAM may vary as studies regarding mutants of enzymes of the origin progress.

The type II CRISPR enzyme may be Cas9.

The Cas9 may be derived from various microorganisms such as *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus Desulforudis, Clostridium botulinum, Clostridium difficile, Finegoldia magna, Natranaerobius thermophilus, Pelotomaculum the rmopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, and *Acaryochloris marina.*

The Cas9 is an enzyme which binds to gRNA so as to cleave or modify a target sequence or position on a target gene or nucleic acid, and may consist of an HNH domain capable of cleaving a nucleic acid strand forming a complementary bond with gRNA, an RuvC domain capable of cleaving a nucleic acid strand forming a non-complementary bond with gRNA, and an REC domain recognizing a target and a PI domain recognizing PAM. Hiroshi Nishimasu, et al. (2014) Cell 156:935-949 may be referenced for specific structural characteristics of Cas9.

The Cas9 may be isolated from a microorganism existing in nature or non-naturally produced by a recombinant or synthetic method.

Additionally, the CRISPR enzyme may be Type V CRISPR enzyme.

Type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains which interact with a target, and a PI domain recognizing PAM. Takashi Yamano et al. (2016) Cell 165:949-962 may be referenced for specific structural characteristics of the type V CRISPR enzyme.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a target gene or nucleic acid is dependent on the PAM sequence.

The PAM sequence is a sequence present in a target gene or nucleic acid, and may be recognized by the PI domain of the type V CRISPR enzyme. The PAM sequence may vary according to the origin of the type V CRISPR enzyme. That is, there are different PAM sequences which are able to be specifically recognized depending on a species. For example, the PAM sequence recognized by Cpf1 may be 5'-TTN-3' (N is A, T, C or G). However, although it is commonly understood that the PAM is determined according to the origin of the enzyme as described above, the PAM may vary as studies regarding mutants of enzymes of the origin progress.

The Type V CRISPR enzyme may be Cpf1.

The Cpf1 may be a Cpf1 which is derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella*, Bacteroidetes, *Helcococcus, Letospira, Desulfovibrio, Desulfonatronum, Opitutaceae, Tuberibacillus, Bacillus, Brevibacilus, Methylobacterium*, or *Acidaminococcus.*

The Cpf1 includes similar RuvC domains corresponding to the RuvC domains of the type II CRISPR enzyme, and may consist of an Nuc domain, instead of the HNH domain of the Cpf1, REC and WED domains which interact with a target, and a PI domain recognizing PAM. Takashi Yamano et al. (2016) Cell 165:949-962 may be referenced for specific structural characteristics of the Cpf1.

The Cpf1 may be isolated from a microorganism existing in nature or non-naturally produced by a recombinant or synthetic method.

The CRISPR enzyme may be a nuclease or a restriction enzyme having a function which cleaves a double strand of the target gene or nucleic acid.

The CRISPR enzyme may be a complete active CRISPR enzyme.

Here, the “complete active” refers to a state having the same function as a function of a wild type CRISPR enzyme, and CRISPR enzymes in this state are referred as “complete active CRISPR enzyme”. Here, the “function of wild type CRISPR enzyme” refers to a state having the function cleaving the double strand of DNA, that is, a state having both the first function cleaving a first strand of the double strand of DNA, and the second function cleaving a second strand of the double strand of DNA.

The complete active CRISPR enzyme may be a wild type CRISPR enzyme cleaving the double strand of DNA.

The complete active CRISPR enzyme may be a CRISPR enzyme mutant in which a wild type CRISPR enzyme cleaving the double strand of DNA is modified or manipulated.

The CRISPR enzyme mutant may be an enzyme in which one or more amino acid in the amino acid sequence of a wild type CRISPR enzyme is substituted with another amino acid, or one or more amino acid is removed.

The CRISPR enzyme mutant may be an enzyme in which one or more amino acid is added in the amino acid sequence of a wild type CRISPR enzyme. Here, the location of the added amino acid may be N-terminus, C-terminus or within the amino acid sequence of the wild type enzyme.

The CRISPR enzyme mutant may be a complete active enzyme in which the function is improved compared to that of the wild type CRISPR enzyme.

For example, a specific modified or manipulated form of a wild type CRISPR enzyme, that is, a CRISPR enzyme mutant may cleave the double strand of DNA without binding to the double strand of DNA to be cleaved or while maintaining a certain distance. In this case, the modified or manipulated form may be a complete active CRISPR enzyme in which the function activity is improved compared to that of the wild type CRISPR enzyme.

The CRISPR enzyme mutant may be a complete active enzyme in which the function is reduced compared to that of the wild type CRISPR enzyme.

For example, a specific modified or manipulated form of a wild type CRISPR enzyme, that is, a CRISPR enzyme mutant may cleave the double strand of DNA at a specific distance or closer to the double strand of DNA to be cleaved, or at a presence of certain bonding. Here, the certain bonding may be, for example, a bond between the amino acid in a specific location of the enzyme and the DNA nucleotide sequence in the cleavage location. In this case, the modified or manipulated form may be a complete active CRISPR enzyme in which the function activity is reduced compared to that of the wild type CRISPR enzyme.

The CRISPR enzyme may be an incomplete or partially active CRISPR enzyme.

The term "incomplete or partially active" refers to a state having a function selected from the function of the wild type CRISPR enzyme, that is, the first function cleaving a first strand of the double strand of DNA, and the second function cleaving a second strand of the double strand of DNA. Additionally, the incomplete or partially active CRISPR enzyme may be referred to as nickase.

The term "nickase" refers to a CRISPR enzyme manipulated or modified to cleave only one strand of the double strand of the target gene or nucleic acid, and the nickase has nuclease activity of cleaving a single strand, for example, a strand that is not complementary or complementary to gRNA of the target gene or nucleic acid. Therefore, to cleave the double strand, nuclease activity of the two nickases is needed.

The nickase may have nuclease activity by the RuvC domain of the CRISPR enzyme. That is, the nickase may not include nuclease activity by the HNH domain of the CRISPR enzyme, and to this end, the HNH domain may be manipulated or modified.

In one example, when the CRISPR enzyme is the type II CRISPR enzyme, the nickase may be the Type II CRISPR enzyme including a modified HNH domain.

For example, when the type II CRISPR enzyme is a wild type SpCas9, the nickase may be a SpCas9 mutant in which the residue 840 in the amino acid sequence of the wild type SpCas9 is mutated from histidine to alanine and the nuclease activity of the HNH domain is inactivated. Here, the produced nickase, that is, SpCas9 mutant, has nuclease activity by the RuvC domain, and therefore is capable of cleaving a strand which does not form a complementary bond with a non-complementary strand of the target gene or nucleic acid, that is, gRNA.

In another example, when the type II CRISPR enzyme is a wild type CjCas9, the nickase may be a CjCas9 mutant in which the residue 559 in the amino acid sequence of the wild type CjCas9 is mutated from histidine to alanine and the nuclease activity by the HNH domain is inactivated. Here, the produced nickase, that is, CjCas9 mutant, has nuclease activity by the RuvC domain, and therefore is capable of cleaving a strand which does not form a complementary bond with a non-complementary strand of the target gene or nucleic acid, that is, gRNA.

Additionally, the nickase may have nuclease activity by the HNH domain of the CRISPR enzyme. That is, the nickase may not include the nuclease activity by the RuvC domain of the CRISPR enzyme, and to this end, the RuvC domain may be manipulated or modified.

In one example, when the CRISPR enzyme is the type II CRISPR enzyme, the nickase may be the type II CRISPR enzyme including a modified RuvC domain.

For example, when the type II CRISPR enzyme is a wild type SpCas9, the nickase may be a SpCas9 mutant in which the residue 10 in the amino acid sequence of the wild type SpCas9 is mutated from aspartic acid to alanine and the nuclease activity of the RuvC domain is inactivated. Here, the produced nickase, that is, SpCas9 mutant, has nuclease activity by the HNH domain, and therefore is capable of cleaving a strand which does not form a complementary bond with a complementary strand of the target gene or nucleic acid, that is, gRNA.

In another example, when the type II CRISPR enzyme is a wild type CjCas9, the nickase may be a CjCas9 mutant in which the residue 8 in the amino acid sequence of the wild type CjCas9 is mutated from aspartic acid to alanine and the nuclease activity of the RuvC domain is inactivated. Here, the produced nickase, that is, CjCas9 mutant, has nuclease activity by the HNH domain, and therefore is capable of cleaving a strand which does not form a complementary bond with a complementary strand of the target gene or nucleic acid, that is, gRNA.

The CRISPR enzyme may be an inactive CRISPR enzyme.

The term "inactive" refers to a state having completely lost the function of the wild type CRISPR enzyme, that is, the first function cleaving a first strand of the double strand of DNA, and the second function cleaving a second strand of the double strand of DNA. The CRISPR enzymes in this state are referred to as inactive CRISPR enzyme.

The inactive CRISPR enzyme may have inactivated nuclease by mutation in the domain of the wild type CRISPR enzyme having nuclease activity.

The inactive CRISPR enzyme may be one in which the nuclease activities of the RuvC domain and the HNH domain are inactivated due to mutation. That is, the inactive CRISPR enzyme may not include nuclease activity by the RuvC domain and the HNH domain of the CRISPR enzyme, and to this end, the RuvC domain and the HNH domain may be manipulated or modified.

In one example, when the CRISPR enzyme is the type II CRISPR enzyme, the inactive CRISPR enzyme may be the type II CRISPR enzyme including a modified RuvC domain and HNH domain.

For example, when the type II CRISPR enzyme is the wild type SpCas9, the inactive CRISPR enzyme may be an SpCas9 mutant in which the nuclease activities by the RuvC domain and the HNH domain are inactivated, by mutating both the residues 10 and 840 in the amino acid sequence of the wild type SpCas9 from aspartic acid and histidine to alanine, respectively. Here, the produced inactive CRISPR enzyme, that is, the SpCas9 mutant has inactivated nuclease activities of the RuvC domain and the HNH domain, and therefore the double strand of the target gene or nucleic acid cannot be cleaved completely.

In another example, when the type II CRISPR enzyme is the wild type CjCas9, the inactive CRISPR enzyme may be a CjCas9 mutant in which the nuclease activities by the RuvC domain and the HNH domain are inactivated, by mutating both the residues 8 and 559 in the amino acid sequence of the wild type CjCas9 from aspartic acid and histidine to alanine, respectively. Here, the produced inactive CRISPR enzyme, that is, the CjCas9 mutant has inactivated nuclease activities of the RuvC domain and the HNH domain, and therefore the double strand of the target gene or nucleic acid cannot be cleaved completely.

In addition to the nuclease activity described above, the CRISPR enzyme may have helicase activity, that is, an ability to anneal the helix structure of the double-stranded nucleic acid.

Additionally, the CRISPR enzyme may be modified to completely, incompletely, or partially activate helicase activity of CRISPR enzyme.

The CRISPR enzyme may be a CRISPR enzyme mutant having artificially manipulated or modified a wild type CRISPR enzyme.

The CRISPR enzyme mutant may be an artificially manipulated or modified CRISPR enzyme mutant to modify the function of the wild type CRISPR enzyme, that is, the first function cleaving a first strand of the double strand of DNA, and/or the second function cleaving a second strand of the double strand of DNA.

For example, the CRISPR enzyme mutant may be a form having lost the first function of the function of the wild type CRISPR enzyme.

Alternatively, the CRISPR enzyme mutant may be a form having lost the second function of the function of the wild type CRISPR enzyme.

For example, the CRISPR enzyme mutant may be a form having lost the function of the wild type CRISPR enzyme, that is, both the first function and the second function.

The CRISPR enzyme mutant may form a gRNA-CRISPR enzyme complex by interacting with a gRNA.

The CRISPR enzyme mutant may be an artificially manipulated or modified CRISPR enzyme mutant to modify the function of the wild type CRISPR enzyme interacting with the gRNA.

For example, the CRISPR enzyme mutant may be a form having a decreased interaction with the gRNA compared to the wild type CRISPR enzyme.

Alternatively, the CRISPR enzyme mutant may be a form having an increased interaction with the gRNA compared to the wild type CRISPR enzyme.

For example, the CRISPR enzyme mutant may be a form having the first function of the wild type CRISPR enzyme and a decreased interaction with the gRNA.

Alternatively, the CRISPR enzyme mutant may be a form having the first function of the wild type CRISPR enzyme and an increased interaction with the gRNA.

For example, the CRISPR enzyme mutant may be a form having the second function of the wild type CRISPR enzyme and a decreased interaction with the gRNA.

Alternatively, the CRISPR enzyme mutant may be a form having the second function of the wild type CRISPR enzyme and an increased interaction with the gRNA.

For example, the CRISPR enzyme mutant may be a form not having the first function and the second function of the wild type CRISPR enzyme and having a decreased interaction with the gRNA.

Alternatively, the CRISPR enzyme mutant may be a form not having the first function and the second function of the wild type CRISPR enzyme and having an increased interaction with the gRNA.

Here, various gRNA-CRISPR enzyme complex may be formed depending on the intensity of interaction between the gRNA and the CRISPR enzyme mutant, and the function of approaching to or cleaving the target sequence may vary depending on the CRISPR enzyme mutant.

For example, the gRNA-CRISPR enzyme complex formed by the CRISPR enzyme mutant having reduced interaction with gRNA is capable of cleaving the double strand or single strand of the target sequence only when approaching or localized to the target sequence forming a complete complementary bond with the gRNA.

The CRISPR enzyme mutant may have at least one of the amino acids of a wild type CRISPR enzyme modified.

In one example, the CRISPR enzyme mutant may have at least one of the amino acids of a wild type CRISPR enzyme substituted.

In another example, the CRISPR enzyme mutant may have at least one of the amino acids of a wild type CRISPR enzyme removed.

In yet another example, the CRISPR enzyme mutant may have at least one of the amino acids of a wild type CRISPR enzyme added.

In one example, the CRISPR enzyme mutant may have at least one of the amino acids of a wild type CRISPR enzyme substituted, removed and/or added.

Additionally, other than the original function of the wild type CRISPR enzyme, that is, the first function cleaving a first strand of the double strand of DNA and the second function cleaving a second strand of the double strand of DNA, the CRISPR enzyme mutant may further include an optional functional domain. Here, the CRISPR enzyme mutant may have an additional function other than the original function of the wild type CRISPR enzyme.

The functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

The functional domain may be a deaminase.

For example, an incomplete or partial CRISPR enzyme may additionally include a cytidine deaminase as a functional domain. In one exemplary embodiment, a cytidine deaminase, for example, apolipoprotein B editing complex 1 (APOBEC1) may be added to SpCas9 nickase, thereby producing a fusion protein. The [SpCas9 nickase]-[APOBEC1] formed thereby may be used in nucleotide repair or editing of the nucleotide C into T or U, or the nucleotide G into A.

In another example, an incomplete or partial CRISPR enzyme may further include a cytidine deaminase as a functional domain. In one embodiment, an adenine deaminase, for example, TadA variants, ADAR2 variants, ADAT2 variants, etc., may be added to SpCas9 nickase, thereby producing a fusion protein. The [SpCas9 nickase]-[TadA variant], [SpCas9 nickase]-[ADAR2 variant], or [SpCas9 nickase]-[ADAT2 variant] formed thereby modifies the nucleotide A into inosine, and the modified inosine is recognized as the nucleotide G by polymerase and substantially exhibits an effect of repairing or editing the nucleotide A into G, therefore may be used in nucleotide repair or editing of the nucleotide A into G, or the nucleotide T into C.

The functional domain may be a nuclear localization sequence or signal (NLS) or a nuclear export sequence or signal (NES).

In one example, the CRISPR enzyme may include one or more NLSs. Here, one or more NLSs may be included at an N-terminus of a CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV; NLS from nucleoplasmin (e.g., nucleoplasmin bipartite NLS having the sequence KRPAATKKAGQAKKKK); c-myc NLS having the amino acid sequence PAAKRVKLD or RQRRNELKRSP; hRNPA1 M9 NLS having the sequence NQSSNFGPMKGGNFGGRSSGPYGGGGQYFAKPRNQGGY; the sequence RMRIZFKNKGKDTAELRRRRVEVSVELRKAKKDEQILKRRNV of the IBB domain from importin-α; the sequences VSRKRPRP and PPKKARED of a myoma T protein; the sequence POPKKKPL of human p53; the sequence SALIKKKKKMAP of mouse c-abl IV; the sequences DRLRR and PKQKKRK of influenza virus NS1; the sequence RKLKKKIKKL of a hepatitis delta virus antigen; the sequence REKKKFLKRR of a mouse Mx1 protein; the sequence KRKGDEVDGVDEVAKKKSKK of a human poly (ADP-ribose) polymerase; or the NLS sequence RKCLQAGMNLEARKTKK, derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

The split-type CRISPR enzyme may be a completely, incompletely or partially active enzyme or inactive enzyme.

For example, when the CRISPR enzyme is SpCas9, a split SpCas9 may be produced by dividing between the residue 656, tyrosine, and the residue 657, threonine into two portions.

The split-type CRISPR enzyme may selectively include an additional domain, peptide, polypeptide or protein for reconstitution.

The additional domain, peptide, polypeptide or protein for the reconstitution may be assembled such that the split-type CRISPR enzyme is structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycine is present, thereby producing a reconstituted CRISPR enzyme.

The CRISPR enzyme or CRISPR enzyme mutant described in the present invention may be a polypeptide, protein or nucleic acid having a sequence encoding the same, and may be codon-optimized for a subject to introduce the CRISPR enzyme or CRISPR enzyme mutant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

The gRNA, CRISPR enzyme or gRNA-CRISPR enzyme complex disclosed by the present specification may be delivered or introduced into a subject in various forms.

The explanation of the above subject is as described above.

In an embodiment, the gRNA and/or CRISPR enzyme may be delivered or introduced into a subject by a vector including the nucleic acid sequence encoding thereof, respectively.

The vector may include a nucleic acid sequence encoding the gRNA and/or CRISPR enzyme.

In one example, the vector may simultaneously include the nucleic acid sequences encoding the gRNA and CRISPR enzyme.

In another example, the vector may include the nucleic acid sequences encoding the gRNA.

For example, the domains included in the gRNA may be entirely included in a vector, or the domains may be separated and individually included in vectors.

In another example, the vector may include the nucleic acid sequences encoding the CRISPR enzyme.

For example, for the CRISPR enzyme, the nucleic acid sequence encoding the CRISPR enzyme may be entirely included in a vector, or may be divided and individually included in vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be, but is not limited to, a retrovirus, a lentivirus, an adenovirus, adeno-associated virus (AAV), vaccinia virus, a poxvirus or a herpes simplex virus.

In one example, a nucleic acid sequence encoding a gRNA and/or CRISPR enzyme may be delivered or introduced by a recombinant lentivirus.

In another example, a nucleic acid sequence encoding a gRNA and/or CRISPR enzyme may be delivered or introduced by a recombinant adenovirus.

In still another example, a nucleic acid sequence encoding a gRNA and/or CRISPR enzyme may be delivered or introduced by recombinant AAV.

In yet another example, a nucleic acid sequence encoding a gRNA and/or CRISPR enzyme may be delivered or introduced by a hybrid virus, for example, one or more hybrids of the virus listed herein.

In an embodiment, a gRNA-CRISPR enzyme complex form may be delivered or introduced into a subject.

For example, the gRNA may be a DNA, RNA, or a mixture thereof. The CRISPR enzyme may be a peptide, polypeptide or protein.

In one example, the gRNA and the CRISPR enzyme may be delivered or introduced into a subject in the form of a gRNA-CRISPR enzyme complex containing an RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The gRNA-CRISPR enzyme complex disclosed by the present specification may be used for artificially manipulating or modifying the target gene, that is, the immunity regulating gene.

The target gene may be manipulated or modified using the above-described gRNA-CRISPR enzyme complex, that is, the CRISPR complex. Here, the manipulation or modification of the target gene includes all of the stages of i) cleaving or damaging the target gene and ii) repairing or restoring the damaged target gene.

The i) cleaving or damaging the target gene may be cleaving or damaging the target gene using the CRISPR complex, specifically, cleaving or damaging the target sequence in the target gene.

The target sequence may be a target of the gRNA-CRISPR enzyme complex, and the target sequence may include or may not include the PAM sequence recognized by the CRISPR enzyme. Such target sequence may provide the practitioner with important criteria for the design of a gRNA.

The target sequence may be specifically recognized by the gRNA of the gRNA-CRISPR enzyme complex, and thereby gRNA-CRISPR enzyme complex may be placed in proximity with the recognized target sequence.

The "cleavage" at a target site refers to a breakage of a covalent backbone of a polynucleotide. The cleavage may include, but is not limited to, enzymatic or chemical hydrolysis of a phosphodiester linkage, and may be performed by various other methods. Both the cleavage of a single strand and cleavage of a double strand may be possible, and the cleavage of a double strand may occur as a result of the cleavage of two distinct single strands. The cleavage of double strands may produce blunt ends or staggered ends.

In one example, cleaving or damaging the target gene using the CRISPR complex may be completely cleaving or damaging the double strand of a target sequence.

In an embodiment, when the CRISPR enzyme is wild type SpCas9, the CRISPR complex may completely cleave the double strand of a target sequence forming a complementary bond to gRNA.

In another embodiment, when the CRISPR enzyme is SpCas9 nickase (D10A) and SpCas9 nickase (H840A), each CRISPR complex may individually cleave the two single strands of a target sequence forming a complementary bond with gRNA. That is, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In another example, cleaving or damaging the target gene or nucleic acid using the CRISPR complex may be cleaving or damaging only the single strand of the double strand of a target sequence. Here, the single strand may be a guide nucleic acid binding sequence of the target sequence forming a complementary bond with gRNA, that is, a complementary single strand, or a guide nucleic acid non-binding sequence that does not form a complementary bond with gRNA, that is, a single strand non-complementary to gRNA.

In an embodiment, when the CRISPR enzyme is SpCas9 nickase (D10A), the CRISPR complex may cleave the guide nucleic acid binding sequence of the target sequence forming a complementary bond with gRNA, that is, a complementary single strand may be cleaved by the SpCas9 nickase (D10A), and the guide nucleic acid non-binding sequence that does not form a complementary bond with gRNA, that is, a single strand non-complementary to gRNA, may not be cleaved.

In another embodiment, when the CRISPR enzyme is SpCas9 nickase (H840A), the CRISPR complex may cleave the guide nucleic acid non-binding sequence of the target sequence that does not form a complementary bond with gRNA, that is, a single strand non-complementary to gRNA may be cleaved by the SpCas9 nickase (H840A), and the guide nucleic acid binding sequence of the target sequence forming a complementary bond with gRNA, that is, a complementary single strand, may not be cleaved.

In yet another example, the cleavage or damage of a target gene or nucleic acid using the CRISPR complex may be partial removal of a nucleic acid fragment.

In an embodiment, when the CRISPR complex is formed by two gRNAs forming complementary bonds with individually different target sequences and the wild type SpCas9, a double strand of a target sequence forming a complementary bond with a first gRNA may be cleaved, and a double strand of a target sequence forming a complementary bond with the second gRNA may be cleaved, resulting in the removal of nucleic acid fragments by the first and second gRNAs and the SpCas9.

The ii) repairing or recovering the damaged target gene may be repaired or restored by non-homologous end joining (NHEJ) or homology-directed repair (HDR).

The non-homologous end joining (NHEJ) is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because the mutation in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a gene targeted by the CRISPR complex may be performed using such NHEJ. A double strand or two single strands of a target gene or nucleic acid may be cleaved using the CRISPR enzyme such as Cas9 or Cpf1, and the broken double strand or two single strands of the target gene or nucleic acid may have indels through the NHEJ, thereby inducing specific knockout of the target gene or nucleic acid. Here, the site of a target gene or nucleic acid cleaved by the CRISPR enzyme may be a non-coding or coding region, and in addition, the site of the target gene or nucleic acid restored by NHEJ may be a non-coding or coding region.

In one example, various insertion and deletion (indel) may occur in a restored region due to a process of cleaving the double strand of the target gene by using a CRISPR complex and restoring by NHEJ.

The term “indel” collectively refers to a mutation in which some nucleotides are inserted or deleted in the nucleotide sequence of DNA. As described above, when a guide nucleic acid-editor protein complex cleaves the nucleic acid (DNA, RNA) of an immunity regulating gene, indel may be one which is introduced to a target sequence in the process of repair by homologous recombination (HDR) or non-homologous end-joining (NHEJ) mechanism.

The homology directed repairing (HDR) is a correction method without an error, which uses a homologous sequence as a template to repair or restore a damaged gene or nucleic acid, and generally, to repair or restore broken DNA, that is, to restore innate information of cells, and the broken DNA is repaired or restored using information of an unmodified complementary nucleotide sequence or information of a sister chromatid. The most common type of HDR is homologous recombination (HR). HDR is a repair or restoration method usually occurring in the S or G2/M phase of actively dividing cells.

To repair or restore damaged DNA using HDR, rather than using a complementary nucleotide sequence or sister chromatid of the cells, a DNA template artificially synthesized using information of a complementary nucleotide sequence or homologous nucleotide sequence, that is, a nucleic acid template including a complementary nucleotide sequence or homologous nucleotide sequence may be provided to the cells, thereby repairing or restoring the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be, but is not limited to, a nucleic acid sequence or nucleic acid fragment for correcting the target gene or nucleic acid modified by a mutation to a normal gene or nucleic acid, or a gene or nucleic acid desired to be expressed in cells.

In one example, a double or single strand of a target gene or nucleic acid may be cleaved using the CRISPR complex, a nucleic acid template including a nucleotide sequence complementary to a nucleotide sequence adjacent to the cleavage site may be provided to cells to repair or restore the cleaved nucleotide sequence of the target gene or nucleic acid through HDR method.

Here, the nucleic acid template including the complementary nucleotide sequence may have broken DNA, that is, a cleaved double or single strand of a complementary nucleotide sequence, and further include a nucleic acid sequence or nucleic acid fragment desired to be inserted into the broken DNA. An additional nucleic acid sequence or nucleic acid fragment may be inserted into a cleaved site of the broken DNA, that is, the target gene or nucleic acid using the nucleic acid template including a nucleic acid sequence or nucleic acid fragment to be inserted into the complementary base sequence. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The complementary nucleotide sequence may be a nucleotide sequence forming a complementary bond with broken DNA, that is, right and left nucleotide sequences of the cleaved double or single strand of the target gene or nucleic acid. Alternatively, the complementary nucleotide sequence may be a nucleotide sequence forming a complementary bond with broken DNA, that is, 3' and 5' ends of the cleaved double or single strand of the target gene or nucleic acid. The complementary nucleotide sequence may be a 15 bp to 3000 bp nucleotide sequence, a length or size of the complementary nucleotide sequence may be suitably designed according to a size of the nucleic acid template, or the target gene or nucleic acid. Here, as the nucleic acid template, a double- or single-stranded nucleic acid may be used, or it may be linear or circular, but the present invention is not limited thereto.

In another example, a double- or single-stranded target gene or nucleic acid may be cleaved using the CRISPR complex, a nucleic acid template including a homologous nucleotide sequence with a nucleotide sequence adjacent to a cleavage site may be provided to cells to repair or restore the cleaved nucleotide sequence of the target gene or nucleic acid by HDR method.

Here, the nucleic acid template including the homologous nucleotide sequence may have broken DNA, that is, a cleaved double- or single-stranded homologous nucleotide sequence, and further include a nucleic acid sequence or nucleic acid fragment desired to be inserted into the broken DNA. An additional nucleic acid sequence or nucleic acid fragment may be inserted into broken DNA, that is, a cleaved site of a target gene or nucleic acid using the nucleic acid template including a homologous base sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The homologous nucleotide sequence may be a nucleotide sequence having homology with broken DNA, that is, right and left nucleotide sequences of the cleaved double or single strand of the target gene or nucleic acid. Alternatively, the complementary nucleotide sequence may be a nucleotide sequence having homology with broken DNA, that is, the 3' and 5' ends of a cleaved double or single strand of a target gene or nucleic acid. The homologous nucleotide sequence may be a 15 bp to 3000 bp nucleotide sequence, and a length or size of the homologous nucleotide sequence may be suitably designed according to a size of the nucleic acid template, or the target gene or nucleic acid. Here, as the nucleic acid template, a double- or single-stranded nucleic acid may be used and may be linear or circular, but the present invention is not limited thereto.

Other than the NHEJ and HDR, there are methods of repairing or restoring broken target genes. For example, the methods of repairing or restoring broken target genes may be single-strand annealing, single-strand break repair, mismatch repair, or nucleotide break repair or a method using nucleotide break repair.

The single-strand annealing (SSA) is a method of repairing double strand breaks between two repeat sequences present in a target nucleic acid, and may generally use a repeat sequence of more than 30 bp nucleotide sequence. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

SSA, similar to HDR, utilizes a complementary sequence, that is, a complementary repeat sequence, and in contrast, does not requires a nucleic acid template for modifying or correcting a target nucleic acid sequence.

Single strand breaks in a genome may be repaired or restored through a separate mechanism, single-strand break repair (SSBR), from the above-described repair mechanisms. In the case of single-strand DNA breaks, PARP1 and/or PARP2 recognize the breaks and recruit a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing generally involves repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a dislocated single nucleotide. After DNA gap filling, a DNA ligase promotes end joining.

The mismatch repair (MMR) may work on mismatched DNA nucleotides. Each of MSH2/6 or MSH2/3 complex has ATPase activity and thus plays an important role in recognizing a mismatch and initiating a repair, and the MSH2/6 primarily recognizes nucleotide-nucleotide mismatches and identifies one or two nucleotide mismatches, while the MSH2/3 primarily recognizes a larger mismatch.

The base excision repair (BER) is a repair method which is active throughout the entire cell cycle, and is used to remove a small non-helix-distorting nucleotide damaged region from the genome.

In the damaged DNA, damaged nucleotides are removed by cleaving an N-glycosidic bond joining a base to the phosphate-deoxyribose backbone, and then the phosphodiester backbone is cleaved, thereby generating breaks in single-strand DNA. The broken single strand ends formed thereby are removed, a gap generated due to the removed single strand is filled with a new complementary base, and then an end of the newly-filled complementary base is ligated with the backbone by a DNA ligase, resulting in repair or restoration of the damaged DNA.

NER (Nucleotide excision repair) is an excision mechanism important for removing large helix-distorting damage from DNA, and when the damage is recognized, a short single-strand DNA segment containing the damaged region is removed, resulting in a single strand gap of a 22 bp to 30 bp nucleotide sequence. The generated gap is filled with new complementary bases, and an end of the newly filled complementary bases is ligated with the backbone by a DNA ligase, resulting in repair or restoration of the damaged DNA.

Effects of artificially manipulating a target gene, that is, the immunity regulating gene, with the gRNA-CRISPR complex may largely be knockout, knockdown, and knockin.

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when a target gene or chromosome is edited or corrected using a gRNA-CRISPR enzyme complex, that is, a CRISPR complex, the target gene or chromosome may be cleaved using the CRISPR complex. The damaged target gene or chromosome may be restored through NHEJ using the CRISPR complex. The damaged target gene or chromosome may have indels due to NHEJ, and thereby, specific knockout for the target gene or chromosome may be induced.

In another example, when a target gene or chromosome is edited or corrected using a gRNA-CRISPR enzyme complex, that is, a CRISPR complex, and a donor, the target gene or nucleic acid may be cleaved using the CRISPR complex. The target gene or nucleic acid damaged by the CRISPR complex may be restored through HDR using a donor. Here, the donor includes a complementary nucleotide sequence and nucleotide sequences desired to be inserted. Here, the number of the nucleotide sequences desired to be inserted may be adjusted according to the location or purpose of insertion. When the damaged gene or chromosome is recovered by using a donor, the nucleotide sequence desired to be inserted is inserted into the damaged nucleotide sequence region, and thereby, specific knockout for the target gene or chromosome may be induced.

The term "knockdown" refers to a decrease in transcription and/or translation of a target gene or nucleic acid or a decrease in expression of a target protein. The onset of a disease may be prevented or a disease may be treated by regulating the overexpression of a gene or protein with the knockdown.

For example, when a target gene or chromosome is edited or corrected using a gRNA-CRISPR inactive enzyme-transcription inhibitory activity domain complex, that is, a CRISPR inactive complex including a transcription inhibitory activity domain, the CRISPR inactive complex may specifically bind to the target gene or chromosome, transcription of the target gene or chromosome may be inhibited by the transcription inhibitory activity domain included in the CRISPR inactive complex, and thereby inducing knockdown in which expression of the corresponding gene or chromosome is inhibited.

In another example, when a target gene or chromosome is edited or corrected using a gRNA-CRISPR enzyme complex, that is, a CRISPR complex, the promoter and/or enhancer region of the target gene or chromosome may be cleaved by the CRISPR complex. Here, the gRNA may recognize a portion of nucleotide sequences in the promoter and/or enhancer region of the target gene or chromosome as the target sequence. The target gene or chromosome damaged by the CRISPR complex may be restored through NHEJ. The damaged target gene or chromosome may have indels due to NHEJ, and thereby, specific knockout for the target gene or chromosome may be induced. Alternatively, when a donor is selectively used, the target gene or chromosome damaged by the CRISPR complex may be restored through HDR. When the damaged gene or chromosome is restored using a donor, the nucleotide sequence desired to be inserted is inserted into the damaged nucleotide sequence region, and thereby, specific knockdown for the target gene or chromosome may be induced.

The term "knockin" refers to insertion of a specific nucleic acid or gene into a target gene or nucleic acid, and in particular, the term "specific nucleic acid or gene" refers to a nucleic acid or gene intended to be inserted or desired to be expressed. Knockin may be used for the treatment of diseases by precisely correcting a mutant gene that causes a disease or inducing normal gene expression by inserting a normal gene.

In addition, knockin may require an additional donor.

For example, when a target gene or nucleic acid is edited or corrected using a gRNA-CRISPR enzyme complex, that is, a CRISPR complex, and a donor, the target gene or nucleic acid may be cleaved using the CRISPR complex. The damaged target gene or nucleic acid may be restored with HDR using the CRISPR complex. Here, the donor includes a specific nucleic acid or gene, and the specific nucleic acid or gene may be inserted into a damaged gene or chromosome using the donor. Here, the specific nucleic acid or gene inserted may induce expression of a protein.

As an embodiment disclosed by the present specification, the gRNA-CRISPR enzyme complex may artificially manipulate or modify PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The gRNA-CRISPR enzyme complex may specifically recognize the target sequence of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be specifically recognized by the gRNA of the gRNA-CRISPR enzyme complex, and thereby locating the gRNA-CRISPR enzyme complex close to the recognized target sequence.

The target sequence may be a region or an area where an artificial modification is made to PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence located in the promoter region of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence located in the intron region of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence located in the exon region of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence located in the enhancer region of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence located in the 3'-UTR region of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence located in the 5'-UTR region of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The target sequence may be a continuous 10 bp to 25 bp nucleotide sequence region adjacent to the 5' end and/or 3' end of a proto-spacer-adjacent motif (PAM) sequence in the nucleotide sequence of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

Here, the PAM sequence may be, for example, one or more of the following sequences (described in the 5' to 3' direction)

(N is A, T, C or G);

NNNNRYAC (N is each independently A, T, C or G, R is A or G, Y is C or T);

NNAGAAW (N is each independently A, T, C or G, W is A or T);

NNNNGATT (N is each independently A, T, C or G);

NNGRR(T) (N is each independently A, T, C or G, R is A or G, Y is C or T); and

TTN (N is A, T, C or G).

In an embodiment, the target sequence may be one or more nucleotide sequence selected from the nucleotide sequences described in table 1.

The gRNA-CRISPR enzyme complex may be formed with gRNA and CRISPR enzyme.

The gRNA may include a guide domain capable of forming a partially or perfectly complementary bond with the guide nucleic acid binding sequence in the target sequence of PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The guide domain may be a nucleotide sequence complementary to the guide nucleic acid binding sequence, which has, for example, at least 70%, 75%, 80%, 85%, 90%, or 95% or more complementarity or complete complementarity.

The guide domain may include a nucleotide sequence complementary to the guide nucleic acid binding sequence in the target sequence of PD-1 gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of CTLA-4 gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of A20 gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of DGKA gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of DGKZ gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of FAS gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of EGR2 gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of PPP2r2d gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of TET2 gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of PSGL-1 gene. Here, the complementary nucleotide sequence may include 0 to 5, 0 to 4, 0 to 3, or 0 to 2 mismatching.

The guide domain may include a nucleotide sequence complementary to the guide nucleic acid binding sequence in the target sequence of KDM6A gene. Here, the complementary nucleotide sequence may include 0 to 5, 0 to 4, 0 to 3, or 0 to 2 mismatching.

The gRNA may include one or more domains selected from the group consisting of a first complementary domain, a linking domain, a second complementary domain, a proximal domain and a tail domain.

The CRISPR enzyme may be one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein. In one example, The editor protein may be a *Campylobacter jejuni*-derived Cas9 protein or a *Streptococcus aureus*-derived Cas9 protein.

The gRNA-CRISPR enzyme complex, according to the type of the gRNA and the CRISPR enzyme, may artificially manipulate or modify PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

In one example, when the CRISPR enzyme is a SpCas9 protein, one or more modifications of the following may be included in a continuous 1 bp to 50 bp, 1 bp to 40 bp, 1 bp to 30 bp, and preferably 1 bp to 25 bp nucleotide sequence region located adjacent to the 5' end and/or 3' end of the 5'-NGG-3' (N is A, T, G, or C) PAM sequence which is present in the target region of the artificially manipulated or modified PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene:

i) deletion of one or more nucleotides ii) substitution of one or more nucleotides into nucleotides different from the wild type gene iii) insertion of one or more nucleotides, or iv) combination of two or more selections from the above i) to iii).

In an another example, when the CRISPR enzyme is a CjCas9 protein, one or more modifications of the following may be included in a continuous 1 bp to 50 bp, 1 bp to 40 bp, 1 bp to 30 bp, and preferably 1 bp to 25 bp nucleotide sequence region located adjacent to the 5' end and/or 3' end of the 5'-NNNNRYAC-3' (N is each independently A, T, G, or C, R is A or G, and Y is C or T) PAM sequence which is present in the target region of the artificially manipulated or modified PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene:

i) deletion of one or more nucleotides ii) substitution of one or more nucleotides into nucleotides different from the wild type gene iii) insertion of one or more nucleotides, or iv) combination of two or more selections from the above i) to iii).

In yet another example, when the CRISPR enzyme is a StCas9 protein, one or more modifications of the following may be included in a continuous 1 bp to 50 bp, 1 bp to 40 bp, 1 bp to 30 bp, and preferably 1 bp to 25 bp nucleotide sequence region located adjacent to the 5' end and/or 3' end of the 5'-NNAGAAW-3' (N is each independently A, T, G, or C, and W is A or T) PAM sequence which is present in the target region of the artificially manipulated or modified PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene:

i) deletion of one or more nucleotides ii) substitution of one or more nucleotides into nucleotides different from the wild type gene iii) insertion of one or more nucleotides, or iv) combination of two or more selections from the above i) to iii).

In one example, when the CRISPR enzyme is a NmCas9 protein, one or more modifications of the following may be included in a continuous 1 bp to 50 bp, 1 bp to 40 bp, 1 bp to 30 bp, and preferably 1 bp to 25 bp nucleotide sequence region located adjacent to the 5' end and/or 3' end of the 5'-NNNNGATT-3' (N is each independently A, T, G, or C) PAM sequence which is present in the target region of the artificially manipulated or modified PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene:

i) deletion of one or more nucleotides ii) substitution of one or more nucleotides into nucleotides different from the wild type gene iii) insertion of one or more nucleotides, or iv) combination of two or more selections from the above i) to iii).

In another example, when the CRISPR enzyme is a SaCas9 protein, one or more modifications of the following may be included in a continuous 1 bp to 50 bp, 1 bp to 40 bp, 1 bp to 30 bp, and preferably 1 bp to 25 bp nucleotide sequence region located adjacent to the 5' end and/or 3' end of the 5'-NNGRR(T)-3' (N is each independently A, T, G, or C, R is A or G, and (T) is any sequence that can be optionally included) PAM sequence which is present in the target region of the artificially manipulated or modified PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene:

i) deletion of one or more nucleotides ii) substitution of one or more nucleotides into nucleotides different from the wild type gene iii) insertion of one or more nucleotides, or iv) combination of two or more selections from the above i) to iii).

In yet another example, when the CRISPR enzyme is a Cpf1 protein, one or more modifications of the following may be included in a continuous 1 bp to 50 bp, 1 bp to 40 bp, 1 bp to 30 bp, and preferably 1 bp to 25 bp nucleotide sequence region located adjacent to the 5' end and/or 3' end of the 5'-TTN-3' (N is each independently A, T, G, or C) PAM sequence which is present in the target region of the artificially manipulated or modified PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene:

i) deletion of one or more nucleotides ii) substitution of one or more nucleotides into nucleotides different from the wild type gene iii) insertion of one or more nucleotides, or iv) combination of two or more selections from the above i) to iii).

The effect of artificially manipulating PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene by the gRNA-CRISPR enzyme complex may be knockout.

The effect of artificially manipulating PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene by the gRNA-CRISPR enzyme complex may inhibit expression of proteins encoded by PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

The effect of artificially manipulating PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene by the gRNA-CRISPR enzyme complex may be knockdown.

The effect of artificially manipulating PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene by the gRNA-CRISPR enzyme complex may reduce expression of proteins encoded by PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene, respectively.

The effect of artificially manipulating PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene by the gRNA-CRISPR enzyme complex may be knockin.

Here, the knockin effect may be induced by the gRNA-CRISPR enzyme complex and additionally, by a donor including a foreign nucleotide sequence or gene.

The effect of artificially manipulating PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene by the gRNA-CRISPR enzyme complex may express peptides or proteins encoded by a foreign nucleotide sequence or gene.

One aspect disclosed by the present specification relates to manipulated immune cell.

"Immune cell" is a cell involved in immune responses, and it includes all cells that are directly or indirectly involved in the immune response and the pre-differentiated cells thereof.

Immune cells may have the function of cytokine secretion, differentiation into other immune cells, and cytotoxicity. Immune cells also include cells that have undergone mutations from the natural state.

The immune cells differentiate from hematopoietic stem cells in the bone marrow and they largely include lymphoid progenitor cells and myeloid progenitor cells; and also include all of T cells and B cells in which lymphoid progenitor cells differentiate and are responsible for acquired immunity; and macrophages, eosinophils, neutrophils, basophils, megakaryocytes, erythrocytes, etc. differentiated from myeloid progenitor cells.

Specifically, the cells may be at least one selected from the group consisting of T cells, for example, CD8+ T cells (e.g., CD8+ naive T cells, CD8+ effector T cells, central memory T cells, or effector memory T cells), CD4+ T cells, natural killer T cells (NKT cells), regulatory T cells (Treg), stem cell memory T cells, lymphoid progenitor cells, hematopoietic stem cells, natural killer cells (NK cells), dendritic cells, cytokine induced killer cells (CIK), peripheral blood mononuclear cells (PBMC), monocytes, macrophages, natural killer T (NKT) cells, etc.

The "manipulated immune cell" means an immune cell that has been subjected to an artificial manipulation, not in a natural state. Recently, techniques for enhancing immunity by extracting immune cells from the body and applying artificial manipulation have been actively studied. Such manipulated immune cell has been shown to be a new therapeutic method because of the excellent immune efficacy against certain diseases. In particular, studies on manipulated immune cells have been actively performed in connection with cancer treatment.

The manipulated immune cell may be an immune cell artificially manipulated or modified by the composition for immune cell manipulation. Here, the term "composition for immune cell manipulation" refers to one or more materials, such as DNA, RNA, nucleic acid, protein, virus, composition that are used to artificially modify or manipulate immune cells, and for example, the composition for immune cell manipulation may include a portion of or the entire composition for gene manipulation, and may also include a nucleic acid encoding an exogenous protein for expressing the exogenous protein.

The manipulated immune cell may be an immune cell produced by gene manipulation.

Here, the gene manipulation may be performed considering the regulatory process of gene expression.

In one example, the gene manipulation may be performed in steps of transcriptional regulation, RNA processing regulation, RNA transport regulation, RNA degradation regulation, translation regulation or protein modification regulation, by selecting a manipulation means suitable for each step For example, the gene manipulation may control the expression of gene information by preventing mRNA using RNA interference (RNAi) or RNA silencing, and in some cases, by destroying so as to prevent the delivery of the information of protein synthesis during the intermediate step.

In another example, the gene manipulation may use a wild-type or variant enzyme capable of catalyzing the hydrolysis (cleavage) of DNA or RNA molecules, preferably bonds between nucleic acids in a DNA molecule. A guide nucleic acid-editor protein complex may be used.

For example, the gene manipulation may control the expression of gene information by manipulating genes using one or more nuclease selected from the group consisting of meganuclease, zinc finger nuclease, CRISPR/Cas9 (Cas9 protein), CRISPR-Cpf1 (Cpf1 protein) and TALE-nuclease.

In a preferred example, without limitation, the gene manipulation may be performed by a guide nucleic acid-editor protein complex, and the explanation on the above guide nucleic acid-editor protein is as described above.

Additionally, the manipulated immune cell may be an immune cell with function modified due to the lost or damaged function of a specific protein.

Here, the function of the specific protein may be lost or damaged by a compound.

The compound may bind with a specific protein and hinder the function of the immune regulatory factor.

Additionally, the compound may bind with a specific protein and modify the structure of the immune regulatory factor, thereby hindering the normal function thereof.

Alternatively, the function of the specific protein may be lost or damaged by modification of the protein binding with a specific protein.

A manipulated immune cell may be a functionally manipulated immune cell or a hybrid manipulated immune cell.

As an embodiment disclosed by the present invention, the manipulated immune cell may be a functionally manipulated immune cell.

The term "functionally manipulated immune cell" refers to an immune cell, in which the natural expression of a wild type immune regulatory factor has been modified or artificially manipulated to damage the function of the immune regulating factor.

The term "immune regulatory factor" refers to a polypeptide or a protein encoded by the immunity regulating gene, and may be also referred to as an immune regulatory protein transcripted, translated and expressed by the immunity regulating gene.

The functionally manipulated immune cell may be an immune cell manipulated to suppress or inhibit the expression of the immune regulatory factor.

Here, the functionally manipulated immune cell may be an immune cell in which the immunity regulating gene is manipulated to suppress or inhibit the expression of the immune regulatory factor.

The functionally manipulated immune cell may be one in which the immune cell activity regulatory gene is manipulated.

Here, the functionally manipulated immune cell may be one in which one or more genes selected from SHP-1, PD-1, CTLA-4, CBLB, ILT-2, KIR2DL4, and PSGL-1 are inactivated.

The functionally manipulated immune cell may be one in which immune cell growth regulatory gene is manipulated.

Here, the functionally manipulated immune cell may be one in which one or more genes selected from DGK-alpha, DGK-zeta, FAS, EGR2, EGR3, PPP2r2d, and A20 are inactivated. In a preferred embodiment, one or more genes selected from DGK-alpha, DGK-zeta, EGR2, PPP2r2d, and A20 are inactivated.

The functionally manipulated immune cell may be one in which immune cell death regulatory gene is manipulated.

Here, the functionally manipulated immune cell may be an immune cell in which one or more genes selected from DAXX, BIM, BID, BAD, PD-1, and CTLA-4 are inactivated.

Additionally, the functionally manipulated immune cell may be an immune cell in which an element that induces self-death is inserted.

The functionally manipulated immune cell may be an immune cell in which immune cell exhaustion regulating element is manipulated.

Here, the functionally manipulated immune cell may be an immune cell in which one or more genes selected from TET2, WNT and AKT are inactivated.

The functionally manipulated immune cell may be one in which cytokine secretion element is manipulated.

The functionally manipulated immune cell may be one in which an antigen binding regulatory element is manipulated.

Here, the functionally manipulated immune cell may be an immune cell in which one or more genes selected from dCK, CD52, B2M, and MHC are inactivated.

The functionally manipulated immune cell may be one in which an immunity regulating gene different from the aforementioned genes is manipulated.

The functionally manipulated immune cell may be one in which one or more immunity regulating genes are simultaneously manipulated. Here, one or more kinds of immunity regulating genes may be manipulated.

Here, when manipulating one immunity regulating gene, a novel immune efficacy is not necessarily exhibited. The manipulation of one immunity regulating gene may cause or inhibit a variety of new immune efficacy.

The functionally manipulated immune cell may be an immune cell in which, in addition to an immunity regulating gene, a gene encoding wild type receptors is manipulated.

Here, the wild type receptor may be a T cell receptor (TCR).

The functionally manipulated immune cell may be one in which the wild type receptors are absent or present at a lower rate on the surface.

The functionally manipulated immune cell may be one in which the wild type receptors are present at a greater proportion on the surface.

The functionally manipulated immune cell may be one in which the wild type receptors have an enhanced recognition ability for specific antigens.

The functionally manipulated immune cell may have new immunological efficacies by manipulating the wild type receptors and immunity regulating genes.

The new immune efficacy may be one in which the ability to recognize a specific antigen is regulated.

The new immune efficacy may be one in which the ability to recognize a specific antigen is improved.

In particular, the specific antigen may be an antigen of disease, for example, an antigen of cancer cells.

The new immune efficacy may be one in which the ability to recognize a specific antigen is deteriorated.

The new immune efficacy may be one in which the new immune efficacy is improved.

The new immune efficacy may be one in which the growth of immune cells is regulated. In particular, the immune efficacy may be one in which the growth and differentiation are promoted or delayed.

The new immune efficacy may be one in which the death of immune cells is regulated. In particular, the immune efficacy may be to prevent the death of immune cells. Additionally, the immune efficacy may be to cause the immune cells to kill themselves when appropriate time has elapsed.

The new immune efficacy may be one in which the loss of functions of immune cells is alleviated.

The new immune efficacy may be one in which the cytokine secretion of immune cells is regulated. In particular, the immune efficacy may be to promote or inhibit the secretion of cytokines.

The new immune efficacy may be to regulate the antigen binding ability of wild-type receptors in an immune cell. In particular, the immune efficacy may be to improve the specificity of wild-type receptors for specific antigens.

Additionally, the functionally manipulated immune cell may be an immune cell manipulated such that the function of the immune regulatory factor is damaged.

Here, the function of the immune regulatory factor may be lost or damaged by a compound.

The compound may bind with a immune regulatory factor or a specific protein interacting with the immune regulatory factor and hinder the function of the immune regulatory factor.

Additionally, the compound may bind with a immune regulatory factor and artificially modify the three-dimensional structure of the immune regulatory factor, thereby hindering the normal function thereof.

Alternatively, the function of the immune regulatory factor may be lost or damaged by modification of the protein interacting with the immune regulatory factor.

As an embodiment disclosed by the present specification, the manipulated immune cell may be a functionally manipulated immune cell in which an immunity regulating gene is artificially manipulated.

Here, the immunity regulating gene may be PD-1 gene, CTLA-4 gene, DGKA gene DGKZ gene, FAS gene, EGR2 gene, PPP2r2d gene, TET2 gene, PSGL-1 gene, A20 gene, and/or KDM6A gene.

The functionally manipulated immune cell may be manipulated by the composition for gene manipulation.

The explanation on the above composition for gene manipulation is as described above.

The functionally manipulated immune cell may include one or more artificially manipulated or modified immunity regulating gene.

Here, the artificially modified immunity regulating gene may include one or more modifications of the following in the target sequence or in a 1 bp to 50 bp nucleotide sequence region located adjacent to the 5' end and/or 3' end of the target sequence:

i) deletion of one or more nucleotides ii) substitution of one or more nucleotides into nucleotides different from the wild type gene iii) insertion of one or more nucleotides, or iv) combination of two or more selections from the above i) to iii).

In one example, the functionally manipulated immune cell may include one or more artificially manipulated or modified immunity regulating gene.

Here, the artificially manipulated or modified immunity regulating gene may include one or more nucleotides deleted in the target sequence or in a 1 bp to 50 bp nucleotide sequence region adjacent to the 5' end and/or 3' end of the target sequence.

For example, the artificially manipulated or modified immunity regulating gene may include one or more nucleotides deleted in the nucleotide sequence region located in the target sequence.

Figure 1:
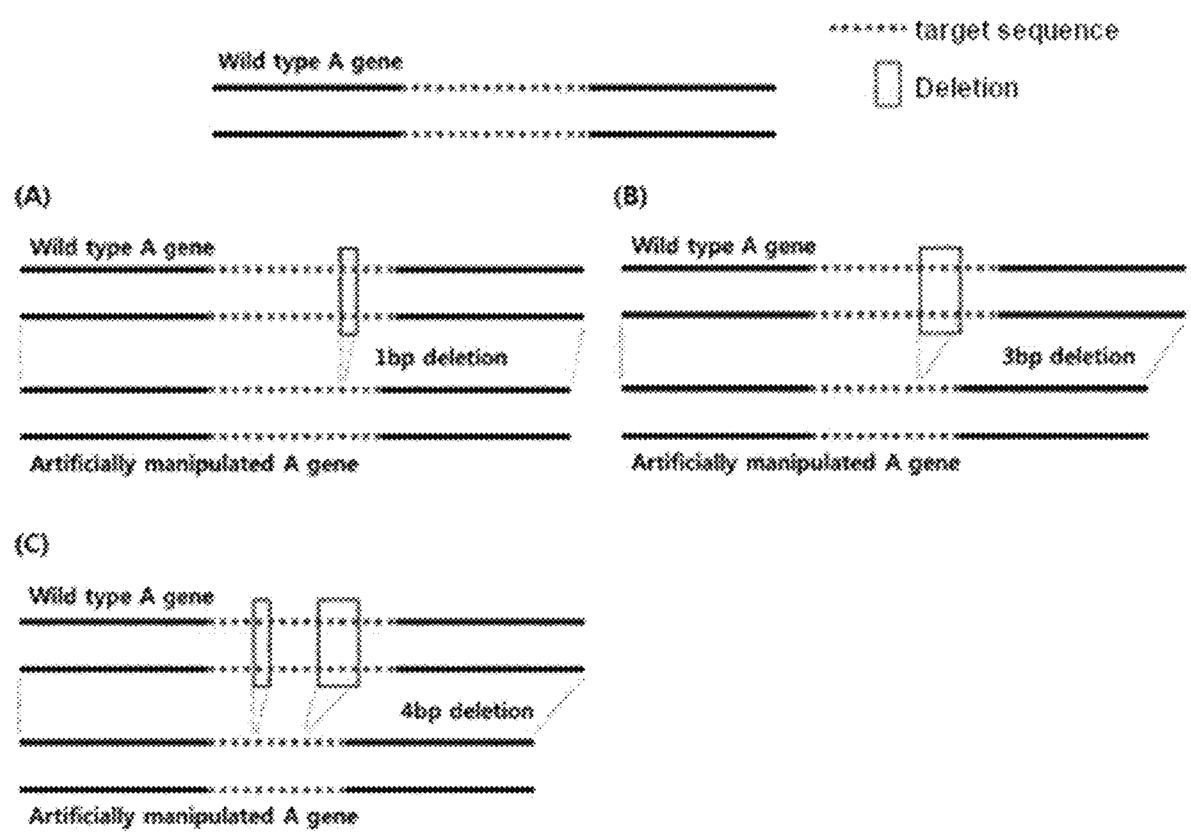
FIGS. 1, 2, 3, 4, 5, 6, 7, 8, 9, 10, 11, 12, 13, 14, 15, 16, 17, 18, 19, 20, 21, 22, 23, 24, 25, 26 and 27 illustrate examples of artificially modified or manipulated target genes.

Here, the deleted nucleotides may be 1 bp to 50 bp nucleotides in which continuous, discontinuous, or both forms (that is, continuous and discontinuous) are mixed. For example, the deleted nucleotide may be a 1 bp nucleotide located in the target sequence. Alternatively, the deleted nucleotide may be a 1 bp nucleotide located in the target sequence. Alternatively, the deleted nucleotide may be a continuous 3 bp nucleotide. Alternatively, the deleted nucleotide may be discontinuous 4 bp nucleotides located in the target sequence, in which the discontinuous 4 bp nucleotides may be a 1 bp nucleotide and continuous 3 bp nucleotides, or continuous 2 bp nucleotides and another continuous 2 bp nucleotides (FIG. 1). For example, the deleted nucleotide may be discontinuous 30 bp nucleotides located in the target sequence, in which the discontinuous 30 bp nucleotides may be continuous 25 bp nucleotides, continuous 4 bp nucleotides and a discontinuous 1 bp nucleotide.

Figure 2:
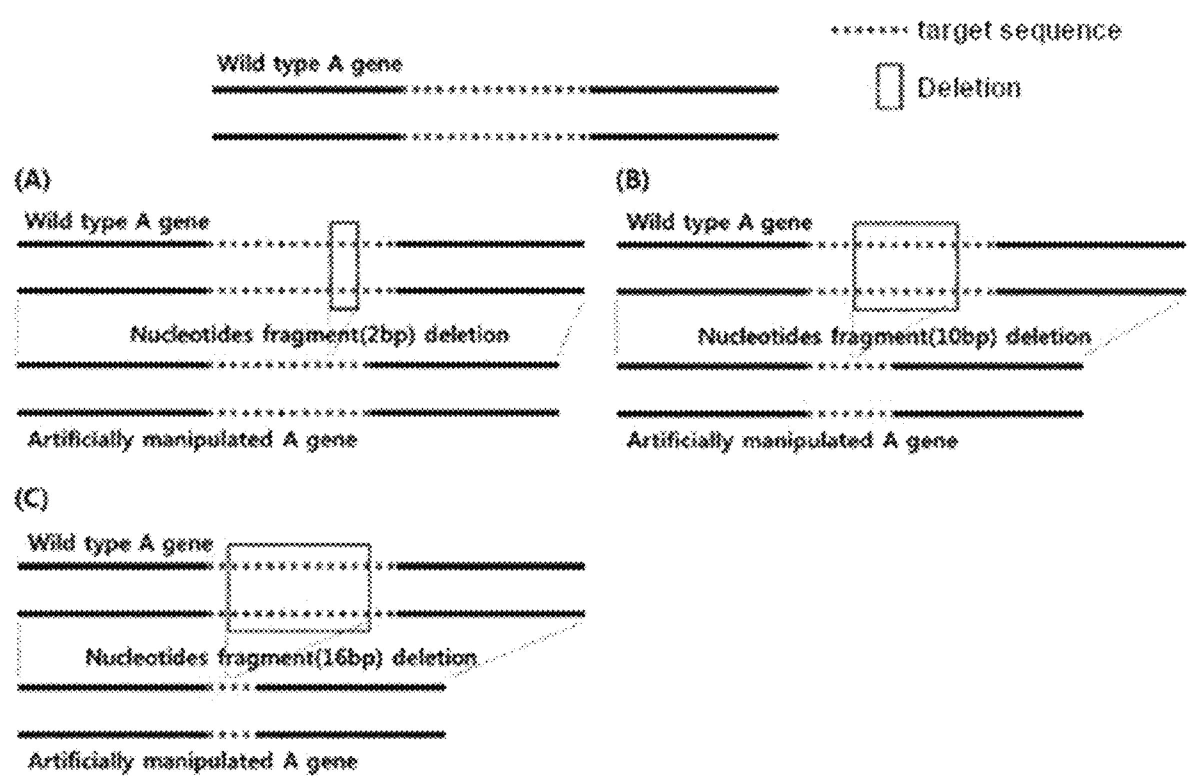

Alternatively here, the deleted nucleotide may be a nucleotide fragment including 2 bp or more of nucleotides. The nucleotide fragment may be, 2 bp to 5 bp, 6 bp to 10 bp, 11 bp to 15 bp, 16 bp to 20 bp, 21 bp to 25 bp, 26 bp to 30 bp, 31 bp to 35 bp, 36 bp to 40 bp, 41 bp to 45 bp, or 46 bp to 50 bp. For example, the deleted nucleotide may be a 2 bp nucleotide fragment located in the target sequence. Alternatively, the deleted nucleotide may be a 10 bp nucleotide fragment located in the target sequence. Alternatively, the deleted nucleotide may be a 16 bp nucleotide fragment located in the target sequence (FIG. 2).

Figure 3:
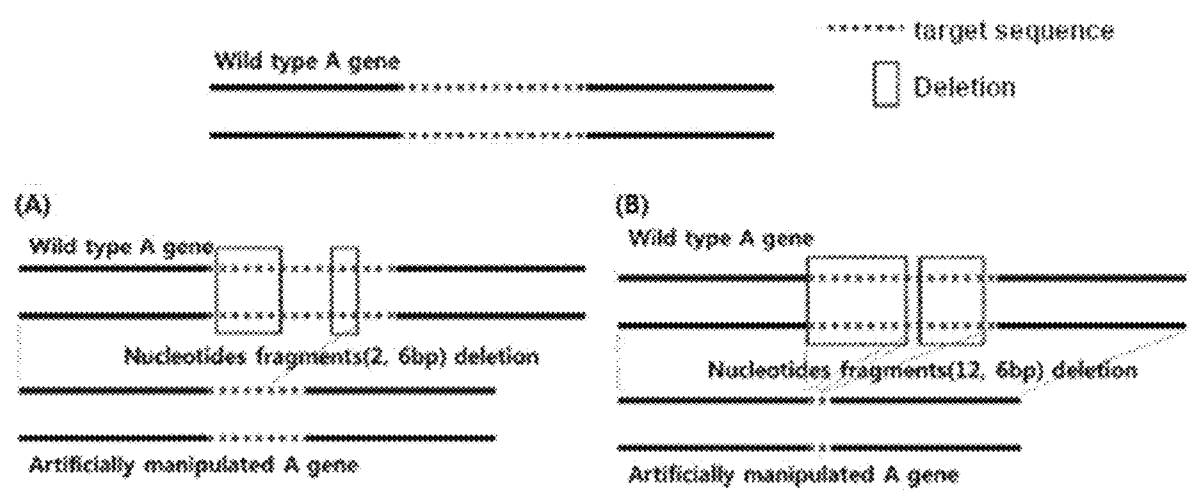

Alternatively here, the deleted nucleotide may be a nucleotide fragment including 2 bp or more of nucleotides. Here, the nucleotide fragment including 2 bp or more of nucleotides may be individual nucleotide fragments having discontinuous nucleotide sequences, that is, having one or more nucleotide sequence gaps, and two or more deletion region may be produced by the two or more deleted nucleotide fragments. For example, the deleted nucleotides may be a 2 bp nucleotide fragment and a 6 bp nucleotide fragment located in the target sequence. Alternatively, the deleted nucleotides may be a 12 bp nucleotide fragment and a 6 bp nucleotide fragment located in the target sequence (FIG. 3).

In another example, the artificially manipulated or modified immunity regulating gene may include one or more nucleotides deleted in a 1 bp to 50 bp nucleotide sequence region adjacent to the 5' end and/or 3' end of the target sequence.

Figure 4:
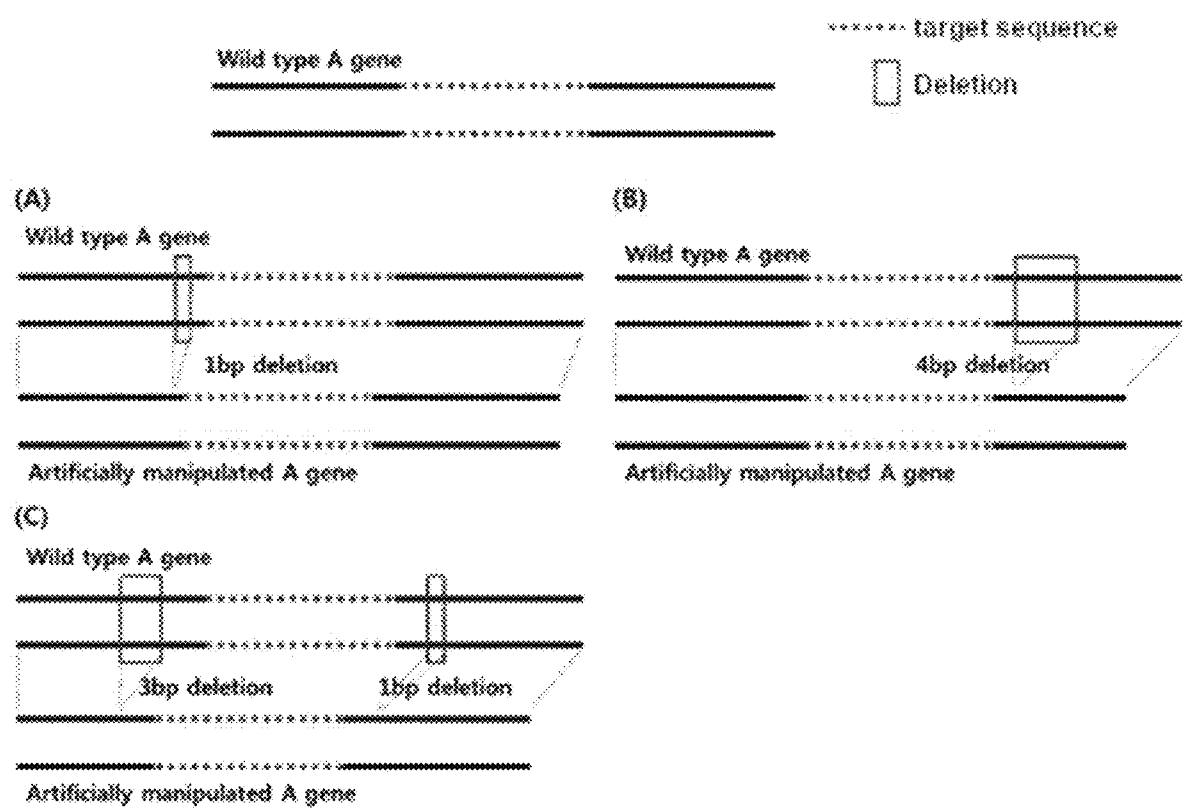

Here, the deleted nucleotides may be 1 bp to 50 bp nucleotides in which continuous, discontinuous, or both forms (that is, continuous and discontinuous) are mixed. For example, the deleted nucleotide may be a 1 bp nucleotide located in the target sequence. Alternatively, the deleted nucleotide may be continuous 4 bp nucleotides located adjacent to the 3' end of the target sequence. Alternatively, the deleted nucleotide may be discontinuous 4 bp nucleotides located adjacent to the 5' end and/or 3' end of the target sequence, in which the discontinuous 4 bp nucleotides may be continuous 3 bp nucleotides located adjacent to the 5' end of the target sequence, and a 1 bp nucleotide located adjacent to the 3' end of the target sequence (FIG. 4). For example, the deleted nucleotide may be discontinuous 25 bp nucleotides located in the target sequence, in which the discontinuous 25 bp nucleotides may be continuous 15 bp nucleotides, continuous 8 bp nucleotides, a discontinuous 1 bp nucleotide and a discontinuous 1 bp nucleotide.

Figure 5:
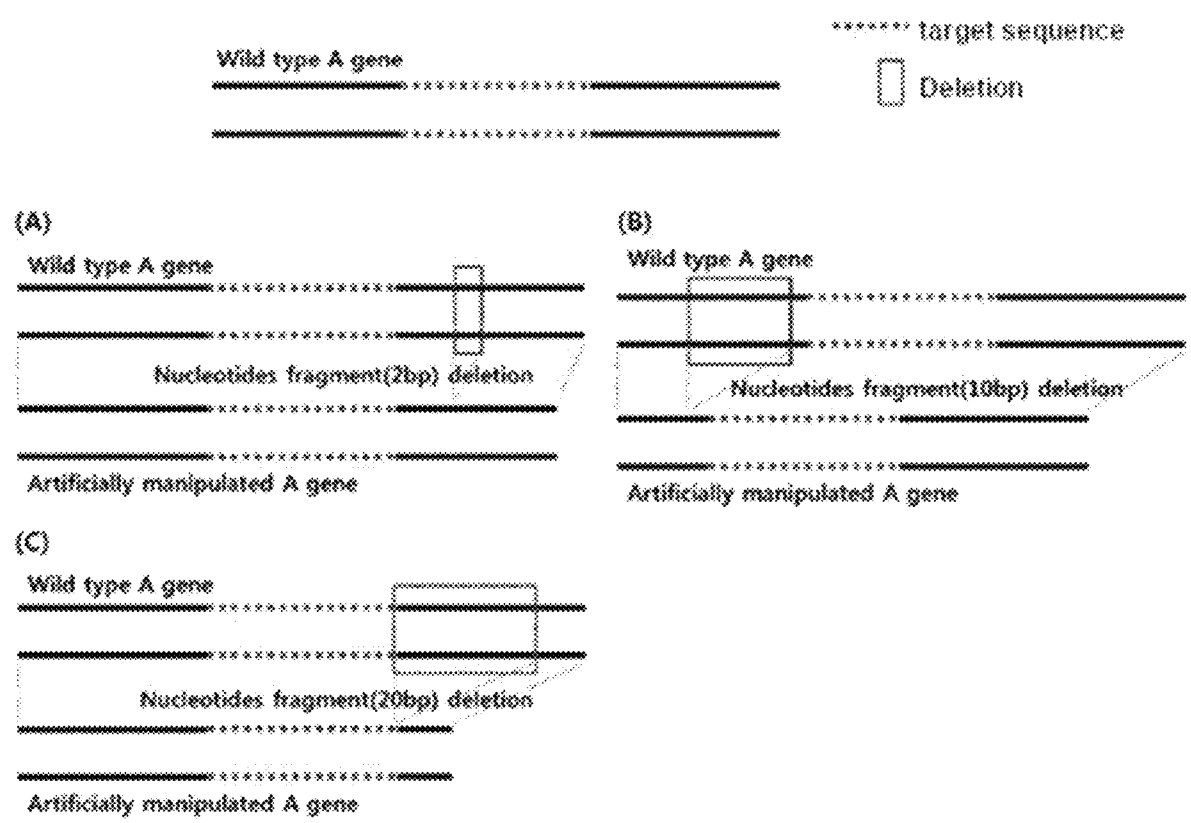

Alternatively here, the deleted nucleotide may be a nucleotide fragment including continuous 2 bp or more nucleotides. The nucleotide fragment may be, 2 bp to 5 bp, 6 bp to 10 bp, 11 bp to 15 bp, 16 bp to 20 bp, 21 bp to 25 bp, 26 bp to 30 bp, 31 bp to 35 bp, 36 bp to 40 bp, 41 bp to 45 bp, or 46 bp to 50 bp. For example, the deleted nucleotide may be a 2 bp nucleotide fragment located adjacent to the 3' end of the target sequence. Alternatively, the deleted nucleotide may be a 10 bp nucleotide fragment located adjacent to the 5' end of the target sequence. Alternatively, the deleted nucleotide may be a 20 bp nucleotide fragment located adjacent to the 3' end of the target sequence (FIG. 5).

Figure 6:
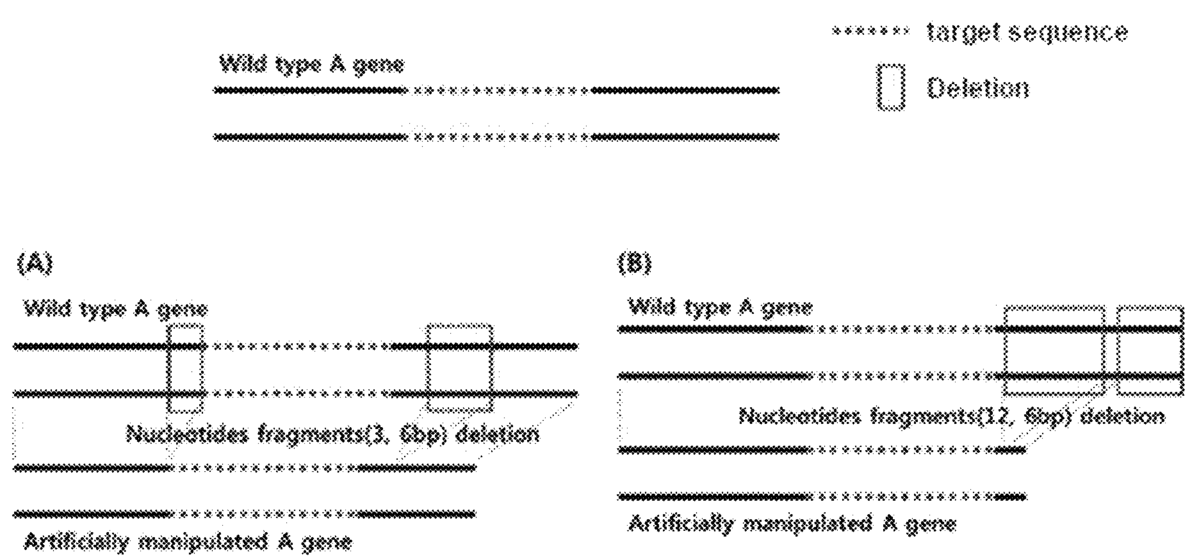

Alternatively here, the deleted nucleotide may be a nucleotide fragment including 2 bp or more nucleotides. Here, the nucleotide fragment including 2 bp or more nucleotides may be individual nucleotide fragments having discontinuous nucleotide sequences, that is, having one or more nucleotide sequence gaps, and two or more deletion region may be produced with the two or more deleted nucleotide fragments. For example, the deleted nucleotides may be a 3 bp nucleotide fragment located adjacent to the 5' end of the target sequence and a 6 bp nucleotide fragment located adjacent to the 3' end of the target sequence. Alternatively, the deleted nucleotides may be a 12 bp nucleotide fragment and a 6 bp nucleotide fragment located adjacent to the 3' end of the target sequence (FIG. 6).

In still another example, the artificially manipulated or modified immunity regulating gene may include one or more nucleotides deleted in the target sequence and in a 1 bp to 50 bp nucleotide sequence region located adjacent to the 5' end and/or 3' end of the target sequence.

Figure 7:
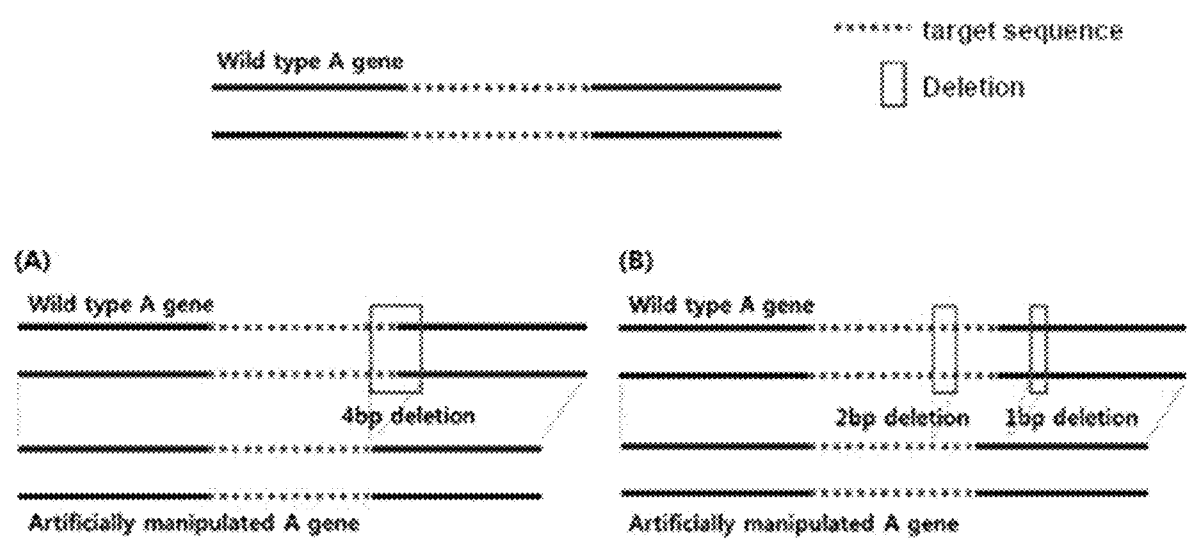

Here, the deleted nucleotides may be 1 bp to 50 bp nucleotides in which continuous, discontinuous, or both forms (that is, continuous and discontinuous) are mixed. For example, the deleted nucleotide may be continuous 4 bp nucleotides located in the target sequence and adjacent to the 3' end of the target sequence. Alternatively, the deleted nucleotide may be discontinuous 3 bp nucleotides located in the target sequence and adjacent to the 3' end of the target sequence, and the discontinuous 3 bp nucleotides may be continuous 2 bp nucleotides located in the target sequence and a 1 bp nucleotide located adjacent to the 3' end of the target sequence (FIG. 7). For example, the deleted nucleotide may be discontinuous 40 bp nucleotides located in the target sequence, and the discontinuous 25 bp nucleotides may be continuous 10 bp nucleotides, continuous 8 bp nucleotides, and discontinuous 5 bp (discontinuous 1 bp, 1 bp, 1 bp, 1 bp, and 1 bp) nucleotides.

Figure 8:
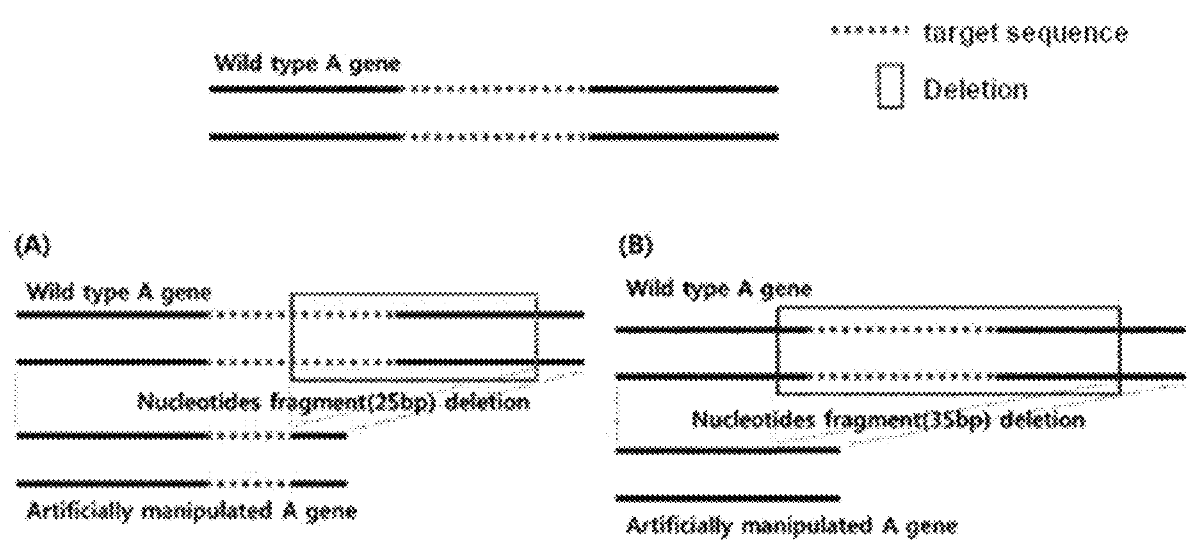

Alternatively here, the deleted nucleotide may be a nucleotide fragment including 2 bp or more nucleotides. The nucleotide fragment may be, 2 bp to 5 bp, 6 bp to 10 bp, 11 bp to 15 bp, 16 bp to 20 bp, 21 bp to 25 bp, 26 bp to 30 bp, 31 bp to 35 bp, 36 bp to 40 bp, 41 bp to 45 bp, or 46 bp to 50 bp. For example, the deleted nucleotides may be a 25 bp nucleotide fragment located in the target sequence and adjacent to the 3' end of the target sequence. Alternatively, the deleted nucleotides may be a 35 bp nucleotide fragment located in the target sequence, and adjacent to the 5' end and the 3' end of the target sequence (FIG. 8).

Figure 9:
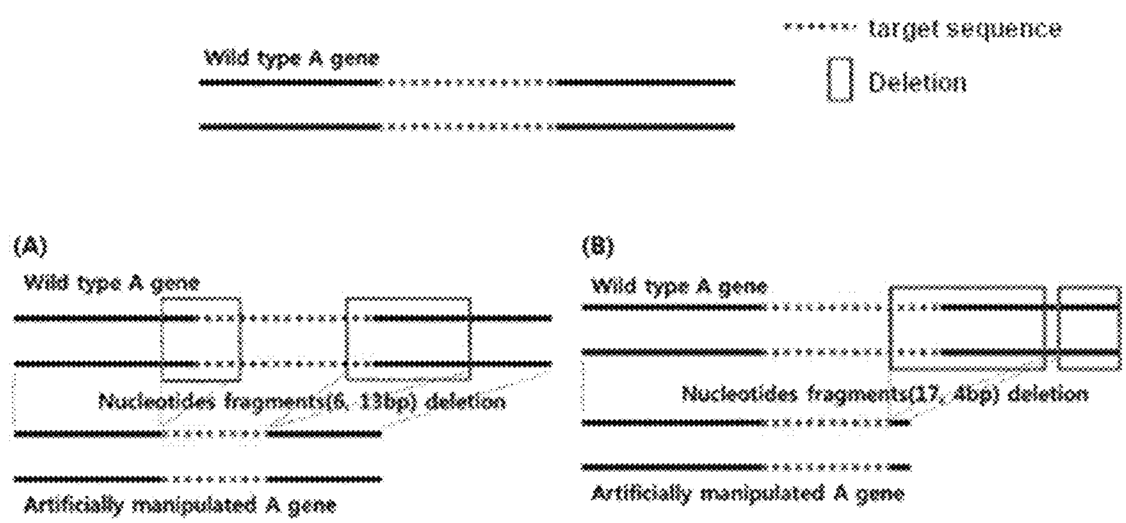

Alternatively here, the deleted nucleotide may be two or more nucleotide fragments. Here, the two or more nucleotide fragments may be individual nucleotide fragments having discontinuous nucleotide sequences, that is, having one or more nucleotide sequence gaps, and two or more deletion region may be produced with the two or more deleted nucleotide fragments. For example, the deleted nucleotides may be a 6 bp nucleotide fragment located in the target sequence and adjacent to the 5' end of the target sequence and a 13 bp nucleotide fragment located in the target sequence and adjacent to the 3' end of the target sequence. Alternatively, the deleted nucleotides may be a 17 bp nucleotide fragment in the target sequence and adjacent to the 3' end of the target sequence and a 4 bp nucleotide fragment located adjacent to the 3' end of the target sequence (FIG. 9).

In another example, the functionally manipulated immune cell may include one or more artificially manipulated or modified immunity regulating gene.

Here, the artificially manipulated or modified immunity regulating gene may include one or more nucleotides inserted in the target sequence or in a 1 bp to 50 bp nucleotide sequence region located adjacent to the 5' end and/or 3' end of the target sequence.

For example, the artificially manipulated or modified immunity regulating gene may include one or more nucleotides inserted in the nucleotide sequence region lactated in the target sequence.

Figure 10:
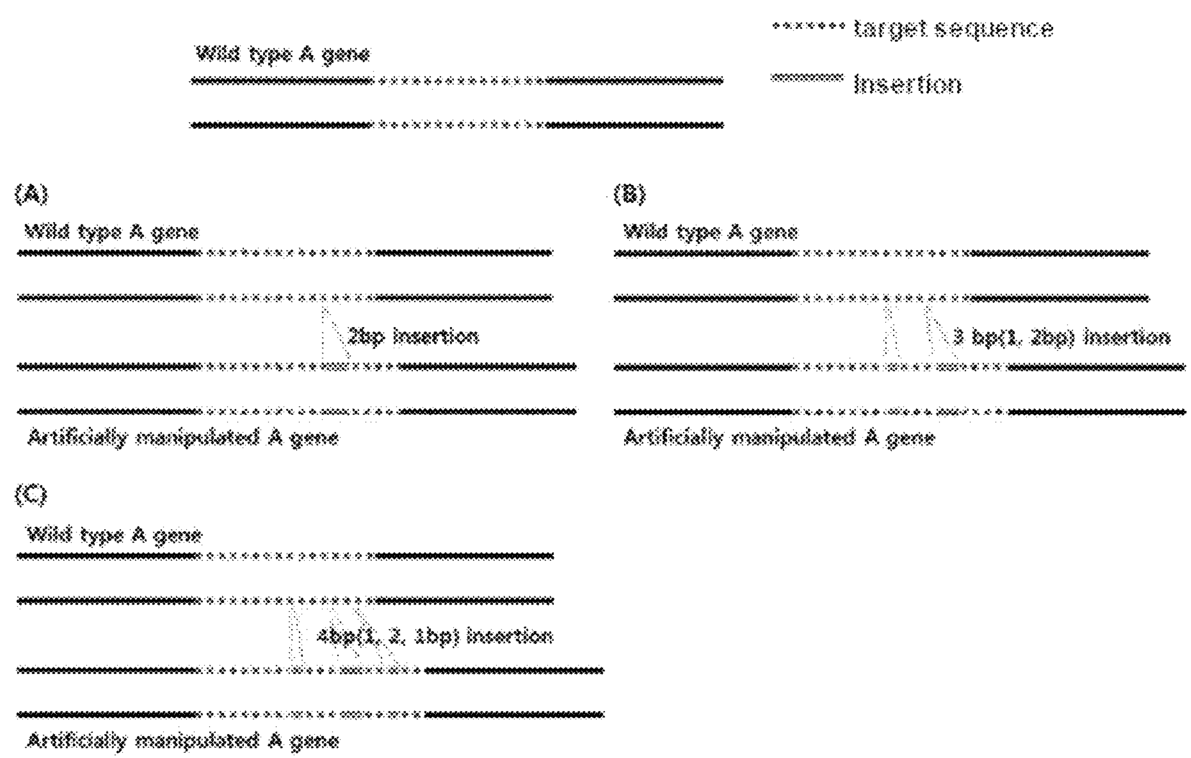

Here, the inserted nucleotides may be 1 bp to 50 bp nucleotides in which continuous, discontinuous, or both forms (that is, continuous and discontinuous) are mixed. For example, the inserted nucleotide may be continuous 2 bp nucleotides inserted in the nucleotide sequence region in the target sequence. Alternatively, the inserted nucleotide may be discontinuous 3 bp nucleotides inserted in the nucleotide sequence region in the target sequence, and the discontinuous 3 bp nucleotides may be a 1 bp nucleotide and continuous 2 bp nucleotides. Alternatively, the inserted nucleotide may be discontinuous 4 bp nucleotides inserted in the nucleotide sequence region in the target sequence, and the discontinuous 4 bp nucleotides may be a 1 bp nucleotide, continuous 2 bp nucleotides and another 1 bp nucleotide (FIG. 10). For example, the inserted nucleotide may be discontinuous 30 bp nucleotides inserted in the nucleotide sequence region in the target sequence, and the discontinuous 30 bp nucleotides may be continuous 15 bp nucleotides, continuous 12 bp nucleotides, and discontinuous 3 bp (discontinuous 1 bp, 1 bp, and 1 bp) nucleotides.

Figure 11:
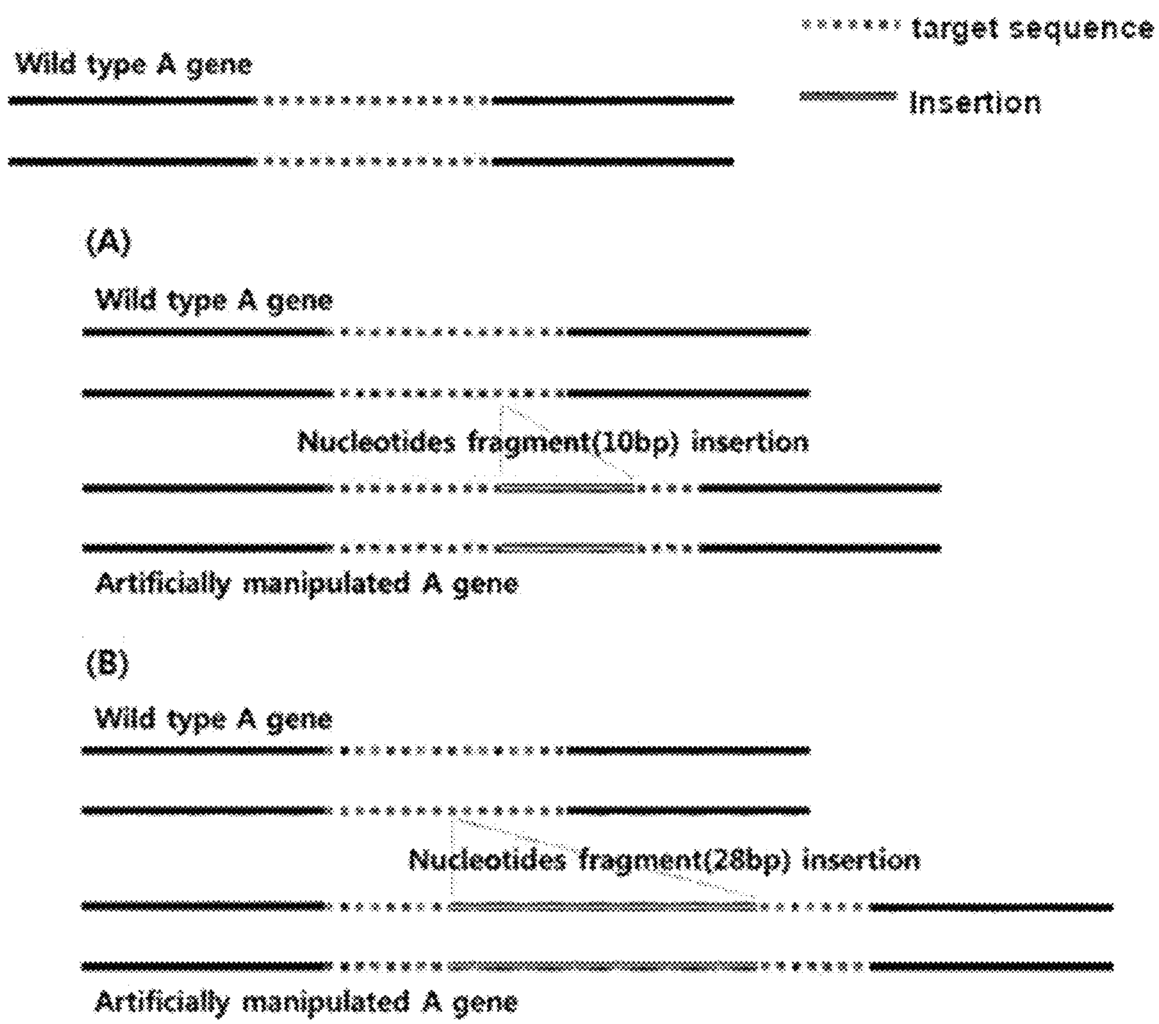

Alternatively here, the inserted nucleotide may be a nucleotide fragment including continuous 5 bp or more nucleotides. The nucleotide fragment may be 5 bp to 10 bp, 11 bp to 50 bp, 50 bp to 100 bp, 100 bp to 200 bp, 200 bp to 300 bp, 300 bp to 400 bp, 400 bp to 500 bp, 500 bp to 750 bp, or 750 bp to 1000 bp. For example, the inserted nucleotide may be a 10 bp nucleotide fragment inserted in the nucleotide sequence region in the target sequence. Alternatively, the inserted nucleotide may be a 28 bp nucleotide fragment inserted in the nucleotide sequence region in the target sequence (FIG. 11).

Figure 12:
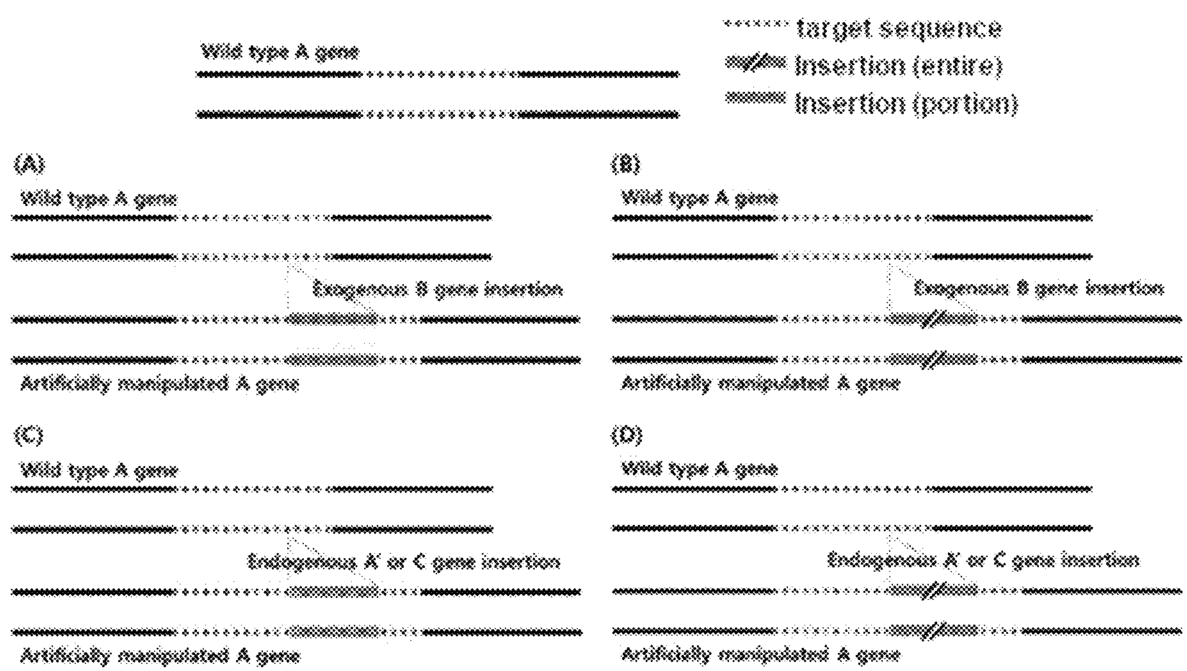

Alternatively here, the inserted nucleotide may be a portion of or the entire nucleotide sequence of a specific gene. The specific gene may be a gene introduced from an external region not included in a subject including the immunity regulating gene, for example, a human cell. Alternatively, the specific gene may be a gene existing in a subject including the immunity regulating gene, for example, a human cell, and for example, the genes existing in the human cell genome. For example, the inserted nucleotide may be a portion of nucleotide sequence in exogenous gene inserted in the nucleotide sequence region in the target sequence. Alternatively, the inserted nucleotide may be the entire nucleotide sequence in exogenous gene inserted in the nucleotide sequence region in the target sequence. Alternatively, the inserted nucleotide may be a portion of nucleotide sequence in endogenous gene inserted in the nucleotide sequence region in the target sequence, and the endogenous gene may be an allele of the target gene, that is, the immunity regulating gene, or genes other than the target gene. Alternatively, the inserted nucleotide may be the entire nucleotide sequence in endogenous gene inserted in the nucleotide sequence region in the target sequence, and the endogenous gene may be an allele of the target gene, that is, the immunity regulating gene, or genes other than the target gene (FIG. 12).

In another example, the artificially manipulated or modified immunity regulating gene may include one or more nucleotides inserted in the target sequence or in a 1 bp to 50 bp nucleotide sequence region located adjacent to the 5' end and/or 3' end of the target sequence.

Figure 13:
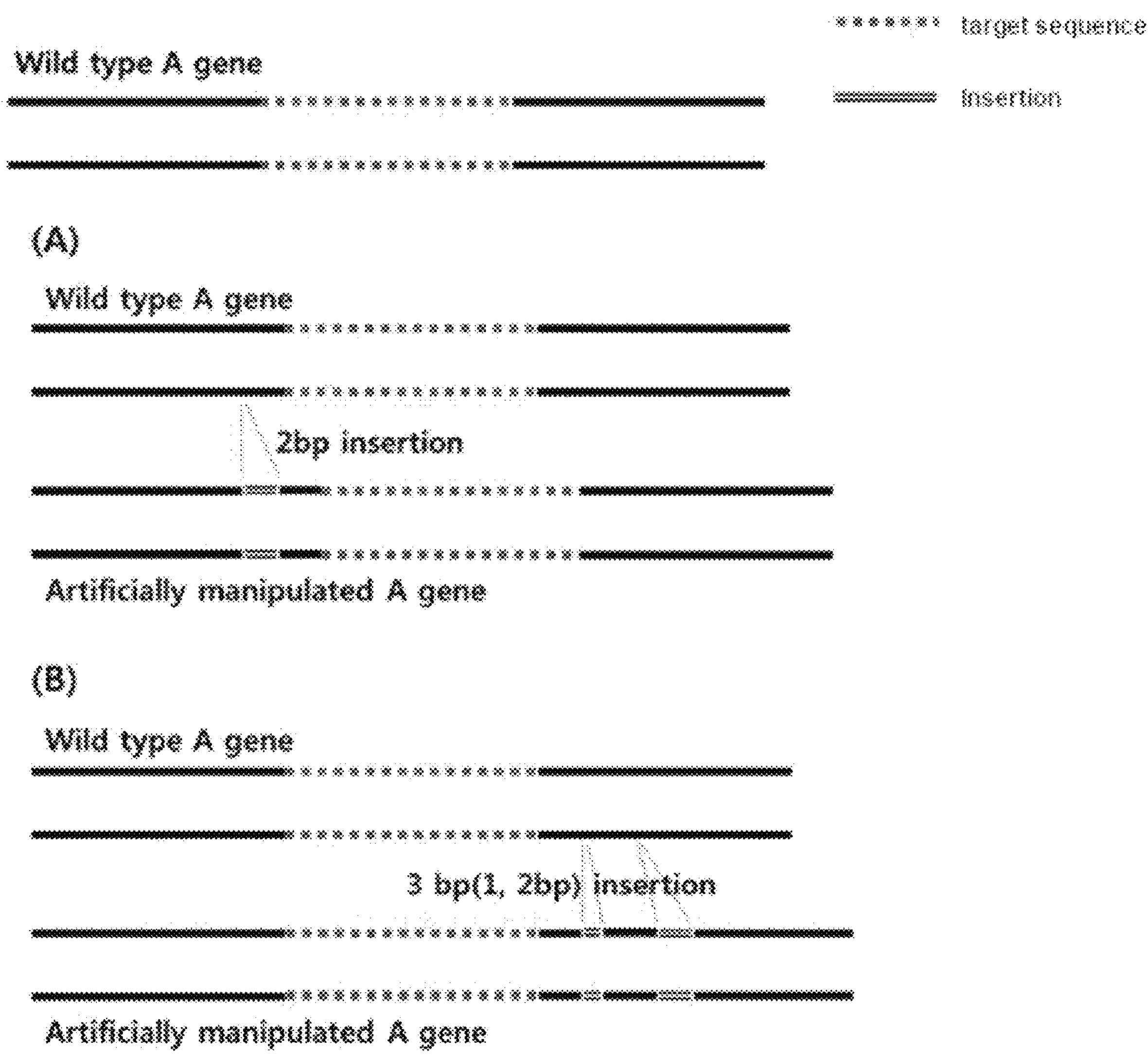

Here, the inserted nucleotides may be 1 bp to 50 bp nucleotides in which continuous, discontinuous, or both forms (that is, continuous and discontinuous) are mixed. For example, the inserted nucleotide may be continuous 2 bp nucleotides inserted in the nucleotide sequence region located adjacent to the 5' end of the target sequence. Alternatively, the inserted nucleotide may be discontinuous 3 bp nucleotides inserted in the nucleotide sequence region located adjacent to the 3' end of the target sequence, and the discontinuous 3 bp nucleotides may be a 1 bp nucleotide and continuous 2 bp nucleotides (FIG. 13). For example, the inserted nucleotide may be discontinuous 40 bp nucleotides inserted in the nucleotide region in the target sequence, and the discontinuous 40 bp nucleotides may be continuous 15 bp nucleotides, continuous 20 bp nucleotides, and continuous 5 bp nucleotides.

Figure 14:
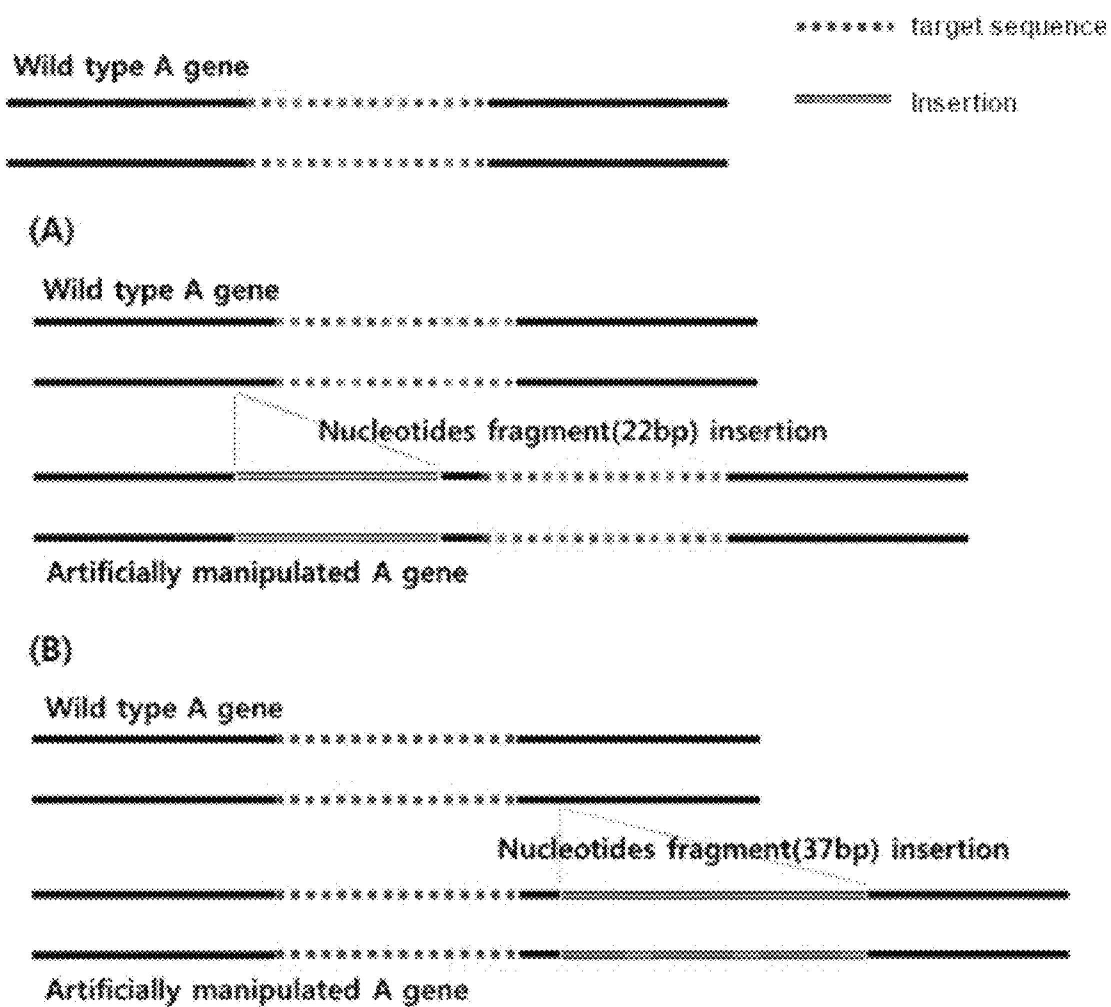

Alternatively here, the inserted nucleotide may be a nucleotide fragment including continuous 5 bp or more nucleotides. The nucleotide fragment may be 5 bp to 10 bp, 11 bp to 50 bp, 50 bp to 100 bp, 100 bp to 200 bp, 200 bp to 300 bp, 300 bp to 400 bp, 400 bp to 500 bp, 500 bp to 750 bp, or 750 bp to 1000 bp. For example, the inserted nucleotide may be a 22 bp nucleotide fragment inserted in the nucleotide sequence region located adjacent to the 5' end of the target sequence. Alternatively, the inserted nucleotide may be a 37 bp nucleotide fragment inserted in the nucleotide sequence region located adjacent to the 3' end of the target sequence (FIG. 14).

Figure 15:
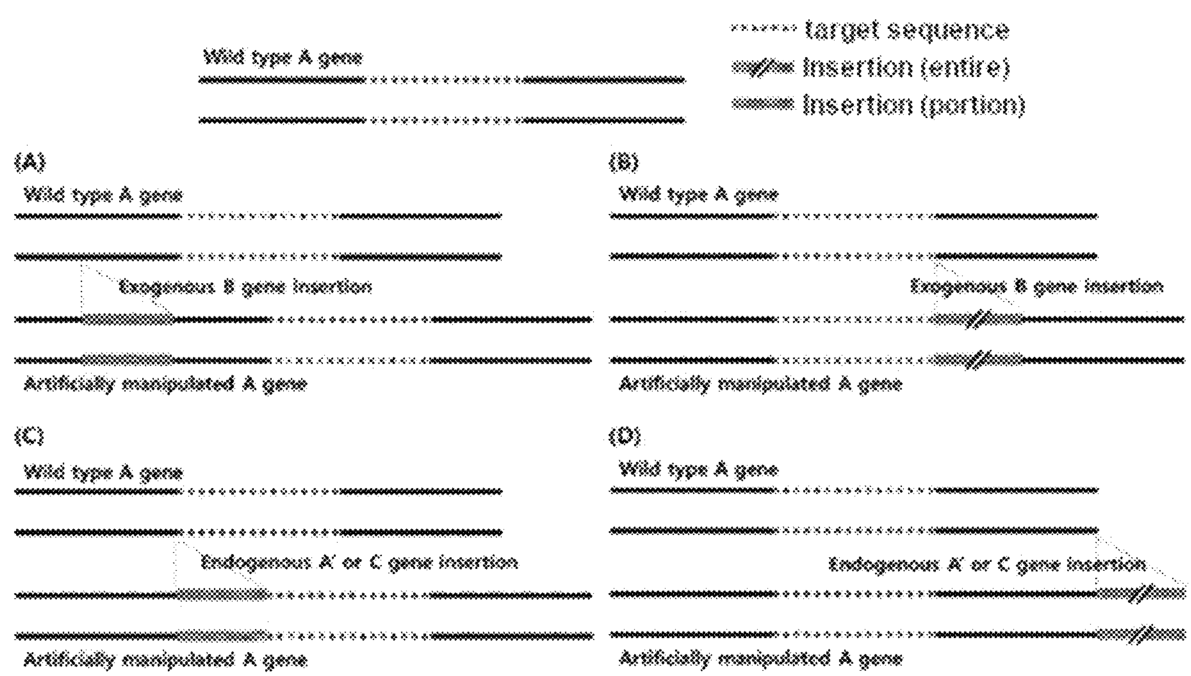

Alternatively here, the inserted nucleotide may be a portion of or the entire nucleotide sequence of a specific gene. The specific gene may be a gene introduced from an external region not included in a subject including the immunity regulating gene, for example, a human cell. Alternatively, the specific gene may be a gene included in a subject including the immunity regulating gene, for example, a human cell, and for example, the genes existing in the human cell genome. For example, the inserted nucleotide may be a portion of nucleotide sequence in exogenous gene inserted in the nucleotide sequence region located adjacent to the 5' end of the target sequence. Alternatively, the inserted nucleotide may be the entire nucleotide sequence in exogenous gene inserted in the nucleotide sequence region located adjacent to the 3' end of the target sequence. Alternatively, the inserted nucleotide may be a portion of nucleotide sequence in endogenous gene inserted in the nucleotide sequence region located adjacent to the 5' end of the target sequence, and the endogenous gene may be an allele of the target gene, that is, the immunity regulating gene, or genes other than the target gene. Alternatively, the inserted nucleotide may be the entire nucleotide sequence in endogenous gene inserted in the nucleotide sequence region located adjacent to the 3' end of the target sequence, and the endogenous gene may be an allele of the target gene, that is, the immunity regulating gene, or genes other than the target gene (FIG. 15).

In yet another example, the functionally manipulated immune cell may include one or more artificially manipulated or modified immunity regulating gene.

Here, the artificially manipulated or modified immunity regulating gene may include one or more nucleotides deleted and inserted in the target sequence or in a 1 bp to 50 bp nucleotide sequence region located adjacent to the 5' end and/or 3' end of the target sequence.

For example, the artificially manipulated or modified immunity regulating gene may include one or more nucleotides deleted and inserted in the nucleotide sequence region located in the target sequence.

Here, the deleted nucleotides may be 1 bp to 50 bp nucleotides in which continuous, discontinuous, or both forms (that is, continuous and discontinuous) are mixed.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously.

The inserted nucleotide fragment may be 5 bp to 10 bp, 11 bp to 50 bp, 50 bp to 100 bp, 100 bp to 200 bp, 200 bp to 300 bp, 300 bp to 400 bp, 400 bp to 500 bp, 500 bp to 750 bp, or 750 bp to 1000 bp.

The specific gene may be a gene introduced from an external region not included in a subject including the immunity regulating gene, for example, a human cell. Alternatively, the specific gene may be a gene included in a subject including the immunity regulating gene, for example, a human cell, and for example, the genes existing in the human cell genome.

Figure 16:
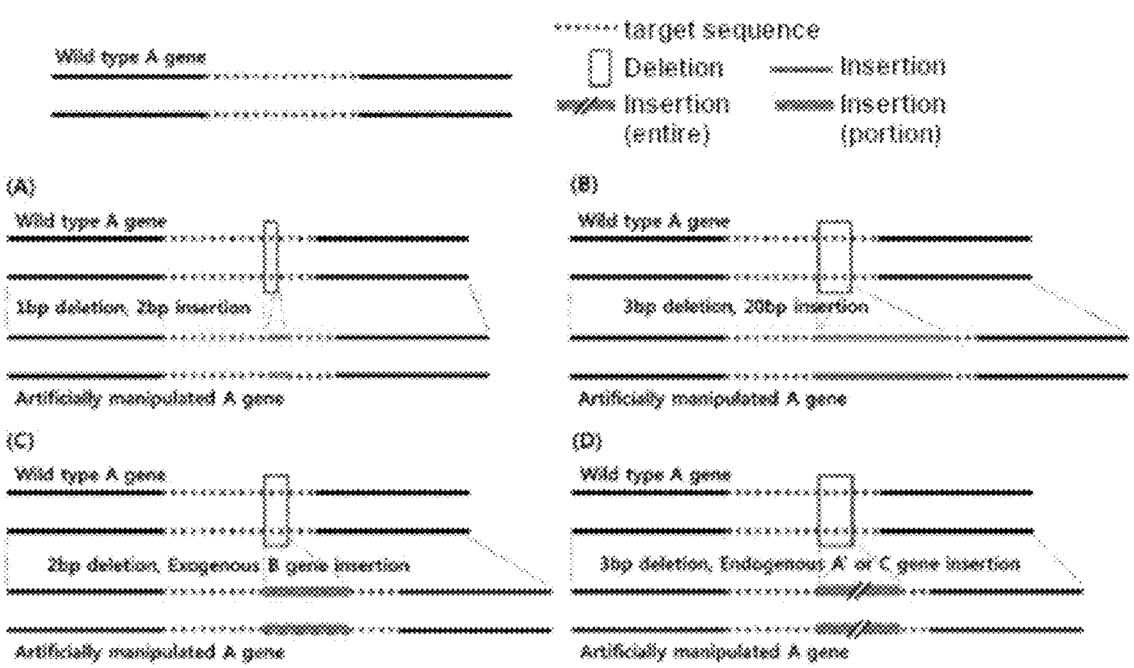

For example, the deletion and insertion of the nucleotide may take place in similar locations in the target sequence, and the deleted nucleotide may be a 1 bp nucleotide located in the target sequence, and in this case, the inserted nucleotide may be continuous 2 bp nucleotides inserted in the location of the deleted nucleotide sequence. Alternatively, the deleted nucleotide may be continuous 3 bp nucleotides located in the target sequence, and in this case, the inserted nucleotide may be a continuous 20 bp nucleotide fragment inserted in the location of the deleted nucleotide sequence. Alternatively, the deleted nucleotide may be continuous 2 bp nucleotides located in the target sequence, and in this case, the inserted nucleotide may be a portion of exogenous gene nucleotide sequence inserted in the location of the deleted nucleotide sequence. Alternatively, the deleted nucleotide may be continuous 3 bp nucleotides located in the target sequence, and in this case, the inserted nucleotide may be the entire endogenous gene nucleotide sequence inserted in the location of the deleted nucleotide sequence, and the endogenous gene may be an allele of the target gene, that is, the immunity regulating gene, or genes other than the target gene (FIG. 16).

Figure 17:
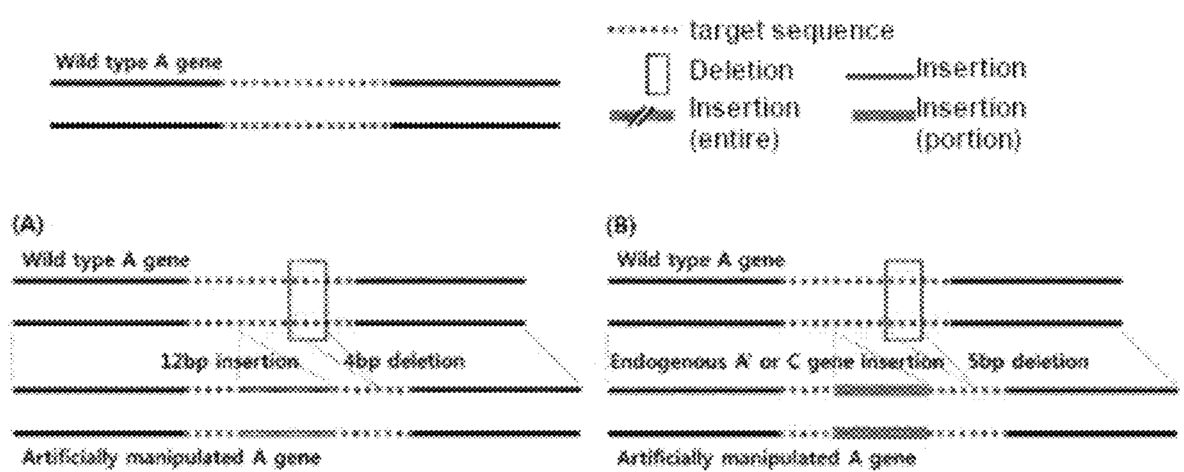

For example, the deletion and insertion of the nucleotide may take place in different locations in the target sequence, and the deleted nucleotide may be continuous 4 bp nucleotides located in the target sequence, and in this case, the inserted nucleotide may be a continuous 12 bp nucleotide fragment inserted in a non-deleted different location in the target sequence. Alternatively, the deleted nucleotide may be continuous 5 bp nucleotides located in the target sequence, and in this case, the inserted nucleotide may be a portion of endogenous gene nucleotide sequence inserted in a non-deleted different location in the target sequence, and the endogenous gene may be the target gene, that is, the allele of the immunity regulating gene, or genes other than the target gene (FIG. 17).

Figure 18:
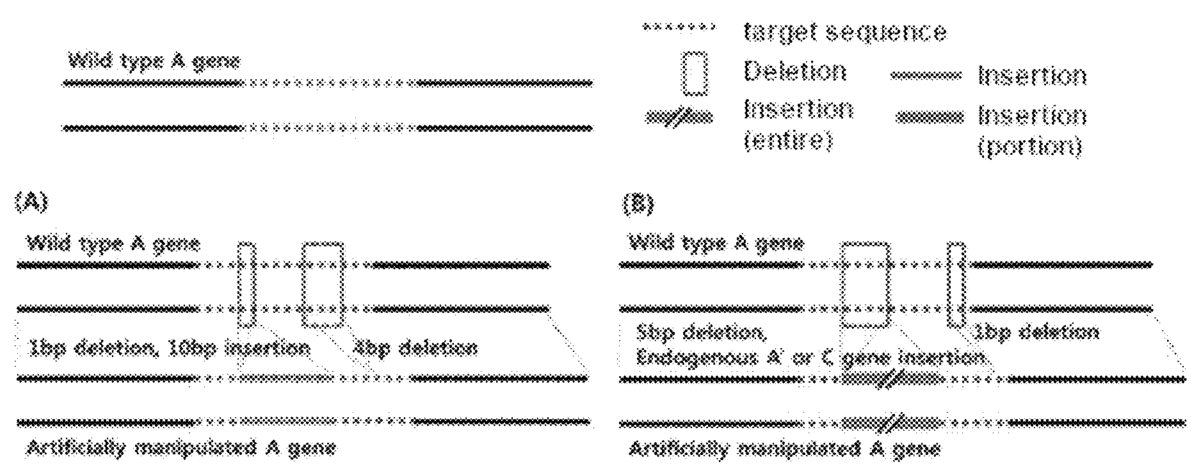

For example, the deletion and insertion of the nucleotide may take place in similar or different locations in the target sequence, and the deleted nucleotides may be a 1 bp nucleotide and continuous 4 bp nucleotides located in the target sequence, and in this case, the inserted nucleotide may be a continuous 10 bp nucleotide fragment inserted in one of the two deleted location of the target sequence, that is, the location of the 1 bp nucleotide deletion. Alternatively, the deleted nucleotides may be continuous 5 bp nucleotides and a 1 bp nucleotide located in the target sequence, and in this case, the inserted nucleotide may be the entire endogenous gene nucleotide sequence inserted in one of the two deleted location, that is, the location of the continuous 5 bp nucleotide deletion, and the endogenous gene may be the target gene, that is, the allele of the immunity regulating gene, or genes other than the target gene (FIG. 18).

Alternatively here, the deleted nucleotide may be a nucleotide fragment including 2 bp or more nucleotides.

The deleted nucleotide fragment may be 2 bp to 5 bp, 6 bp to 10 bp, 11 bp to 15 bp, 16 bp to 20 bp, 21 bp to 25 bp, 26 bp to 30 bp, 31 bp to 35 bp, 36 bp to 40 bp, 41 bp to 45 bp, or 46 bp to 50 bp.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously.

Figure 19:
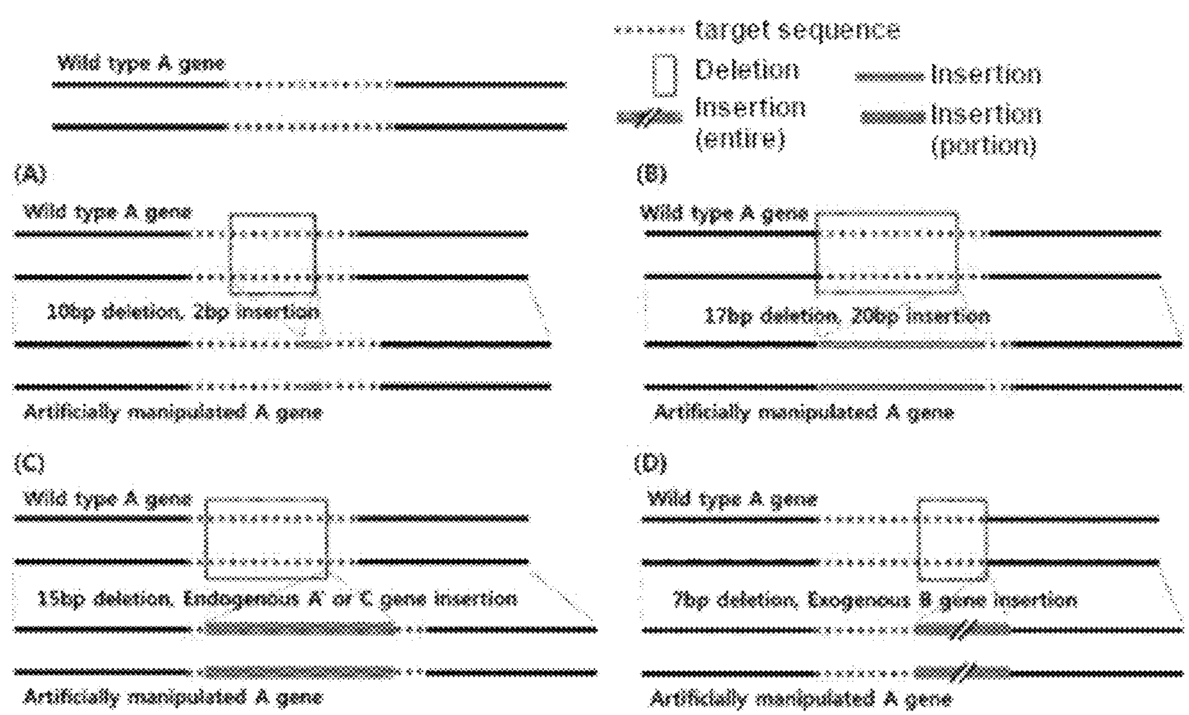

For example, the deletion and insertion of the nucleotide may take place in similar locations in the target sequence, and the deleted nucleotide may be a 10 bp nucleotide fragment located in the target sequence, and in this case, the inserted nucleotide may be continuous 2 bp nucleotides inserted in the location of the deleted nucleotide sequence. Alternatively, the deleted nucleotide may be a continuous 17 bp nucleotide fragment located in the target sequence, and in this case, the inserted nucleotide may be a continuous 20 bp nucleotide fragment inserted in the location of the deleted nucleotide sequence. Alternatively, the deleted nucleotide may be a 15 bp nucleotide fragment located in the target sequence, and in this case, the inserted nucleotide may be a portion of endogenous gene nucleotide sequence inserted in the location of the deleted nucleotide sequence, and the endogenous gene may be the target gene, that is, an allele of the immunity regulating gene, or genes other than the target gene. Alternatively, the deleted nucleotide may be a 7 bp nucleotide fragment located in the target sequence, and in this case, the inserted nucleotide may be the entire exogenous gene nucleotide sequence inserted in the location of the deleted nucleotide sequence (FIG. 19).

Alternatively here, the deleted nucleotide may be a nucleotide fragment including 2 bp or more nucleotides.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously. Additionally, the insertion may take place in a portion of, or the entire region of the two or more deleted regions.

Figure 20:
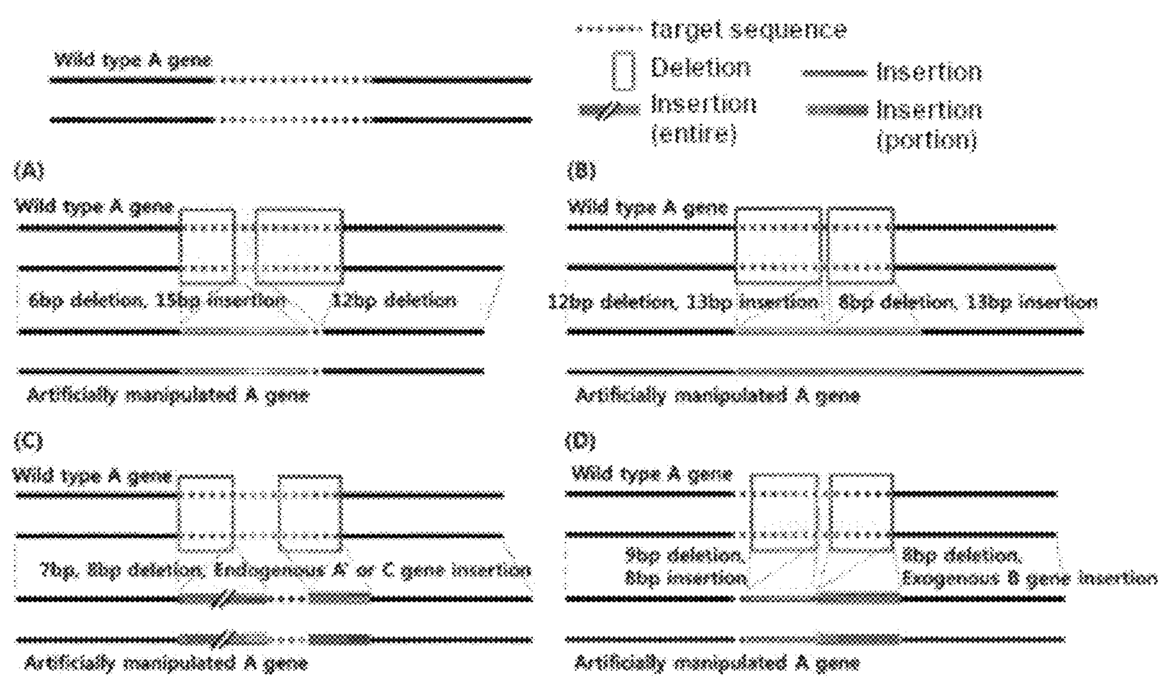

For example, the deletion and insertion of the nucleotide may take place in similar and/or different locations of the target sequence, and the deleted nucleotide may be a 6 bp nucleotide fragment and a 12 bp nucleotide fragment located in the target sequence, and in this case, the inserted nucleotide may be a 15 bp nucleotide fragment in one of the two deleted location of the target sequence, that is, the location of the 6 bp nucleotide deletion. Alternatively, the deleted nucleotide may be a 12 bp nucleotide fragment and a 8 bp nucleotide fragment located in the target sequence, and in this case, the inserted nucleotide may be a 13 bp nucleotide fragment inserted in the two deleted nucleotide sequences, respectively, that is, a 13 bp nucleotide fragment inserted in the location of the deleted 12 bp nucleotide fragment, and a 13 bp nucleotide fragment inserted in the location of the deleted 8 bp nucleotide. Alternatively, the deleted nucleotide may be a 7 bp nucleotide fragment and a 8 bp nucleotide fragment located in the target sequence, and in this case, the inserted nucleotide may be a portion of or the entire endogenous gene nucleotide sequence inserted in the two deleted nucleotide sequences, respectively, that is, the entire endogenous gene nucleotide sequence inserted in the location of the deleted 7 bp nucleotide fragment, and a portion of endogenous gene nucleotide sequence inserted in the location of the deleted 8 bp nucleotide fragment. Alternatively, the deleted nucleotide may be a 9 bp nucleotide fragment and a 8 bp nucleotide fragment located in the target sequence, and in this case, the inserted nucleotide may be the entire of a 8 bp nucleotide fragment and a portion of exogenous gene nucleotide sequence inserted in the two deleted nucleotide sequences, respectively, that is, a 8 bp nucleotide fragment inserted in the location of the deleted 9 bp nucleotide fragment, and a portion of exogenous gene nucleotide sequence inserted in the location of the deleted 8 bp nucleotide fragment (FIG. 20).

In another example, the artificially manipulated or modified immunity regulating gene may include one or more nucleotides deleted and inserted in a 1 bp to 50 bp nucleotide sequence region located adjacent to the 5' end and/or 3' end of the target sequence.

Here, the deleted nucleotides may be 1 bp to 50 bp nucleotides in which continuous, discontinuous, or both forms (that is, continuous and discontinuous) are mixed.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously.

The inserted nucleotide fragment may be 5 bp to 10 bp, 11 bp to 50 bp, 50 bp to 100 bp, 100 bp to 200 bp, 200 bp to 300 bp, 300 bp to 400 bp, 400 bp to 500 bp, 500 bp to 750 bp, or 750 bp to 1000 bp.

The specific gene may be a gene introduced from an external region not included in a subject including the immunity regulating gene, for example, a human cell. Alternatively, the specific gene may be a gene included in a subject including the immunity regulating gene, for example, a human cell, and for example, the genes existing in the human cell genome.

Figure 21:
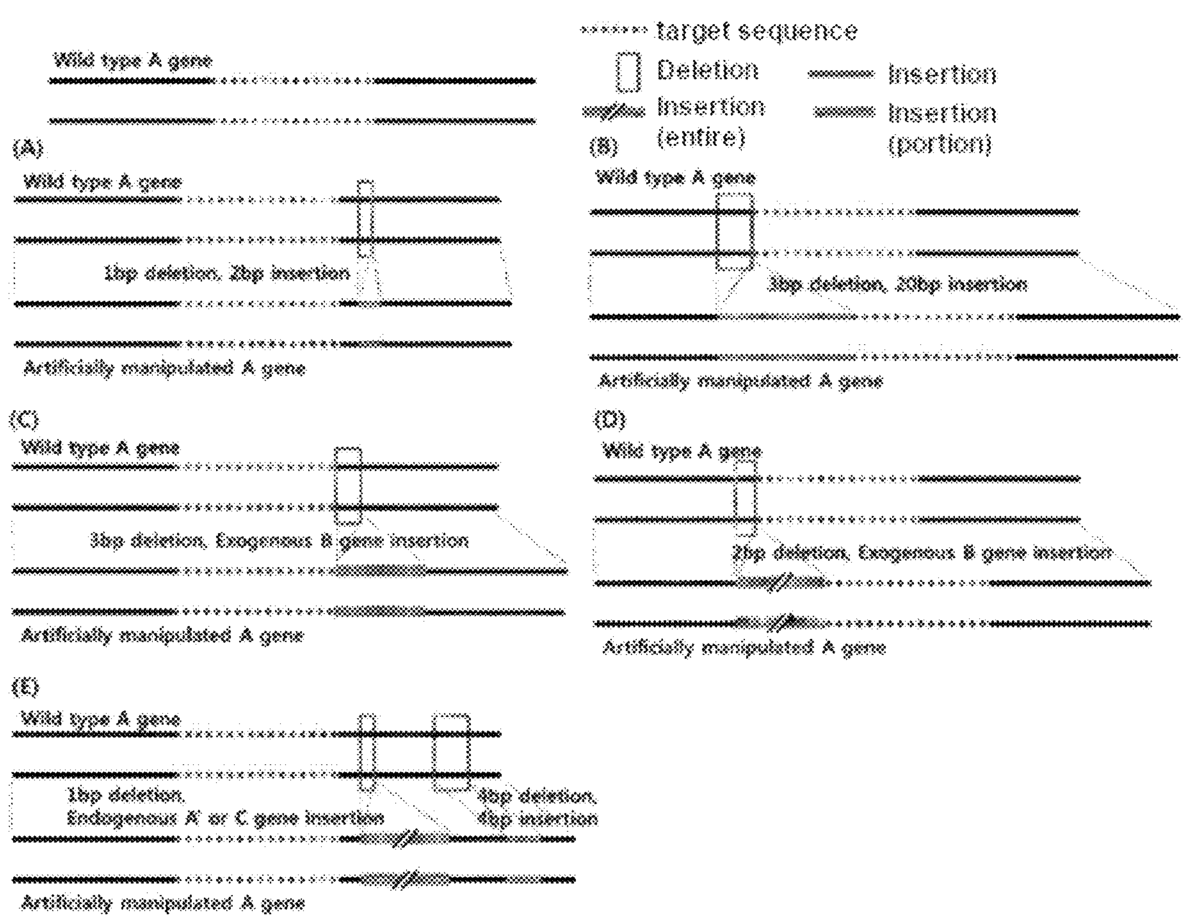

For example, the deletion and insertion of the nucleotide may take place in similar locations adjacent to the 5' end and/or the 3' end of the target sequence, the deleted nucleotide may be a 1 bp nucleotide located adjacent to the 3' end of the target sequence, and in this case, the inserted nucleotide may be continuous 2 bp nucleotides inserted in the location of the deleted nucleotide sequence. Alternatively, the deleted nucleotide may be continuous 3 bp nucleotides located adjacent to the 5' end of the target sequence, and in this case, the inserted nucleotide may be 20 bp nucleotides inserted in the location of the deleted nucleotide sequence. Alternatively, the deleted nucleotide may be continuous 3 bp nucleotides located adjacent to the 3' end of the target sequence, and in this case, the inserted nucleotide may be a portion of endogenous gene nucleotide sequence inserted in the location of the deleted nucleotide sequence. Alternatively, the deleted nucleotide may be continuous 2 bp nucleotides located adjacent to the 5' end of the target sequence, and in this case, the inserted nucleotide may be the entire exogenous gene nucleotide sequence inserted in the location of the deleted nucleotide sequence. Alternatively, the deleted nucleotide may be a 1 bp nucleotide and continuous 4 bp nucleotides located adjacent to the 3' end of the target sequence, and in this case, the inserted nucleotides may be the entire endogenous gene nucleotide sequence and continuous 4 bp nucleotide sequence inserted in the two deleted nucleotide sequences, respectively, that is, the entire endogenous gene nucleotide sequence inserted in the location of the deleted 1 bp nucleotide sequence, and continuous 4 bp nucleotide sequence inserted in the location of the deleted continuous 4 bp nucleotide (FIG. 21).

Figure 22:
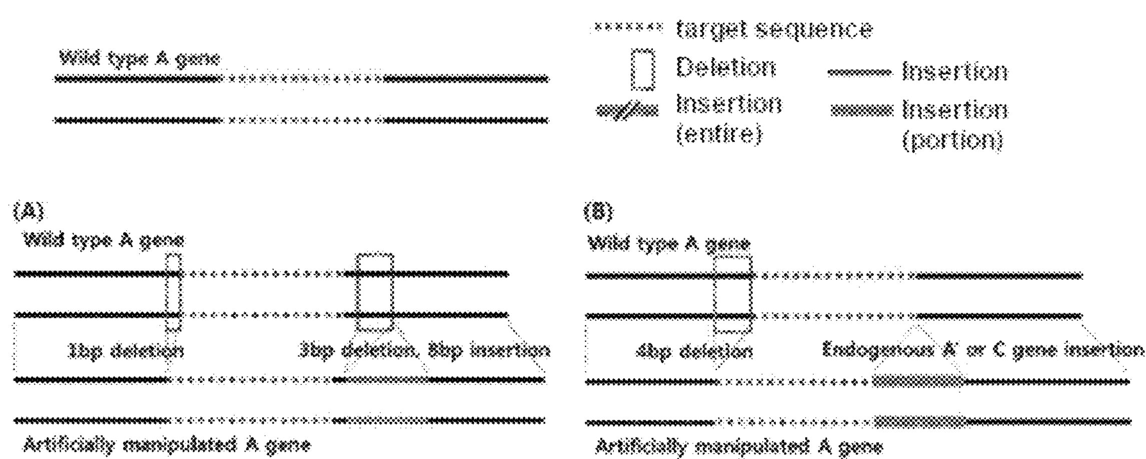

For example, the deletion and insertion of the nucleotide may take place in similar or different locations of nucleotide sequences located adjacent to the 5' end and/or the 3' end of the target sequence, the deleted nucleotides may be a 1 bp nucleotide located adjacent to the 5' end of the target sequence and continuous 3 bp nucleotides located adjacent to the 3' end of the target sequence, and in this case, the inserted nucleotide may be a 8 bp nucleotide fragment inserted in one of the location of the deleted nucleotide sequence, that is, the location of the deleted continuous 3 bp nucleotides. Alternatively, the deleted nucleotide may be a continuous 4 bp nucleotides located adjacent to the 5' end of the target sequence, and in this case, the inserted nucleotide may be a portion of endogenous gene nucleotide sequence inserted in a non-deleted different location adjacent to the 3' end of the target sequence (FIG. 22).

Alternatively here, the deleted nucleotide may be a nucleotide fragment including 2 bp or more nucleotides.

The deleted nucleotide fragment may be 2 bp to 5 bp, 6 bp to 10 bp, 11 bp to 15 bp, 16 bp to 20 bp, 21 bp to 25 bp, 26 bp to 30 bp, 31 bp to 35 bp, 36 bp to 40 bp, 41 bp to 45 bp, or 46 bp to 50 bp.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously.

Figure 23:
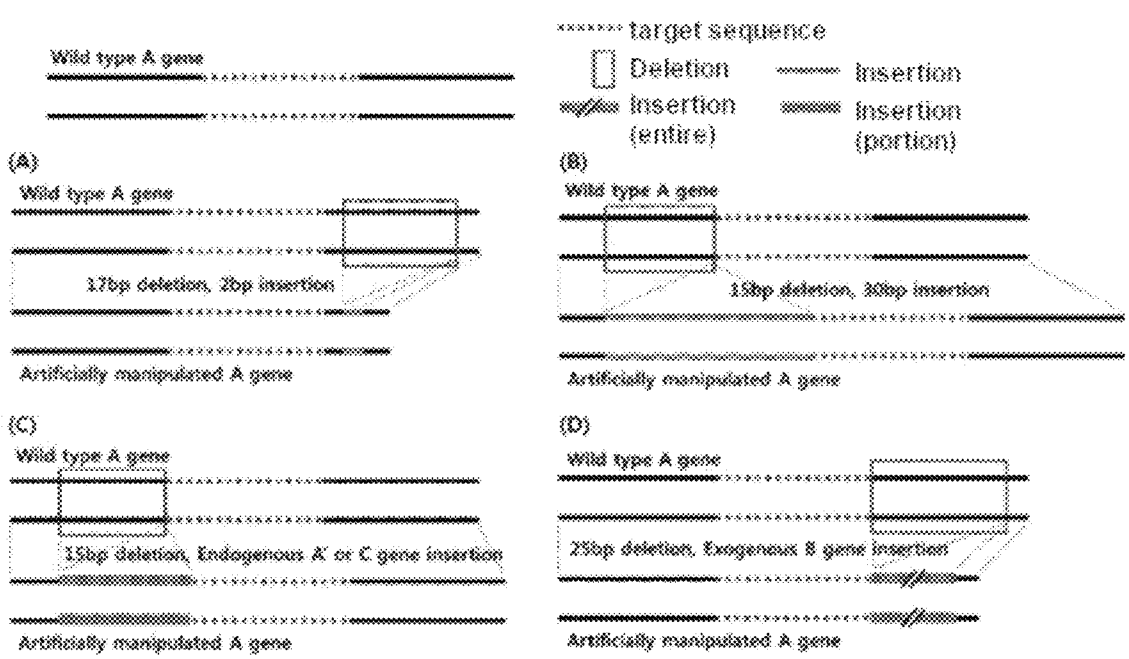

For example, the deletion and insertion of the nucleotide may take place in similar locations adjacent to the 5' end and/or the 3' end of the target sequence, the deleted nucleotide may be a 17 bp nucleotide fragment located adjacent to the 3' end of the target sequence, and in this case, the inserted nucleotide may be continuous 2 bp nucleotides inserted in the location of the deleted nucleotide sequence. Alternatively, the deleted nucleotide may be a 15 bp nucleotide fragment located adjacent to the 5' end of the target sequence, and in this case, the inserted nucleotide may be a 30 bp nucleotide fragment inserted in the location of the deleted nucleotide sequence. Alternatively, the deleted nucleotide may be a 15 bp nucleotide fragment located adjacent to the 5' end of the target sequence, and in this case, the inserted nucleotide may be a portion of endogenous gene nucleotide sequence inserted in the location of the deleted nucleotide sequence. Alternatively, the deleted nucleotide may be a 25 bp nucleotide fragment located adjacent to the 3' end of the target sequence, and in this case, the inserted nucleotide may be the entire endogenous gene nucleotide sequence inserted in the location of the deleted nucleotide sequence (FIG. 23).

Alternatively here, the deleted nucleotide may be a nucleotide fragment including 2 bp or more nucleotides.

Here, the inserted nucleotides may be 1, 2, 3, 4 or 5 bp; a nucleotide fragment; or a portion of or the entire nucleotide sequence of a specific gene, and the deletion and the insertion may take place sequentially or simultaneously. Alternatively, the insertion may take place in a portion of or the entire region of the two or more deleted regions.

Figure 24:
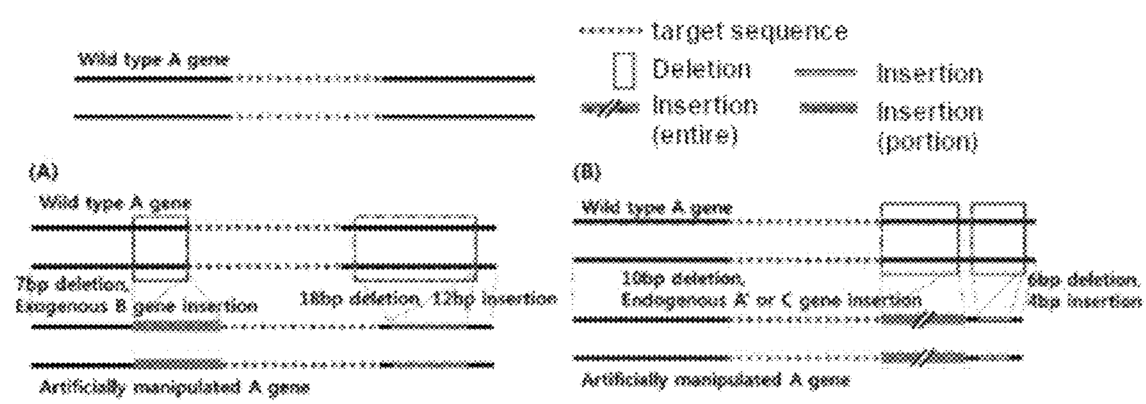

For example, the deletion and insertion of the nucleotide may take place in similar locations adjacent to the 5' end and/or the 3' end of the target sequence, the deleted nucleotides may be a 7 bp nucleotide fragment located adjacent to the 5' end of the target sequence and a 18 bp nucleotide fragment located adjacent to the 3' end of the target sequence, and in this case, the inserted nucleotides may be a portion of exogenous gene nucleotide sequence and a 12 bp nucleotide fragment inserted in the two deleted nucleotide sequences, respectively, that is, a portion of exogenous gene nucleotide sequence inserted in the location of the deleted 7 bp nucleotide fragment, and a 12 bp nucleotide fragment inserted in the location of the deleted 18 bp nucleotide fragment. Alternatively, the deleted nucleotides may be a 10 bp nucleotide fragment located adjacent to the 3' end of the target sequence and a 6 bp nucleotide fragment located adjacent to the 5' end of the target sequence, and in this case, the inserted nucleotides may be the entire endogenous gene nucleotide sequence and continuous 4 bp nucleotides inserted in the two deleted nucleotide sequences, respectively, that is, the entire endogenous gene nucleotide sequence inserted in the location of the deleted 10 bp nucleotide fragment, and continuous 4 bp nucleotides inserted in the location of the deleted 6 bp nucleotide fragment (FIG. 24).

In yet another example, the artificially manipulated or modified immunity regulating gene may include one or more nucleotides deleted and inserted in the target sequence and in a 1 bp to 50 bp nucleotide sequence region located adjacent to the 5' end and/or 3' end of the target sequence.

Here, the deleted nucleotides may be 1 bp to 50 bp nucleotides in which continuous, discontinuous, or both forms (that is, continuous and discontinuous) are mixed.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously.

The inserted nucleotide fragment may be 5 bp to 10 bp, 11 bp to 50 bp, 50 bp to 100 bp, 100 bp to 200 bp, 200 bp to 300 bp, 300 bp to 400 bp, 400 bp to 500 bp, 500 bp to 750 bp, or 750 bp to 1000 bp.

The specific gene may be a gene introduced from an external region not included in a subject including the immunity regulating gene, for example, a human cell. Alternatively, the specific gene may be a gene included in a subject including the immunity regulating gene, for example, a human cell, and for example, the genes existing in the human cell genome.

Figure 25:
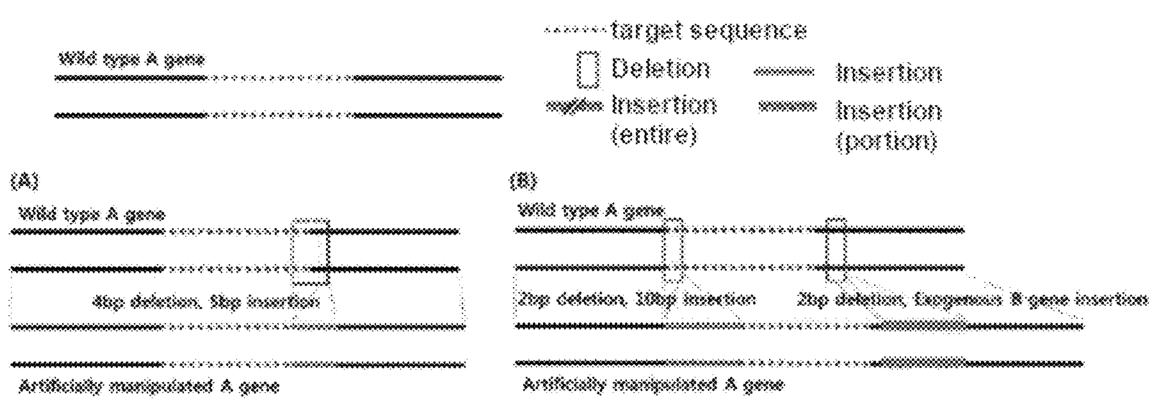

For example, the deletion and insertion of the nucleotide may take place in similar locations of the nucleotide sequence located in the target sequence, and adjacent to the 5' end and/or the 3' end of the target sequence, the deleted nucleotides may be continuous 4 bp nucleotides located in the target sequence and adjacent to the 3' end of the target sequence, and in this case, the inserted nucleotides may be 5 bp nucleotide fragments inserted in the locations of the deleted nucleotide sequence. Alternatively, the deleted nucleotides may be continuous 2 bp nucleotides located in the target sequence and continuous 2 bp nucleotides located adjacent to the 3' end of the target sequence, and in this case, the inserted nucleotide may be a 10 bp nucleotide fragment and a portion of exogenous gene nucleotide sequence inserted in the two deleted nucleotide sequences, respectively, that is, a 10 bp nucleotide fragment inserted in the location of the deleted continuous 2 bp nucleotide sequence located in the target sequence and a portion of exogenous gene nucleotide sequence inserted in the location of the deleted continuous 2 bp nucleotide sequence located adjacent to the 3' end of the target sequence (FIG. 25).

Alternatively here, the deleted nucleotide may be a nucleotide fragment including 2 bp or more nucleotides.

The deleted nucleotide fragment may be 2 bp to 5 bp, 6 bp to 10 bp, 11 bp to 15 bp, 16 bp to 20 bp, 21 bp to 25 bp, 26 bp to 30 bp, 31 bp to 35 bp, 36 bp to 40 bp, 41 bp to 45 bp, or 46 bp to 50 bp.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously.

Figure 26:
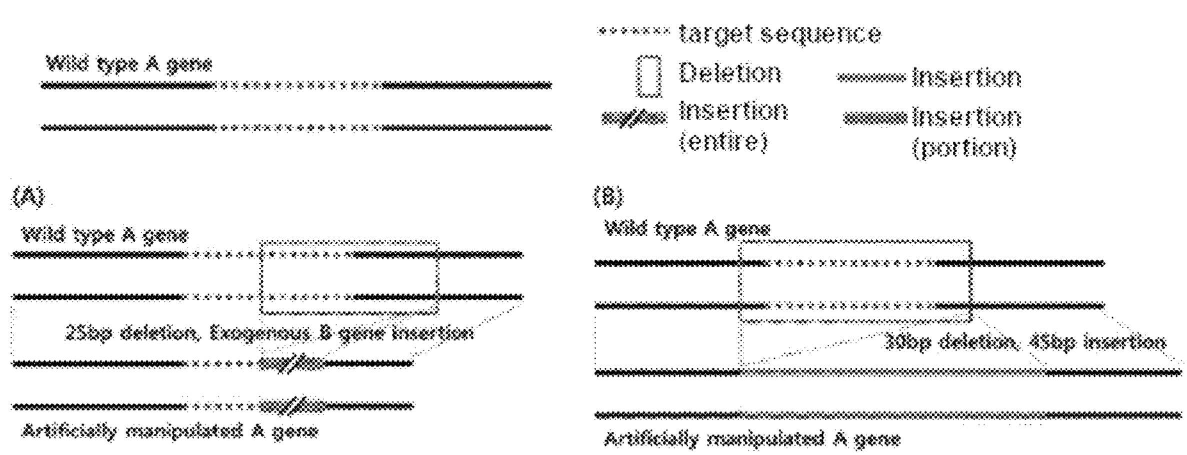

For example, the deletion and insertion of the nucleotide may take place in similar locations of the nucleotide sequence located in the target sequence, and adjacent to the 5' end and/or the 3' end of the target sequence, the deleted nucleotides may be 25 bp nucleotide fragments located in the target sequence and adjacent to the 3' end of the target sequence, and in this case, the inserted nucleotide may be the entire exogenous gene nucleotide sequences inserted in the locations of the deleted nucleotide sequence. Alternatively, the deleted nucleotides may be 30 bp nucleotide fragments located in the target sequence and adjacent to the 5' end or the 3' end of the target sequence, and in this case, the inserted nucleotides may be 45 bp nucleotide fragments inserted in the locations of the deleted nucleotide sequence (FIG. 26).

Alternatively here, the deleted nucleotide may be a nucleotide fragment including 2 bp or more nucleotides.

Here, the inserted nucleotides may be 1 bp to 50 bp nucleotides in which continuous, discontinuous, or both forms (that is, continuous and discontinuous) are mixed; a nucleotide fragment; or a portion of or the entire nucleotide sequence of a specific gene, and the deletion and the insertion may take place sequentially or simultaneously. Additionally, the insertion may take place in a portion of, or the entire region of the two or more deleted regions.

Figure 27:
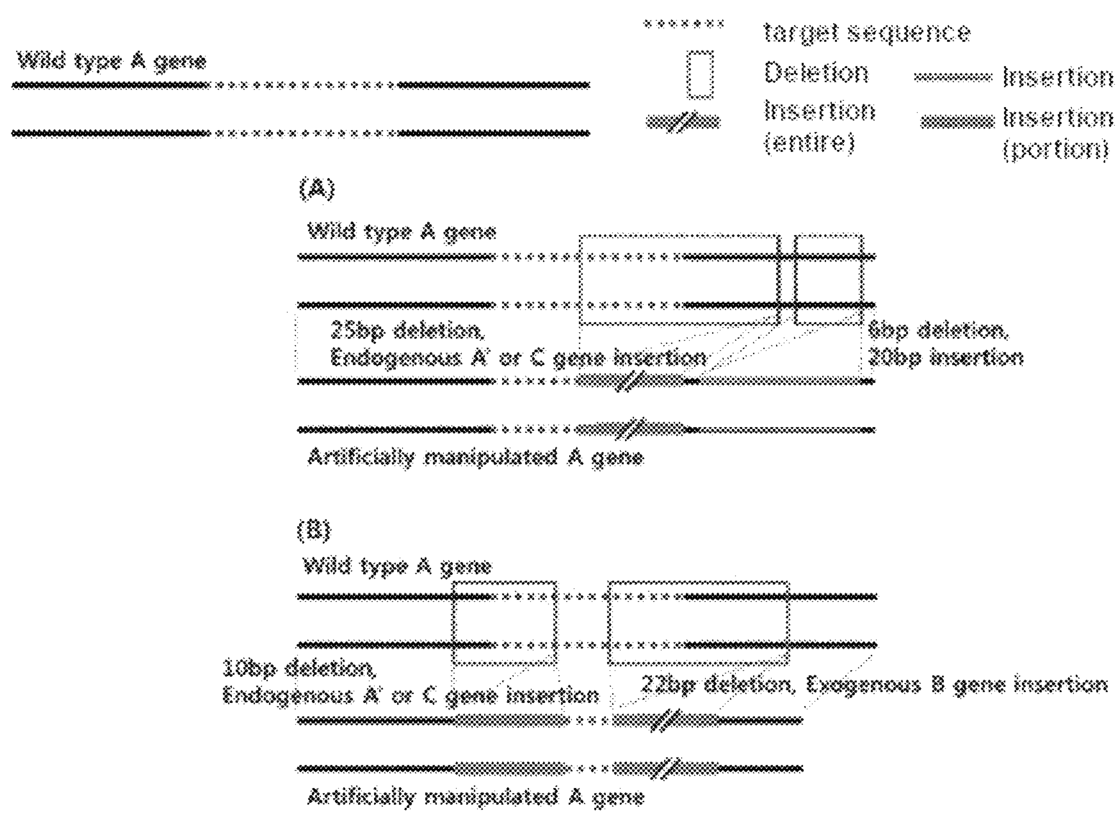

For example, the deletion and insertion of the nucleotide may take place in similar locations of the nucleotide sequence located in the target sequence, and adjacent to the 5' end and/or the 3' end of the target sequence, the deleted nucleotides may be 25 bp nucleotide fragments located in the target sequence and adjacent to the 3' end of the target sequence, a 6 bp nucleotide fragment located adjacent to the 3' end of the target sequence, and in this case, the inserted nucleotide may be the entire endogenous gene nucleotide sequences and a 20 bp nucleotide fragment inserted in the two deleted nucleotide sequences, respectively, that is, the entire endogenous gene nucleotide sequences inserted in the location of the deleted 25 bp nucleotide fragments, and a 20 bp nucleotide fragment inserted in the location of the deleted 6 bp nucleotide fragment. Alternatively, the deleted nucleotides may be 10 bp nucleotide fragments located in the target sequence and adjacent to the 5' end of the target sequence, and 22 bp nucleotide fragments located in the target sequence and adjacent to the 3' end of the target sequence, and in this case, the inserted nucleotides may be a portion of endogenous gene nucleotide sequence and the entire exogenous nucleotide sequence inserted in the two deleted nucleotide sequence, respectively, that is, a portion of endogenous gene nucleotide sequence inserted in the location of the deleted 10 bp nucleotide fragments, and the entire exogenous nucleotide sequence inserted in the location of the deleted 22 bp nucleotide fragments (FIG. 27).

The functionally manipulated immune cell may include one or more artificially manipulated or modified immunity regulating genes.

The artificially manipulated or modified immunity regulating gene may include one or more modifications of the following in a continuous 1 bp to 50 bp nucleotide sequence region located adjacent to the 5' end and/or 3' end of the PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

In one example, when the CRISPR enzyme is a SpCas9 protein, the artificially manipulated or modified immunity regulating gene may include one or more modifications of the following in a continuous 1 bp to 50 bp, 1 bp to 40 bp, 1 bp to 30 bp, or 1 bp to 25 bp nucleotide sequence region located adjacent to the 5' end and/or 3' end of the 5'-NGG-3' (N is A, T, G, or C) PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

In an another example, when the CRISPR enzyme is a CjCas9 protein, the artificially manipulated or modified immunity regulating gene may include one or more modifications of the following in a continuous 1 bp to 50 bp, 1 bp to 40 bp, 1 bp to 30 bp, or 1 bp to 25 bp nucleotide sequence region located adjacent to the 5' end and/or 3' end of the 5'-NNNNRYAC-3' (N is each independently A, T, C, or G, R is A or G, and Y is C or T) PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

In yet another example, when the CRISPR enzyme is a StCas9 protein, the artificially manipulated or modified immunity regulating gene may include one or more modifications of the following in a continuous 1 bp to 50 bp, 1 bp to 40 bp, 1 bp to 30 bp, and 1 bp to 25 bp nucleotide sequence region located adjacent to the 5' end and/or 3' end of the 5'-NNAGAAW-3' (N is each independently A, T, C, or G, W is A or T) PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

In one example, when the CRISPR enzyme is a NmCas9 protein, the artificially manipulated or modified immunity regulating gene may include one or more modifications of the following in a continuous 1 bp to 50 bp, 1 bp to 40 bp, 1 bp to 30 bp, or 1 bp to 25 bp nucleotide sequence region located adjacent to the 5' end and/or 3' end of the 5'-NNNNGATT-3' (N is each independently A, T, C, or G) PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

In another example, when the CRISPR enzyme is a SaCas9 protein, the artificially manipulated or modified immunity regulating gene may include one or more modifications of the following in a continuous 1 bp to 50 bp, 1 bp to 40 bp, 1 bp to 30 bp, and 1 bp to 25 bp nucleotide sequence region adjacent to the 5' end and/or 3' end of the 5'-NNGRR(T)-3' (N is each independently A, T, C, or G, R is A or G, and (T) is any sequence that can be optionally included) PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

In yet another example, when the CRISPR enzyme is a Cpf1 protein, the artificially manipulated or modified immunity regulating gene may include one or more modifications of the following in a continuous 1 bp to 50 bp, 1 bp to 40 bp, 1 bp to 30 bp, and 1 bp to 25 bp nucleotide sequence region located adjacent to the 5' end and/or 3' end of the 5'-TTN-3' (N is A, T, C, or G) PAM sequence existing in the nucleotide sequence of the immunity regulating gene:

i) deletion of one or more nucleotides
ii) substitution of one or more nucleotides into nucleotides different from the wild type gene
iii) insertion of one or more nucleotides, or
iv) combination of two or more selections from the above i) to iii).

The functionally manipulated immune cell may include one or more knockout artificially manipulated or modified immunity regulating genes.

Here, the knockout may be an effect by an artificial manipulation or modification of an immunity regulating gene.

Here, the knockout may be an inhibition of the expression of a protein encoded by an immunity regulating gene through the artificial manipulation or modification.

The functionally manipulated immune cell may include one or more knockdown artificially manipulated or modified immunity regulating genes.

Here, the knockdown may be an effect by an artificial manipulation or modification of an immunity regulating gene.

Here, the knockdown may be an inhibition of the expression of a protein encoded by an immunity regulating gene through the artificial manipulation or modification.

The functionally manipulated immune cell may include one or more knockin foreign nucleic acids or foreign genes.

Here, the one or more knockin foreign nucleic acids or foreign genes may be introduced by an artificial manipulation or modification of an immunity regulating gene.

Here, the one or more knockin foreign nucleic acids or foreign genes may express an encoding foreign peptide or a foreign protein.

Additionally, the functionally manipulated immune cell may be an immune cell with suppressed or inhibited expression of immune regulatory factor.

Here, the immune regulatory factor may be a polypeptide or a protein expressed by an immunity regulating gene, that is, PD-1 gene, CTLA-4 gene, DGKA gene, DGKZ gene, FAS gene, EGR2 gene, PPP2r2d gene, TET2 gene, PSGL-1 gene, A20 gene, and/or KDM6A gene.

Here, the quantity of modified immune regulatory factor expressed by the functionally modified immunity cells is reduced by at least 30% when compared with the quantity of immune regulatory factor expressed by wild type immune cells, that is, naturally-occurring immune cells. Here, the quantity of immune regulatory factor expressed by the wild type immune cell for standard of comparison may be, the average quantity of immune regulatory factor expressed by naturally-occurring immune cells collected from healthy human with no immunological diseases, for example, cancer and acquired immune deficiency syndrome (AIDS), and in this case, the population, that is, the number of healthy human from whom the wild type immune cell is acquirable, may be at least 50.

Here, the quantity of modified immune regulatory factor expressed by the functionally modified immunity cells is reduced by at least 30% when compared with the quantity of immune regulatory factor expressed by wild type immune cells, that is, immune cells prior to artificial manipulation. Here, the quantity of immune regulatory factor expressed by the wild type immune cell for standard of comparison may be the average quantity of immune regulatory factor expressed by wild type immune cells, that is, immune cells prior to artificial manipulation, for example, immune cells separated from human that are prior to treatment of immunity regulating gene-targeting composition for gene manipulation or composition for immune cell manipulation As an embodiment disclosed by the present specification, the manipulated immune cell may be a hybrid manipulated immune cell.

The term "hybrid manipulated immune cell" is an immune cell, and refers to an functionally manipulated immune cell in which one or more artificial structure is supplemented by artificial manipulation, or an artificial structure supplemented immune cell in which artificial manipulation is made to modify expression of natural immune regulatory factor or damage functions of immune regulatory factor.

The term "artificial structure supplemented immune cell" refers to an immune cell with one or more artificial structures supplemented.

For example, the artificial structure may be an artificial receptor.

The term "artificial receptor" refers to a functional entity, which is not a wild-type receptor but artificially prepared, and has an ability to recognize antigens and performs a specific function.

Such an artificial receptor may contribute to enhancement of immune response with improved ability to recognize specific antigens or by producing reinforced immune response signals.

As an example, the artificial receptor may have the following constitutions:

(i) Antigen Recognition Part

An artificial receptor includes an antigen recognition part.

The term "antigen recognition part", which is a part of artificial receptor, refers to a region that recognizes an antigen.

The antigen recognition part may be one which has improved recognition of specific antigens compared to wild-type receptors. In particular, the specific antigen may be an antigen of cancer cell. In addition, the specific antigen may be an antigen of common cells in the body.

The antigen recognition part may have a binding affinity for antigens.

The antigen recognition part may generate a signal while binding to the antigen. The signal may be an electrical signal. The signal may be a chemical signal.

The antigen recognition part may include a signal sequence.

The signal sequence refers to a peptide sequence that allows a protein to be delivered to a specific site during the process of protein synthesis.

The signal sequence may be located close to the N-terminus of the antigen recognition part. In particular, the distance from the N-terminus may be about 100 amino acids. The signal sequence may be located close to the C-terminus of the antigen recognition part. In particular, the distance from the C-terminus may be about 100 amino acids.

The antigen recognition part may have an organic functional relationship with a first signal generating part.

The antigen recognition part may be homologous to a fragment antigen binding (Fab) domain of an antibody.

The antigen recognition part may be a single-chain variable fragment (scFv).

The antigen recognition part may recognize antigens by itself or by forming an antigen recognition structure.

The antigen recognition structure can recognize antigens by establishing a specific structure, and the monomeric units constituting the specific structure and the binding of the monomeric units can be easily understood by those of ordinary skill in the art. In addition, the antigen recognition structure may consist of one or two or more monomeric units.

The antigen recognition structure may be a structure in which the monomeric units are connected in series or may be a structure in which the monomeric units are connected in parallel.

The structure connected in series refers to a structure in which two or more monomeric units are continuously connected in one direction, whereas the structure connected in parallel refers to a structure in which each of two or more monomeric units is concurrently connected at the distal end of one monomeric unit, for example, in different directions.

For example, the monomeric unit may be an inorganic material.

The monomeric unit may be a biochemical ligand.

The monomeric unit may be homologous to an antigen recognition part of a wild-type receptor.

The monomeric unit may be homologous to an antibody protein.

The monomeric unit may be a heavy chain of an immunoglobulin or may be homologous thereto.

The monomeric unit may a light chain of an immunoglobulin or may be homologous thereto.

The monomeric unit may include a signal sequence.

Meanwhile, the monomeric unit may be linked by a chemical bond or may be bonded through a specific combining part.

The term "antigen recognition unit combining part" is a region where antigen recognition units are connected to each other, and it may be an optional constitutuion which is present when an antigen recognition structure consisting of two or more antigen recognition units is present.

The antigen recognition unit combining part may be a peptide. In particular, the combining part may have high proportions of serine and threonine.

The antigen recognition unit combining part may be a chemical binding

The antigen recognition unit combining part can aid in the expression of the three-dimensional structure of the antigen recognition unit by having a specific length.

The antigen recognition unit combining part can aid the function of the antigen recognition structure by having a specific positional relationship between the antigen recognition units.

(ii) Receptor Body

The artificial receptor includes a receptor body.

The term "receptor body" is a region where the connection between the antigen recognition part and the signal generating part are mediated, and the antigen recognition part and the signal generating part may be physically connected.

The function of the receptor body may be to deliver the signal produced in the antigen recognition part or the signal generating part.

The structure of the receptor body may have the function of the signal generating part at the same time depending on cases.

The function of the receptor body may be to allow that the artificial receptor to be immobilized on the immune cells.

The receptor body may include an amino acid helical structure.

The structure of the receptor body may include a part which is homologous to a part of the common receptor protein present in the body. The homology may be in a range of 50% to 100%.

The structure of the receptor body may include a part which is homologous to the proteins on immune cells. The homology may be in a range of 50% to 100%.

For example, the receptor body may be a CD8 transmembrane domain.

The receptor body may be a CD28 transmembrane domain. In particular, when a second signal generating part is CD28, CD28 can perform the functions of the second signal generating part and the receptor body.

(iii) Signal Generating Part

The artificial receptor may include a signal generating part.

The term "first signal generating part", which is a part of the artificial receptor, refers to a part that produces an immune response signal.

The term "second signal generating part", which is a part of the artificial receptor, refers to a part that produces an immune response signal by interacting with the first signal generating part or independently.

The artificial receptor may include the first signal generating part and/or the second signal generating part.

The artificial receptor may include two or more of the first and/or second signal generating part, respectively.

The first and/or second signal generating part may include a specific sequence motif The sequence motif may be homologous to the motifs of cluster of designation (CD) proteins.

In particular, the CD proteins may be CD3, CD247, and CD79.

The sequence motif may be an amino acid sequence of YxxL/I.

The sequence motif may be multiple in the first and/or second signal generating part.

In particular, a first sequence motif may be located at a distance of 1 to 200 amino acids from the start position of the first signal generating part. A second sequence motif may be located at a distance of 1 to 200 amino acids from the start position of the second signal generating part.

In addition, the distance between each sequence motif may be 1 to 15 amino acids.

In particular, the preferred distance between each sequence motif is 6 to 8 amino acids.

For example, the first and/or second signal generating part may be CD3 ζ.

The first and/or second signal generating part may be FcεRIγ.

The first and/or second signal generating part may be those which produce an immune response only when a specific condition is met.

The specific condition may be that the antigen recognition part recognizes antigens.

The specific condition may be that the antigen recognition part forms a binding with an antigen.

The specific condition may be that the signal generated is delivered when the antigen recognition part forms a binding with the antigen.

The specific condition may be that the antigen recognition part recognizes an antigen or the antigen recognition part is separated from an antigen while binding with the antigen.

The immune response signal may be a signal associated with the growth and differentiation of immune cells.

The immune response signal may be a signal associated with the death of immune cells.

The immune response signal may be a signal associated with the activity of immune cells.

The immune response signal may be a signal associated with the aid of immune cells.

The immune response signal may be activated to be specific for the signal produced in the antigen recognition part.

The immune response signal may be a signal that regulates the expression of a gene of interest.

The immune response signal may be a signal that suppresses immune responses.

In an embodiment, the signal generating part may include an additional signal generating part.

The term "additional signal generating part", which is a part of an artificial receptor, refers to a region that produces an additional immune response signal with regard to the immune response signal produced by the first and/or second signal generating parts.

Hereinafter, the additional signal generating part is referred to as the $n^{th}$ signal generating part ($n \neq 1$) according to the order.

The artificial receptor may include an additional signal generating part, in addition to the first signal generating part.

Two or more additional signal generating parts can be included in an artificial receptor.

The additional signal generating part may be a structure in which immune response signals of 4-1BB, CD27, CD28, ICOS, and OX40, or other signals thereof may be produced.

The conditions that the additional signal generating part produces an immune response signal and the characteristics of the immune response signals produced thereof include the details that correspond to the immune response signals of the first and/or second signal generating parts.

The immune response signal may be one which promotes the synthesis of cytokines. The immune response signal may be one which promotes or inhibits the secretion of cytokines. In particular, the cytokine may be, preferably, IL-2, TNFα or IFN-γ.

The immune response signal may be a signal that helps the growth or differentiation of other immune cells.

The immune response signal may be a signal that attracts other immune cells to a location where the signal occurs.

The present invention includes all possible binding relationships of artificial receptors. Accordingly, the aspects of the artificial receptors of the present invention are not limited to those described herein.

The artificial receptor may consist of an antigen recognition part-a receptor body-a first signal generating part. The receptor body may be optionally included.

The artificial receptor may consist of an antigen recognition part-a receptor body-a second signal generating part-a first signal generating part. The receptor body may be optionally included. In particular, the positions of the first signal generating part and the second signal generating part may be changed.

The artificial receptor may consist of antigen recognition part-a receptor body-a second signal generating part-a third signal generating part-a first signal generating part. The receptor body may be optionally included. In particular, the positions of from the first signal generating part to the third signal generating part may be changed.

In the artificial receptor, the number of signal generating parts is not limited to 1 to 3, but it may be included to have more than three.

In addition to the above embodiment, the artificial receptor may have the structure of an antigen recognition part-signal generating part-a receptor body. The structure may be advantageous at the time when an immune response signal that acts out of a cell which has the artificial receptor, must be produced.

The artificial receptor may function in a manner corresponding to the wild-type receptor.

The artificial receptor may function to form a specific positional relationship by forming a binding with a specific antigen.

The artificial receptor may function to recognize an antigen and produce an immune response signal that promotes an immune response against the specific antigen.

The artificial receptor may function to recognize the antigens of a general cell in the body and inhibit an immune response against the cell in the body.

(iv) Signal Sequence

In an embodiment, the artificial receptor may optionally include a signal sequence.

When the artificial receptor includes a signal sequence of a specific protein, this may aid the artificial receptor in being easily located on the membrane of an immune cell. Preferably, when the artificial receptor includes a signal sequence of a transmembrane protein, this may aid the artificial receptor in penetrating through the membrane of the immune cell to be located on the external membrane of the immune cell.

The artificial receptor may include one or more signal sequences.

The signal sequence may include many positively charged amino acids.

The signal sequence may include a positively charged amino acid at a location close to the N- or C-terminus.

The signal sequence may be a signal sequence of the transmembrane protein.

The signal sequence may be a signal sequence of a protein located on the external membrane of an immune cell.

The signal sequence, preferably, may be a signal sequence of a scFv.

The signal sequence may be included in the structure that the artificial receptor possesses, that is, an antigen recognition part, a receptor body, a first signal generating part, and additional signal generating part.

In particular, the signal sequence may be located at a position close to the N- or C-terminus of each structure.

In particular, the distance of the signal sequence from the N- or C-terminus may be about 100 amino acids.

In an embodiment, the artificial receptor may be a chimeric antigen receptor (CAR).

The chimeric antigen receptor may be an receptor having binding specificity to one or more antigens.

The one or more antigens may be antigens expressed specifically by cancer cells and/or virus.

The one or more antigens may be tumor associated antigens.

The one or more antigens, may be, but are not limited to, A33, ALK, alpha-fetoprotein (AFP), adrenoreceptor beta 3 (ADRB3), alpha-folate receptor, AD034, AKT1, BCMA, beta-human chorionic gonadotropin, B7H3 (CD276), BST2, BRAP, CD5, CD13, CD19, CD20, CD22, CD24, CD30, CD33, CD38, CD40, CD44v6, CD52, CD72, CD79a, CD79b, CD89, CD97, CD123, CD138, CD160, CD171, CD179a, carbonic anhydrase IX (CAIX), CA-125, carcinoembryonic antigen (CEA), CCR4, C-type lectin-like molecules (CLL-1 or CLECL1), claudin6 (CLDN6), CXORF61, CAGE, CDX2, CLP, CT-7, CT8/HOM-TES-85, cTAGE-1, ERBB2, epidermal growth factor receptor (EGFR), EGFR variants III (EGFRvIII), epithelial cell adhesion molecule (EPCAM), E74-like factor 2 mutation (ELF2M), Ephrin type-A receptor 2 (EphA2), EMR2, Fms-like tyrosine kinase 3 (FLT3), FCRL5, fibulin-1, G250, GD2, glycoprotein 36 (gp36), glycoprotein 100 (gp100), glucocorticoid-induced tumor necrosis factor receptor (GITR), GPRC5D, GloboH, G protein-coupled receptor 20 (GPR20), GPC3, hsp70-2, human high molecular weight-melanoma-associated antigen (HMWMAA), hepatitis A virus cellular receptor 1 (HAVCR1), human papillomavirus E6 (HPV E6), human papillomavirus E7 (HPV E7), HAGE, HCA587/MAGE-C2, hCAP-G, HCE661, HER2/neu, HLA-Cw, HOM-HD-21/galectin9, HOM-MEEL-40/SSX2, HOM-RCC-3.1.3/CAXII, HOXA7, HOXB6, Hu, HUB 1, insulin growth factor (IGF1)-I, IGF-II, IGFI receptor, interleukin-13 receptor subunit alpha-2 (IL-13Ra2 or CD213A2), interleukin 11 receptor alpha (IL-11Ra), IGLL1, KIT (CD117), KM-HN-3, KM-KN-1, KOC1, KOC2, KOC3, KOC3, LAGA-1a, LAGE-1, LAIR1, LILRA2, LY75, Lewis Y antigen, MUC1, MN-CA IX, M-CSF, MAGE-1, MAGE-4a, mesothelin, MAGE-A1, MAD-CT-1, MAD-CT-2, MART1, MPP11, MSLN, neural cell adhesion molecule (NCAM), NY-ESO-1, NY-ESO-5, Nkp30, NKG2D, NY-BR-1, NY-BR-62, NY-BR-85, NY-CO-37, NY-CO-38, NNP-1, NY-LU-12, NY-REN-10, NY-REN-19/LKB/STK11, NY-REN-21, NY-REN-26/BCR, NY-REN-3/NY-CO-38, NY-REN-33/SNC6, NY-REN-43, NY-REN-65, NY-REN-9, NY-SAR-35, o-acetyl-GD2 ganglioside (OAcGD2), OGFr, PSMA, prostatic acid phosphatase (PAP), p53, prostate carcinoma tumor antigen-1 (PCTA-1), prostate stem cell antigen (PSCA), serine protease 21 (testisin or PRSS21), platelet-derived growth factor receptor-beta (PDGFR-beta), PLAC1, pannexin 3 (PANX3), PLU-1, ROR-1, RAGE-1, RU1, RU2, Rab38, RBPJ kappa, RHAMM, stage-specific embryonic antigen-4 (SSEA-4), SCP1, SSX3, SSX4, SSX5, Tyrp-1, TAG72, thyroglobulin, human telomerase reverse transcriptase (hTERT), 5T4, tumor-associated glycoprotein (TAG72), tyrosinase, transglutaminase 5 (TGS5), TEM1, TEM7R, thyroid-stimulating hormone receptor (TSHR), Tie 2, TRP-2, TOP2A, TOP2B, uroplakin 2 (UPK2), vimentin, vascular endothelial growth factor receptor 2 (VEGFR2), Wilms tumor protein 1 (WT1), and lewis (Y) antigen.

As an embodiment disclosed by the present specification, the hybrid manipulated immune cell may be an artificially manipulated immune cell including all of the following:

(i) one or more artificially manipulated or modified immunity regulating genes and/or the expression product thereof; and (ii) an artificial receptor protein and/or the nucleic acid encoding thereof.

The explanation on the above one or more artificially manipulated or modified immunity regulating genes is as described above.

The expression product of (i) may be mRNA or protein expressed by one or more artificially manipulated or modified immunity regulating genes.

Additionally, the explanation on the above artificial receptor is as described above.

For example, the hybrid manipulated immune cell may be a functionally manipulated immune cell including an artificial receptor.

Here, the artificial receptor may be a chimeric antigen receptor, and the explanation related thereto is as described above.

The hybrid manipulated immune cell may be an immune cell with one or more artificially manipulated or modified immunity regulating genes including one or more chimeric antigen receptors. Here, the immune cell with one or more artificially manipulated or modified immunity regulating genes may be a functionally manipulated immune cell, and the explanation related thereto is as described above.

The hybrid manipulated immune cell may be an immune cell in which expression of one or more immunity regulating genes including one or more chimeric antigen receptors is suppressed or inhibited. Here, the immune cell in which expression of one or more immunity regulating genes is suppressed or inhibited may be a functionally manipulated immune cell, and the explanation related thereto is as described above.

As an example, the hybrid manipulated immune cell may be an immune cell produced by artificially introducing one or more nucleic acids or genes encoding chimeric antigen receptor into a functionally manipulated immune cell.

Here, the nucleic acids or genes encoding chimeric antigen receptor may exist in cells in a form not inserted into the genome of the functionally manipulated immune cell.

Here, the nucleic acids or genes encoding chimeric antigen receptor may be inserted into a specific locus in the genome of the functionally manipulated immune cell. The specific locus may be an intron, an exon, a promoter, or an enhancer locus of the immunity regulating gene.

Here, the nucleic acids or genes encoding chimeric antigen receptor may be randomly inserted into one or more introns existing in the genome of the functionally manipulated immune cell.

Here, the nucleic acids or genes encoding chimeric antigen receptor may be randomly inserted into one or more exons existing in the genome of the functionally manipulated immune cell.

Here, the nucleic acids or genes encoding chimeric antigen receptor may be randomly inserted into one or more promoters existing in the genome of the functionally manipulated immune cell.

Here, the nucleic acids or genes encoding chimeric antigen receptor may be randomly inserted into one or more enhancers existing in the genome of the functionally manipulated immune cell.

Here, the nucleic acids or genes encoding chimeric antigen receptor may be randomly inserted into one or more regions other than introns, exons, promoters, and enhancers existing in the genome of the functionally manipulated immune cell.

The chimeric antigen receptor artificially introduced into the functionally manipulated immune cell may be expressed as a form of protein in the hybrid manipulated immune cell, and the protein-expressed chimeric antigen receptor may be located on the surface of the hybrid manipulated immune cell. Here, the functionally manipulated immune cell in which nucleic acids or genes encoding chimeric antigen receptor are artificially introduced may be a form of the hybrid manipulated immune cell.

In another example, the hybrid manipulated immune cell may be an immune cell produced by artificially introducing one or more chimeric antigen receptor proteins into a functionally manipulated immune cell.

The chimeric antigen receptor protein artificially introduced to the functionally manipulated immune cell may be located on the surface of a hybrid manipulated immune cell. Here, the functionally manipulated immune cell in which chimeric antigen receptor protein is artificially introduced may be a form of the hybrid manipulated immune cell.

In another example, the hybrid manipulated immune cell may be an artificial structure supplemented immune cell including one or more artificially manipulated or modified immunity regulating gene.

Here, the artificial structure supplemented immune cell may be an immune cell including an artificial receptor. The artificial receptor may be a chimeric antigen receptor.

The artificial structure supplemented immune cell including one or more artificially manipulated or modified immunity regulating gene may have suppressed or inhibited expression of immune regulatory factor. Here, the artificial structure supplemented immune cell in which one or more immunity regulating genes are artificially modified may be a form of a hybrid manipulated immune cell.

In yet another example, the hybrid manipulated immune cell may be an artificial structure supplemented immune cell in which expression of one or more immune regulatory factors is suppressed or inhibited.

An aspect disclosed by the present specification relates to a method of producing manipulated immune cells.

The explanation described above may be referenced for the explanation related to the artificially modified immunity regulating gene. Hereinafter, the method will be explained being focused on representative embodiments of manipulated immune cells.

As an example, the method for producing the manipulated immune cell may be a method of producing functionally manipulated immune cell. The method may be carried out in vivo, ex vivo or in vitro.

In some embodiments, the method includes sample-extracting a cell or a cell group from humans or nonhuman animals, and modifying the cell or the cells. Cultivation may take place at any step, ex vivo. The cell or the cells may even be reintroduced to the nonhuman animals or plants.

In an embodiment, the method may be a method for producing functionally manipulated immune cells including one or more artificially manipulated immunity regulating genes, including contacting the following:

(a) an immune cell;

(b) a composition for gene manipulation capable of artificially manipulating at least one immunity regulating gene selected from the group consisting of PD-1 gene, CTLA-4 gene, DGKA gene, DGKZ gene, FAS gene, EGR2 gene, PPP2r2d gene, TET2 gene, PSGL-1 gene, A20 gene, and KDM6A gene.

Here, the (a) immune cell may be isolated from a human body, or may be an immune cell differentiated from a stem cell.

The (b) composition for gene manipulation comprises the following:

(b') a guide nucleic acid that is homologous or capable of forming a complementary bond to the target sequences of SEQ ID NOS: 1 to 289 in nucleic acid sequences of one or more genes selected from the group consisting of PD-1 gene, CTLA-4 gene, DGKA gene, DGKZ gene, FAS gene, EGR2 gene, PPP2r2d gene, TET2 gene, PSGL-1 gene, A20 gene, and KDM6A gene; and (b") an editor protein which is one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein.

The explanation of the above composition for gene manipulation is as described above.

The contacting may be performed ex vivo.

The contacting may include introducing (b) composition for gene manipulation into (a) an immune cell.

The method may be performed in vivo or in vitro, e.g. ex vivo.

For example, the contacting may be performed in vitro and the contacted cells may be returned to the body of the subject after the contacting.

The method may use immune cells in a living body or immune cells isolated from living bodies, for example, human bodies, or artificially produced immune cells. As an example, the contacting cells from a subject suffering from cancer may be included.

The immune cells used in the method may be immune cells derived from mammals including primates (e.g., humans, monkeys, etc.) and rodents (e.g., mice, rats, etc.). For example, the immune cells may be NKT cells, NK cells, T cells, etc. Here, the immune cells may be manipulated immune cells to which immune receptors are supplemented (e.g., chimeric antigen receptors (CAR) or manipulated T-cell receptors (TCR) are supplemented).

The method may be performed in an appropriate medium for immune cells, which can contain serum (e.g., bovine fetal serum or human serum), interleukin-2 (IL-2), insulin, IFN-gamma, IL-4, IL-7, GM-CSF, IL-10, IL-15, TGF-beta, and TNF-alpha; or in an appropriate medium which may contain factors necessary for proliferation and viability, including other additives for growth of cells known to those skilled in the art (e.g., minimal essential media, RPMI Media 1640, or X-vivo-10, -15, -20, (Lonza)), but the medium is not limited thereto.

In another example, the method of producing the manipulated immune cells may be a method of producing hybrid manipulated immune cells. The method may be carried out in vivo, ex vivo or in vitro.

In some embodiments, the method includes sample-extracting a cell or a cell group from humans or nonhuman animals, and modifying the cell or the cells. Cultivation may take place at any step, ex vivo. The cell or the cells may even be reintroduced to the nonhuman animals or plants.

In an embodiment, the method may be a method for producing hybrid manipulated immune cells including one or more artificially manipulated immunity regulating genes and one or more artificial receptors, including contacting the following:

(a) an immune cell;

(b) a composition for artificial receptor expression or an artificial receptor protein; and (c) a composition for gene manipulation capable of artificially manipulating one or more immunity regulating genes selected from the group consisting of PD-1 gene, CTLA-4 gene, DGKA gene, DGKZ gene, FAS gene, EGR2 gene, PPP2r2d gene, TET2 gene, PSGL-1 gene, A20 gene, and KDM6A gene.

The (a) immune cell may be isolated from a human body, or may be an immune cell differentiated from a stem cell.

The (b) composition for artificial receptor expression may be a composition containing a vector having a nucleotide sequence encoding the chimeric antigen receptor.

The (b) composition for artificial receptor expression may be introduced into the immune cell with one or more methods selected from electroporation, liposome, plasmid, viral vector, nanoparticles, and protein translocation domain (PTD) fusion protein method.

For example, the viral vector may be one or more selected from the group consisting of a retrovirus, a lentivirus, an adenovirus, an adeno-associated virus (AAV), a vaccinia virus, a poxvirus or a herpes simplex virus.

The (c) composition for gene manipulation may comprise the following:

(c') a guide nucleic acid that is homologous or capable of forming a complementary bond to the target sequences of SEQ ID NOS: 1 to 289 in nucleic acid sequences of one or more immunity regulating genes selected from the group consisting of PD-1 gene, CTLA-4 gene, DGKA gene, DGKZ gene, FAS gene, EGR2 gene, PPP2r2d gene, TET2 gene, PSGL-1 gene, A20 gene, and KDM6A gene; and (c") an editor protein which is one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein.

The explanation on the above composition for gene manipulation is as described above.

The contacting may be performed ex vivo.

The contacting may sequentially or simultaneously contact (a) an immune cell with (b) a composition for artificial receptor expression and (c) a composition for gene manipulation.

The contacting may sequentially or simultaneously contact (a) an immune cell with (c) a composition for gene manipulation and (b) a composition for artificial receptor expression.

The contacting may include introducing (b) a composition for artificial receptor expression and (c) a composition for gene manipulation into (a) an immune cell.

The method may be carried out in vivo or ex vivo, for example, outside a human body.

For example, the contacting may be performed ex vivo, and the contacted cells may be returned to the body of the subject after the contacting.

The method may employ immune cells or organisms in an organism, for example, immune cells isolated from the human body or artificially produced immune cells. In one example, contacting the cells from the subject suffering from cancer may be included.

The immune cells used in the above method may be immune cells derived from mammals including primates (e.g., humans, monkeys, etc.) and rodents (e.g., mice, rats, etc.). For example, the immune cells may be NKT cells, NK cells, T cells, etc. In particular, the immune cells may be manipulated immune cells to which immune receptors are supplemented (e.g., chimeric antigen receptors (CAR) or manipulated T-cell receptors (TCR) are supplemented).

The method may be performed in an appropriate medium for immune cells, which may contain serum (e.g., bovine fetal serum or human serum), interleukin-2 (IL-2), insulin, IFNgamma, IL-4, IL-7, GM-CSF, IL-10, IL-15, TGF-beta, and TNF-alpha; or in an appropriate medium (e.g., Minimal Essential Media, RPMI Media 1640, or X-vivo-10, -15, -20, (Lonza)) which may contain factors necessary for proliferation and viability, including other additives for growth of cells known to those skilled in the art, but the medium is not limited thereto.

An aspect disclosed by the present specification relates to a method of disease treatment using the manipulated immune cells.

An embodiment disclosed by the present specification is the use for disease treatment using an immunotherapy approach which includes administration of artificially modified cells for a subject, for example, genetically modified immune cells containing chimeric antigen receptors.

The subject to be treated may be mammals including primates (e.g., humans, monkeys, etc.) and rodents (e.g., mice, rats, etc.)

An embodiment disclosed by the present specification is a pharmaceutical composition to be used in disease treatment using artificially modified immune cells.

The pharmaceutical composition may be used in disease treatment using immune responses. For example, the pharmaceutical composition is a composition containing modified immune cells. The pharmaceutical composition may be referred to as composition for treatment or cell therapy product.

In one example, the pharmaceutical composition may include functionally modified immune cells.

Here, the functionally modified immune cell population included in the pharmaceutical composition may take 50% to 60%, 60% to 70%, 70% to 80%, 80% to 90%, or 90% to 100% portion of the total immune cell population included in the pharmaceutical composition.

In another example, the pharmaceutical composition may include hybrid manipulated immune cells.

Here, the functionally modified immune cell population include d in the pharmaceutical composition may take 50% to 60%, 60% to 70%, 70% to 80%, 80% to 90%, or 90% to 100% portion of the total immune cell population included in the pharmaceutical composition.

In yet another example, the pharmaceutical composition may include functionally manipulated immune cells and hybrid manipulated immune cells.

Here, the functionally modified immune cell population included in the pharmaceutical composition may take 1% to 20%, 20% to 60%, 60% to 80%, or 80% to 99% portion of the total immune cell population included in the pharmaceutical composition, and in this case, the hybrid modified immune cell population contained in the pharmaceutical composition may take 80% to 99%, 60% to 80%, 40% to 60%, 20% to 40% or 1% to 20% portion of the total immune cell population included in the pharmaceutical composition.

Here, the pharmaceutical composition may further include an additional component.

For example, the pharmaceutical composition may include an immune checkpoint inhibitor.

Here, the immune checkpoint inhibitor may be an inhibitor of PD-1, PD-L1, LAG-3, TIM-3, CTLA-4, TIGIT, BTLA, IDO, VISTA, ICOS, KIRs, CD160, CD244, or CD39. Here, the inhibitor may be, but is not limited to, an antibody; a compound; nucleic acid, peptide, polypeptide or protein capable of binding or interacting with immune checkpoint; microRNA (miRNA), small interfering RNA (siRNA) or short hairpin RNA (shRNA) for RNA interference (RNAi); or nucleases for knockout or knockdown of the immune checkpoint gene, such as Zinc finger nuclease (ZFN), Transcription activator-like effector nucleases (TALEN) or CRISPR/Cas.

The pharmaceutical composition may include antigen binding mediator.

The pharmaceutical composition may include cytokine.

The pharmaceutical composition may include cytokine secretion stimulant or suppressant.

The pharmaceutical composition may include an appropriate carrier for delivering the manipulated immune cells into a body.

Here, the immune cells included in the pharmaceutical composition may be autologous cells of the patient or allogeneic cells of the patient.

Another embodiment disclosed by the present specification is a method for treating disease in a patient including production of the pharmaceutical composition explained above and administration of the pharmaceutical composition to the patients needed thereof Disease to be Treated The disease may be an immune disease.

In particular, immune disease may be a disease in which immune competence is deteriorated.

The immune disease may be an autoimmune disease.

For example, the autoimmune disease may include graft versus host disease (GVHD), systemic lupus erythematosus, celiac disease, diabetes mellitus type 1, graves disease, inflammatory bowel disease, psoriasis, rheumatoid arthritis, multiple sclerosis, etc.

Additionally, the disease may be an intractable disease in which pathogens are known but the treatment is unknown.

The intractable disease may be a virus infectious disea cancse.

The intractable disease may be a prion pathogen-derived disease.

The intractable disease may be a cancer.

Immunity-Enhancing Treatment

For patients with significantly decreased immunity, even mild infections can result in fatal consequences. Decreased immunity is caused by the functional decline of immune cells, a decreased amount of immune cell production, etc. As methods for enhancing immunity to treat the deterioration in immune function, one may be a permanent treatment method that activates the production of normal immune cells, and the other may be a temporary treatment method in which immune cells are temporarily injected.

The immunity-enhancing treatment may be intended to inject the therapeutic composition into the body of a patient to permanently enhance the immunity.

The immunity-enhancing treatment may be a method of injecting the therapeutic composition into a specific body part of the patient. In particular, the specific body part may be a part having tissues supply immune cell sources.

The immunity-enhancing treatment may be to create a new source of immune cells in the body of the patient. In particular, in one example, the therapeutic composition may include stem cells. In particular, the stem cells may be hematopoietic stem cells.

The immunity-enhancing treatment may be intended to inject the therapeutic composition into the body of a patient to temporarily enhance the immunity.

The immunity-enhancing treatment may be to inject a therapeutic composition into the body of a patient.

In particular, a preferred therapeutic composition may contain differentiated immune cells.

The therapeutic composition used in the immunity-enhancing treatment may contain a specific number of immune cells.

The specific number may vary depending on the degree of deterioration of the immunity.

The specific number may vary depending on the volume of the body.

The specific number can be adjusted according to the amount of cytokines released from the patient.

Treatment of Refractory Disease

Immune cell manipulation techniques may provide a method for treating diseases in which complete treatment for pathogens such as HIV, prions, and cancer is not known. Although pathogens for these diseases are known, in many cases, these diseases are difficult to treat because there are problems in that antibodies are hardly formed, the diseases are rapidly progressed and inactivate immune system of the patient, and the pathogens have a latent period in the body. Manipulated immune cells may be a powerful means to solve these problems.

Treatment of refractory disease may be performed by injecting the therapeutic composition into the body. In particular, a preferred therapeutic composition may contain manipulated immune cells. In addition, the therapeutic composition may be injected into a specific part of the body.

Manipulated immune cells may be those in which the immune cells have an improved ability of recognizing the pathogen of the target disease.

Manipulated immune cells may be those in which the intensity or activity of the immune response is enhanced.

Gene-Correction Treatment

In addition to the treatment method using exogenously extracted immune cells, there may be a treatment method that directly affects the expression of immune cells by manipulating the gene of a living body. Such a treatment method may be achieved by directly injecting a gene-correction composition for manipulating a gene into the body.

The gene-correction composition may contain a guide nucleic acid-editor protein complex.

The gene-correction composition may be injected into a specific part of the body.

The specific part of the body can be an immune cell source, for example, bone marrow.

The subject to be administered may be a mammal including primates, e.g., humans, monkeys, etc.; and rodents, e.g., mice, rats, etc.

Administration of the composition may be performed in any convenient manner, e.g., injection, transfusion, implantation, transplantation, etc. The route of administration may be selected from subcutaneous, intradermal, intratumoral, intranodal, intramedullary, intramuscular, intravenous, intralymphatic, intraperitoneal administrations, etc.

A single dose of the composition (a pharmaceutically effective amount for achieving the desired effect) may be selected from among all the integer values in the range of about $10^4$ to $10^9$ cells/kg of body weight of the subject (e.g., about $10^5$ to $10^6$ cells/kg (body weight)) to be administered, but the dose is not limited thereto, and the single dose of the composition may be appropriately prescribed considering the age, health conditions and weight of the subject to be administered, kind of concurrent treatment, if any, frequency of treatment, and the nature of the desired effect.

For example, when the immunity regulating genes are artificially manipulated and controlled by the composition for gene manipulation disclosed by the present specification, the immune efficacies involved in survival, proliferation, persistency, cytotoxicity, cytokine-release and/or infiltration, etc. of immune cells may be improved. Additionally, immune diseases and intractable diseases may be alleviated or cured by the pharmaceutical compositions including the manipulated immune cells disclosed by the present specification and the treatment methods using the pharmaceutical compositions

EXPERIMENTAL EXAMPLES

1. Design of sgRNA

CRISPR/Cas9 target regions of human PD-1 gene (PDCD1; NCBI Accession No. NM_005018.2), CTLA-4 gene (NCBI Accession No. NM_001037631.2), A20 gene (TNFAIP3; NCBI Accession No. NM_001270507.1), Dgk-alpha gene (NCBI Accession No. NM_001345.4), Dgk-zeta gene (NCBI Accession No. NM_001105540.1), Egr2 gene (NCBI Accession No. NM_000399.4), PPP2r2d gene (NCBI Accession No. NM_001291310.1), PSGL-1 gene (NCBI Accession No. NP_001193538.1), and Tet2 gene (NCBI Accession No. NM_017628.4) were selected using CRISPR RGEN Tools (Institute for Basic Science, Korea) and estimated by off-target test. For CRISPR/Cas9 target regions, DNA sequences without 0-, 1-, or 2 bp mismatch sites were selected as target regions of the sgRNA, except for the on-target sequence regions in the human genome (GRCh38/hg38).

2. Synthesis of sgRNA

Templates for sgRNA synthesis were PCR-amplified by annealing and extending two complementary oligonucleotides.

The target regions sequence used at this time, the primer sequence for amplifying them, and the DNA target sequence targeted by the sgRNA obtained therefrom are described in Table 2 below.

In vitro transcription was performed using T7 RNA polymerase (New England Biolabs) for the template DNA (except for NGG' at the 3' end of the target sequence), RNA was synthesized according to the manufacturer's instructions, and then DNAase (Ambion) was used to remove template DNA. The transcribed RNA was purified by Expin Combo kit (GeneAll) and isopropanol precipitation In experiments using T cells, in order to minimize the immunogenicity and degradation of sgRNA, the 5'terminal phosphate residues were removed from the sgRNA synthesized by the above method using alkaline phosphatase (New England Biolabs) and then the RNA was purified again by the Expin Combo kit (GeneAll) and isopropanol precipitation. In addition, chemically synthesized sgRNA (Trilink) was used in some T cell experiments.

The chemically synthesized sgRNA used in a certain example was sgRNA modified with 2'OMe and phosphorothioate.

For example, DGKα sgRNA #11 used in this example has a structure of 5'-2'OMe(C(ps)U(ps)C(ps)) UCA AGC UGA GUG GGU CCG UUU UAG AGC UAG AAA UAG CAA GUU AAA AUA AGG CUA GUC CGU UAU CAA CUU GAA AAA GUG GCA CCG AGU CGG UGC 2'OMe(U (ps)U(ps)U(ps)U-3' (2'OMe=2'-methyl RNA and ps=phosphorothioate).

In another example, A20 sgRNA #1 used in this embodiment is GCUUGUGGCGCUGAAAACGAAGUUUUA-GAGCUAGAAAUAGCAAGUUAAAAUAAGGCUA GUCCGUUAUCAACUUGAAAAAGUGGCACCGAGU CGGUGCUUUUUUU (the bold part is the sequence being that hybridizes to the target sequence region; sgRNA for other target gene or other target sequence is that the bold sequence has a target sequence (just, T is changed to U)), modified thereof in which the three nucleotides at the 3'end of the sequence and the three nucleotides at the 5' end is modified with 2'-OMe and a phosphorothioate backbone introduction.

TABLE 2

| Gene | # | DNA target sequence | Forward primer sequence | Reverse primer | SEQ ID NO |
|---|---|---|---|---|---|
| A20 | 1 | CTTGTGGCGCTGA AAACGAACGG | GAAATTAATACGAC TCACTATAGCTTGT GGCGCTGAAAACG AAGTTTTAGAGCTA GAAATAGC | AAAAAAAGC ACCGACTCG GTGCCACTTT TTCAAGTTGA TAACGGACT AGCCTTATTT TAACTTGCTA TTTCTAGCTC TAAAAC | SEQ ID NO 1 |
| | 2 | ATGCCACTTCTCA GTACATGTGG | GAAATTAATACGAC TCACTATAGATGCC ACTTCTCAGTACAT GGTTTTAGAGCTAG AAATAGC | | SEQ ID NO 2 |
| | 3 | GCCACTTCTCAGT ACATGTGGGG | GAAATTAATACGAC TCACTATAGGCCAC TTCTCAGTACATGT GGTTTTAGAGCTAG AAATAGC | | SEQ ID NO 3 |
| | 4 | GCCCCACATGTAC TGAGAAGTGG | GAAATTAATACGAC TCACTATAGGCCCC ACATGTACTGAGAA GGTTTTAGAGCTAG AAATAGC | | SEQ ID NO 4 |
| | 5 | TCAGTACATGTGG GGCGTTCAGG | GAAATTAATACGAC TCACTATAGTCAGT ACATGTGGGGCGTT CGTTTTAGAGCTAG AAATAGC | | SEQ ID NO 5 |
| | 6 | **GGGCGTTCAGGA CACAGACTTGG** | GAAATTAATACGAC TCACTATAGGGGCG TTCAGGACACAGAC TGTTTTAGAGCTAG AAATAGC | | SEQ ID NO 6 |
| | 7 | CACAGACTTGGTA CTGAGGAAGG | GAAATTAATACGAC TCACTATAGCACAG ACTTGGTACTGAGG AGTTTTAGAGCTAG AAATAGC | | SEQ ID NO 7 |
| | 8 | GGCGCTGTTCAGC ACGCTCAAGG | GAAATTAATACGAC TCACTATAGGGCGC TGTTCAGCACGCTC AGTTTTAGAGCTAG AAATAGC | | SEQ ID NO 8 |
| | 9 | CACGCAACTTTAA ATTCCGCTGG | GAAATTAATACGAC TCACTATAGCACGC AACTTTAAATTCCG CGTTTTAGAGCTAG AAATAGC | | SEQ ID NO 9 |
| | 10 | CGGGGCTTTGCTA TGATACTCGG | GAAATTAATACGAC TCACTATAGCGGGG CTTTGCTATGATACT GTTTTAGAGCTAGA AATAGC | | SEQ ID NO 10 |
| | 11 | **GGCTTCCACAGA CACACCCATGG** | GAAATTAATACGAC TCACTATAGGGCTT CCACAGACACACCC AGTTTTAGAGCTAG AAATAGC | | SEQ ID NO 11 |
| | 12 | TGAAGTCCACTTC GGGCCATGGG | GAAATTAATACGAC TCACTATAGTGAAG TCCACTTCGGGCCA TGTTTTAGAGCTAG AAATAGC | | SEQ ID NO 12 |
| DGKα | 1 | CTGTACGACACG GACAGAAATGG | GAAATTAATACGAC TCACTATAGCTGTA CGACACGGACAGA AAGTTTTAGAGCTA GAAATAGC | AAAAAAAGC ACCGACTCG GTGCCACTTT TTCAAGTTGA TAACGGACT AGCCTTATTT TAACTTGCTA TTTCTAGCTC TAAAAC | SEQ ID NO 13 |
| | 2 | TGTACGACACGG ACAGAAATGGG | GAAATTAATACGAC TCACTATAGTGTAC GACACGGACAGAA ATGTTTTAGAGCTA GAAATAGC | | SEQ ID NO 14 |

TABLE 2-continued

| Gene | # | DNA target sequence | Forward primer sequence | Reverse primer | SEQ ID NO |
|---|---|---|---|---|---|
| | 3 | CACGGACAGAAA TGGGATCCTGG | GAAATTAATACGAC TCACTATAGCACGG ACAGAAATGGGATC CGTTTTAGAGCTAG AAATAGC | | SEQ ID NO 15 |
| | 4 | GATGCGAGTGGC TGAATACCTGG | GAAATTAATACGAC TCACTATAGGATGC GAGTGGCTGAATAC CGTTTTAGAGCTAG AAATAGC | | SEQ ID NO 16 |
| | 5 | GAGTGGCTGAAT ACCTGGATTGG | GAAATTAATACGAC TCACTATAGGAGTG GCTGAATACCTGGA TGTTTTAGAGCTAG AAATAGC | | SEQ ID NO 17 |
| | 6 | AGTGGCTGAATAC CTGGATTGGG | GAAATTAATACGAC TCACTATAGAGTGG CTGAATACCTGGAT TGTTTTAGAGCTAG AAATAGC | | SEQ ID NO 18 |
| | 7 | **ATTGGGATGTGT CTGAGCTGAGG** | GAAATTAATACGAC TCACTATAGATTGG GATGTGTCTGAGCT GGTTTTAGAGCTAG AAATAGC | | SEQ ID NO 19 |
| | 8 | **ATGAAAGAGATT GACTATGATGG** | GAAATTAATACGAC TCACTATAGATGAA AGAGATTGACTATG AGTTTTAGAGCTAG AAATAGC | | SEQ ID NO 20 |
| | 9 | **CTCTGTCTCTCAA GCTGAGTGGG** | GAAATTAATACGAC TCACTATAGCTCTG TCTCTCAAGCTGAG TGTTTTAGAGCTAG AAATAGC | | SEQ ID NO 21 |
| | 10 | TCTCTCAAGCTGA GTGGGTCCGG | GAAATTAATACGAC TCACTATAGTCTCTC AAGCTGAGTGGGTC GTTTTAGAGCTAGA AATAGC | | SEQ ID NO 22 |
| | 11 | **CTCTCAAGCTGA GTGGGTCCGGG** | GAAATTAATACGAC TCACTATAGCTCTC AAGCTGAGTGGGTC CGTTTTAGAGCTAG AAATAGC | | SEQ ID NO 23 |
| | 12 | CAAGCTGAGTGG GTCCGGGCTGG | GAAATTAATACGAC TCACTATAGCAAGC TGAGTGGGTCCGG GCGTTTTAGAGCTA GAAATAGC | | SEQ ID NO 24 |
| EGR2 | 1 | **TTGACATGACTG GAGAGAAGAGG** | GAAATTAATACGAC TCACTATAGTTGAC ATGACTGGAGAGA AGGTTTTAGAGCTA GAAATAGC | AAAAAAAGC ACCGACTCG GTGCCACTTT TTCAAGTTGA TAACGGACT | SEQ ID NO 25 |
| | 2 | GACTGGAGAGAA GAGGTCGTTGG | GAAATTAATACGAC TCACTATAGGACTG GAGAGAAGAGGTC GTGTTTTAGAGCTA GAAATAGC | AGCCTTATTT TAACTTGCTA TTTCTAGCTC TAAAAC | SEQ ID NO 26 |
| | 3 | GAGACGGGAGCA AAGCTGCTGGG | GAAATTAATACGAC TCACTATAGGAGAC GGGAGCAAAGCTG CTGTTTTAGAGCTA GAAATAGC | | SEQ ID NO 27 |
| | 4 | AGAGACGGGAGC AAAGCTGCTGG | GAAATTAATACGAC TCACTATAGAGAGA CGGGAGCAAAGCT GCGTTTTAGAGCTA GAAATAGC | | SEQ ID NO 28 |
| | 5 | TGGTTTCTAGGTG CAGAGACGGG | GAAATTAATACGAC TCACTATAGTGGTTT CTAGGTGCAGAGAC GTTTTAGAGCTAGA AATAGC | | SEQ ID NO 29 |

TABLE 2-continued

| Gene | # | DNA target sequence | Forward primer sequence | Reverse primer | SEQ ID NO |
|---|---|---|---|---|---|
| | 6 | TAAGTGAAGGTCT GGTTTCTAGG | GAAATTAATACGAC TCACTATAGTAAGT GAAGGTCTGGTTTC TGTTTTAGAGCTAG AAATAGC | | SEQ ID NO 30 |
| | 7 | TGCCCATGTAAGT GAAGGTCTGG | GAAATTAATACGAC TCACTATAGTGCCC ATGTAAGTGAAGGT CGTTTTAGAGCTAG AAATAGC | | SEQ ID NO 31 |
| | 8 | GAACTTGCCCATG TAAGTGAAGG | GAAATTAATACGAC TCACTATAGGAACT TGCCCATGTAAGTG AGTTTTAGAGCTAG AAATAGC | | SEQ ID NO 32 |
| | 9 | TCCATTGACCCTC AGTACCCTGG | GAAATTAATACAC TCACTATAGTCCATT GACCCTCAGTACCC GTTTTAGAGCTAGA AATAGC | | SEQ ID NO 33 |
| | 10 | TATGCCTTCTGGG ATGCAGCTGG | GAAATTAATACGAC TCACTATAGTATGC CTTCTGGGTAGCAG CGTTTTAGAGCTAG AAATAGC | | SEQ ID NO 34 |
| | 11 | TGAGTGCAGGCAT CTTGCAAGGG | GAAATTAATACGAC TCACTATAGTGAGT GCAGGCATCTTGCA AGTTTTAGAGCTAG AAATAGC | | SEQ ID NO 35 |
| | 12 | GAGTGCAGGCAT CTTGCAAGGGG | GAAATTAATACGAC TCACTATAGGAGTG CAGGCATCTTGCAA GGTTTTAGAGCTAG AAATAGC | | SEQ ID NO 36 |
| | 13 | GATGAGGCTGTG GTTGAAGCTGG | GAAATTAATACGAC TCACTATAGGATGA GGCTGTGGTTGAAG CGTTTTAGAGCTAG AAATAGC | | SEQ ID NO 37 |
| | 14 | CCACTGGCCACA GGACCCCTGGG | GAAATTAATACGAC TCACTATAGCCACT GGCCACAGGACCC CTGTTTTAGAGCTA GAAATAGC | | SEQ ID NO 38 |
| | 15 | GGGACATGGTGC ACACACCCAGG | GAAATTAATACGAC TCACTATAGGGGAC ATGGTGCACACACC CGTTTTAGAGCTAG AAATAGC | | SEQ ID NO 39 |
| | 16 | GAGTACAGGTGG TCCAGGTCAGG | GAAATTAATACGAC TCACTATAGGAGTA CAGGTGGTCCAGGT CGTTTTAGAGCTAG AAATAGC | | SEQ ID NO 40 |
| | 17 | GCGGAGAGTACA GGTGGTCCAGG | GAAATTAATACGAC TCACTATAGGCGGA GAGTACAGGTGGTC CGTTTTAGAGCTAG AAATAGC | | SEQ ID NO 41 |
| | 18 | GCGGTGGCGGAG AGTACAGGTGG | GAAATTAATACGAC TCACTATAGGCGGT GGCGGAGAGTACA GGGTTTTAGAGCTA GAAATAGC | | SEQ ID NO 42 |
| | 19 | TCTCCTGCACAGC CAGAATAAGG | GAAATTAATACGAC TCACTATAGTCTCCT GCACAGCCAGAAT AGTTTTAGAGCTAG AAATAGC | | SEQ ID NO 43 |
| | 20 | ACGCAGAAGGGT CCTGGTAGAGG | GAAATTAATACGAC TCACTATAGACGCA GAAGGGTCCTGGTA GGTTTTAGAGCTAG AAATAGC | | SEQ ID NO 44 |
| | 21 | AGGTGGTGGGTA GGCCAGAGAGG | GAAATTAATACGAC TCACTATAGAGGTG | | SEQ ID NO 45 |

TABLE 2-continued

| Gene | # | DNA target sequence | Forward primer sequence | Reverse primer | SEQ ID NO |
|---|---|---|---|---|---|
| | | | GTGGGTAGGCCAG AGGTTTTAGAGCTA GAAATAGC | | |
| | 22 | CCCAAGCCAGCC ACGGACCCAGG | GAAATTAATACGAC TCACTATAGCCCAA GCCAGCCACGGAC CCGTTTTAGAGCTA GAAATAGC | | SEQ ID NO 46 |
| | 23 | ACCTGGGTCCGTG GCTGGCTTGG | GAAATTAATACGAC TCACTATAGACCTG GGTCCGTGGCTGGC TGTTTTAGAGCTAG AAATAGC | | SEQ ID NO 47 |
| | 24 | AAGAGACCTGGG TCCGTGGCTGG | GAAATTAATACGAC TCACTATAGAAGAG ACCTGGGTCCGTGG CGTTTTAGAGCTAG AAATAGC | | SEQ ID NO 48 |
| | 25 | GGATCATTGGGA AGAGACCTGGG | GAAATTAATACGAC TCACTATAGGGATC ATTGGGAAGAGAC CTGTTTTAGAGCTA GAAATAGC | | SEQ ID NO 49 |
| | 26 | GGGATCATTGGG AAGAGACCTGG | GAAATTAATACGAC TCACTATAGGGGAT CATTGGGAAGAGA CCGTTTTAGAGCTA GAAATAGC | | SEQ ID NO 50 |
| | 27 | CAGGATAGTCTGG GATCATTGGG | GAAATTAATACGAC TCACTATAGCAGGA TAGTCTGGGATCAT TGTTTTAGAGCTAG AAATAGC | | SEQ ID NO 51 |
| | 28 | GGAAAGAATCCA GGATAGTCTGG | GAAATTAATACGAC TCACTATAGGGAAA GAATCCAGGATAGT CGTTTTAGAGCTAG AAATAGC | | SEQ ID NO 52 |
| | 29 | CAGTGCCAGAGA GACCTACATGG | GAAATTAATACGAC TCACTATAGCAGTG CCAGAGAGACCTAC AGTTTTAGAGCTAG AAATAGC | | SEQ ID NO 53 |
| | 30 | CTGTACCATGTAG GTCTCTCTGG | GAAATTAATACGAC TCACTATAGCTGTA CCATGTAGGTCTCT CGTTTTAGAGCTAG AAATAGC | | SEQ ID NO 54 |
| | 31 | AGAGACCTACAT GGTACAGCTGG | GAAATTAATACGAC TCACTATAGAGAGA CCTACATGGTACAG CGTTTTAGAGCTAG AAATAGC | | SEQ ID NO 55 |
| | 32 | CTGGGCCAGCTGT ACCATGTAGG | GAAATTAATACGAC TCACTATAGCTGGG CCAGCTGTACCATG TGTTTTAGAGCTAG AAATAGC | | SEQ ID NO 56 |
| | 33 | AGGGAAAGGGCT TACGGTCTGGG | GAAATTAATACGAC TCACTATAGAGGGA AAGGGCTTACGGTC TGTTTTAGAGCTAG AAATAGC | | SEQ ID NO 57 |
| | 34 | CAGGGAAAGGGC TTACGGTCTGG | GAAATTAATACGAC TCACTATAGCAGGG AAAGGGCTTACGGT CGTTTTAGAGCTAG AAATAGC | | SEQ ID NO 58 |
| PPP2R2D | 5 | TCTGGAGATCTTC TTGCAACAGG | GAAATTAATACGAC TCACTATAGTCTGG AGATCTTCTTGCAA CGTTTTAGAGCTAG AAATAGC | | SEQ ID NO 59 |
| | 6 | CTCCGGTTCATGA CTTTGAAAGG | GAAATTAATACGAC TCACTATAGCTCCG GTTCATGACTTTGA | | SEQ ID NO 60 |

TABLE 2-continued

| Gene | # | DNA target sequence | Forward primer sequence | Reverse primer | SEQ ID NO |
|---|---|---|---|---|---|
| | | | AGTTTTAGAGCTAG AAATAGC | | |
| | 7 | GTCTTCCATCTTC GTCTTTCAGG | GAAATTAATACGAC TCACTATAGGTCTT CCATCTTCGTCTTTC GTTTTAGAGCTAGA AATAGC | | SEQ ID NO 61 |
| | 8 | GAAGACTTCGAG ACCCATTTAGG | GAAATTAATACGAC TCACTATAGGAAGA CTTCGAGACCCATT TGTTTTAGAGCTAG AAATAGC | | SEQ ID NO 62 |
| | 9 | TCGAGACCCATTT AGGATCACGG | GAAATTAATACGAC TCACTATAGTCGAG ACCCATTTAGGATC AGTTTTAGAGCTAG AAATAGC | | SEQ ID NO 63 |
| | 10 | **GTAGCGCCGTGA TCCTAAATGGG** | GAAATTAATACGAC TCACTATAGGTAGC GCCGTGATCCTAAA TGTTTTAGAGCTAG AAATAGC | | SEQ ID NO 64 |
| | 11 | CGTAGCGCCGTG ATCCTAAATGG | GAAATTAATACGAC TCACTATAGCGTAG CGCCGTGATCCTAA AGTTTTAGAGCTAG AAATAGC | | SEQ ID NO 65 |
| | 12 | CATTTAGGATCAC GGCGCTACGG | GAAATTAATACGAC TCACTATAGCATTTA GGATCACGGCGCTA GTTTTAGAGCTAGA AATAGC | | SEQ ID NO 66 |
| | 13 | GGTCCCAATATTG AAGCCCATGG | GAAATTAATACGAC TCACTATAGGGTCC CAATATTGAAGCCC AGTTTTAGAGCTAG AAATAGC | | SEQ ID NO 67 |
| | 14 | GATCCATGGGCTT CAATATTGGG | GAAATTAATACGAC TCACTATAGGATCC ATGGGCTTCAATAT TGTTTTAGAGCTAG AAATAGC | | SEQ ID NO 68 |
| | 15 | AGATCCATGGGCT TCAATATTGG | GAAATTAATACGAC TCACTATAGAGATC CATGGGCTTCAATA TGTTTTAGAGCTAG AAATAGC | | SEQ ID NO 69 |
| | 16 | GCTTCTACCATAA GATCCATGGG | GAAATTAATACGAC TCACTATAGGCTTC TACCATAAGATCCA TGTTTTAGAGCTAG AAATAGC | | SEQ ID NO 70 |
| | 17 | CGCTTCTACCATA AGATCCATGG | GAAATTAATACGAC TCACTATAGCGCTT CTACCATAAGATCC AGTTTTAGAGCTAG AAATAGC | | SEQ ID NO 71 |
| | 18 | GCATTTGCAAAAA TTCGCCGTGG | GAAATTAATACGAC TCACTATAGGCATT TGCAAAAATTCGCC GGTTTTAGAGCTAG AAATAGC | | SEQ ID NO 72 |
| | 19 | ATGACCTGAGAAT TAATTTATGG | GAAATTAATACGAC TCACTATAGATGAC CTGAGAATTAATTT AGTTTTAGAGCTAG AAATAGC | | SEQ ID NO 73 |
| | 20 | CCATGCACTCCCA GACATCGTGG | GAAATTAATACGAC TCACTATAGCCATG CACTCCCAGACATC GGTTTTAGAGCTAG AAATAGC | | SEQ ID NO 74 |
| | 21 | GCACTGGTGCGG GTGGAACTCGG | GAAATTAATACGAC TCACTATAGGCACT GGTGCGGGTGGAA CTGTTTTAGAGCTA GAAATAGC | | SEQ ID NO 75 |

TABLE 2-continued

| Gene | # | DNA target sequence | Forward primer sequence | Reverse primer | SEQ ID NO |
|---|---|---|---|---|---|
| | 22 | ACACGTTGCACTG GTGCGGGTGG | GAAATTAATACGAC TCACTATAGACACG TTGCACTGGTGCGG GGTTTTAGAGCTAG AAATAGC | | SEQ ID NO 76 |
| | 23 | CGAACACGTTGCA CTGGTGCGGG | GAAATTAATACGAC TCACTATAGCGAAC ACGTTGCACTGGTG CGTTTTAGAGCTAG AAATAGC | | SEQ ID NO 77 |
| | 24 | ACGAACACGTTGC ACTGGTGCGG | GAAATTAATACGAC TCACTATAGACGAA CACGTTGCACTGGT GGTTTTAGAGCTAG AAATAGC | | SEQ ID NO 78 |
| | 25 | TGTAGACGAACA CGTTGCACTGG | GAAATTAATACGAC TCACTATAGTGTAG ACGAACACGTTGCA CGTTTTAGAGCTAG AAATAGC | | SEQ ID NO 79 |
| | 26 | GCGCATGTCACAC AGGCGGATGG | GAAATTAATACGAC TCACTATAGGCGCA TGTCACACAGGCGG AGTTTTAGAGCTAG AAATAGC | | SEQ ID NO 80 |
| | 27 | AGGAGCGCATGT CACACAGGCGG | GAAATTAATACGAC TCACTATAGAGGAG CGCATGTCACACAG GGTTTTAGAGCTAG AAATAGC | | SEQ ID NO 81 |
| | 28 | CCGAGGAGCGCA TGTCACACAGG | GAAATTAATACGAC TCACTATAGCCGAG GAGCGCATGTCACA CGTTTTAGAGCTAG AAATAGC | | SEQ ID NO 82 |
| | 29 | CCTGTGTGACATG CGCTCCCTCGG | GAAATTAATACGAC TCACTATAGCCTGT GTGACATGCGCTCC TGTTTTAGAGCTAG AAATAGC | | SEQ ID NO 83 |
| PD-1 | 1 | CGACTGGCCAGG GCGCCTGTGGG | GAAATTAATACGAC TCACTATAGCGACT GGCCAGGGCGCCT GTGTTTTAGAGCTA GAAATAGC | AAAAAAAGC ACCGACTCG GTGCCACTTT TTCAAGTTGA TAACGGACT | SEQ ID NO 84 |
| | 2 | ACCGCCCAGACG ACTGGCCAGGG | GAAATTAATACGAC TCACTATAGACCGC CCAGACGACTGGCC AGTTTTAGAGCTAG AAATAGC | AGCCTTATTT TAACTTGCTA TTTCTAGCTC TAAAAC | SEQ ID NO 85 |
| | 3 | CACCGCCCAGAC GACTGGCCAGG | GAAATTAATACGAC TCACTATAGCACCG CCCAGACGACTGGC CGTTTTAGAGCTAG AAATAGC | | SEQ ID NO 86 |
| | 4 | **GTCTGGGCGGTG CTACAACTGGG** | GAAATTAATACGAC TCACTATAGGTCTG GGCGGTGCTACAAC TGTTTTAGAGCTAG AAATAGC | | SEQ ID NO 87 |
| | 5 | CTACAACTGGGCT GGCGGCCAGG | GAAATTAATACGAC TCACTATAGCTACA ACTGGGCTGGCGG CCGTTTTAGAGCTA GAAATAGC | | SEQ ID NO 88 |
| | 6 | **CACCTACCTAAG AACCATCCTGG** | GAAATTAATACGAC TCACTATAGCACCT ACCTAAGAACCATC CGTTTTAGAGCTAG AAATAGC | | SEQ ID NO 89 |
| | 7 | CGGTCACCACGA GCAGGGCTGGG | GAAATTAATACGAC TCACTATAGCGGTC ACCACGAGCAGGG CTGTTTTAGAGCTA GAAATAGC | | SEQ ID NO 90 |

TABLE 2-continued

| Gene | # | DNA target sequence | Forward primer sequence | Reverse primer | SEQ ID NO |
|---|---|---|---|---|---|
| | 8 | GCCCTGCTCGTGG TGACCGAAGG | GAAATTAATACGAC TCACTATAGGCCCT GCTCGTGGTGACCG AGTTTTAGAGCTAG AAATAGC | | SEQ ID NO 91 |
| | 9 | CGGAGAGCTTCGT GCTAAACTGG | GAAATTAATACGAC TCACTATAGCGGAG AGCTTCGTGCTAAA CGTTTTAGAGCTAG AAATAGC | | SEQ ID NO 92 |
| | 10 | CAGCTTGTCCGTC TGGTTGCTGG | GAAATTAATACGAC TCACTATAGCAGCT TGTCCGTCTGGTTG CGTTTTAGAGCTAG AAATAGC | | SEQ ID NO 93 |
| | 11 | AGGCGGCCAGCT TGTCCGTCTGG | GAAATTAATACGAC TCACTATAGAGGCG GCCAGCTTGTCCGT CGTTTTAGAGCTAG AAATAGC | | SEQ ID NO 94 |
| | 12 | CCGGGCTGGCTG CGGTCCTCGGG | GAAATTAATACGAC TCACTATAGCCGGG CTGGCTGCGGTCCT CGTTTTAGAGCTAG AAATAGC | | SEQ ID NO 95 |
| | 13 | CGTTGGGCAGTTG TGTGACACGG | GAAATTAATACGAC TCACTATAGCGTTG GGCAGTTGTGTGAC AGTTTTAGAGCTAG AAATAGC | | SEQ ID NO 96 |
| CTLA-4 | 1 | CATAAAGCCATG GCTTGCCTTGG | GAAATTAATACGAC TCACTATAGCATAA AGCCATGGCTTGCC TGTTTTAGAGCTAG AAATAGC | AAAAAAAGC ACCGACTCG GTGCCACTTT TTCAAGTTGA TAACGGACT | SEQ ID NO 97 |
| | 2 | CCTTGGATTTCAG CGGCACAAGG | GAAATTAATACGAC TCACTATAGCCTTG GATTTCAGCGGCAC AGTTTTAGAGCTAG AAATAGC | AGCCTTATTT TAACTTGCTA TTTCTAGCTC TAAAAC | SEQ ID NO 98 |
| | 3 | CCTTGTGCCGCTG AAATCCAAGG | GAAATTAATACGAC TCACTATAGCCTTG TGCCGCTGAAATCC AGTTTTAGAGCTAG AAATAGC | | SEQ ID NO 99 |
| | 4 | CACTCACCTTTGC AGAAGACAGG | GAAATTAATACGAC TCACTATAGCACTC ACCTTTGCAGAAGA CGTTTTAGAGCTAG AAATAGC | | SEQ ID NO 100 |
| | 5 | TTCCATGCTAGCA ATGCACGTGG | GAAATTAATACGAC TCACTATAGTTCCAT GCTAGCAATGCACG GTTTTAGAGCTAGA AATAGC | | SEQ ID NO 101 |
| | 6 | GGCCACGTGCATT GCTAGCATGG | GAAATTAATACGAC TCACTATAGGGCCA CGTGCATTGCTAGC AGTTTTAGAGCTAG AAATAGC | | SEQ ID NO 102 |
| | 7 | GGCCCAGCCTGCT GTGGTACTGG | GAAATTAATACGAC TCACTATAGGGCCC AGCCTGCTGTGGTA CGTTTTAGAGCTAG AAATAGC | | SEQ ID NO 103 |
| | 8 | AGGTCCGGGTGA CAGTGCTTCGG | GAAATTAATACGAC TCACTATAGAGGTC CGGGTGACAGTGCT TGTTTTAGAGCTAG AAATAGC | | SEQ ID NO 104 |
| | 9 | CCGGGTGACAGT GCTTCGGCAGG | GAAATTAATACGAC TCACTATAGCCGGG TGACAGTGCTTCGG CGTTTTAGAGCTAG AAATAGC | | SEQ ID NO 105 |

TABLE 2-continued

| Gene | # | DNA target sequence | Forward primer sequence | Reverse primer | SEQ ID NO |
|---|---|---|---|---|---|
| | 10 | CTGTGCGGCAACC TACATGATGG | GAAATTAATACGAC TCACTATAGCTGTG CGGCAACCTACATG AGTTTTAGAGCTAG AAATAGC | | SEQ ID NO 106 |
| | 11 | **CAACTCATTCCCC ATCATGTAGG** | GAAATTAATACGAC TCACTATAGCAACT CATTCCCCATCATG TGTTTTAGAGCTAG AAATAGC | | SEQ ID NO 107 |
| | 12 | CTAGATGATTCCA TCTGCACGGG | GAAATTAATACGAC TCACTATAGCTAGA TGATTCCATCTGCA CGTTTTAGAGCTAG AAATAGC | | SEQ ID NO 108 |
| DGKζ | 1 | **GGCTAGGAGTCA GCGACATATGG** | GAAATTAATACGAC TCACTATAGGGCTA GGAGTCAGCGACAT AGTTTTAGAGCTAG AAATAGC | AAAAAAAGC ACCGACTCG GTGCCACTTT TTCAAGTTGA TAACGGACT | SEQ ID NO 109 |
| | 2 | **GCTAGGAGTCAG CGACATATGGG** | GAAATTAATACGAC TCACTATAGGCTAG GAGTCAGCGACATA TGTTTTAGAGCTAG AAATAGC | AGCCTTATTT TAACTTGCTA TTTCTAGCTC TAAAAC | SEQ ID NO 110 |
| | 3 | **CTAGGAGTCAGC GACATATGGGG** | GAAATTAATACGAC TCACTATAGCTAGG AGTCAGCGACATAT GGTTTTAGAGCTAG AAATAGC | | SEQ ID NO 111 |
| | 4 | **GTACTGTGTAGC CAGGATGCTGG** | GAAATTAATACGAC TCACTATAGGTACT GTGTAGCCAGGATG CGTTTTAGAGCTAG AAATAGC | | SEQ ID NO 112 |
| | 5 | **ACGAGCACTCAC CAGCATCCTGG** | GAAATTAATACGAC TCACTATAGACGAG CACTCACCAGCATC CGTTTTAGAGCTAG AAATAGC | | SEQ ID NO 113 |
| | 6 | AGGCTCCAGGAA TGTCCGCGAGG | GAAATTAATACGAC TCACTATAGAGGCT CCAGGAATGTCCGC GGTTTTAGAGCTAGA AATAGC | | SEQ ID NO 114 |
| | 7 | ACTTACCTCGCGG ACATTCCTGG | GAAATTAATACGAC TCACTATAGACTTA CCTCGCGGACATTC CGTTTTAGAGCTAG AAATAGC | | SEQ ID NO 115 |
| | 8 | CACCCTGGGCACT TACCTCGCGG | GAAATTAATACGAC TCACTATAGCACCC TGGGCACTTACCTC GGTTTTAGAGCTAG AAATAGC | | SEQ ID NO 116 |
| | 9 | GTGCCGTACAAA GGTTGGCTGGG | GAAATTAATACGAC TCACTATAGGTGCC GTACAAAGGTTGGC TGTTTTAGAGCTAG AAATAGC | | SEQ ID NO 117 |
| | 10 | GGTGCCGTACAA AGGTTGGCTGG | GAAATTAATACGAC TCACTATAGGGTGC CGTACAAAGGTTGG CGTTTTAGAGCTAG AAATAGC | | SEQ ID NO 118 |
| | 11 | CTCTCCTCAGTAC CACAGCAAGG | GAAATTAATACGAC TCACTATAGCTCTC CTCAGTACCACAGC AGTTTTAGAGCTAG AAATAGC | | SEQ ID NO 119 |
| | 12 | CCTGGGGCCTCC GGGCGCGGAGG | GAAATTAATACGAC TCACTATAGCCTGG GGCCTCCGGGCGC GGGTTTTAGAGCTA GAAATAGC | | SEQ ID NO 120 |

TABLE 2-continued

| Gene | # | DNA target sequence | Forward primer sequence | Reverse primer | SEQ ID NO |
|---|---|---|---|---|---|
| | 13 | AGTACTCACCTGG GGCCTCCGGG | GAAATTAATACGAC TCACTATAGAGTAC TCACCTGGGGCCTC CGTTTTAGAGCTAG AAATAGC | | SEQ ID NO 121 |
| | 14 | AGGGTCTCCAGC GGCCCTCCTGG | GAAATTAATACGAC TCACTATAGAGGGT CTCCAGCGGCCCTC CGTTTTAGAGCTAG AAATAGC | | SEQ ID NO 122 |
| | 15 | GCAAGTACTTACG CCTCCTTGGG | GAAATTAATACGAC TCACTATAGGCAAG TACTTACGCCTCCTT GTTTTAGAGCTAGA AATAGC | | SEQ ID NO 123 |
| | 16 | TTGCGGTACATCT CCAGCCTGGG | GAAATTAATACGAC TCACTATAGTTGCG GTACATCTCCAGCC TGTTTTAGAGCTAG AAATAGC | | SEQ ID NO 124 |
| | 17 | TTTGCGGTACATC TCCAGCCTGG | GAAATTAATACGAC TCACTATAGTTTGC GGTACATCTCCAGC CGTTTTAGAGCTAG AAATAGC | | SEQ ID NO 125 |
| Tet2 | 1 | **GCAAAACCTGTC CACTCTTATGG** | GAAATTAATACGAC TCACTATAGGCAAA ACCTGTCCACTCTT AGTTTTAGAGCTAG AAATAGC | AAAAAAAGC ACCGACTCG GTGCCACTTT TTCAAGTTGA TAACGGACT | SEQ ID NO 126 |
| | 2 | TTGGTGCCATAAG AGTGGACAGG | GAAATTAATACGAC TCACTATAGTTGGT GCCATAAGAGTGG ACGTTTTAGAGCTA GAAATAGC | AGCCTTATTT TAACTTGCTA TTTCTAGCTC TAAAAC | SEQ ID NO 127 |
| | 3 | **GGTGCAAGTTTC TTATATGTTGG** | GAAATTAATACGAC TCACTATAGGGTGC AAGTTTCTTATATGT GTTTTAGAGCTAGA AATAGC | | SEQ ID NO 128 |
| | 4 | **ACCTGATGCATA TAATAATCAGG** | GAAATTAATACGAC TCACTATAGACCTG ATGCATATAATAAT CGTTTTAGAGCTAG AAATAGC | | SEQ ID NO 129 |
| | 5 | ACCTGATTATTAT ATGCATCAGG | GAAATTAATACGAC TCACTATAGACCTG ATTATTATATGCATC GTTTTAGAGCTAGA AATAGC | | SEQ ID NO 130 |
| | 6 | CAGAGCACCAGA GTGCCGTCTGG | GAAATTAATACGAC TCACTATAGCAGAG CACCAGAGTGCCGT CGTTTTAGAGCTAG AAATAGC | | SEQ ID NO 131 |
| | 7 | AGAGCACCAGAG TGCCGTCTGGG | GAAATTAATACGAC TCACTATAGAGAGC ACCAGAGTGCCGTC TGTTTTAGAGCTAG AAATAGC | | SEQ ID NO 132 |
| | 8 | AGAGTGCCGTCTG GGTCTGAAGG | GAAATTAATACGAC TCACTATAGAGAGT GCCGTCTGGGTCTG AGTTTTAGAGCTAG AAATAGC | | SEQ ID NO 133 |
| | 9 | AGGAAGGCCGTC CATTCTCAGGG | GAAATTAATACGAC TCACTATAGAGGAA GGCCGTCCATTCTC AGTTTTAGAGCTAG AAATAGC | | SEQ ID NO 134 |
| | 10 | GGATAGAACCAA CCATGTTGAGG | GAAATTAATACGAC TCACTATAGGGATA GAACCAACCATGTT GGTTTTAGAGCTAG AAATAGC | | SEQ ID NO 135 |

TABLE 2-continued

| Gene | # | DNA target sequence | Forward primer sequence | Reverse primer | SEQ ID NO |
|---|---|---|---|---|---|
| | 11 | TCTGTTGCCCTCA ACATGGTTGG | GAAATTAATACGAC TCACTATAGTCTGTT GCCCTCAACATGGT GTTTTAGAGCTAGA AATAGC | | SEQ ID NO 136 |
| | 12 | TTAGTCTGTTGCC CTCAACATGG | GAAATTAATACGAC TCACTATAGTTAGT CTGTTGCCCTCAAC AGTTTTAGAGCTAG AAATAGC | | SEQ ID NO 137 |
| | 13 | GTCTGGCAAATGG GAGGTGATGG | GAAATTAATACGAC TCACTATAGGTCTG GCAAATGGGAGGT GAGTTTTAGAGCTA GAAATAGC | | SEQ ID NO 138 |
| | 14 | CAGAGGTTCTGTC TGGCAAATGG | GAAATTAATACGAC TCACTATAGCAGAG GTTCTGTCTGGCAA AGTTTTAGAGCTAG AAATAGC | | SEQ ID NO 139 |
| | 15 | TTGTAGCCAGAGG TTCTGTCTGG | GAAATTAATACGAC TCACTATAGTTGTA GCCAGAGGTTCTGT CGTTTTAGAGCTAG AAATAGC | | SEQ ID NO 140 |
| | 16 | ACTTCTGGATGAG CTCTCTCAGG | GAAATTAATACGAC TCACTATGACTTCT GGATGAGCTCTCTC GTTTTAGAGCTAGA AATAGC | | SEQ ID NO 141 |
| | 17 | AGAGCTCATCCAG AAGTAAATGG | GAAATTAATACGAC TCACTATAGAGAGC TCATCCAGAAGTAA AGTTTTAGAGCTAG AAATAGC | | SEQ ID NO 142 |
| | 18 | TTGGTGTCTCCAT TTACTTCTGG | GAAATTAATACGAC TCACTATAGTTGGT GTCTCCATTTACTTC GTTTTAGAGCTAGA AATAGC | | SEQ ID NO 143 |
| | 19 | TTCTGGCTTCCCTT CATACAGGG | GAAATTAATACGAC TCACTATAGTTCTG GCTTCCCTTCATAC AGTTTTAGAGCTAG AAATAGC | | SEQ ID NO 144 |
| | 20 | CAGGACTCACAC GACTATTCTGG | GAAATTAATACGAC TCACTATAGCAGGA CTCACACGACTATT CGTTTTAGAGCTAG AAATAGC | | SEQ ID NO 145 |
| | 21 | CTACTTTCTTGTGT AAAGTCAGG | GAAATTAATACGAC TCACTATAGCTACTT TCTTGTGTAAAGTC GTTTTAGAGCTAGA AATAGC | | SEQ ID NO 146 |
| | 22 | GACTTTACACAAG AAAGTAGAGG | GAAATTAATACGAC TCACTATAGGACTT TACACAAGAAAGTA GGTTTTAGAGCTAG AAATAGC | | SEQ ID NO 147 |
| | 23 | GTCTTTCTCCATTA GCCTTTTGG | GAAATTAATACGAC TCACTATAGGTCTTT CTCCATTAGCCTTTG TTTTAGAGCTAGAA ATAGC | | SEQ ID NO 148 |
| | 24 | AATGGAGAAAGA CGTAACTTCGG | GAAATTAATACGAC TCACTATAGAATGG AGAAAGACGTAACT TGTTTTAGAGCTAG AAATAGC | | SEQ ID NO 149 |
| | 25 | ATGGAGAAAGAC GTAACTTCGGG | GAAATTAATACGAC TCACTATAGATGGA GAAAGACGTAACTT CGTTTTAGAGCTAG AAATAGC | | SEQ ID NO 150 |

TABLE 2-continued

| Gene | # | DNA target sequence | Forward primer sequence | Reverse primer | SEQ ID NO |
|---|---|---|---|---|---|
| | 26 | TGGAGAAAGACG TAACTTCGGGG | GAAATTAATACGAC TCACTATAGTGGAG AAAGACGTAACTTC GGTTTTAGAGCTAG AAATAGC | | SEQ ID NO 151 |
| | 27 | TTTGGTTGACTGC TTTCACCTGG | GAAATTAATACGAC TCACTATAGTTTGGT TGACTGCTTTCCC GTTTTAGAGCTAGA AATAGC | | SEQ ID NO 152 |
| | 28 | TCACTCAAATCGG AGACATTTGG | GAAATTAATACGAC TCACTATAGTCACT CAAATCGGAGACAT TGTTTTAGAGCTAG AAATAGC | | SEQ ID NO 153 |
| | 29 | ATCTGAAGCTCTG GATTTTCAGG | GAAATTAATACGAC TCACTATAGATCTG AAGCTCTGGATTTT CGTTTTAGAGCTAG AAATAGC | | SEQ ID NO 154 |
| | 30 | GCTTCAGATTCTG AATGAGCAGG | GAAATTAATACGAC TCACTATAGGCTTC AGATTCTGAATGAG CGTTTTAGAGCTAG AAATAGC | | SEQ ID NO 155 |
| | 31 | CAGATTCTGAATG AGCAGGAGGG | GAAATTAATACGAC TCACTATAGCAGAT TCTGAATGAGCAGG AGTTTTAGAGCTAG AAATAGC | | SEQ ID NO 156 |
| | 32 | AAGGCAGTGCTA ATGCCTAATGG | GAAATTAATACGAC TCACTATAGAAGGC AGTGCTAATGCCTA AGTTTTAGAGCTAG AAATAGC | | SEQ ID NO 157 |
| | 33 | GCAGAAACTGTA GCACCATTAGG | GAAATTAATACGAC TCACTATAGGCAGA AACTGTAGCACCAT TGTTTTAGAGCTAG AAATAGC | | SEQ ID NO 158 |
| | 34 | ACCGCAATGGAA ACACAATCTGG | GAAATTAATACGAC TCACTATAGACCGC AATGGAAACACAAT CGTTTTAGAGCTAG AAATAGC | | SEQ ID NO 159 |
| | 35 | TGTGGTTTTCTGC ACCGCAATGG | GAAATTAATACGAC TCACTATAGTGTGG TTTTCTGCACCGCA AGTTTTAGAGCTAG AAATAGC | | SEQ ID NO 160 |
| | 36 | CATAAATGCCATT AACAGTCAGG | GAAATTAATACGAC TCACTATAGCATAA ATGCCATTAACAGT CGTTTTAGAGCTAG AAATAGC | | SEQ ID NO 161 |
| | 37 | ATTAGTAGCCTGA CTGTTAATGG | GAAATTAATACGAC TCACTATAGATTAG TAGCCTGACTGTTA AGTTTTAGAGCTAG AAATAGC | | SEQ ID NO 162 |
| | 38 | CGATGGGTGAGT GATCTCACAGG | GAAATTAATACGAC TCACTATAGCGATG GGTGAGTGATCTCA CGTTTTAGAGCTAG AAATAGC | | SEQ ID NO 163 |
| | 39 | ACTCACCCATCGC ATACCTCAGG | GAAATTAATACGAC TCACTATAGACTCA CCCATCGCATACCT CGTTTTAGAGCTAG AAATAGC | | SEQ ID NO 164 |
| | 40 | CTCACCCATCGCA TACCTCAGGG | GAAATTAATACGAC TCACTATAGCTCAC CCATCGCATACCTC AGTTTTAGAGCTAG AAATAGC | | SEQ ID NO 165 |

TABLE 2-continued

| Gene | # | DNA target sequence | Forward primer sequence | Reverse primer | SEQ ID NO |
|---|---|---|---|---|---|
| PSGL-1 | 1 | AGCAACAGGAGG AGTTGCAGAGG | GAAATTAATACGAC TCACTATAGAGCAA CAGGAGGAGTTGC AGGTTTTAGAGCTA GAAATAGC | AAAAAAAGC ACCGACTCG GTGCCACTTT TTCAAGTTGA TAACGGACT | SEQ ID NO 166 |
| | 2 | CCAGTAGGATCA GCAACAGGAGG | GAAATTAATACGAC TCACTATAGCCAGT AGGATCAGCAACA GGGTTTTAGAGCTA GAAATAGC | AGCCTTATTT TAACTTGCTA TTTCTAGCTC TAAAAC | SEQ ID NO 167 |
| | 3 | CTCCTGTTGCTGA TCCTACTGGG | GAAATTAATACGAC TCACTATAGCTCCT GTTGCTGATCCTAC TGTTTTAGAGCTAG AAATAGC | | SEQ ID NO 168 |
| | 4 | GGCCCAGTAGGA TCAGCAACAGG | GAAATTAATACGAC TCACTATAGGGCCC AGTAGGATCAGCAA CGTTTTAGAGCTAG AAATAGC | | SEQ ID NO 169 |
| | 5 | TTGCTGATCCTAC TGGGCCCTGG | GAAATTAATACGAC TCACTATAGTTGCT GATCCTACTGGGCC CGTTTTAGAGCTAG AAATAGC | | SEQ ID NO 170 |
| | 6 | TGGCAACAGCTTG CAGCTGTGGG | GAAATTAATACGAC TCACTATAGTGGCA ACAGCTTGCAGCTG TGTTTTAGAGCTAG AAATAGC | | SEQ ID NO 171 |
| | 7 | CTTGGGTCCCCTG CTTGCCCGGG | GAAATTAATACGAC TCACTATAGCTTGG GTCCCCTGCTTGCC CGTTTTAGAGCTAG AAATAGC | | SEQ ID NO 172 |
| | 8 | GTCCCCTGCTTGC CCGGGACCGG | GAAATTAATACGAC TCACTATAGGTCCC CTGCTTGCCCGGGA CGTTTTAGAGCTAG AAATAGC | | SEQ ID NO 173 |
| | 9 | CTCCGGTCCCGG GCAAGCAGGGG | GAAATTAATACGAC TCACTATAGCTCCG GTCCCGGGCAAGC AGGTTTTAGAGCTA GAAATAGC | | SEQ ID NO 174 |
| | 10 | TCTCCGGTCCCGG GCAAGCAGGG | GAAATTATACGAC TCACTATAGTCTCC GGTCCCGGGCAAG CAGTTTTAGAGCTA GAAATAGC | | SEQ ID NO 175 |
| | 11 | GTCTCCGGTCCCG GGCAAGCAGG | GAAATTAATACGAC TCACTATAGGTCTC CGGTCCCGGGCAA GCGTTTTAGAGCTA GAAATAGC | | SEQ ID NO 176 |
| | 12 | GCTTGCCCGGGA CCGGAGACAGG | GAAATTAATACGAC TCACTATAGGCTTG CCCGGGACCGGAG ACGTTTTAGAGCTA GAAATAGC | | SEQ ID NO 177 |
| | 13 | GGTGGCCTGTCTC CGGTCCCGGG | GAAATTAATACGAC TCACTATAGGGTGG CCTGTCTCCGGTCC CGTTTTAGAGCTAG AAATAGC | | SEQ ID NO 178 |
| | 14 | CGGTGGCCTGTCT CCGGTCCCGG | GAAATTAATACGAC TCACTATAGCGGTG GCCTGTCTCCGGTC CGTTTTAGAGCTAG AAATAGC | | SEQ ID NO 179 |
| | 15 | CATATTCGGTGGC CTGTCTCCGG | GAAATTAATACGAC TCACTATAGCATATT CGGTGGCCTGTCTC GTTTTAGAGCTAGA AATAGC | | SEQ ID NO 180 |

TABLE 2-continued

| Gene | # | DNA target sequence | Forward primer sequence | Reverse primer | SEQ ID NO |
|---|---|---|---|---|---|
| | 16 | ATCTAGGTACTCA TATTCGGTGG | GAAATTAATACGAC TCACTATAGATCTA GGTACTCATATTCG GGTTTTAGAGCTAG AAATAGC | | SEQ ID NO 181 |
| | 17 | **ATAATCTAGGTA CTCATATTCGG** | GAAATTAATACGAC TCACTATAGATAAT CTAGGTACTCATAT TGTTTTAGAGCTAG AAATAGC | | SEQ ID NO 182 |
| | 18 | TTATGATTTCCTG CCAGAAACGG | GAAATTAATACGAC TCACTATAGTTATG ATTTCCTGCCAGAA AGTTTTAGAGCTAG AAATAGC | | SEQ ID NO 183 |
| | 19 | ATTTCTGGAGGCT CCGTTTCTGG | GAAATTAATACGAC TCACTATAGATTTCT GGAGGCTCCGTTTC GTTTTAGAGCTAGA AATAGC | | SEQ ID NO 184 |
| | 20 | ACTGACACCACTC CTCTGACTGG | GAAATTAATACGAC TCACTATAGACTGA CACCACTCCTCTGA CGTTTTAGAGCTAG AAATAGC | | SEQ ID NO 185 |
| | 21 | CTGACACCACTCC TCTGACTGGG | GAAATTAATACGAC TCACTATAGCTGAC ACCACTCCTCTGAC TGTTTTAGAGCTAG AAATAGC | | SEQ ID NO 186 |
| | 22 | ACCACTCCTCTGA CTGGGCCTGG | GAAATTAATACGAC TCACTATAGACCAC TCCTCTGACTGGGC CGTTTTAGAGCTAG AAATAGC | | SEQ ID NO 187 |
| | 23 | AACCCCTGAGTCT ACCACTGTGG | GAAATTAATACGAC TCACTATAGAACCC CTGAGTCTACCACT GGTTTTAGAGCTAG AAATAGC | | SEQ ID NO 188 |
| | 24 | CTCCACAGTGGTA GACTCAGGGG | GAAATTAATACGAC TCACTATAGCTCCA CAGTGGTAGACTCA GGTTTTAGAGCTAG AAATAGC | | SEQ ID NO 189 |
| | 25 | GCTCCACAGTGGT AGACTCAGGG | GAAATTAATACGAC TCACTATAGGCTCC ACAGTGGTAGACTC AGTTTTAGAGCTAG AAATAGC | | SEQ ID NO 190 |
| | 26 | GGCTCCACAGTG GTAGACTCAGG | GAAATTAATACGAC TCACTATAGGGCTC CACAGTGGTAGACT CGTTTTAGAGCTAG AAATAGC | | SEQ ID NO 191 |
| | 27 | CCTGCTGCAAGGC GTTCTACTGG | GAAATTAATACGAC TCACTATAGCCTGC TGCAAGGCGTTCTA CGTTTTAGAGCTAG AAATAGC | | SEQ ID NO 192 |
| | 28 | CCAGTAGAACGC CTTGCAGCAGG | GAAATTAATACGAC TCACTATAGCCAGT AGAACGCCTTGCAG CGTTTTAGAGCTAG AAATAGC | | SEQ ID NO 193 |
| | 29 | CGTTCTACTGGCC TGGATGCAGG | GAAATTAATACGAC TCACTATAGCGTTC TACTGGCCTGGATG CGTTTTAGAGCTAG AAATAGC | | SEQ ID NO 194 |
| | 30 | TCTACTGGCCTGG ATGCAGGAGG | GAAATTAATACGAC TCACTATAGTCTACT GGCCTGGATGCAG GGTTTTAGAGCTAG AAATAGC | | SEQ ID NO 195 |
| | 31 | CCACGGAGCTGG CCAACATGGGG | GAAATTAATACGAC TCACTATAGCCACG | | SEQ ID NO 196 |

TABLE 2-continued

| Gene | # | DNA target sequence | Forward primer sequence | Reverse primer | SEQ ID NO |
|---|---|---|---|---|---|
| | | | GAGCTGGCCAACAT CGTTTTAGAGCTAG AAATAGC | | |
| | 32 | CGTGGACAGGTTC CCCATGTTGG | GAAATTAATACGAC TCACTATAGCGTGG ACAGGTTCCCCATG TGTTTTAGAGCTAG AAATAGC | | SEQ ID NO 197 |
| | 33 | GTCCACGGATTCA GCAGCTATGG | GAAATTAATACGAC TCACTATAGGTCCA CGGATTCAGCAGCT AGTTTTAGAGCTAG AAATAGC | | SEQ ID NO 198 |
| | 34 | GACCACTCAACCA GTGCCCACGG | GAAATTAATACGAC TCACTATAGGACCA CTCAACCAGTGCCC AGTTTTAGAGCTAG AAATAGC | | SEQ ID NO 199 |
| | 35 | GGAGTGGTCTGTG CCTCCGTGGG | GAAATTAATACGAC TCACTATAGGGAGT GGTCTGTGCCTCCG TGTTTTAGAGCTAG AAATAGC | | SEQ ID NO 200 |
| | 36 | GGCACAGACAAC TCGACTGACGG | GAAATTAATACGAC TCACTATAGGGCAC AGACAACTCGACTG AGTTTTAGAGCTAG AAATAGC | | SEQ ID NO 201 |
| | 37 | GACAACTCGACTG ACGGCCACGG | GAAATTAATACGAC TCACTATAGGACAA CTCGACTGACGGCC AGTTTTAGAGCTAG AAATAGC | | SEQ ID NO 202 |
| | 38 | AACTCGACTGACG GCCACGGAGG | GAAATTAATACGAC TCACTATAGAACTC GACTGACGGCCAC GGGTTTTAGAGCTA GAAATAGC | | SEQ ID NO 203 |
| | 39 | CACAGAACCCAG TGCCACAGAGG | GAAATTAATACGAC TCACTATAGCACAG AACCCAGTGCCACA GGTTTTAGAGCTAG AAATAGC | | SEQ ID NO 204 |
| | 40 | GGTAGTAGGTTCC ATGGACAGGG | GAAATTAATACGAC TCACTATAGGGTAG TAGGTTCCATGGAC AGTTTTAGAGCTAG AAATAGC | | SEQ ID NO 205 |
| | 41 | TGGTAGTAGGTTC CATGGACAGG | GAAATTAATACGAC TCACTATAGTGGTA GTAGGTTCCATGGA CGTTTTAGAGCTAG AAATAGC | | SEQ ID NO 206 |
| | 42 | TCTTTTGGTAGTA GGTTCCATGG | GAAATTAATACGAC TCACTATGTCTTTT GGTAGTAGGTTCCA GTTTTAGAGCTAGA AATAGC | | SEQ ID NO 207 |
| | 43 | ATGGAACCTACTA CCAAAAGAGG | GAAATTAATACGAC TCACTATAGATGGA ACCTACTACCAAAA GGTTTTAGAGCTAG AAATAGC | | SEQ ID NO 208 |
| | 44 | AACAGACCTCTTT TGGTAGTAGG | GAAATTAATACGAC TCACTATAGAACAG ACCTCTTTTGGTAGT GTTTTAGAGCTAGA AATAGC | | SEQ ID NO 209 |
| | 45 | GGGTATGAACAG ACCTCTTTTGG | GAAATTAATACGAC TCACTATAGGGGTA TGAACAGACCTCTT TGTTTTAGAGCTAG AAATAGC | | SEQ ID NO 210 |
| | 46 | TGTGTCCTCTGTT ACTCACAAGG | GAAATTAATACGAC TCACTATAGTGTGT CCTCTGTTACTCAC | | SEQ ID NO 211 |

TABLE 2-continued

| Gene | # | DNA target sequence | Forward primer sequence | Reverse primer | SEQ ID NO |
|---|---|---|---|---|---|
| | | | AGTTTTAGAGCTAG AAATAGC | | |
| | 47 | GTGTCCTCTGTTA CTCACAAGGG | GAAATTAATACGAC TCACTATAGGTGTC CTCTGTTACTCACA AGTTTTAGAGCTAG AAATAGC | | SEQ ID NO 212 |
| | 48 | GTAGTTGACGGAC AAATTGCTGG | GAAATTAATACGAC TCACTATAGGTAGT TGACGGACAAATTG CGTTTTAGAGCTAG AAATAGC | | SEQ ID NO 213 |
| | 49 | TTTGTCCGTCAAC TACCCAGTGG | GAAATTAATACGAC TCACTATAGTTTGTC CGTCAACTACCCAG GTTTTAGAGCTAGA AATAGC | | SEQ ID NO 214 |
| | 50 | TTGTCCGTCAACT ACCCAGTGGG | GAAATTAATACGAC TCACTATAGTTGTC CGTCAACTACCCAG TGTTTTAGAGCTAG AAATAGC | | SEQ ID NO 215 |
| | 51 | TGTCCGTCAACTA CCCAGTGGGG | GAAATTAATACGAC TCACTATAGTGTCC GTCAACTACCCAGT GGTTTTAGAGCTAG AAATAGC | | SEQ ID NO 216 |
| | 52 | GTCCGTCAACTAC CCAGTGGGGG | GAAATTAATACGAC TCACTATAGGTCCG TCAACTACCCAGTG GGTTTTAGAGCTAG AAATAGC | | SEQ ID NO 217 |
| | 53 | CTCTGTGAAGCAG TGCCTGCTGG | GAAATTAATACGAC TCACTATAGCTCTG TGAAGCAGTGCCTG CGTTTTAGAGCTAG AAATAGC | | SEQ ID NO 218 |
| | 54 | CCTGCTGGCCATC CTAATCTTGG | GAAATTAATACGAC TCACTATAGCCTGC TGGCCATCCTAATC TGTTTTAGAGCTAG AAATAGC | | SEQ ID NO 219 |
| | 55 | CCAAGATTAGGAT GGCCAGCAGG | GAAATTAATACGAC TCACTATAGCCAAG ATTAGGATGGCCAG CGTTTTAGAGCTAG AAATAGC | | SEQ ID NO 220 |
| | 56 | GGCCATCCTAATC TTGGCGCTGG | GAAATTAATACGAC TCACTATAGGGCCA TCCTAATCTTGGCG CGTTTTAGAGCTAG AAATAGC | | SEQ ID NO 221 |
| | 57 | CACCAGCGCCAA GATTAGGATGG | GAAATTAATACGAC TCACTATAGCACCA GCGCCAAGATTAGG AGTTTTAGAGCTAG AAATAGC | | SEQ ID NO 222 |
| | 58 | AGTGCACACGAA GAAGATAGTGG | GAAATTAATACGAC TCACTATAGAGTGC ACACGAAGAAGAT AGGTTTTAGAGCTA GAAATAGC | | SEQ ID NO 223 |
| | 59 | TATCTTCTCGTGT GCACTGTGG | GAAATTAATACGAC TCACTATAGTATCTT CTTCGTGTGCACTG GTTTTAGAGCTAGA AATAGC | | SEQ ID NO 224 |
| | 60 | CTTCGTGTGCACT GTGGTGCTGG | GAAATTAATACGAC TCACTATAGCTTCG TGTGCACTGTGGTG CGTTTTAGAGCTAG AAATAGC | | SEQ ID NO 225 |
| | 61 | GGCGGTCCGCCT CTCCCGCAAGG | GAAATTAATACGAC TCACTATAGGGCGG TCCGCCTCTCCCGC AGTTTTAGAGCTAG AAATAGC | | SEQ ID NO 226 |

TABLE 2-continued

| Gene | # | DNA target sequence | Forward primer sequence | Reverse primer | SEQ ID NO |
|---|---|---|---|---|---|
| | 62 | GCGGTCCGCCTCTCCCGCAAGGG | GAAATTAATACGACTCACTATAGGCGGTCCGCCTCTCCCGCAAGTTTTAGAGCTAGAAATAGC | | SEQ ID NO 227 |
| | 63 | AATTACGCACGGGGTACATGTGG | GAAATTAATACGACTCACTATAGAATTACGCACGGGGTACATGGTTTTAGAGCTAGAAATAGC | | SEQ ID NO 228 |
| | 64 | TGGGGGAGTAATTACGCACGGGG | GAAATTAATACGACTCACTATAGTGGGGGAGTAATTACGCACGGTTTTAGAGCTAGAAATAGC | | SEQ ID NO 229 |
| | 65 | GTGGGGGAGTAATTACGCACGGG | GAAATTAATACGACTCACTATAGGTGGGGGAGTAATTACGCACGTTTTAGAGCTAGAAATAGC | | SEQ ID NO 230 |
| | 66 | GGTGGGGGAGTAATTACGCACGG | GAAATTAATACGACTCACTATAGGGTGGGGGAGTAATTACGCAGTTTTAGAGCTAGAAATAGC | | SEQ ID NO 231 |
| | 67 | TAATTACTCCCCCACCGAGATGG | GAAATTAATACGACTCACTATAGTAATTACTCCCCCACCGAGAGTTTTAGAGCTAGAAATAGC | | SEQ ID NO 232 |
| | 68 | AGATGCAGACCATCTCGGTGGGG | GAAATTAATACGACTCACTATAGAGATGCAGACCATCTCGGTGGTTTTAGAGCTAGAAATAGC | | SEQ ID NO 233 |
| | 69 | GAGATGCAGACCATCTCGGTGGG | GAAATTAATACGACTCACTATAGGAGATGCAGACCATCTCGGTGTTTTAGAGCTAGAAATAGC | | SEQ ID NO 234 |
| | 70 | TGAGATGCAGACCATCTCGGTGG | GAAATTAATACGACTCACTATAGTGAGATGCAGACCATCTCGGGTTTTAGAGCTAGAAATAGC | | SEQ ID NO 235 |
| | 71 | GGATGAGATGCAGACCATCTCGG | GAAATTAATACGACTCACTATAGGGATGAGATGCAGACCATCTGTTTTAGAGCTAGAAATAGC | | SEQ ID NO 236 |
| | 72 | ATCTCATCCCTGTTGCCTGATGG | GAAATTAATACGACTCACTATAGATCTCATCCCTGTTGCCTGAGTTTTAGAGCTAGAAATAGC | | SEQ ID NO 237 |
| | 73 | TCATCCCTGTTGCCTGATGGGGG | GAAATTAATACGACTCACTATAGTCATCCCTGTTGCCTGATGGGTTTTAGAGCTAGAAATAGC | | SEQ ID NO 238 |
| | 74 | CTCACCCCCATCAGGCAACAGGG | GAAATTAATACGACTCACTATAGCTCACCCCCATCAGGCAACAGTTTTAGAGCTAGAAATAGC | | SEQ ID NO 239 |
| | 75 | GAGGGCCCCTCACCCCCATCAGG | GAAATTAATACGACTCACTATAGGAGGGCCCCTCACCCCCATCGTTTTAGAGCTAGAAATAGC | | SEQ ID NO 240 |
| | 76 | GGGCCCTCTGCCACAGCCAATGG | GAAATTAATACGACTCACTATAGGGGCCCTCTGCCACAGCCAAGTTTTAGAGCTAGAAATAGC | | SEQ ID NO 241 |
| | 77 | CCCTCTGCCACAGCCAATGGGGG | GAAATTAATACGACTCACTATAGCCCTC | | SEQ ID NO 242 |

TABLE 2-continued

| Gene | # | DNA target sequence | Forward primer sequence | Reverse primer | SEQ ID NO |
|---|---|---|---|---|---|
| | | | TGCCACAGCCAATG GGTTTTAGAGCTAG AAATAGC | | |
| | 78 | CCCCCATTGGCTG TGGCAGAGGG | GAAATTAATACGAC TCACTATAGCCCCC ATTGGCTGTGGCAG AGTTTTAGAGCTAG AAATAGC | | SEQ ID NO 243 |
| | 79 | GCCCCCATTGGCT GTGGCAGAGG | GAAATTAATACGAC TCACTATAGGCCCC CATTGGCTGTGGCA GGTTTTAGAGCTAG AAATAGC | | SEQ ID NO 244 |
| | 80 | GGACAGGCCCCC ATTGGCTGTGG | GAAATTAATACGAC TCACTATAGGACA GGCCCCCATTGGCT GGTTTTAGAGCTAG AAATAGC | | SEQ ID NO 245 |
| | 81 | CCGGGCTCTTGGC CTTGGACAGG | GAAATTAATACGAC TCACTATAGCCGGG CTCTTGGCCTTGCA CGTTTTAGAGCTAG AAATAGC | | SEQ ID NO 246 |
| | 82 | CTGTCCAAGGCCA AGAGCCCGGG | GAAATTAATACGAC TCACTATAGCTGTC CAAGGCCAAGAGC CCGTTTTAGAGCTA GAAATAGC | | SEQ ID NO 247 |
| | 83 | TGGCGTCAGGCC CGGGCTCTTGG | GAAATTAATACGAC TCACTATAGTGGCG TCAGGCCCGGGCTC TGTTTTAGAGCTAG AAATAGC | | SEQ ID NO 248 |
| | 84 | CGGGCCTGACGC CAGAGCCCAGG | GAAATTAATACGAC TCACTATAGCGGGC CTGACGCCAGAGCC CGTTTTAGAGCTAG AAATAGC | | SEQ ID NO 249 |
| FAS | 1 | CAACAACCATGCT GGGCATCTGG | GAAATTAATACGAC TCACTATAGCAACA ACCATGCTGGGCAT CGTTTTAGAGCTAG AAATAGC | AAAAAAAGC ACCGACTCG GTGCCACTTT TTCAAGTTGA TAACGGACT | SEQ ID NO 250 |
| | 2 | GAGGGTCCAGAT GCCCAGCATGG | GAAATTAATACGAC TCACTATAGGAGGG TCCAGATGCCCAGC AGTTTTAGAGCTAG AAATAGC | AGCCTTATTT TAACTTGCTA TTTCTAGCTC TAAAAC | SEQ ID NO 251 |
| | 3 | **CATCTGGACCCT CCTACCTCTGG** | GAAATTAATACGAC TCACTATAGCATCT GGACCCTCCTACCT CGTTTTAGAGCTAG AAATAGC | | SEQ ID NO 252 |
| | 4 | AGGGCTCACCAG AGGTAGGAGGG | GAAATTAATACGAC TCACTATAGAGGGC TCACCAGAGGTAGG AGTTTTAGAGCTAG AAATAGC | | SEQ ID NO 253 |
| | 5 | **GGAGTTGATGTC AGTCACTTGGG** | GAAATTAATACGAC TCACTATAGGGAGT TGATGTCAGTCACT TGTTTTAGAGCTAG AAATAGC | | SEQ ID NO 254 |
| | 6 | TGGAGTTGATGTC AGTCACTTGG | GAAATTAATACGAC TCACTATAGTGGAG TTGATGTCAGTCAC TGTTTTAGAGCTAG AAATAGC | | SEQ ID NO 255 |
| | 7 | AGTGACTGACATC AACTCCAAGG | GAAATTAATACGAC TCACTATAGAGTGA CTGACATCAACTCC AGTTTTAGAGCTAG AAATAGC | | SEQ ID NO 256 |
| | 8 | **GTGACTGACATC AACTCCAAGGG** | GAAATTAATACGAC TCACTATAGGTGAC TGACATCAACTCCA | | SEQ ID NO 257 |

TABLE 2-continued

| Gene | # | DNA target sequence | Forward primer sequence | Reverse primer | SEQ ID NO |
|---|---|---|---|---|---|
| | | | AGTTTTAGAGCTAG AAATAGC | | |
| | 9 | ACTCCAAGGGATT GGAATTGAGG | GAAATTAATACGAC TCACTATAGACTCC AAGGGATTGGAATT GGTTTTAGAGCTAG AAATAGC | | SEQ ID NO 258 |
| | 10 | CTTCCTCAATTCC AATCCCTTGG | GAAATTAATACGAC TCACTATAGCTTCCT CAATTCCAATCCCT GTTTTAGAGCTAGA AATAGC | | SEQ ID NO 259 |
| | 11 | TACAGTTGAGACT CAGAACTTGG | GAAATTAATACGAC TCACTATAGTACAG TTGAGACTCAGAAC TGTTTTAGAGCTAG AAATAGC | | SEQ ID NO 260 |
| | 12 | TTGGAAGGCCTGC ATCATGATGG | GAAATTAATACGAC TCACTATAGTTGGA AGGCCTGCATCATG AGTTTTAGAGCTAG AAATAGC | | SEQ ID NO 261 |
| | 13 | AGAATTGGCCATC ATGATGCAGG | GAAATTAATACGAC TCACTATAGAGAAT TGGCCATCATGATG CGTTTTAGAGCTAG AAATAGC | | SEQ ID NO 262 |
| | 14 | GACAGGGCTTATG GCAGAATTGG | GAAATTAATACGAC TCACTATAGGACAG GGCTTATGGCAGAA TGTTTTAGAGCTAG AAATAGC | | SEQ ID NO 263 |
| | 15 | **TGTAACATACCT GGAGGACAGGG** | GAAATTAATACGAC TCACTATAGTGTAA CATACCTGGAGGAC AGTTTTAGAGCTAG AAATAGC | | SEQ ID NO 264 |
| | 16 | GTGTAACATACCT GGAGGACAGG | GAAATTAATACGAC TCACTATAGGTGTA ACATACCTGGAGGA CGTTTTAGAGCTAG AAATAGC | | SEQ ID NO 265 |
| KDM6A | 1 | CGTACCTGTGCAA CTCCTGTTGG | GAAATTAATACGAC TCACTATAGCGTAC CTGTGCAACTCCTG TGTTTTAGAGCTAG AAATAGC | AAAAAAAGC ACCGACTCG GTGCCACTTT TTCAAGTTGA TAACGGACT | SEQ ID NO 266 |
| | 2 | GATCTACTGGAAT TCCTAATGGG | GAAATTAATACGAC TCACTATAGGATCT ACTGGAATTCCTAA TGTTTTAGAGCTAG AAATAGC | AGCCTTATTT TAACTTGCTA TTTCTAGCTC TAAAAC | SEQ ID NO 267 |
| | 3 | GAGTCAGCTGTTG GCCCATTAGG | GAAATTAATACGAC TCACTATAGGAGTC AGCTGTTGGCCCAT TGTTTTAGAGCTAG AAATAGC | | SEQ ID NO 268 |
| | 4 | CTGCCTACAAACT CAGTCTCTGG | GAAATTAATACGAC TCACTATAGCTGCC TACAAACTCAGTCT CGTTTTAGAGCTAG AAATAGC | | SEQ ID NO 269 |
| | 5 | GGGCAGGCAGGA CGGACTCCAGG | GAAATTAATACGAC TCACTATAGGGGCA GGCAGGACGGACT CCGTTTTAGAGCTA GAAATAGC | | SEQ ID NO 270 |
| | 6 | GGAGTCCGTCCTG CCTGCCCTG | GAAATTAATACGAC TCACTATAGGGAGT CCGTCCTGCCTGCC CGTTTTAGAGCTAG AAATAGC | | SEQ ID NO 271 |
| | 7 | GAGTCCGTCCTGC CTGCCCTGGG | GAAATTAATACGAC TCACTATAGGAGT CGTCCTGCCTGCCC | | SEQ ID NO 272 |

TABLE 2-continued

| Gene | # | DNA target sequence | Forward primer sequence | Reverse primer | SEQ ID NO |
|---|---|---|---|---|---|
| | | | TGTTTTAGAGCTAG AAATAGC | | |
| | 8 | GAAAAGGGTCCA TTGGCCAAAGG | GAAATTAATACGAC TCACTATAGGAAAA GGGTCCATTGGCCA AGTTTTAGAGCTAG AAATAGC | | SEQ ID NO 273 |
| | 9 | GCCTGCAGAAAA GGGTCCATTGG | GAAATTAATACGAC TCACTATAGGCCTG CAGAAAAGGGTCC ATGTTTTAGAGCTA GAAATAGC | | SEQ ID NO 274 |
| | 10 | TTGATGTGCTACA GGGAACATGG | GAAATTAATACGAC TCACTATAGTTGAT GTGCTACAGGGAAC AGTTTTAGAGCTAG AAATAGC | | SEQ ID NO 275 |
| | 11 | AGCGTTCTTGATG TGCTACAGGG | GAAATTAATACGAC TCACTATAGAGCGT TCTTGATGTGCTAC AGTTTTAGAGCTAG AAATAGC | | SEQ ID NO 276 |
| | 12 | CAGCGTTCTTGAT GTGCTACAGG | GAAATTAATACGAC TCACTATAGCAGCG TTCTTGATGTGCTAC GTTTTAGAGCTAGA AATAGC | | SEQ ID NO 277 |
| | 13 | CTGTAGCACATCA AGAACGCTGG | GAAATTAATACGAC TCACTATAGCTGTA GCACATCAAGAAC GCGTTTTAGAGCTA GAAATAGC | | SEQ ID NO 278 |
| | 14 | TGTAGCACATCAA GAACGCTGGG | GAAATTAATACGAC TCACTATAGTGTAG CACATCAAGAACGC TGTTTTAGAGCTAG AAATAGC | | SEQ ID NO 279 |
| | 15 | ATAGGCAATAATC ATATAACAGG | GAAATTAATACGAC TCACTATAGATAGG CAATAATCATATAA CGTTTTAGAGCTAG AAATAGC | | SEQ ID NO 280 |
| | 16 | AGTGCGTTTCGCT GCAGGTAAGG | GAAATTAATACGAC TCACTATAGAGTGC GTTTCGCTGCAGGT AGTTTTAGAGCTAG AAATAGC | | SEQ ID NO 281 |
| | 17 | GAGTGAGTGCGTT TCGCTGCAGG | GAAATTAATACGAC TCACTATAGGAGTG AGTGCGTTTCGCTG CGTTTTAGAGCTAG AAATAGC | | SEQ ID NO 282 |
| | 18 | GTCAGGTTTGTGC GGTTATGAGG | GAAATTAATACGAC TCACTATAGGTCAG GTTTGTGCGGTTAT GGTTTTAGAGCTAG AAATAGC | | SEQ ID NO 283 |
| | 19 | CGCTGCTGGTCAG GTTTGTGCGG | GAAATTAATACGAC TCACTATAGCGCTG CTGGTCAGGTTTGT GGTTTTAGAGCTAG AAATAGC | | SEQ ID NO 284 |
| | 20 | **AAACCTGACCAG CAGCGCAGAGG** | GAAATTAATACGAC TCACTATAGAAACC TGACCAGCAGCGC AGGTTTTAGAGCTA GAAATAGC | | SEQ ID NO 285 |
| | 21 | CCAGCAGCGCAG AGGAGCCGTGG | GAAATTAATACGAC TCACTATAGCCAGC AGCGCAGAGGAGC CGGTTTTAGAGCTA GAAATAGC | | SEQ ID NO 286 |
| | 22 | CCACGGCTCCTCT GCGCTGCTGG | GAAATTAATACGAC TCACTATAGCCACG GCTCCTCTGCGCTG CGTTTTAGAGCTAG AAATAGC | | SEQ ID NO 287 |

TABLE 2-continued

| Gene | # | DNA target sequence | Forward primer sequence | Reverse primer | SEQ ID NO |
|---|---|---|---|---|---|
| | 23 | CCAACTATCTAACTCCACTCAGG | GAAATTAATACGACTCACTATAGCCAACTATCTAACTCCACTCGTTTTAGAGCTAGAAATAGC | | SEQ ID NO 288 |
| | 24 | CCTGAGTGGAGTTAGATAGTTGG | GAAATTAATACGACTCACTATAGCCTGAGTGGAGTTAGATAGTGTTTTAGAGCTAGAAATAGC | | SEQ ID NO 289 |

Meanwhile, sgRNA was produced in the same method as the above for PSGL-1 gene with respect to the DNA target sequences of SEQ ID NOS: 1 to 84 described in the table 1.

Example 3. Screening of sgRNAs in Jurkat Cells

Activities of the above synthesized sgRNAs targeting the exons of A20, Dgkα, Egr2, PPP2r2d, PD-1, CTLA-4, Dgk, PSGL-1, KDM6A and Tet2 were tested in Jurkat cells.

Jurkat cells (ATCC TIB-152; immortalized cell line of human T cell) was cultured in RPMI 1640 medium supplemented with 10% (v/v) fetal bovine serum (GeneAll). The cells were cultured in an incubator under conditions of 37° C. and 5% $CO_2$.

For cell activation, the concentration of cells in the medium were each individually $1\times10^6$ cells/mL.

CD2/CD3/CD28 beads (anti-CD2/3/CD28 Dynabeads; Miltenyi Biotec) were added at 3:1 ratio (beads:cells; based on numbers of the beads and the cells), and the cells were cultured in an incubator under conditions of 37° C. and 5% $CO_2$. The cell activation was performed for 72 hours, the CD2/CD3/CD28 beads were removed using a magnet, and the cells were cultured for additional 12-24 hours without the beads.

1 μg (microgram) of the synthesized in vitro transcribed sgRNA and 4 μg of Cas9 protein (ToolGen) were introduced to $1\times10^6$ of the cultured Jurkat cells via electroporation (in vitro). Genes were introduced under the following condition using a 10 μL tip of Neon Transfection System (ThermoFisher Scientific, Grand Island, NY): Jurkats (Buffer R): 1,400 V, 20 ms, 2 pulses.

The transfected cells were plated on 500 μL of antibiotics-free medium and were cultured in an incubator under conditions of 37° C. and 5% $CO_2$.

The indel ratio at the transfected Jurkat cells (indicated as '+ aRGEN') was tested in comparison to the Jurkat cells (indicated as '-aRGEN') without transfection. The tested CRISPR/Cas9 target sequences were summarized in table 3, and the indel ratio of each sgRNA is summarized in table 4.

TABLE 3

| Gene | # | DNA target sequence | Mismatch 0 bp | 1 bp | 2 bp |
|---|---|---|---|---|---|
| A20 | 1 | CTTGTGGCGCTGAAAACGAACGG | 1 | 0 | 0 |
| | 2 | ATGCCACTTCTCAGTACATGTGG | 1 | 0 | 0 |
| | 3 | GCCACTTCTCAGTACATGTGGGG | 1 | 0 | 0 |
| | 4 | GCCCCACATGTACTGAGAAGTGG | 1 | 0 | 0 |
| | 5 | TCAGTACATGTGGGGCGTTCAGG | 1 | 0 | 0 |
| | 6 | **GGGCGTTCAGGACACAGACTTGG** | 1 | 0 | 0 |
| | 7 | CACAGACTTGGTACTGAGGAAGG | 1 | 0 | 0 |
| | 8 | GGCGCTGTTCAGCACGCTCAAGG | 1 | 0 | 0 |
| | 9 | CACGCAACTTTAAATTCCGCTGG | 1 | 0 | 0 |
| | 10 | CGGGGCTTTGCTATGATACTCGG | 1 | 0 | 0 |
| | 11 | **GGCTTCCACAGACACACCCATGG** | 1 | 0 | 0 |
| | 12 | TGAAGTCCACTTCGGGCCATGGG | 1 | 0 | 0 |
| DGKα | 1 | CTGTACGACACGGACAGAAATGG | 1 | 0 | 0 |
| | 2 | TGTACGACACGGACAGAAATGGG | 1 | 0 | 0 |
| | 3 | CACGGACAGAAATGGGATCCTGG | 1 | 0 | 0 |
| | 4 | GATGCGAGTGGCTGAATACCTGG | 1 | 0 | 0 |
| | 5 | GAGTGGCTGAATACCTGGATTGG | 1 | 0 | 0 |
| | 6 | AGTGGCTGAATACCTGGATTGGG | 1 | 0 | 0 |
| | 7 | **ATTGGGATGTGTCTGAGCTGAGG** | 1 | 0 | 0 |
| | 8 | **ATGAAAGAGATTGACTATGATGG** | 1 | 0 | 0 |
| | 9 | **CTCTGTCTCTCAAGCTGAGTGGG** | 1 | 0 | 0 |
| | 10 | TCTCTCAAGCTGAGTGGGTCCGG | 1 | 0 | 0 |
| | 11 | **CTCTCAAGCTGAGTGGGTCCGGG** | 1 | 0 | 0 |
| | 12 | CAAGCTGAGTGGGTCCGGGCTGG | 1 | 0 | 0 |
| EGR2 | 1 | **TTGACATGACTGGAGAGAAGAGG** | 1 | 0 | 0 |
| | 2 | GACTGGAGAGAAGAGGTCGTTGG | 1 | 0 | 0 |
| | 3 | GAGACGGGAGCAAAGCTGCTGGG | 1 | 0 | 0 |
| | 4 | AGAGACGGGAGCAAAGCTGCTGG | 1 | 0 | 0 |
| | 5 | TGGTTTCTAGGTGCAGAGACGGG | 1 | 0 | 0 |
| | 6 | TAAGTGAAGGTCTGGTTTCTAGG | 1 | 0 | 0 |
| | 7 | TGCCCATGTAAGTGAAGGTCTGG | 1 | 0 | 0 |
| | 8 | GAACTTGCCCATGTAAGTGAAGG | 1 | 0 | 0 |
| | 9 | TCCATTGACCCTCAGTACCCTGG | 1 | 0 | 0 |
| | 10 | TATGCCTTCTGGGTAGCAGCTGG | 1 | 0 | 0 |
| | 11 | TGAGTGCAGGCATCTTGCAAGGG | 1 | 0 | 0 |
| | 12 | GAGTGCAGGCATCTTGCAAGGGG | 1 | 0 | 0 |
| | 13 | GATGAGGCTGTGGTTGAAGCTGG | 1 | 0 | 0 |
| | 14 | CCACTGGCCACAGGACCCCTGGG | 1 | 0 | 0 |
| | 15 | GGGACATGGTGCACACACCCAGG | 1 | 0 | 0 |
| | 16 | GAGTACAGGTGGTCCAGGTCAGG | 1 | 0 | 0 |
| | 17 | GCGGAGAGTACAGGTGGTCCAGG | 1 | 0 | 0 |
| | 18 | GCGGTGGCGGAGAGTACAGGTGG | 1 | 0 | 0 |
| | 19 | TCTCCTGCACAGCCAGAATAAGG | 1 | 0 | 0 |
| | 20 | ACGCAGAAGGGTCCTGGTAGAGG | 1 | 0 | 0 |
| | 21 | AGGTGGTGGGTAGGCCAGAGAGG | 1 | 0 | 0 |
| | 22 | CCCAAGCCAGCCACGGACCCAGG | 1 | 0 | 0 |
| | 23 | ACCTGGGTCCGTGGCTGGCTTGG | 1 | 0 | 0 |
| | 24 | AAGAGACCTGGGTCCGTGGCTGG | 1 | 0 | 0 |
| | 25 | GGATCATTGGGAAGAGACCTGGG | 1 | 0 | 0 |
| | 26 | GGGATCATTGGGAAGAGACCTGG | 1 | 0 | 0 |
| | 27 | CAGGATAGTCTGGGATCATTGGG | 1 | 0 | 0 |
| | 28 | GGAAAGAATCCAGGATAGTCTGG | 1 | 0 | 0 |
| | 29 | CAGTGCCAGAGAGACCTACATGG | 1 | 0 | 0 |
| | 30 | CTGTACCATGTAGGTCTCTCTGG | 1 | 0 | 0 |
| | 31 | AGAGACCTACATGGTACAGCTGG | 1 | 0 | 0 |
| | 32 | CTGGGCCAGCTGTACCATGTAGG | 1 | 0 | 0 |
| | 33 | AGGGAAAGGGCTTACGGTCTGGG | 1 | 0 | 0 |
| | 34 | CAGGGAAAGGGCTTACGGTCTGG | 1 | 0 | 0 |
| PPP2R2D | 5 | TCTGGAGATCTTCTTGCAACAGG | 1 | 0 | 0 |
| | 6 | CTCCGGTTCATGACTTTGAAAGG | 1 | 0 | 0 |
| | 7 | GTCTTCCATCTTCGTCTTTCAGG | 1 | 0 | 0 |
| | 8 | GAAGACTTCGAGACCCATTTAGG | 1 | 0 | 0 |

TABLE 3-continued

| Gene | # | DNA target sequence | Mismatch 0 bp | 1 bp | 2 bp |
|---|---|---|---|---|---|
| | 9 | TCGAGACCCATTTAGGATCACGG | 1 | 0 | 0 |
| | 10 | **GTAGCGCCGTGATCCTAAATGGG** | 1 | 0 | 0 |
| | 11 | CGTAGCGCCGTGATCCTAAATGG | 1 | 0 | 0 |
| | 12 | CATTTAGGATCACGGCGCTACGG | 1 | 0 | 0 |
| | 13 | GGTCCCAATATTGAAGCCCATGG | 1 | 0 | 0 |
| | 14 | GATCCATGGGCTTCAATATTGGG | 1 | 0 | 0 |
| | 15 | AGATCCATGGGCTTCAATATTGG | 1 | 0 | 0 |
| | 16 | GCTTCTACCATAAGATCCATGGG | 1 | 0 | 0 |
| | 17 | CGCTTCTACCATAAGATCCATGG | 1 | 0 | 0 |
| | 18 | GCATTTGCAAAAATTCGCCGTGG | 1 | 0 | 0 |
| | 19 | ATGACCTGAGAATTAATTTATGG | 1 | 0 | 0 |
| | 20 | CCATGCACTCCCAGACATCGTGG | 1 | 0 | 0 |
| | 21 | GCACTGGTGCGGGTGGAACTCGG | 1 | 0 | 0 |
| | 22 | ACACGTTGCACTGGTGCGGGTGG | 1 | 0 | 0 |
| | 23 | CGAACACGTTGCACTGGTGCGGG | 1 | 0 | 0 |
| | 24 | ACGAACACGTTGCACTGGTGCGG | 1 | 0 | 0 |
| | 25 | TGTAGACGAACACGTTGCACTGG | 1 | 0 | 0 |
| | 26 | GCGCATGTCACACAGGCGGATGG | 1 | 0 | 0 |
| | 27 | AGGAGCGCATGTCACACAGGCGG | 1 | 0 | 0 |
| | 28 | CCGAGGAGCGCATGTCACACAGG | 1 | 0 | 0 |
| | 29 | CCTGTGTGACATGCGCTCCTCGG | 1 | 0 | 0 |
| PD-1 | 1 | CGACTGGCCAGGGCGCCTGTGGG | 1 | 0 | 0 |
| | 2 | ACCGCCCAGACGACTGGCCAGGG | 1 | 0 | 0 |
| | 3 | CACCGCCCAGACGACTGGCCAGG | 1 | 0 | 0 |
| | 4 | **GTCTGGGCGGTGCTACAACTGGG** | 1 | 0 | 0 |
| | 5 | CTACAACTGGGCTGGCGGCCAGG | 1 | 0 | 0 |
| | 6 | **CACCTACCTAAGAACCATCCTGG** | 1 | 0 | 0 |
| | 7 | CGGTCACCACGAGCAGGGCTGGG | 1 | 0 | 0 |
| | 8 | GCCCTGCTCGTGGTGACCGAAGG | 1 | 0 | 0 |
| | 9 | CGGAGAGCTTCGTGCTAAACTGG | 1 | 0 | 0 |
| | 10 | CAGCTTGTCCGTCTGGTTGCTGG | 1 | 0 | 0 |
| | 11 | AGGCGGCCAGCTTGTCCGTCTGG | 1 | 0 | 0 |
| | 12 | CCGGGCTGGCTGCGGTCCTCGGG | 1 | 0 | 0 |
| | 13 | CGTTGGGCAGTTGTGTGACACGG | 1 | 0 | 0 |
| CTLA-4 | 1 | CATAAAGCCATGGCTTGCCTTGG | 1 | 0 | 0 |
| | 2 | CCTTGGATTTCAGCGGCACAAGG | 1 | 0 | 0 |
| | 3 | CCTTGTGCCGCTGAAATCCAAGG | 1 | 0 | 0 |
| | 4 | CACTCACCTTTGCAGAAGACAGG | 1 | 0 | 0 |
| | 5 | TTCCATGCTAGCAATGCACGTGG | 1 | 0 | 0 |
| | 6 | GGCCACGTGCATTGCTAGCATGG | 1 | 0 | 0 |
| | 7 | GGCCCAGCCTGCTGTGGTACTGG | 1 | 0 | 0 |
| | 8 | AGGTCCGGGTGACAGTGCTTCGG | 1 | 0 | 0 |
| | 9 | CCGGGTGACAGTGCTTCGGCAGG | 1 | 0 | 0 |
| | 10 | CTGTGCGGCAACCTACATGATGG | 1 | 0 | 0 |
| | 11 | **CAACTCATTCCCCATCATGTAGG** | 1 | 0 | 0 |
| | 12 | CTAGATGATTCCATCTGCACGGG | 1 | 0 | 0 |
| DGKζ | 1 | **GGCTAGGAGTCAGCGACATATGG** | 1 | 0 | 0 |
| | 2 | **GCTAGGAGTCAGCGACATATGGG** | 1 | 0 | 0 |
| | 3 | **CTAGGAGTCAGCGACATATGGGG** | 1 | 0 | 0 |
| | 4 | **GTACTGTGTAGCCAGGATGCTGG** | 1 | 0 | 0 |
| | 5 | **ACGAGCACTCACCAGCATCCTGG** | 1 | 0 | 0 |
| | 6 | AGGCTCCAGGAATGTCCGCGAGG | 1 | 0 | 0 |
| | 7 | ACTTACCTCGCGGACATTCCTGG | 1 | 0 | 0 |
| | 8 | CACCCTGGGCACTTACCTCGCGG | 1 | 0 | 0 |
| | 9 | GTGCCGTACAAAGGTTGGCTGGG | 1 | 0 | 0 |
| | 10 | GGTGCCGTACAAAGGTTGGCTGG | 1 | 0 | 0 |
| | 11 | CTCTCCTCAGTACCACAGCAAGG | 1 | 0 | 0 |
| | 12 | CCTGGGGCCTCCGGGCGCGGAGG | 1 | 0 | 0 |
| | 13 | AGTACTCACCTGGGGCCTCCGGG | 1 | 0 | 0 |
| | 14 | AGGGTCTCCAGCGGCCCTCCTGG | 1 | 0 | 0 |
| | 15 | GCAAGTACTTACGCCTCCTTGGG | 1 | 0 | 0 |
| | 16 | TTGCGGTACATCTCCAGCCTGGG | 1 | 0 | 0 |
| | 17 | TTTGCGGTACATCTCCAGCCTGG | 1 | 0 | 0 |
| Tet2 | 1 | **GCAAAACCTGTCCACTCTTATGG** | 1 | 0 | 0 |
| | 2 | TTGGTGCCATAAGAGTGGACAGG | 1 | 0 | 0 |
| | 3 | **GGTGCAAGTTTCTTATATGTTGG** | 1 | 0 | 0 |
| | 4 | **ACCTGATGCATATAATAATCAGG** | 1 | 0 | 0 |
| | 5 | ACCTGATTATTATATGCATCAGG | 1 | 0 | 0 |
| | 6 | CAGAGCACCAGAGTGCCGTCTGG | 1 | 0 | 0 |
| | 7 | AGAGCACCAGAGTGCCGTCTGGG | 1 | 0 | 0 |
| | 8 | AGAGTGCCGTCTGGGTCTGAAGG | 1 | 0 | 0 |
| | 9 | AGGAAGGCCGTCCATTCTCAGGG | 1 | 0 | 0 |

TABLE 3-continued

| Gene | # | DNA target sequence | Mismatch 0 bp | 1 bp | 2 bp |
|---|---|---|---|---|---|
| | 10 | GGATAGAACCAACCATGTTGAGG | 1 | 0 | 0 |
| | 11 | TCTGTTGCCCTCAACATGGTTGG | 1 | 0 | 0 |
| | 12 | TTAGTCTGTTGCCCTCAACATGG | 1 | 0 | 0 |
| | 13 | GTCTGGCAAATGGGAGGTGATGG | 1 | 0 | 0 |
| | 14 | CAGAGGTTCTGTCTGGCAAATGG | 1 | 0 | 0 |
| | 15 | TTGTAGCCAGAGGTTCTGTCTGG | 1 | 0 | 0 |
| | 16 | ACTTCTGGATGAGCTCTCTCAGG | 1 | 0 | 0 |
| | 17 | AGAGCTCATCCAGAAGTAAATGG | 1 | 0 | 0 |
| | 18 | TTGGTGTCTCCATTTACTTCTGG | 1 | 0 | 0 |
| | 19 | TTCTGGCTTCCCTTCATACAGGG | 1 | 0 | 0 |
| | 20 | CAGGACTCACACGACTATTCTGG | 1 | 0 | 0 |
| | 21 | CTACTTTCTTGTGTAAAGTCAGG | 1 | 0 | 0 |
| | 22 | GACTTTACACAAGAAAGTAGAGG | 1 | 0 | 0 |
| | 23 | GTCTTTCTCCATTAGCCTTTTGG | 1 | 0 | 0 |
| | 24 | AATGGAGAAAGACGTAACTTCGG | 1 | 0 | 0 |
| | 25 | ATGGAGAAAGACGTAACTTCGGG | 1 | 0 | 0 |
| | 26 | TGGAGAAAGACGTAACTTCGGGG | 1 | 0 | 0 |
| | 27 | TTTGGTTGACTGCTTTCACCTGG | 1 | 0 | 0 |
| | 28 | TCACTCAAATCGGAGACATTTGG | 1 | 0 | 0 |
| | 29 | ATCTGAAGCTCTGGATTTTCAGG | 1 | 0 | 0 |
| | 30 | GCTTCAGATTCTGAATGAGCAGG | 1 | 0 | 0 |
| | 31 | CAGATTCTGAATGAGCAGGAGGG | 1 | 0 | 0 |
| | 32 | AAGGCAGTGCTAATGCCTAATGG | 1 | 0 | 0 |
| | 33 | GCAGAAACTGTAGCACCATTAGG | 1 | 0 | 0 |
| | 34 | ACCGCAATGGAAACACAATCTGG | 1 | 0 | 0 |
| | 35 | TGTGGTTTTCTGCACCGCAATGG | 1 | 0 | 0 |
| | 36 | CATAAATGCCATTAACAGTCAGG | 1 | 0 | 0 |
| | 37 | ATTAGTAGCCTGACTGTTAATGG | 1 | 0 | 0 |
| | 38 | CGATGGGTGAGTGATCTCACAGG | 1 | 0 | 0 |
| | 39 | ACTCACCCATCGCATACCTCAGG | 1 | 0 | 0 |
| | 40 | CTCACCCATCGCATACCTCAGGG | 1 | 0 | 0 |
| PSGL-1 | 1 | AGCAACAGGAGGAGTTGCAGAGG | 1 | 0 | 0 |
| | 2 | CCAGTAGGATCAGCAACAGGAGG | 1 | 0 | 0 |
| | 3 | CTCCTGTTGCTGATCCTACTGGG | 1 | 0 | 0 |
| | 4 | GGCCCAGTAGGATCAGCAACAGG | 1 | 0 | 0 |
| | 5 | TTGCTGATCCTACTGGGCCCTGG | 1 | 0 | 0 |
| | 6 | TGGCAACAGCTTGCAGCTGTGGG | 1 | 0 | 0 |
| | 7 | CTTGGGTCCCCTGGTTGCCCGGG | 1 | 0 | 0 |
| | 8 | GTCCCCTGCTTGCCCGGGACCGG | 1 | 0 | 0 |
| | 9 | CTCCGGTCCCGGGCAAGCAGGGG | 1 | 0 | 0 |
| | 10 | TCTCCGGTCCCGGGCAAGCAGGG | 1 | 0 | 0 |
| | 11 | GTCTCCGGTCCCGGGCAAGCAGG | 1 | 0 | 0 |
| | 12 | GCTTGCCCGGGACCGGAGACAGG | 1 | 0 | 0 |
| | 13 | GGTGGCCTGTCTCCGGTCCCGGG | 1 | 0 | 0 |
| | 14 | CGGTGGCCTGTCTCCGGTCCCGG | 1 | 0 | 0 |
| | 15 | CATATTCGGTGGCCTGTCTCCGG | 1 | 0 | 0 |
| | 16 | ATCTAGGTACTCATATTCGGTGG | 1 | 0 | 0 |
| | 17 | **ATAATCTAGGTACTCATATTCGG** | 1 | 0 | 0 |
| | 18 | TTATGATTTCCTGCCAGAAACGG | 1 | 0 | 0 |
| | 19 | ATTTCTGGAGGCTCCGTTTCTGG | 1 | 0 | 0 |
| | 20 | ACTGACACCACTCCTCTGACTGG | 1 | 0 | 0 |
| | 21 | CTGACACCACTCCTCTGACTGGG | 1 | 0 | 0 |
| | 22 | ACCACTCCTCTGACTGGGCCTGG | 1 | 0 | 0 |
| | 23 | AACCCCTGAGTCTACCACTGTGG | 1 | 0 | 0 |
| | 24 | CTCCACAGTGGTAGACTCAGGGG | 1 | 0 | 0 |
| | 25 | GCTCCACAGTGGTAGACTCAGGG | 1 | 0 | 0 |
| | 26 | GGCTCCACAGTGGTACACTCAGG | 1 | 0 | 0 |
| | 27 | CCTGCTGCAAGGCGTTCTACTGG | 1 | 0 | 0 |
| | 28 | CCAGTAGAACGCCTTGCAGCAGG | 1 | 0 | 0 |
| | 29 | CGTTCTACTGGCCTGGATGCAGG | 1 | 0 | 0 |
| | 30 | TCTACTGGCCTGGATGCAGGAGG | 1 | 0 | 0 |
| | 31 | CCACGGAGCTGGCCAACATGGGG | 1 | 0 | 0 |
| | 32 | CGTGGACAGGTTCCCCATGTTGG | 1 | 0 | 0 |
| | 33 | GTCCACGGATTCAGCAGCTATGG | 1 | 0 | 0 |
| | 34 | GACCACTCAACCAGTGCCCACGG | 1 | 0 | 0 |
| | 35 | GGAGTGGTCTGTGCCTCCGTGGG | 1 | 0 | 0 |
| | 36 | GGCACAGACAACTCGACTGACGG | 1 | 0 | 0 |
| | 37 | GACAACTCGACTGACGGCCACGG | 1 | 0 | 0 |
| | 38 | AACTCGACTGACGGCCACGGAGG | 1 | 0 | 0 |
| | 39 | CACAGAACCCAGTGCCACAGAGG | 1 | 0 | 0 |
| | 40 | GGTAGTAGGTTCCATGGACAGGG | 1 | 0 | 0 |
| | 41 | TGGTAGTAGGTTCCATGGACAGG | 1 | 0 | 0 |
| | 42 | TCTTTTGGTAGTAGGTTCCATGG | 1 | 0 | 0 |
| | 43 | ATGGAACCTACTACCAAAAGAGG | 1 | 0 | 0 |
| | 44 | AACAGACCTCTTTTGGTAGTAGG | 1 | 0 | 0 |

TABLE 3-continued

| Gene | # | DNA target sequence | Mismatch 0 bp | 1 bp | 2 bp |
|---|---|---|---|---|---|
| | 45 | GGGTATGAACAGACCTCTTTTGG | 1 | 0 | 0 |
| | 46 | TGTGTCCTCTGTTACTCACAAGG | 1 | 0 | 0 |
| | 47 | GTGTCCTCTGTTACTCACAAGGG | 1 | 0 | 0 |
| | 48 | GTAGTTGACGGACAAATTGCTGG | 1 | 0 | 0 |
| | 49 | TTTGTCCGTCAACTACCCAGTGG | 1 | 0 | 0 |
| | 50 | TTGTCCGTCAACTACCCAGTGGG | 1 | 0 | 0 |
| | 51 | TGTCCGTCAACTACCCAGTGGGG | 1 | 0 | 0 |
| | 52 | GTCCGTCAACTACCCAGTGGGGG | 1 | 0 | 0 |
| | 53 | CTCTGTGAAGCAGTGCCTGCTGG | 1 | 0 | 0 |
| | 54 | CCTGCTGGCCATCCTAATCTTGG | 1 | 0 | 0 |
| | 55 | CCAAGATTAGGATGGCCAGCAGG | 1 | 0 | 0 |
| | 56 | GGCCATCCTAATCTTGGCGCTGG | 1 | 0 | 0 |
| | 57 | CACCAGCGCCAAGATTAGGATGG | 1 | 0 | 0 |
| | 58 | AGTGCACACGAAGAAGATAGTGG | 1 | 0 | 0 |
| | 59 | TATCTTCTTCGTGTGCACTGTGG | 1 | 0 | 0 |
| | 60 | CTTCGTGTGCACTGTGGTGCTGG | 1 | 0 | 0 |
| | 61 | GGCGGTCCGCCTCTCCCGCAAGG | 1 | 0 | 0 |
| | 62 | GCGGTCCGCCTCTCCCGCAAGGG | 1 | 0 | 0 |
| | 63 | AATTACGCACGGGGTACATGTGG | 1 | 0 | 0 |
| | 64 | TGGGGGAGTAATTACGCACGGGG | 1 | 0 | 0 |
| | 65 | GTGGGGGAGTAATTACGCACGGG | 1 | 0 | 0 |
| | 66 | GGTGGGGGAGTAATTACGCACGG | 1 | 0 | 0 |
| | 67 | TAATTACTCCCCCACCGAGATGG | 1 | 0 | 0 |
| | 68 | AGATGCAGACCATCTCGGTGGGG | 1 | 0 | 0 |
| | 69 | GAGATGCAGACCATCTCGGTGGG | 1 | 0 | 0 |
| | 70 | TGAGATGCAGACCATCTCGGTGG | 1 | 0 | 0 |
| | 71 | GGATGAGATGCAGACCATCTCGG | 1 | 0 | 0 |
| | 72 | ATCTCATCCCTGTTGCCTGATGG | 1 | 0 | 0 |
| | 73 | TCATCCCTGTTGCCTGATGGGGG | 1 | 0 | 0 |
| | 74 | CTCACCCCCATCAGGCAACAGGG | 1 | 0 | 0 |
| | 75 | GAGGGCCCCTCACCCCCATCAGG | 1 | 0 | 0 |
| | 76 | GGGCCCTCTGCCACAGCCAATGG | 1 | 0 | 0 |
| | 77 | CCCTCTGCCACAGCCAATGGGGG | 1 | 0 | 0 |
| | 78 | CCCCCATTGGCTGTGGCAGAGGG | 1 | 0 | 0 |
| | 79 | GCCCCCATTGGCTGTGGCAGAGG | 1 | 0 | 0 |
| | 80 | GGACAGGCCCCCATTGGCTGTGG | 1 | 0 | 0 |
| | 81 | CCGGGCTCTTGGCCTTGGACAGG | 1 | 0 | 0 |
| | 82 | CTGTCCAAGGCCAAGAGCCCGGG | 1 | 0 | 0 |
| | 83 | TGGCGTCAGGCCCGGGCTCTTGG | 1 | 0 | 0 |
| | 84 | CGGGCCTGACGCCAGAGCCCAGG | 1 | 0 | 0 |

TABLE 3-continued

| Gene | # | DNA target sequence | Mismatch 0 bp | 1 bp | 2 bp |
|---|---|---|---|---|---|
| FAS | 1 | CAACAACCATGCTGGGCATCTGG | 1 | 0 | 0 |
| | 2 | GAGGGTCCAGATGCCCAGCATGG | 1 | 0 | 0 |
| | 3 | **CATCTGGACCCTCCTACCTCTGG** | 1 | 0 | 0 |
| | 4 | AGGGCTCACCAGAGGTAGGAGGG | 1 | 0 | 0 |
| | 5 | **GGAGTTGATGTCAGTCACTTGGG** | 1 | 0 | 0 |
| | 6 | TGGAGTTGATGTCAGTCACTTGG | 1 | 0 | 0 |
| | 7 | AGTGACTGACATCAACTCCAAGG | 1 | 0 | 0 |
| | 8 | **GTGACTGACATCAACTCCAAGGG** | 1 | 0 | 0 |
| | 9 | ACTCCAAGGGATTGGAATTGAGG | 1 | 0 | 0 |
| | 10 | CTTCCTCAATTCCAATCCCTTGG | 1 | 0 | 0 |
| | 11 | TACAGTTGAGACTCAGAACTTGG | 1 | 0 | 0 |
| | 12 | TTGGAAGGCCTGCATCATGATGG | 1 | 0 | 0 |
| | 13 | AGAATTGGCCATCATGATGCAGG | 1 | 0 | 0 |
| | 14 | GACAGGGCTTATGGCAGAATTGG | 1 | 0 | 0 |
| | 15 | **TGTAACATACCTGGAGGACAGGG** | 1 | 0 | 0 |
| | 16 | GTGTAACATACCTGGAGGACAGG | 1 | 0 | 0 |
| KDM6A | 1 | CGTACCTGTGCAACTCCTGTTGG | 1 | 0 | 0 |
| | 2 | GATCTACTGGAATTCCTAATGGG | 1 | 0 | 0 |
| | 3 | GAGTCAGCTGTTGGCCCATTAGG | 1 | 0 | 0 |
| | 4 | CTGCCTACAAACTCAGTCTCTGG | 1 | 0 | 0 |
| | 5 | GGGCAGGCAGGACGGACTCCAGG | 1 | 0 | 0 |
| | 6 | GGAGTCCGTCCTGCCTGCCCTGG | 1 | 0 | 0 |
| | 7 | GAGTCCGTCCTGCCTGCCCTGGG | 1 | 0 | 0 |
| | 8 | GAAAAGGGTCCATTGGCCAAAGG | 1 | 0 | 0 |
| | 9 | GCCTGCAGAAAAGGGTCCATTGG | 1 | 0 | 0 |
| | 10 | TTGATGTGCTACAGGGAACATGG | 1 | 0 | 0 |
| | 11 | AGCGTTCTTGATGTGCTACAGGG | 1 | 0 | 0 |
| | 12 | CAGCGTTCTTGATGTGCTACAGG | 1 | 0 | 0 |
| | 13 | CTGTAGCACATCAAGAACGCTGG | 1 | 0 | 0 |
| | 14 | TGTAGCACATCAAGAACGCTGGG | 1 | 0 | 0 |
| | 15 | ATAGGCAATAATCATATAACAGG | 1 | 0 | 0 |
| | 16 | AGTGCGTTTCGCTGCAGGTAAGG | 1 | 0 | 0 |
| | 17 | GAGTGAGTGCGTTTCGCTGCAGG | 1 | 0 | 0 |
| | 18 | GTCAGGTTTGTGCGGTTATGAGG | 1 | 0 | 0 |
| | 19 | CGCTGCTGGTCAGGTTTGTGCGG | 1 | 0 | 0 |
| | 20 | **AAACCTGACCAGCAGCGCAGAGG** | 1 | 0 | 0 |
| | 21 | CCAGCAGCGCAGAGGAGCCGTGG | 1 | 0 | 0 |
| | 22 | CCACGGCTCCTCTGCGCTGCTGG | 1 | 0 | 0 |
| | 23 | CCAACTATCTAACTCCACTCAGG | 1 | 0 | 0 |
| | 24 | CCTGAGTGGAGTTAGATAGTTGG | 1 | 0 | 0 |

TABLE 41

The activity of each sgRNA on the Jurkat cells for the target sequence

| Gene | # | Cas9/sgRNA Transfection Total Leads | Ins | Del | Indel ratio (%) | Cas9/sgRNA Transfection Total Leads | Ins | Del | Indel ratio (%) |
|---|---|---|---|---|---|---|---|---|---|
| A20 | 1 | 58003 | 46 | 55 | 0.20% | 63455 | 17711 | 9469 | 42.80% |
| | 2 | 40652 | 0 | 18 | 0.00% | 46245 | 12025 | 6331 | 39.70% |
| | 3 | 40652 | 0 | 18 | 0.00% | 41702 | 301 | 92 | 0.90% |
| | 4 | 40652 | 0 | 18 | 0.00% | 4 | 2 | 2 | 0.00% |
| | 5 | 40652 | 0 | 18 | 0.00% | 52838 | 36339 | 4989 | 78.20% |
| | 6 | 40652 | 0 | 18 | 0.00% | 10641 | 5864 | 3460 | 87.60% |
| | 7 | 40652 | 0 | 18 | 0.00% | 40168 | 10298 | 4194 | 36.10% |
| | 8 | 40652 | 0 | 18 | 0.00% | 43044 | 9494 | 13398 | 53.20% |
| | 9 | 40652 | 0 | 18 | 0.00% | 46853 | 6629 | 2620 | 19.70% |
| | 10 | 40652 | 0 | 18 | 0.00% | 44573 | 17644 | 5168 | 51.20% |
| | 11 | 63969 | 37 | 103 | 0.20% | 61003 | 26844 | 22740 | 81.30% |
| | 12 | 63959 | 37 | 103 | 0.20% | 63321 | 949 | 1464 | 3.80% |
| DGKα | 1 | 61246 | 0 | 4 | 0.00% | 70438 | 4171 | 703 | 7.00% |
| | 2 | 61246 | 0 | 4 | 0.00% | 55262 | 7413 | 662 | 14.60% |
| | 3 | 61246 | 0 | 4 | 0.00% | 62354 | 19424 | 1546 | 33.60% |
| | 4 | 59349 | 0 | 44 | 0.10% | 58402 | 20072 | 5137 | 43.20% |
| | 5 | 59349 | 0 | 44 | 0.10% | 60718 | 14921 | 2484 | 28.70% |
| | 6 | 59349 | 0 | 44 | 0.10% | 67024 | 18760 | 2365 | 31.50% |
| | 7 | 49807 | 0 | 0 | 0.00% | 49459 | 26142 | 2877 | 58.70% |
| | 8 | 49807 | 0 | 0 | 0.00% | 65141 | 29740 | 3324 | 50.80% |

TABLE 41-continued

The activity of each sgRNA on the Jurkat cells for the target sequence

| Gene | # | Cas9/sgRNA Transfection Total Leads | Ins | Del | Indel ratio (%) | Cas9/sgRNA Transfection Total Leads | Ins | Del | Indel ratio (%) |
|---|---|---|---|---|---|---|---|---|---|
| | 9 | 49807 | 0 | 0 | 0.00% | 50760 | 30324 | 3742 | 67.10% |
| | 10 | 49807 | 0 | 0 | 0.00% | 61315 | 8953 | 4772 | 22.40% |
| | 11 | 49807 | 0 | 0 | 0.00% | 78876 | 61415 | 8416 | 88.50% |
| | 12 | 49807 | 0 | 0 | 0.00% | 64641 | 12255 | 1780 | 21.70% |
| EGR2 | 1 | 37189 | 0 | 0 | 0.00% | 53321 | 11060 | 4974 | 30.10% |
| | 2 | 37189 | 0 | 0 | 0.00% | 48475 | 6809 | 1965 | 18.10% |
| | 3 | 37189 | 0 | 0 | 0.00% | 43800 | 8688 | 7796 | 37.60% |
| | 4 | 37189 | 0 | 0 | 0.00% | 43670 | 2921 | 569 | 8.00% |
| | 5 | 37189 | 0 | 0 | 0.00% | 34730 | 3002 | 497 | 10.10% |
| | 6 | 37189 | 0 | 0 | 0.00% | 46018 | 10502 | 1408 | 25.90% |
| | 7 | 37189 | 0 | 0 | 0.00% | 48537 | 5271 | 2475 | 16.00% |
| | 3 | 37189 | 0 | 0 | 0.00% | 36551 | 6457 | 686 | 19.50% |
| | 9 | 37189 | 0 | 0 | 0.00% | 37903 | 6210 | 1671 | 20.80% |
| | 10 | 37189 | 0 | 0 | 0.00% | 44855 | 9524 | 2320 | 26.40% |
| | 11 | 37189 | 0 | 0 | 0.00% | 39615 | 9368 | 2622 | 30.30% |
| | 12 | 37189 | 0 | 0 | 0.00% | 43995 | 2542 | 563 | 7.10% |
| | 13 | | | | | 46228 | 289 | 62 | 0.76% |
| | 14 | | | | | 50220 | 1323 | 821 | 4.27% |
| | 15 | | | | | 33478 | 5638 | 1156 | 20.29% |
| | 16 | | | | | 20489 | 1731 | 483 | 10.81% |
| | 17 | | | | | 26353 | 3835 | 495 | 16.43% |
| | 18 | | | | | 23901 | 1456 | 896 | 9.84% |
| | 19 | | | | | 24352 | 3956 | 1672 | 23.11% |
| | 20 | | | | | 11 | 0 | 0 | 0.00% |
| | 21 | | | | | 34764 | 1522 | 359 | 5.41% |
| | 22 | | | | | 31546 | 91 | 0 | 0.29% |
| | 23 | | | | | 42734 | 10 | 0 | 0.02% |
| | 24 | | | | | 32492 | 59 | 0 | 0.18% |
| | 25 | | | | | 32243 | 1917 | 304 | 6.89% |
| | 26 | | | | | 39333 | 868 | 328 | 3.04% |
| | 27 | | | | | 36373 | 806 | 556 | 3.74% |
| | 28 | | | | | 45819 | 2 | 26 | 0.06% |
| | 29 | | | | | 53425 | 1159 | 584 | 3.26% |
| | 30 | | | | | 36877 | 169 | 47 | 0.59% |
| | 31 | | | | | 36317 | 0 | 76 | 0.21% |
| | 32 | | | | | 37941 | 829 | 122 | 2.51% |
| | 33 | | | | | 47730 | 167 | 2 | 0.35% |
| | 34 | | | | | 38753 | 347 | 62 | 1.06% |
| PPP2R2D | 5 | 38644 | 0 | 31 | 0.10% | 48997 | 2891 | 240 | 6.40% |
| | 6 | 50653 | 2 | 19 | 0.00% | 48327 | 7669 | 1403 | 18.80% |
| | 7 | 36764 | 0 | 0 | 0.00% | 54465 | 670 | 70 | 1.40% |
| | 8 | 36764 | 0 | 0 | 0.00% | 45004 | 11382 | 1569 | 28.80% |
| | 9 | 36764 | 0 | 0 | 0.00% | 54094 | 17825 | 3635 | 39.70% |
| | 10 | 36764 | 0 | 0 | 0.00% | 47800 | 19253 | 3432 | 47.50% |
| | 11 | 36764 | 0 | 0 | 0.00% | 50362 | 966 | 129 | 2.20% |
| | 12 | 36764 | 0 | 0 | 0.00% | 42667 | 12810 | 2318 | 35.50% |
| | 13 | | | | | 57258 | 1380 | 1050 | 3.61% |
| | 14 | | | | | 69925 | 13321 | 3599 | 24.20% |
| | 15 | | | | | 1E+05 | 21836 | 3254 | 24.10% |
| | 16 | | | | | 77282 | 19219 | 7372 | 34.41% |
| | 17 | | | | | 66732 | 3687 | 2227 | 8.86% |
| | 18 | | | | | 96593 | 9524 | 1111 | 11.01% |
| | 19 | | | | | 63082 | 11415 | 4155 | 24.68% |
| | 20 | | | | | 57937 | 4360 | 676 | 8.69% |
| | 21 | | | | | 67752 | 20314 | 4900 | 37.22% |
| | 22 | | | | | 72814 | 2244 | 1198 | 4.73% |
| | 23 | | | | | 79305 | 14047 | 1175 | 19.19% |
| | 24 | | | | | 73629 | 2914 | 571 | 4.73% |
| | 25 | | | | | 85222 | 5472 | 1905 | 8.66% |
| | 26 | | | | | 73094 | 1937 | 288 | 3.04% |
| | 27 | | | | | 94017 | 9895 | 6171 | 17.09% |
| | 28 | | | | | 93118 | 8847 | 2464 | 12.15% |
| | 29 | | | | | 77821 | 5007 | 1962 | 8.96% |
| PD-1 | 1 | 68258 | 581 | 105 | 1.00% | 77910 | 29123 | 7725 | 47.30% |
| | 2 | 68258 | 581 | 105 | 1.00% | 77866 | 1270 | 3816 | 6.50% |
| | 3 | 68258 | 581 | 105 | 1.00% | 66362 | 912 | 94 | 1.50% |
| | 4 | 68258 | 581 | 105 | 1.00% | 55936 | 41594 | 10324 | 92.80% |
| | 5 | 68258 | 581 | 105 | 1.00% | 65077 | 2554 | 192 | 4.20% |
| | 6 | 68258 | 581 | 105 | 1.00% | 71898 | 50678 | 10542 | 85.10% |

TABLE 41-continued

The activity of each sgRNA on the Jurkat cells for the target sequence

| Gene | # | Cas9/sgRNA Transfection Total Leads | Ins | Del | Indel ratio (%) | Cas9/sgRNA Transfection Total Leads | Ins | Del | Indel ratio (%) |
|---|---|---|---|---|---|---|---|---|---|
| | 7 | 68258 | 581 | 105 | 1.00% | 83902 | 17154 | 3246 | 24.30% |
| | 8 | 68258 | 581 | 105 | 1.00% | 79724 | 28304 | 7542 | 45.00% |
| | 9 | 68258 | 581 | 105 | 1.00% | 65936 | 10471 | 649 | 16.90% |
| | 10 | 68258 | 581 | 105 | 1.00% | 66937 | 0 | 29 | 0.00% |
| | 11 | 68258 | 581 | 105 | 1.00% | 77994 | 1135 | 754 | 2.40% |
| | 12 | 68258 | 581 | 105 | 1.00% | 67631 | 0 | 8 | 0.00% |
| | 13 | 68258 | 581 | 105 | 1.00% | 67161 | 30099 | 8037 | 56.80% |
| CTLA-4 | 7 | 68230 | 0 | 0 | 0 | 51173 | 3216 | 714 | 7.70% |
| | 10 | 53694 | 3 | 18 | 0 | 40995 | 11760 | 1803 | 33.10% |
| | 11 | 53694 | 3 | 18 | 0 | 55767 | 33107 | 3935 | 66.40% |
| | 12 | 53333 | 0 | 0 | 0 | 54992 | 19469 | 8396 | 50.70% |
| DGKζ | 1 | 26039 | 3 | 2 | 0.00% | 25450 | 10061 | 2453 | 49.20% |
| | 2 | 26039 | 3 | 2 | 0.00% | 24907 | 17380 | 2591 | 80.20% |
| | 3 | 26039 | 3 | 2 | 0.00% | 21950 | 14819 | 3291 | 82.50% |
| | 4 | 26039 | 3 | 2 | 0.00% | 20959 | 17708 | 1027 | 89.40% |
| | 5 | 26039 | 3 | 2 | 0.00% | 29570 | 26290 | 2120 | 96.10% |
| | 6 | 37268 | 0 | 0 | 0.00% | 32463 | 3663 | 1878 | 17.10% |
| | 7 | 37268 | 0 | 0 | 0.00% | 34154 | 6884 | 1706 | 25.20% |
| | 8 | 37268 | 0 | 0 | 0.00% | 32920 | 13190 | 4952 | 55.10% |
| | 9 | 22544 | 7 | 12 | 0.10% | 40374 | 5391 | 1209 | 16.30% |
| | 10 | 22544 | 7 | 12 | 0.10% | 28637 | 879 | 702 | 5.50% |
| | 11 | 21780 | 0 | 0 | 0.00% | 27636 | 9279 | 1859 | 40.30% |
| | 12 | 21780 | 0 | 0 | 0.00% | 20548 | 9474 | 2164 | 56.60% |
| | 13 | 21780 | 0 | 0 | 0.00% | 19161 | 9909 | 3016 | 67.50% |
| | 14 | 53786 | 0 | 6 | 0.00% | 36736 | 13 | 45 | 0.20% |
| | 15 | 24528 | 0 | 10 | 0.00% | 24319 | 12791 | 1446 | 58.50% |
| | 16 | 24528 | 0 | 10 | 0.00% | 20768 | 1520 | 140 | 8.00% |
| | 17 | 24528 | 0 | 10 | 0.00% | 26158 | 301 | 56 | 1.40% |
| Tet2 | 1 | 42428 | 375 | 573 | 2.23% | 48887 | 35150 | 5438 | 83.02% |
| | 2 | 42428 | 375 | 573 | 2.23% | 44082 | 852 | 1852 | 6.13% |
| | 3 | 42428 | 375 | 573 | 2.23% | 49662 | 24418 | 7469 | 64.21% |
| | 4 | 42428 | 375 | 573 | 2.23% | 39571 | 20708 | 6428 | 68.58% |
| | 5 | 42428 | 375 | 573 | 2.23% | 52562 | 11325 | 2524 | 26.35% |
| | 6 | 38575 | 7 | 14 | 0.10% | 38990 | 3873 | 6433 | 26.43% |
| | 7 | 38575 | 7 | 14 | 0.10% | 36884 | 8795 | 1143 | 26.94% |
| | 8 | 38575 | 7 | 14 | 0.10% | 34674 | 5096 | 1843 | 20.01% |
| | 9 | 38575 | 7 | 14 | 0.10% | 38693 | 16101 | 4895 | 54.26% |
| | 10 | | | | | 17614 | 4770 | 780 | 31.51% |
| | 11 | | | | | 19411 | 1855 | 1416 | 16.85% |
| | 12 | | | | | 14049 | 6887 | 1565 | 60.16% |
| | 13 | | | | | 16272 | 2960 | 2087 | 31.02% |
| | 14 | | | | | 18553 | 110 | 79 | 1.02% |
| | 15 | | | | | 18062 | 1434 | 591 | 11.21% |
| | 16 | | | | | 12053 | 2969 | 2423 | 44.74% |
| | 17 | | | | | 14802 | 738 | 444 | 7.99% |
| | 18 | | | | | 16943 | 395 | 154 | 3.24% |
| | 19 | | | | | 18051 | 2953 | 1070 | 22.29% |
| | 20 | | | | | 14729 | 3041 | 474 | 23.86% |
| | 21 | | | | | 18590 | 1074 | 320 | 7.50% |
| | 22 | | | | | 19329 | 3304 | 1481 | 24.76% |
| | 23 | | | | | 17420 | 36 | 19 | 0.32% |
| | 24 | | | | | 20994 | 5582 | 1354 | 33.04% |
| | 25 | | | | | 16860 | 2573 | 370 | 17.46% |
| | 26 | | | | | 15137 | 1509 | 998 | 16.56% |
| | 27 | | | | | 16035 | 635 | 185 | 5.11% |
| | 28 | | | | | 14636 | 2734 | 1750 | 30.64% |
| | 29 | | | | | 18893 | 133 | 45 | 0.94% |
| | 30 | | | | | 15959 | 0 | 0 | 0.00% |
| | 31 | | | | | 22627 | 216 | 126 | 1.51% |
| | 32 | | | | | 15361 | 368 | 361 | 4.75% |
| | 33 | | | | | 14501 | 1358 | 1939 | 22.74% |
| | 34 | | | | | 3225 | 171 | 21 | 5.95% |
| | 35 | | | | | 20968 | 725 | 209 | 4.45% |
| | 36 | | | | | 15689 | 147 | 155 | 1.92% |
| | 37 | | | | | 17405 | 239 | 18 | 1.48% |
| | 38 | | | | | 20122 | 166 | 134 | 1.49% |
| | 39 | | | | | 12585 | 370 | 106 | 3.78% |
| | 40 | | | | | 15027 | 344 | 378 | 4.80% |

TABLE 41-continued

| The activity of each sgRNA on the Jurkat cells for the target sequence | | | | | | | | | |
|---|---|---|---|---|---|---|---|---|---|
| | | Cas9/sgRNA Transfection | | | | Cas9/sgRNA Transfection | | | |
| Gene | # | Total Leads | Ins | Del | Indel ratio (%) | Total Leads | Ins | Del | Indel ratio (%) |
| PSGL-1 | 5 | 29368 | 0 | 9 | 0.03% | 36584 | 8978 | 2453 | 31.25% |
| | 6 | 29368 | 0 | 9 | 0.03% | 35183 | 6859 | 639 | 21.31% |
| | 7 | 33707 | 125 | 13 | 0.41% | 24237 | 14697 | 2248 | 69.91% |
| | 9 | 33707 | 125 | 13 | 0.41% | 23911 | 9948 | 2001 | 49.97% |
| | 10 | 33707 | 125 | 13 | 0.41% | 30152 | 804 | 207 | 3.35% |
| | 11 | 33707 | 125 | 13 | 0.41% | 28425 | 95 | 6 | 0.36% |
| | 12 | 33707 | 125 | 13 | 0.41% | 25153 | 8931 | 1355 | 40.89% |
| | 15 | 33707 | 125 | 13 | 0.41% | 24798 | 2996 | 414 | 13.75% |
| | 16 | 33707 | 125 | 13 | 0.41% | 23116 | 8737 | 1192 | 42.95% |
| | 17 | 33707 | 125 | 13 | 0.41% | 19094 | 10638 | 2066 | 66.53% |
| | 27 | 29168 | 0 | 3 | 0.41% | 29561 | 9316 | 1202 | 35.58% |
| | 29 | 29168 | 0 | 3 | 0.01% | 36720 | 5836 | 396 | 16.97% |
| | 30 | 29168 | 0 | 3 | 0.01% | 41685 | 3815 | 976 | 11.49% |
| FAS | 1 | | | | | 33594 | 14802 | 6170 | 62.43% |
| | 2 | | | | | 24634 | 7187 | 2668 | 40.01% |
| | 3 | | | | | 32994 | 21062 | 10555 | 95.83% |
| | 4 | | | | | 30374 | 1328 | 529 | 6.11% |
| | 5 | | | | | 40549 | 33991 | 4118 | 93.98% |
| | 6 | | | | | 51209 | 7460 | 173 | 17.96% |
| | 7 | | | | | 24583 | 8997 | 9498 | 75.23% |
| | 8 | | | | | 28815 | 20681 | 6053 | 92.78% |
| | 9 | | | | | 29188 | 17689 | 4990 | 77.70% |
| | 10 | | | | | 25433 | 10120 | 9482 | 77.07% |
| | 11 | | | | | 29184 | 15700 | 7500 | 79.50% |
| | 12 | | | | | 25410 | 18254 | 1737 | 78.67% |
| | 13 | | | | | 28564 | 18560 | 1575 | 70.49% |
| | 14 | | | | | 2482 | 1241 | 325 | 63.09% |
| | 15 | | | | | 29819 | 14067 | 10479 | 82.32% |
| | 16 | | | | | 31325 | 8422 | 3600 | 38.38% |
| KDM6A | 1 | | | | | 33935 | 4337 | 1753 | 17.95% |
| | 2 | | | | | 42016 | 10713 | 3625 | 34.13% |
| | 3 | | | | | 56988 | 1195 | 951 | 3.77% |
| | 4 | | | | | 25006 | 3298 | 1295 | 18.37% |
| | 5 | | | | | 38511 | 43 | 16 | 0.15% |
| | 6 | | | | | 20361 | 598 | 340 | 4.61% |
| | 7 | | | | | 32084 | 2785 | 1161 | 12.30% |
| | 8 | | | | | 31373 | 1616 | 523 | 6.82% |
| | 9 | | | | | 5215 | 199 | 228 | 8.19% |
| | 10 | | | | | 32955 | 4524 | 1097 | 17.06% |
| | 11 | | | | | 38820 | 5726 | 1940 | 19.75% |
| | 12 | | | | | 24536 | 72 | 12 | 0.34% |
| | 13 | | | | | 42251 | 2640 | 475 | 7.37% |
| | 14 | | | | | 44333 | 2018 | 628 | 5.97% |
| | 15 | | | | | 33618 | 722 | 290 | 3.01% |
| | 16 | | | | | 36221 | 466 | 250 | 1.98% |
| | 17 | | | | | 40214 | 1357 | 261 | 4.02% |
| | 18 | | | | | 31381 | 1958 | 714 | 8.51% |
| | 19 | | | | | 40205 | 345 | 151 | 1.23% |
| | 20 | | | | | 32494 | 9665 | 1761 | 35.16% |
| | 21 | | | | | 37911 | 1286 | 381 | 4.40% |
| | 22 | | | | | 30751 | 677 | 103 | 2.54% |
| | 23 | | | | | 38635 | 8932 | 2445 | 29.45% |
| | 24 | | | | | 44475 | 1263 | 978 | 5.04% |

4. Tumor Cell Line Culture

EGFRvIII positive U87 MG glioblastoma cell line (U87vIII) was purchased from Celther Polska. A375P melanoma cell line was purchased from Korean Cell line Bank. The cell lines were cultured in DMEM medium containing 10% fetal bovine serum albumin (FBS).

5. Lentivirus Preparation

Anti-EGFRVIII scFV fused with CD8 hinge, 4-1BB and CD3 domain-containing fusion protein 139 CAR and c259 TCR construct targeting NY-ESO-1 were referenced from the study of Sampson, Choi et al. (Sampson et al. 2014, Rapoport, Stadtmauer et al. 2015). The codon-optimized cDNA CAR and TCR construct were subcloned with pLVX vector. The lentivirus vector and helper plasmids were transfected into 293T cell using Lipofectamine2000 (ThermoFisher SCIENTIFIC), and lentivirus-produced culture supernatant was obtained by culturing the transfected 293T cells. After obtaining the culture supernatant, the lentivirus-containing culture supernatant was overlaid to sucrose-containing buffer (100 mM NaCl, 0.5 mM ethylene diamine tetra acetic acid [EDTA], 50 mM Tri-HCl, pH 7.4) at a ratio of 4:1, and was centrifuged at 4° C. for 4 hours at 10,000 g. After the centrifugation, the supernatant was removed, and resuspended after adding phosphate buffered saline (PBS).

6. Construction of DGK KO 139 CAR-T Cells

Human peripheral blood T cells (pan-T cells) were purchased from STEMCELL TECHNOLOGIES. The thawed T cells were cultured in RPMI medium added with hIL-2 of 50 U/mL, hIL-7 of 5 ng/mL and FBS for overnight prior to activation. Anti-CD3/28 Dynabeads (ThermoFisher Scientific) was used to activate the cells, used at 3:1 ratio (beads:cells) in RPMI medium added with 10% FBS. After 24 hours of activation, the T cells were mixed with 139-CAR lentivirus for 48 hours in a 100 μg/mL retronectin-coated plate. Beads were removed after 3 days of stimulation. Electroporation was performed using Amaxa P3 Primary Cell kit and 4D-Nucleofecter (Lonza). To form Cas9 ribonuclear protein (RNP) complex, 40 μg of recombinant *S. pyogenes* Cas9 (Toolgen) and 10 μg of chemically synthesized tracr/crRNA (Integrated DNA Technologies) were incubated for 20 minutes. Pre-incubated Cas9 RNP complex was added to $3\times10^6$ stimulated T cells resuspended in P3 buffer. Cas9 RNP complex were introduced into a nucleus of the cells using the program EO-115. After the electroporation, the cells were seeded at $5\times10^5$ cells/mL in RPMI medium added with hIL-2 of 50 U/mL, hIL-7 of 5 ng/mL and 10% FBS. The target sequence of crRNA used in the test is as follows: DGKα: CTCTCAAGCTGAGTGGGTCC, DGKζ: ACGAGCACTCACCAGCATCC.

7. Flow Cytometry Staining and Antibodies

Unless otherwise specified, cell staining was performed at 4° C. in PBS added with 1% FBS. The list of antibodies and agents for flow cytometry and functional study is as follows: CellTrace CFSE/Far red (ThermoFisher), 7-AAD (Sigma), anti-CD3: UCHT1 (BD), anti-CD4: RPA-T4 (BD), anti-CD8: HIT8a (BD), anti-CD56: B159 (BD), anti-NKG2D: 1D11 (Biolegend), anti-CD45RO: UCHL1 (BD), anti-CCR7: 150513 (BD), anti-PD-1: EH12.2H7 (Biolegend), anti-CD25: M-A251 (BD), anti-Fas: Dx2 (BD), anti-CD107a: H4A3 (Molecular Probes), anti-EGFRviii: (Biorbyt), goat anti-human IgG: (Biorad). The data was collected in Attune NxT Acoustic Focusing Cytometer, and was analyzed using FlowJo.

8. In Vitro Killing Assay, Cytokine Release, and Proliferation Assay

U87vIII and A375P were stained with CellTrace Far red (Invitrogen). Tumor cell lines were cocultured with T cells at a directed ratio, and $2\times10^4$ to $5\times10^4$ tumor cell lines were dispensed per well in a U-bottom 96-well plate. Rested 139 CAR-T cells and c259 T cells were added to each target cell at a directed effector:target (E:T) ratio. The cells were collected after 18 hours of coculture, and were stained with 7-aminoactinomycin for identifying live/dead cells. The sample was measured with Attune NxT Acoustic Focusing Cytometer, and was analyzed with FlowJo. The cytotoxicity was calculated using the equation of [(% lysis sample % lysis minimum)/(% lysis max [100%]-% lysis minimum]× 100%. The test was repeated for three times. The culture supernatant collected after the coculture was used for measuring the quantity of IL-2 and IFN-γ secretion using ELISA Kit (Biolegend). Celltrace-labeled 139CAR-T cells were cocultured for 4 days with U87vIII cells for proliferation assay, and the distribution of Celltrace in 139 CAR-T cells was evaluated using flow cytometry.

9. Repetitive Tumor Challenging Experiment

For a continuous tumor test, 139 CAR-T was cocultured with U87vIII at a ratio of 3:1 (E:T) in IL-7 medium (Day 0). On day 4, 139 CAR-T cells were collected, and again cocultured with U87vIII at the same E:T ratio in IL-7 medium. The culture supernatant was collected individually 24 hours after a first and a second tumor inoculation to evaluate the release of IFN-γ and IL-2.

10. Western Blot Analysis

To evaluate TCR distal signal of T cells, $1\times10^6$ cells were activated for 15 minutes and 60 minutes by using anti-CD3 activation beads (Miltenyi Biotec) at a ratio of 1:2 (beads: cells). To measure ERK, pERK and GAPDH, cell lysate was prepared using RIPA lysis and extracting buffer. Every antibody used in the test was purchased from Cell Signaling.

11. Calcium Influx

The measurement of T cell calcium influx was performed according to the Calcium assay kit (BD) manual. Briefly, T cells were washed with RPMI medium, were resuspended to the same medium, and were incubated with a pigment for an hour at 37° C. After obtaining the basic standard of FITC signal from non treated cells, anti-CD3 activation beads (Miltenyi Biotec) were added at a beads:cells ratio of 5:1, and were measured with flow cytometry. The data collected from the flow cytometry was analyzed with FlowJo software using kinetic mode.

12. Real-Time PCR

For RNA sequencing, $1\times10^6$ cells were activated for 48 hours using human T activator anti-CD3/28 Dynabeads (Thermofisher) at a ratio of 1:1 (beads:cells). The RNA was extracted using RNeasy Mini Kit (Qiagen), and the cDNA was produced according to the manufacturer's instructions (ABI). The real-time PCR was performed using TaqMan gene expression analysis kit/probe set (Thermofisher). The expression of each gene was normalized with GAPDH expression. Here, the primers used for the test are as follows: hDGKα F: 5'-AATACCTGGATTGGGATGTGTCT-3', hDGKα R: 5'-GTCCGTCGTCCTTCAGAGTC, hDGKζF: 5'-GTACTGGCAACGACTTGGC-3', hDGKζR: 5'-GCCCAGGCTGAAGTAGTTGTT-3 hβF: 5'-GGCACTCTTCCAGCCTTC-3 hβR: 5'-TACAGGTCTTTGCGGATGTC-3', ID2: Hs00747379_ml, PRDM1: HS00153357_ml, IL10: 00174086_ml, IFNG: Hs00174143_ml, IL2: HS00174114.

13. Digenome-Sequencing

The genome DNA of human T cell was separated using DNeasy Tissue kit (Qiagen). The genome DNA (20 μg) was treated with Cas9 protein (10 μg), crRNA (3.8 μg) and tracrRNA (3.8 μg) in 1000 μL of reacting solution (NEB3.1 buffer), and was cultured for 4 hours at 37° C. The digested DNA was cultured for 30 minutes at 37° C. with RNase A (50 μg/mL), and was purified with DNeasy Tissue kit. The digested DNA was fragmented using Covaris system and was connected with an adaptor to form library. The DNA library was applied to the full genome sequence using Illumina HiSeq×Ten Sequencer in THERAGEN ETEX. To form a Bam file, Isaac aligner was used by using the following parameters: ver. 01.14.03.12; Human genome reference, hg19 from UCSC (original GRCh37 from NCBI, February 2009), Mouse genome reference, mm10 from UCSC; Base quality cutoff, 15; Keep duplicate reads, yes; Variable read length support, yes; Realign gaps, no; and Adaptor clipping, yes (adaptor: 5'-AGATCGGAAGAGC-3', 5'-GCTCTTCCGATCT-3')

14. Mouse Xenograft Studies

For U87vIII tumor model, $1\times10^6$ U87vIII cells were hypodermically injected at 100 μL PBS volume to the right flank of 6-8 week female NSC mice (Day 0). On the 28th day after transplant, the tumor size reached 150±50 $mm^2$, and the mice were randomly grouped. Each group consisted of 6-8 mice, and the tumor sizes were smilar. $5\times10^6$ of T cells, 139 AAVS1 CAR-T cells, and 139 DGKαζCAR-T cells were intravenously (IV) or intratumorally (IT) injected to each group, respectively, on the 28th day and the 32nd day. Surface expression of CAR for 139 AAVS1 CAR-T cells and 139 DGKαζCAR-T cells was identified (surface CAR expression range: 25%-70%). Every mouse was intraperitoneally administered with Temozolomide (TMZ) (Sigma) (0.33 mg/mouse/day) every day, from the 32nd to the 35th day. The tumor size was monitored twice a week with a calipers. The mice were sacrificed when the tumor size reached 2000 $mm^3$. For additional study of CAR-T cells after in vivo delivery, peripheral blood, spleen and tumor tissues were separated from each mouse. To separate tumor tissue, tumor samples were trimmed with scissors and were treated for an hour with 100 U/ml collagenase IV and 20 U/ml Dnase in a 37° C. water bath. Afterwards the cells were passed through a sterile cell strainer for an additional investigation. To separate cells from the spleen, the tissue was crushed with a sterile plunger and was passed through a sterile cell strainer. For hemolysis, ACK buffer solution (150 mM NH4Cl, 10 mM KHCO3, 1 mM EDTA, pH 7.2) was additionally treated for 5 minutes to the cell suspension. To analyze effector function of tumor-infiltrated T cells, the cells dissociated from the tumor tissue were reactivated for 5 hours with 50 ng/ml PMA and 1 μg/mL ionomycin in a $CO_2$ incubator, and staining of intracellular IFN-γ and TNFα was performed.

Figure 28:
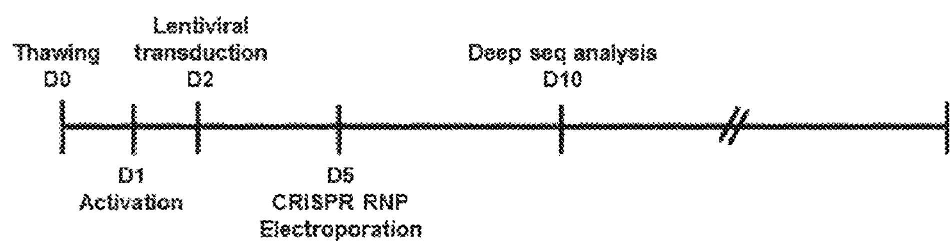
FIG. 28 is a graph showing the CAR expression level in 139 CAR-T cells treated with CRISPR/Cas9.
Figure 28:
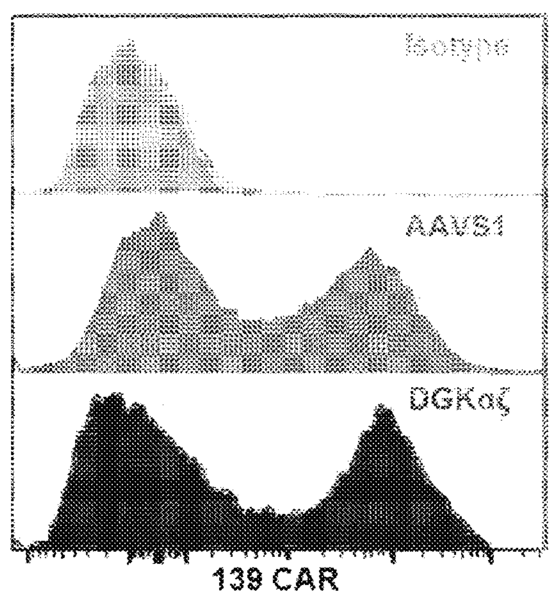
Figure 29:
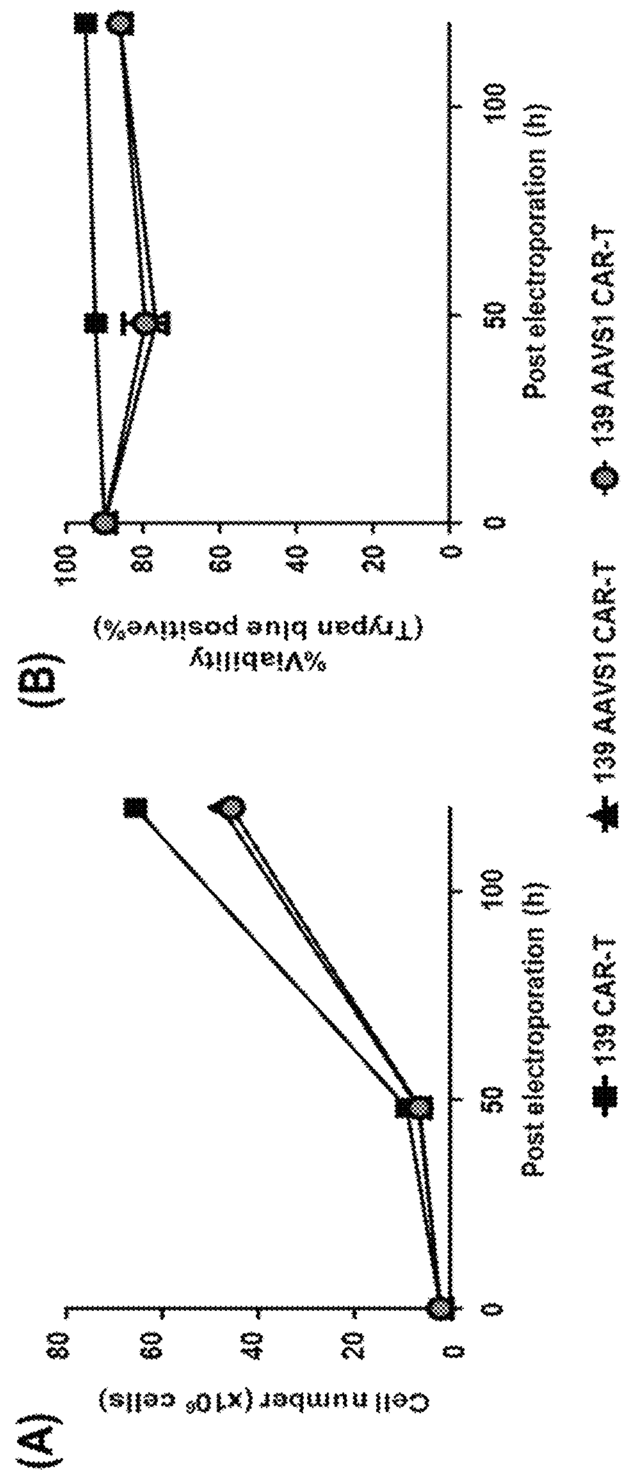
FIG. 29 is a graph showing the growth of T cells after electroporing CRISPR/Cas9 complex.
Figure 30:
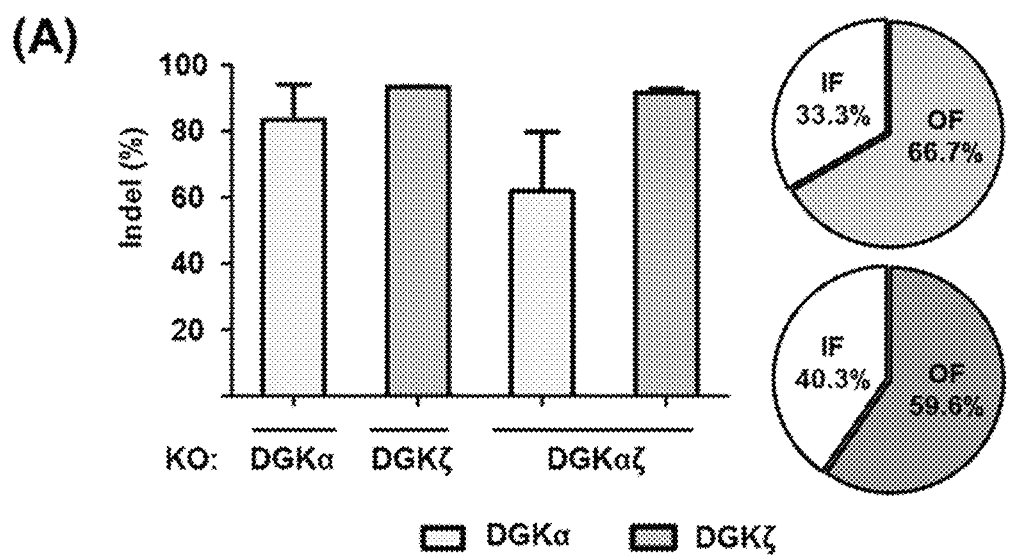
FIG. 30 shows the DGKs knockout selectively by CRISPR/Cas9 in T cells, in which a graph confirms (A) indel (%) of DGKs and (B) protein expression of DGKs.
Figure 30:
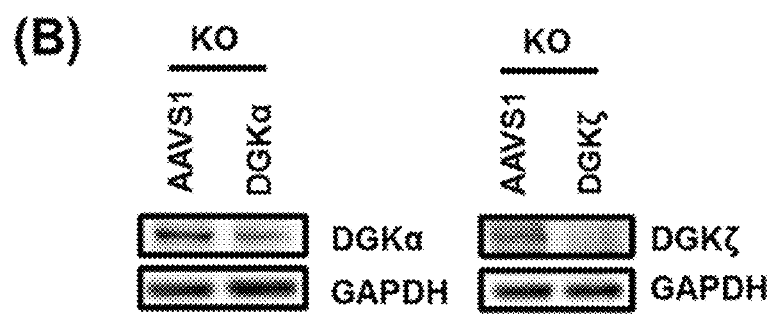
Figure 31:
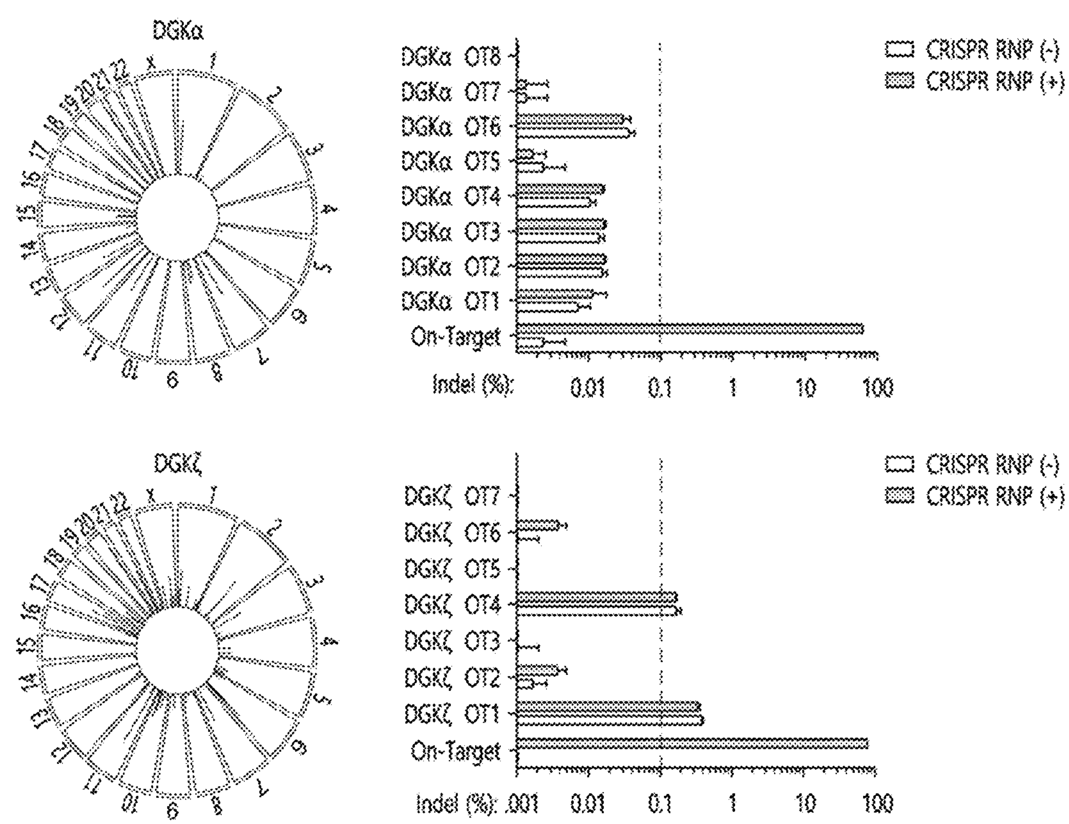
FIG. 31 is a graph illustrating identified off-target sites of gRNA for each DGKs using Digenome-Seq.

Example 1. Effective Inhibition of DGK in Human Primary T Cells by Optimized CRISPR/Cas9 RNP Delivery To identify the role of DGKs in anti-tumor activity of human primary T cells, gRNAs targeting the exon 5-7 of DGKα gene and exon 3-12 of DGK gene, respectively, were screened. After an optimized CRISPR/Cas9 RNP electroporation and lentivirus transfection, the T cells treated with CRISPR/Cas9 showed active CAR expression (FIG. 28). Even though slight reduction in survivability and cell growth was observed, survivability and cell growth were quickly recovered two days after the electroporation (FIG. 29). In an example, 139 CAR, an anti-EGFRvIII CAR having high specificity, was used for targeting glioblastoma cells (Sampson et al. 2014). The expression of EGFRvIII is strictly limited to malignant tissues, and therefore concerns regarding potential safety of manipulated CAR-T cells by using the 139-CAR, for example, on-target effect, was expected to be improved. The indel ratio in a single gene knockout experiment was measured to be approximately 80%-90% based on deep sequencing (FIG. 30). As a result of a detailed sequence analysis in the cleavage site, out-of-frame mutations induced by NHEJ recovery in DGKα and DGKζ139 CAR-T cells were found to be 66.7% and 59.6%, respectively, which was significantly in accordance with the reduction of DGK protein expression (FIG. 30). Since prior studies reported nonoverlapping functions of DGKα and DGKζ, synergy effect was identified by producing DGKαζ double-knockout T cells that exhibits a knockout efficiency comparable to single DGK-knockout 139 T cells (FIG. 30). To investigate off-target of CRISPR/Cas9 targeting DGKs, mismatch-based in silico analysis and Digenome-seq, a method of off-target identification in full genome, were performed in DGKα 139 CAR-T and DGKζ 139 CAR-T (FIG. 31). Overall, the result illustrates that the CRISPR/Cas9-mediated gene manipulation inhibits DGKs efficiently and specifically, while not critically slowing cell growth and CAR expression in human primary T cells.

Figure 32:
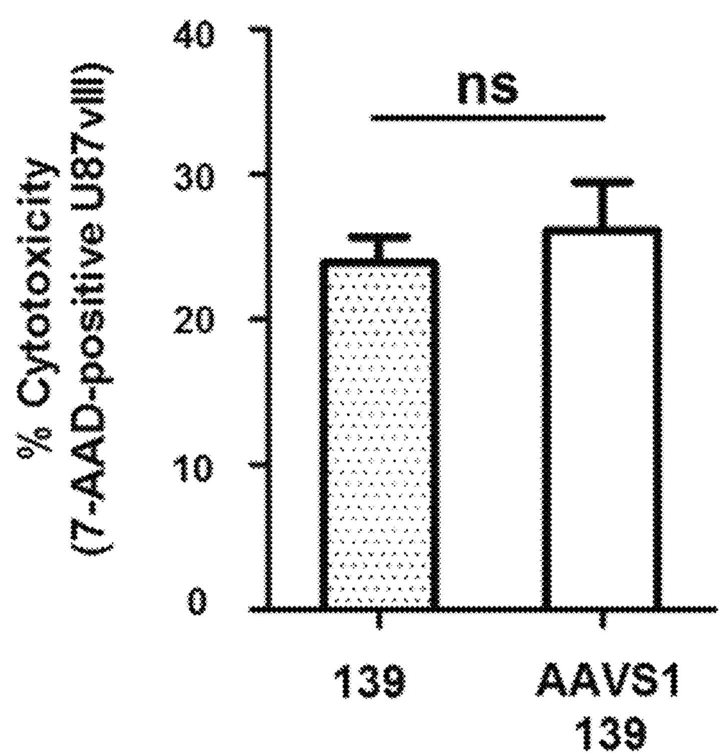
FIG. 32 is a graph showing cytotoxic effect of 139 CAR-T cells, where AAVS1 is knocked out by CRISPR/Cas9.
Figure 33:
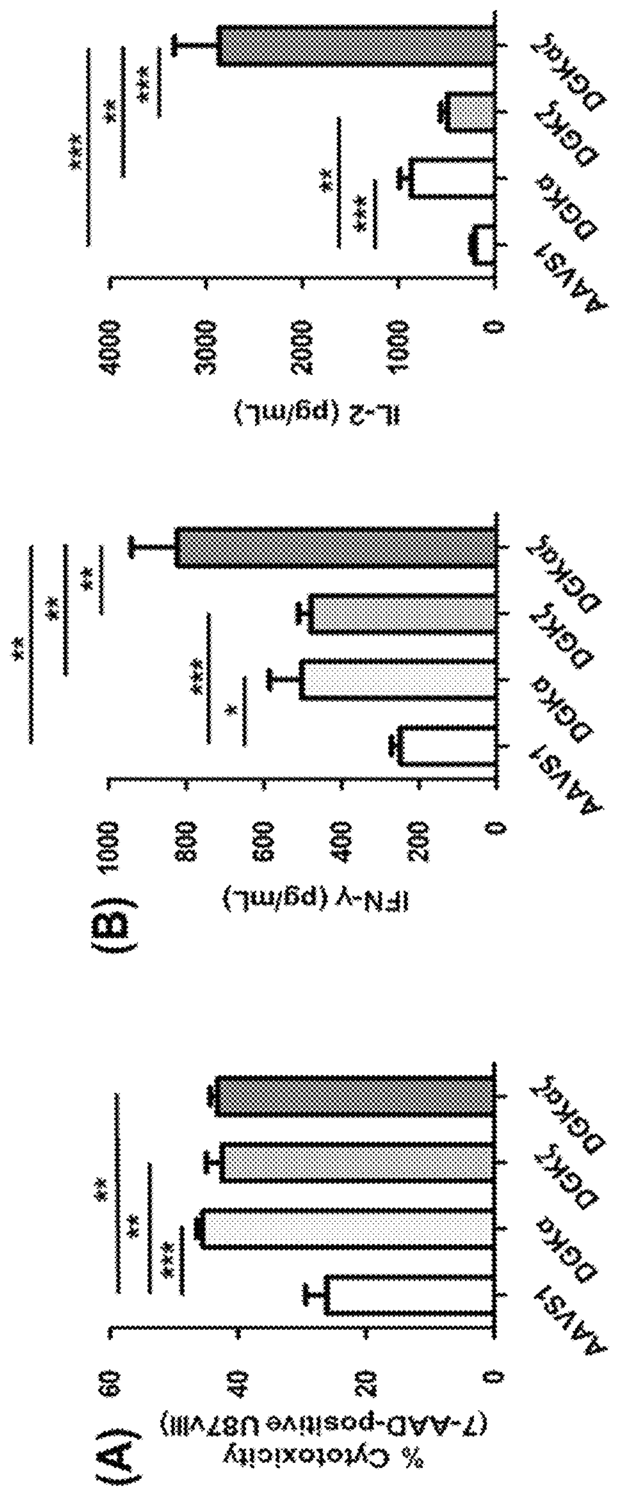
FIG. 33 is a graph comparing (A) cytotoxic effect and (B) cytokine secretion level of 139 CAR-T cells that are either AAVS1-knockout or DGK-knockout by CRISPR/Cas9.
Figure 34:
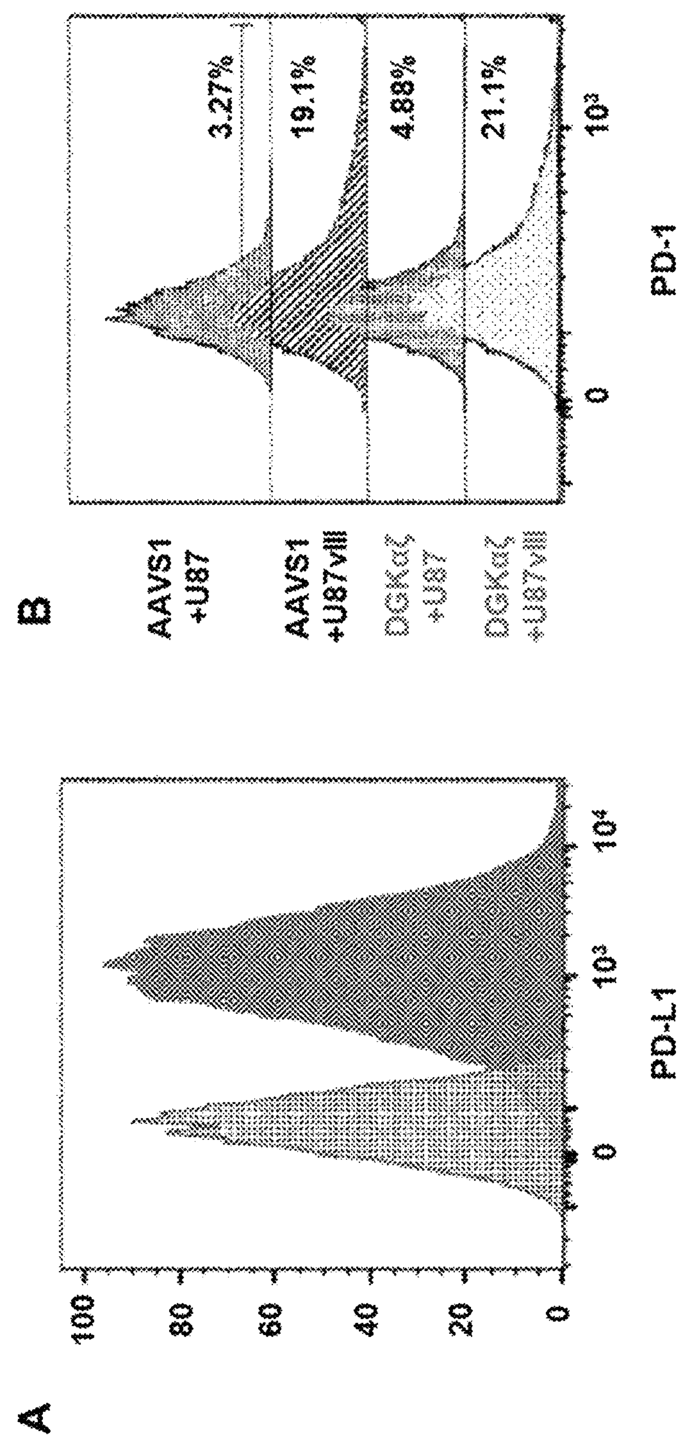
FIG. 34 is a graph comparing (A) the expression level of PDL-1 at U87vIII and (B) the expression level of PD-1 at T cells after co-culturing U87 or U87vIII cells with 139 CAR-T cells.

Example 2 Enhancing Effector Function Presented by CD3 Terminal Signal Amplified by Artificially Manipulated DGK Since the increase of cytokine secretion in DGK-deficient T cells was previously reported from a different group, anti-tumor function of DGK 139 CAR-T cells was evaluated in the example (Shin et al. 2012, Riese et al. 2013). In the in vitro property analysis, AAVS1 139 CAR-T that maintains the cytotoxicity of 139 CAR-T and has more similar physiological status with DGKs 139 CAR-T than 139 CAR-T was used as a negative control (FIG. 32). When cocultured with U87vIII, the DGKs 139 CAR-T exhibited an excellent effector function, such as cytotoxicity and significant increase of cytokine, compared to AAVS1 CAR-T (FIG. 33). Interestingly, DGKαζ139 CAR-T produced more IFN-γ and IL-2 than DGKα or DGKζ139 CAR-T, which strongly signifies existence of synergy effect by DGK double-knockout in anti-tumor activity. Additionally, the expression of PD-1 increased when CAR-T cells and target tumor cell lines were cocultured, and strong expression of PD-L1 in U87vIII glioblastoma cell lines was also identified. This means that synergy effect may exhibit when combined with PD-1 blockades such as PD-1 antibody or PD-1 knockout (FIG. 34).

Figure 35:
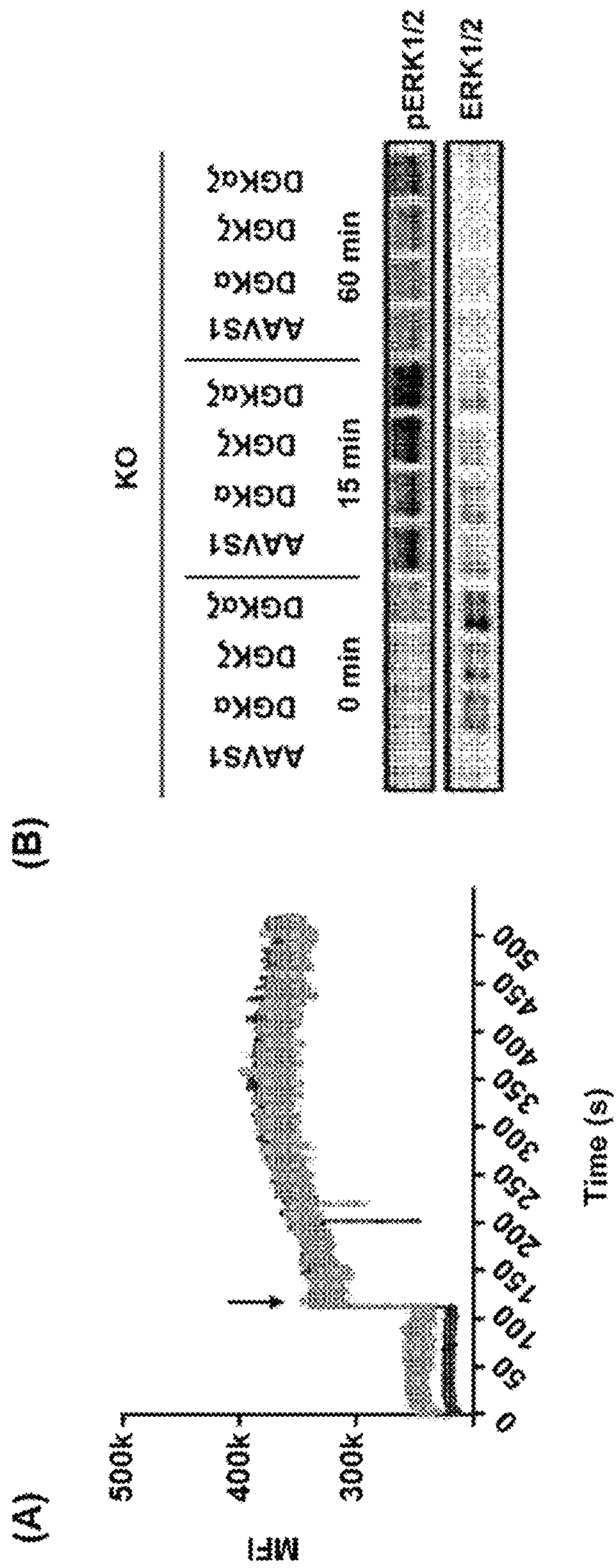
FIG. 35 is an image showing (A) changes in calcium influx and (B) expression of pERK protein in DGK-knockout 139 CAR-T cells.

Next, it was investigated whether signal1 (CD3 signal) pathway is affected by DGK-destruction or not. AAVS1 T cells and DGK T cells were stimulated with anti-CD3 beads for the directed period of time, and calcium influx and ERK that is a peripheral signal of signal1, were measured. The calcium influx was not affected by TCR activation, but phosphorylated ERK signal was amplified, and lasted longer in DGK-knockout mutant (FIG. 35). The significant increase of phosphorylated ERK signal in DGKαζT cells is in accordance with the synergy effect of DGK double-knockout in FIG. 33. Such result illustrates that DGK removal increases TCR peripheral signals, and thereby increasing cytotoxicity of T cells and cytokine release.

Figure 36:
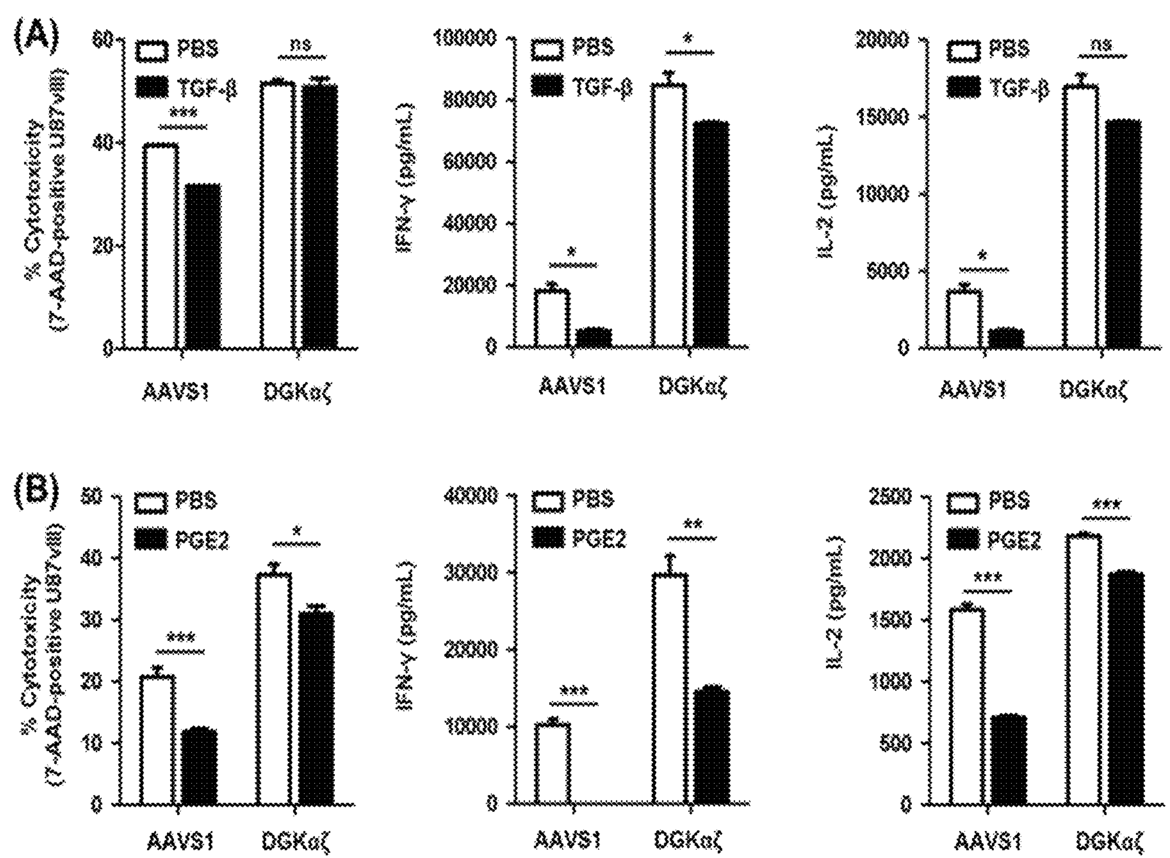
FIG. 36 is a graph comparing cytotoxic effect and cytokine secretion level of AAVS1-knockout or DGK-knockout 139 CAR-T cells in the presence of an immunosuppresive factor, showing (A) in the presence of TGF-β, and (B) in the presence of PEG2, respectively.

Example 3. Evasion of Immune Suppressing Effect of TGF-β and PGE2 bp DGK Artificially Manipulated T Cells After finding that removing DGKs effectively activates TCR signalling from the previous examples, whether artificially manipulated DGKs are capable of reducing sensitivity of T cell for signal1 inhibitor was tested. Since the treatment result of CAR-T treatment method was limited due to the high level of TGF-β and PGE2 in tumor microenvironment (TME), TGF-β and PGE2 were focused among the inhibiting factors (Arumugam, Bluemn et al. 2015, Perng and Lim 2015, O'Rourke, Nasrallah et al. 2017). First, TGF-β inhibition efficacy in CAR-T activity for U87vIII was investigated. Since DGK double-knockout 139 CAR-T showed synergy resistance in PGE2 and TGF-β-mediated immune suppression, DGKαζ139 CAR-T was used for the test (FIG. 36). The tumor death activity, and activities such as production of IFN-γ and IL-2 bp AAVS1 139 CAR-T sharply decreased when exposed to high physiological concentration of TGF-β (10 ng/mL) (FIG. 36) (Xu, Ahmad et al. 2000) (Ivanovic, Todorovic-Rakovic et al. 2003). Meanwhile, DGKαζ139 CAR-T maintained effector function even when treated with TGF-β. In the same manner, contrary to the AAVS1 139 CAR-T in which cytotoxicity ability by PGE2 treatment was critically damaged, the DGKαζ139 CAR-T was relatively insensitive to the inhibiting factor (FIG. 36). In summary, the tumor responsiveness of AAVS1

Figure 37:
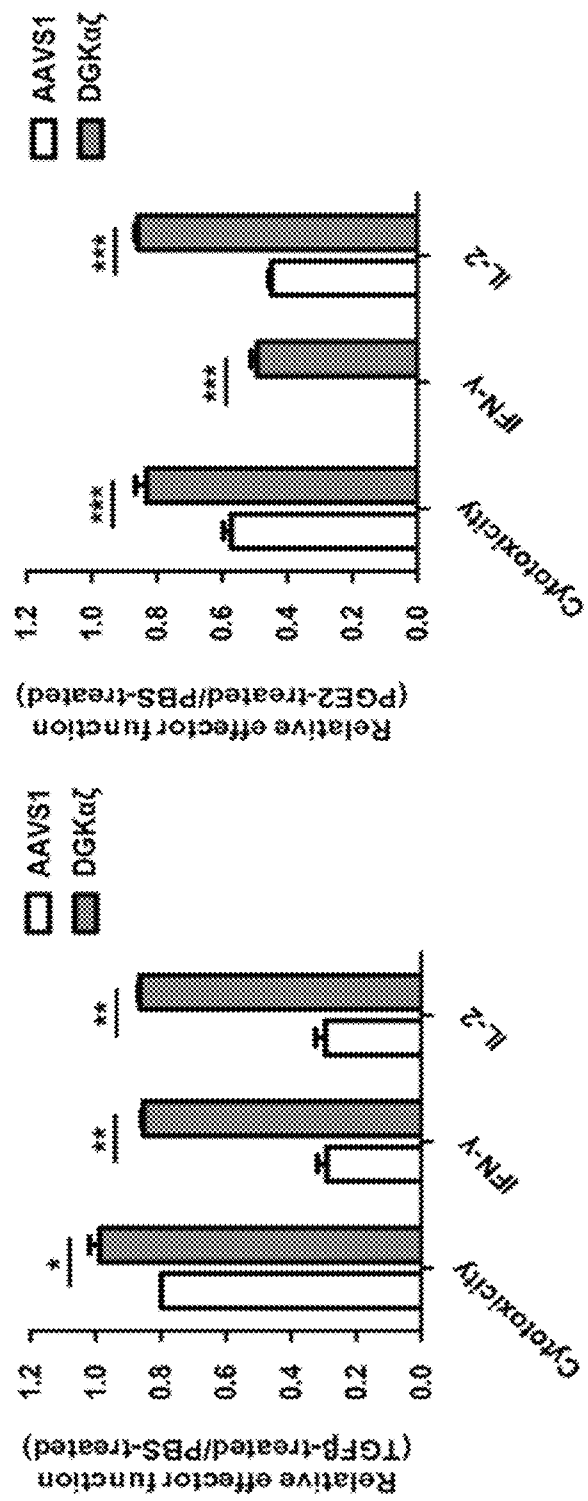
FIG. 37 is a graph showing effector functions of AAVS1-knockout or DGK-knockout 139 CAR-T cells in the presence of an immunosuppresive factor.
Figure 38:
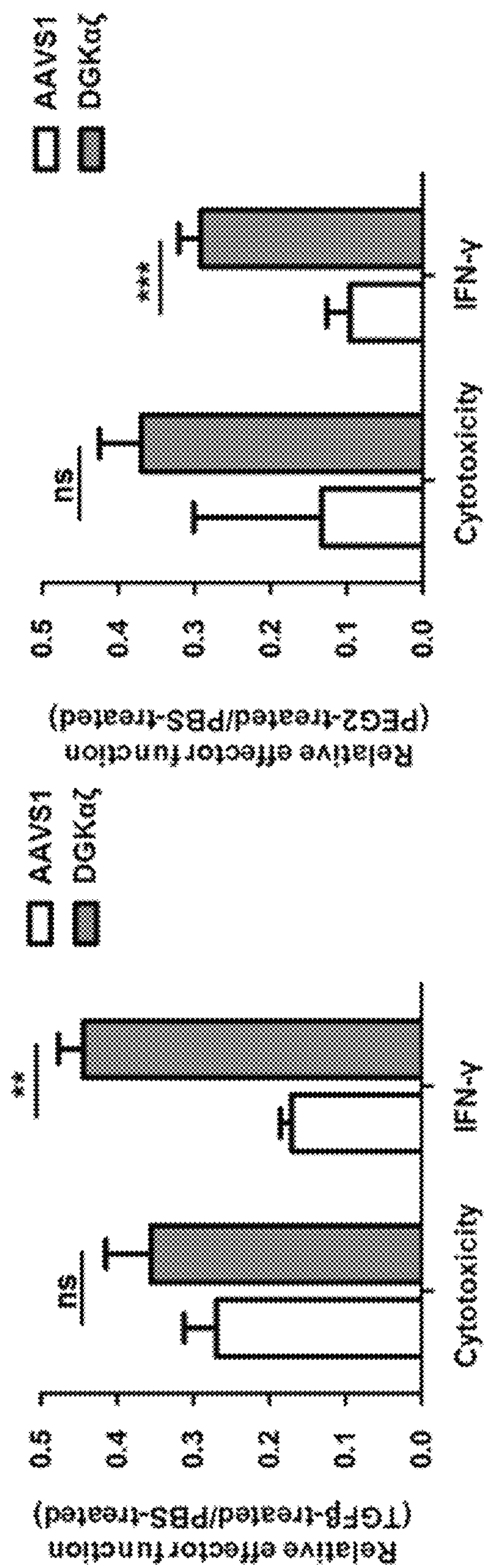
FIG. 38 is a graph showing effector functions of AAVS1-knockout or DGK-knockout c259 TCR T cells in the presence of an immunosuppresive factor.

CAR-T was significantly lost, whereas DGKs CAR-T cells maintained 49%-99% of activity and showed constant anti-tumor function even when exposed to TGF-β and PGE2 (FIG. 37). Additionally, advantageous role of DGK-knockout in c259 TCR-T was identified. When cultured with A375P cells expressing NY-ESO, the DGKs c259 TCR-T was less sensitive to TGF-β and PGE2, showing flexibility of DGK-knockout platform in adoptive cell transfer (FIG. 38). Slight reduction of DGKαζ139 CAR-T anti-tumor activity during TGF-β and PGE2 suppression experiment is considered to be due to incomplete destruction of DGKs, since the out-of-frame knockout rates of DGKα and DGKζ are 66.7% and 59.6%, respectively (FIG. 30). The data signifies that increase of intracellular DAG availability by DGK-knockout enables T cells to overcome immune suppression by signal1 suppressant, and suggests that an effective synergy effect may exhibit when administered in combination with signal 2 suppressant.

Figure 39:
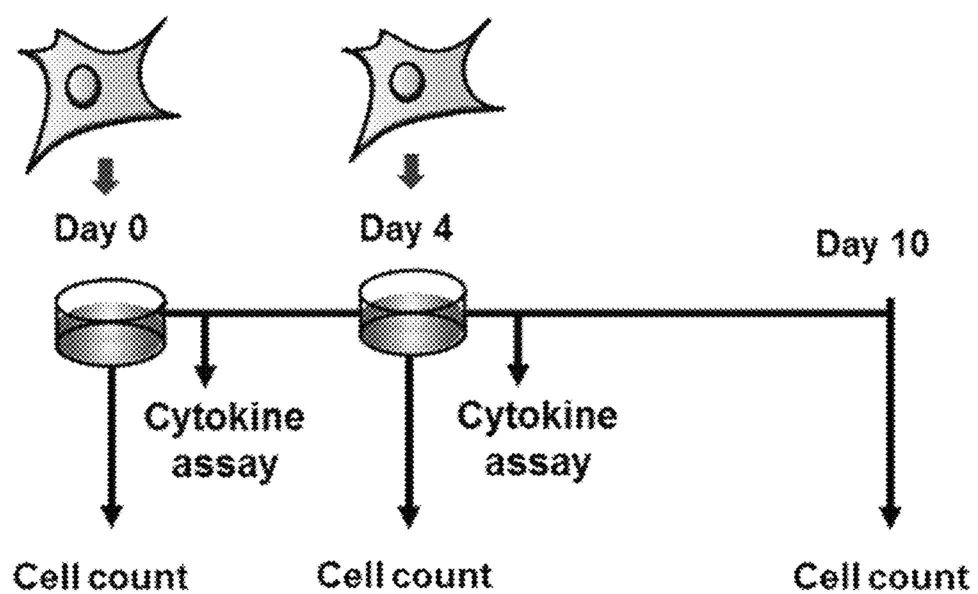
FIG. 39 illustrates the experiment design for identifying the effector activity of DGK-knockout T cells under repeated antigen exposure.
Figure 40:
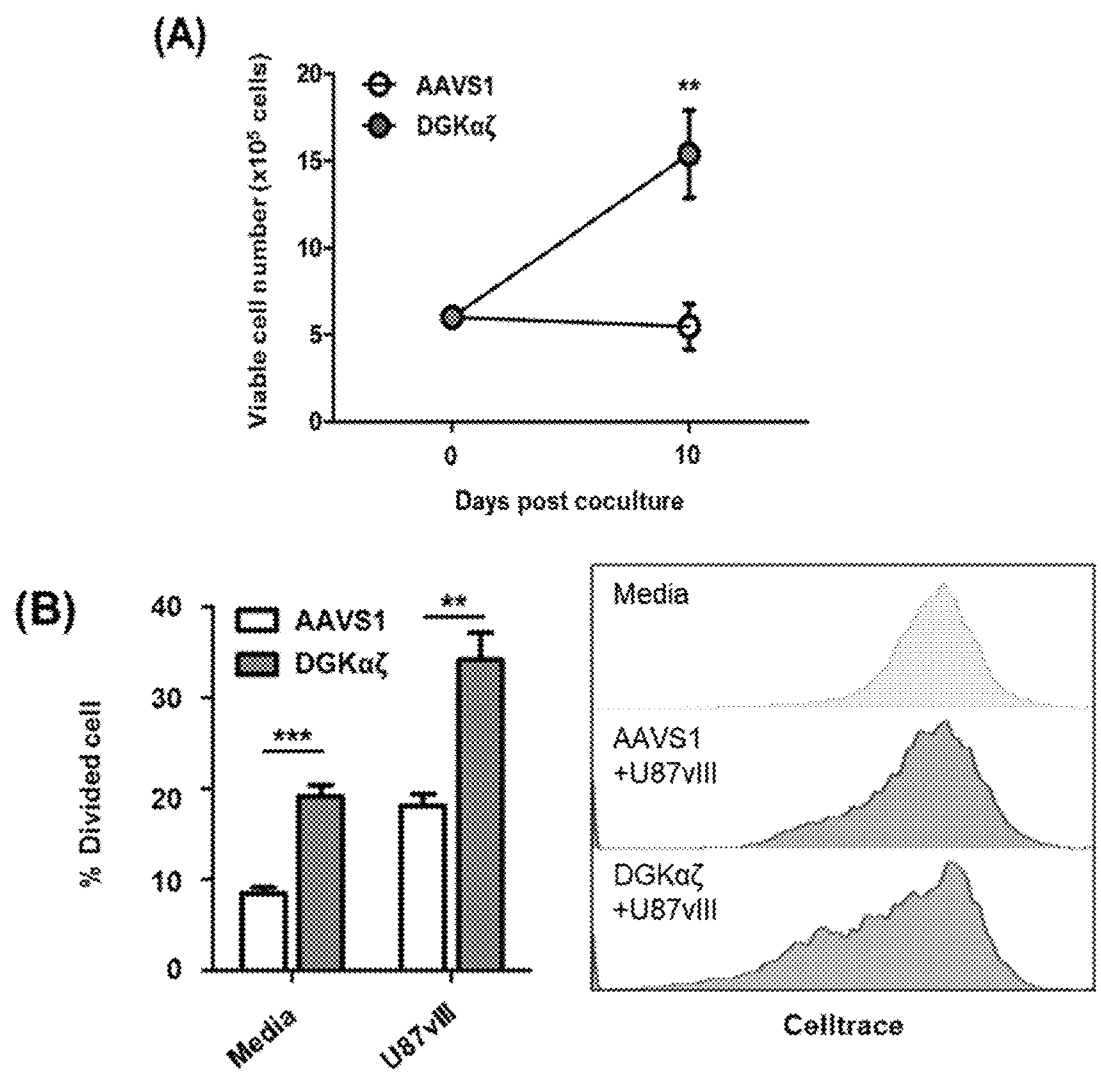
FIG. 40 illustrates cell proliferation of DGK-knockout T cells under repeated antigen exposure, in which a graph compares (A) number of survived cells and (B) number of proliferated cells (%).
Figure 41:
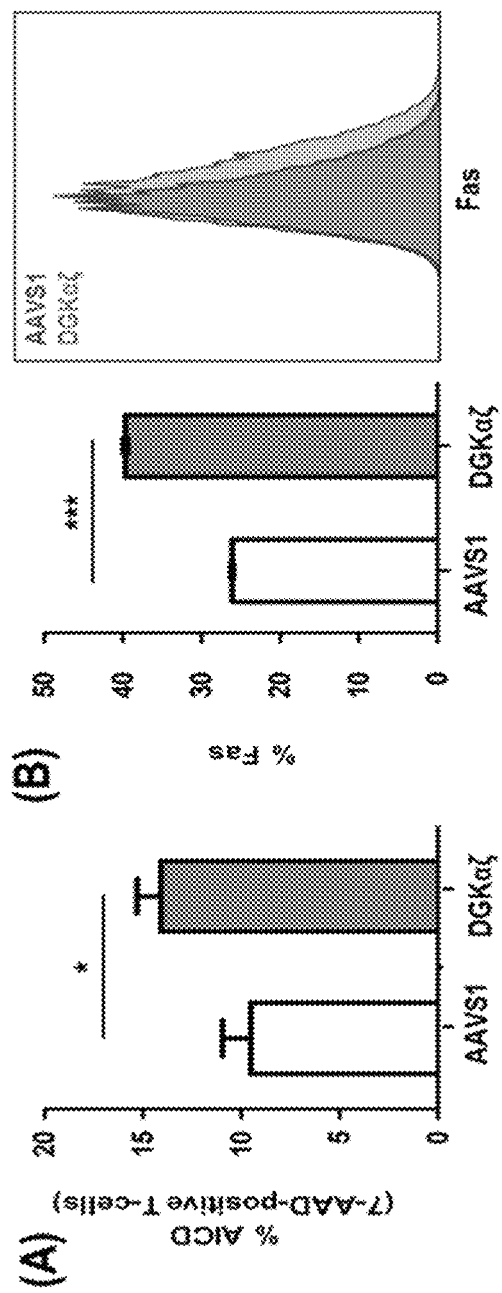
FIG. 41 illustrates Fas-mediated activity that induces cell death in DGK-knockout T cells, in which a graph shows (A) activation induced cell death (AICD, %) and (B) expression level of Fas (%).
Figure 42:
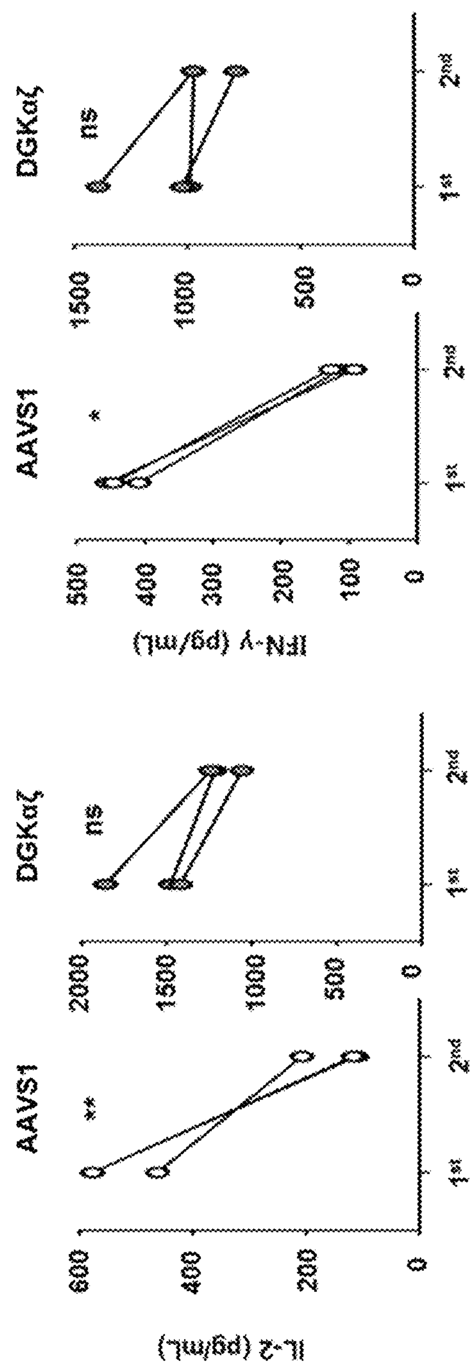
FIG. 42 is a graph showing the cytokine secretion level of AAVS1-knockout or DGK-knockout 139 CAR-T cells followed by repeated tumor inoculation.

Example 4. Maintaining Effector Function of DGK Artificially Manipulated T Cells in Repetitive Antigen Stimulation T cells often go under a depressed state, anergy, in which IL-2 secretion and cytotoxicity are lost, when recognizes antigens repeatedly. DAG metabolism is an important decision factor that regulates T cell activation and anergy (Olenchock, Guo et al. 2006, Zha, Marks et al. 2006). Numbers of studies report that pharmacological suppression of DGKα is capable of reversing anergy state of mouse T cells, and whether DGK artificially manipulated human T cell overcomes T cell anergy was thereby identified (Olenchock, Guo et al. 2006, Moon, Wang et al. 2014). First, the proliferation ability of DGKαζ139 CAR-T during a repeated antigen attack was evaluated. 139 CAR-T cells were cultured with U87vIII for 96 hours, then U87vIII was inoculated again, and the cell proliferation ability of CAR-T was measured by using Celltrace distribution and cell counting (FIG. 39). Unlike AAVS1 139 CAR-T that showed insignificant proliferation, DGKαζ139 CAR-T successfully proliferated under repetitive activation (FIG. 40). To identify whether the excellent expansion of DGKαζ139 CAR-T is a result of enhanced proliferation ability or reduced activation induced cell death (AICD), apoptosis analysis was performed. When 139 CAR T cells met with U87vIII were stained with 7-AAD, the DGKαζ139 CAR-T showed a greater 7-AAD positive T cell population compared to the AAVS1 139 CAR-T (FIG. 41). Since suppression of DGKα is capable of inducing FAS-dependent apoptosis, FAS expression in 139 CAR-T was identified, and as a result, a significant increase of FAS expression on the surface of 139 CAR-T was identified (FIG. 41) (Alonso, Rodriguez et al. 2005). Such data illustrates that the DGKαζ139 CAR-T cells increased by tumor recognition is mostly by cell proliferation ability, and the increase compensates T cell apoptosis induced by tumor recognition. The cytokine secretion of DGKαζ139 CAR-T in multiple tumor inoculation was analyzed (FIG. 42). AAVS1 139 CAR-T cells strongly produced IFN-γ and IL-2 after first exposure to U87vIII, but after collecting the AAVS1 139 CAR-T cells, reexposing the same to new U87vIII, and identifying the production of cytokine using ELISA, considerable reduction of cytokine producing ability was identified. In contrast, DGKαζ139 CAR-T maintained secretion of cytokine by reacting to the activation by U87vIII even after second exposure, showing that the DGK-knockout enables to avoid T cell anergy.

Example 5. Effect of Reprogramming DGK Artificially Manipulated T Cells into Effector Memory T Cells Loss of both DGKα and DGK is reported to let CD8 T cells differentiate into short-life effector cells and effector memory groups (Yang, Zhang et al. 2016). To investigate whether DGKs deficiency changes T cell differentiation, the characteristics of the memory subset of DGKs manipulated CAR-T cells are illustrated while coculturing the DGKs manipulated 139 CAR-T cells with U87vIII for 4 days. Before being inoculated to tumor, DGKαζ139 CAR-T cells showed a naïve T cell population smaller than AAV 139 CAR-T cells (FIG. 43). After 4 days of tumor inoculation, the naïve T cell population of DGKαζ139 CAR-T cells preferentially differentiated into effector memory cells, and as a result formed a smaller naïve and central memory T cell population (FIG. 43). Next, whether or not artificial manipulation of DGK transcriptionally reprograms T cells was investigated. As a result of identifying the related transcription factors after activating T cells for 48 hours using CD3/28 dynabead, a great increase of ID2 and PRDM1, the effector memory controlling factors of DGKαζT cells, was identified (FIG. 44). Additionally, the expression of type I cytokine increased in DGKs artificially manipulated T cells, but transcription of IL-10, a type II cytokine, significantly decreased (FIG. 44). Finally, to identify the effector T cells produced by DGK-knockout has no dysfunction, PD-1 and TIM-3, the depletion markers in DGKαζ139 CAR-T, were investigated. When activating 139 CAR-T cells for 7 days using U87vIII, DGKs 139 CAR-T illustrated a similar level of PD-1 and TIM-3 expression compared to AAVS1 139 CAR-T (FIG. 45). The DGKs artificially manipulated T cells are reprogrammed into effector memory T cells without T cell depletion, and as a result illustrated strong anti-tumor effect ex vivo.

Example 6. Tumor Infiltrating Ability and Tumor Removing Effect of DGKs Artificially Manipulated T Cells To investigate in vivo functional relativity of enhanced effector function of DGKαζ139 CAR-T, AAVS1 139 CAR-T or DGKαζ139 CAR-T were intravenously (IV) or intratumorally (IT) injected into U87vIII transplanted NSG mice. The effect of adopted cell metastasis may greatly vary depending on quantity of existing tumor and number of immune cells. Levi J, Rupp et al. proved in an experiment with mice having low tumor quantity that, in both control group CD19 CAR-T cells and PD1-knockout CD19 CAR-T cells, high T cell injection is capable of completely removing tumor (Rupp, Schumann et al. 2017). Therefore, the present study used low T cell quantity in a high tumor quantity model, to investigate in vivo efficacy of DGK-knockout T cells. T cells were first injected when the volume of tumor reached 150±50 $mm^3$, and second T cell injection was performed after 4 days when the size of tumor reached 400±50 $mm^3$. Here, the first and the second injections were performed at an E:T ratio of approximately 1:10 and 1:20, respectively. Numerous studies report that treating without temozolomide (TMZ) during anti-EGFRvIII glioblastoma-targeting T cell treatment often illustrate inefficient results ((Ohno, Ohkuri et al. 2013, Johnson, Scholler et al. 2015), therefore temozolomide adjuvant was intraperitoneally injected during the second T cell injection to stimulate tumor regression. Every IV injected group showed delay in tumor growth after 32 days of TMZ treatment, but mice injected with AAVS1 139 CAR-T did not express anti-tumor effect compared to the control group T cell mice group (FIG. 46). In contrast, complete tumor regression was found in a DGKαζ139 CAR-T mouse group on the 56th day. In the same manner, although intratumoral injection of AAVS1 139 CAR-T could not remove U87vIII tumor, the adoptive cell metastasis of DGKαζ139 CAR-T showed a meaningful result of tumor cell regression on the 52nd day. To characterize the in vivo function of DGKαζ139 CAR-T, the tumor was extracted on the 49th day, and the number of tumor infiltrated T cells was counted.

To additionally characterize the in vivo function of DGK-knockout 139 CAR-T cells, the survivability of injected AAVS1, αKO, and dKO 139 CAR-T cells was analyzed. As a result, ζKO and dKO 139 CAR-T cells were identified to maintain a significantly large number in the tumors (FIG. 47). This is because dividing T cells, represented with Ki-67 stained cells, exist in larger quantity, and were identified as functionally dominant effector T cells with increase of T-bet expression and enhanced secretion ability of cytokines, such as IFN-γ and TNF-α (FIG. 48).

In conclusion, the data result illustrates that artificial manipulation of DGKs by CRIPSR/Cas9 is capable of enhancing in vivo anti-tumor efficacy of human CAR-T cells.

INDUSTRIAL APPLICABILITY

Effective immune cell therapeutic agents may be obtained with manipulated immune cells including artificially modified immunity regulating genes and artificial receptors. For example, when immune cells artificially manipulated by the composition for immune cell manipulation of the present invention or manipulated immune cells are used, they may be used as effective immune cell therapeutic agents, as the immune efficacy involved in survival, proliferation, persistency, cytotoxicity, cytokine-release and/or infiltration, etc. of immune cells which are capable of specifically binding a specific antigen may be improved.

Sequence Listing Free Text

Target Sequences of Immunity Regulating Gene

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. A manipulated human T cell with an enhanced immune activity comprising:

an engineered genome comprising an engineered endogenous DGKA gene and an engineered endogenous DGKZ gene; and at least one artificial receptor and/or nucleic acid encoding the artificial receptor, wherein the engineered endogenous DGKA gene comprises a first artificial modification, wherein the first artificial modification is a first indel by CRISPR/Cas gene editing and induced in a region of exon 7 of the wild-type DGKA gene, wherein the engineered endogenous DGKA gene does not comprise any further modification other than the first artificial modification, wherein the engineered endogenous DGKZ gene comprises a second artificial modification, wherein the second artificial modification is a second indel by CRISPR/Cas gene editing and induced in a region of exon 3 of the wild-type DGKZ gene, wherein the engineered endogenous DGKZ gene does not comprise any further modification other than the second artificial modification, wherein the first artificial modification causes at least one of a reduced expression of engineered endogenous DGKA gene and a functional impairment of the protein expressed from the engineered endogenous DGKA gene, and the second artificial modification causes at least one of a reduced expression of engineered endogenous DGKZ gene and a functional impairment of the protein expressed from the engineered endogenous DGKZ gene, in a manner that the manipulated human T cell has the enhanced immune activity.

2. The manipulated human T cell according to claim 1, wherein the artificial receptor has a binding specificity for at least one antigen selected from the group consisting of A33, ALK, alpha-fetoprotein (AFP), adrenoreceptor beta 3 (ADRB3), alpha-folate receptor, AD034, AKT1, BCMA, beta-human chorionic gonadotropin, B7H3 (CD276), BST2, BRAP, CD5, CD13, CD19, CD20, CD22, CD24, CD30, CD33, CD38, CD40, CD44v6, CD52, CD72, CD79a, CD79b, CD89, CD97, CD123, CD138, CD160, CD171, CD179a, carbonic anhydrase IX (CAIX), CA-125, carcinoembryonic antigen (CEA), CCR4, C-type lectin-like molecules (CLL-1 or CLECL1), claudin6 (CLDN6), CXORF61, CAGE, CDX2, CLP, CT-7, CT8/HOM-TES-85, cTAGE-1, ERBB2, epidermal growth factor receptor (EGFR), EGFR variants III (EGFRvIII), epithelial cell adhesion molecule (EPCAM), E74-like factor 2 mutation (ELF2M), Ephrin type-A receptor 2 (EphA2), EMR2, Fms-like tyrosine kinase 3 (FLT3), FCRL5, fibulin-1, G250, GD2, glycoprotein 36 (gp36), glycoprotein 100 (gp100), glucocorticoid-induced tumor necrosis factor receptor (GITR), GPRC5D, GloboH, G protein-coupled receptor 20 (GPR20), GPC3, hsp70-2, human high molecular weight-melanoma-associated antigen (HMWMAA), hepatitis A virus cellular receptor 1 (HAVCR1), human papillomavirus E6 (HPV E6), human papillomavirus E7 (HPV E7), HAGE, HCA587/MAGE-C2, hCAP-G, HCE661, HER2/neu, HLA-Cw, HOM-HD-21/galectin9, HOM-MEEL-40/SSX2, HOM-RCC-3.1.3/CAXII, HOXA7, HOXB6, Hu, HUB 1, insulin growth factor (IGF1)-I, IGF-II, IGFI receptor, interleukin-13 receptor subunit alpha-2 (IL-13Ra2 or CD213A2), interleukin 11 receptor alpha (IL-11Ra), IGLL1, KIT (CD117), KM-HN-3, KM-KN-1, KOC1, KOC2, KOC3, KOC3, LAGA-1a, LAGE-1, LAIR1, LILRA2, LY75, Lewis Y antigen, MUC1, MN-CA IX, M-CSF, MAGE-1, MAGE-4a, mesothelin, MAGE-A1, MAD-CT-1, MAD-CT-2, MART1, MPPI 1, MSLN, neural cell adhesion molecule (NCAM), NY-ESO-1, NY-ESO-5, Nkp30, NKG2D, NY-BR-1, NY-BR-62, NY-BR-85, NY-CO-37, NY-CO-38, NNP-1, NY-LU-12, NY-REN-10, NY-REN-19/LKB/STK1 1, NY-REN-21, NY-REN-26/BCR, NY-REN-3/NY-CO-38, NY-REN-33/SNC6, NY-REN-43, NY-REN-65, NY-REN-9, NY-SAR-35, o-acetyl-GD2 ganglioside (OAcGD2), OGFr, PSMA, prostatic acid phosphatase (PAP), p53, prostate carcinoma tumor antigen-1 (PCTA-1), prostate stem cell antigen (PSCA), serine protease 21 (testisin or PRSS21), platelet-derived growth factor receptor-beta (PDGFR-beta), PLAC1, pannexin 3 (PANX3), PLU-1, ROR-1, RAGE-1, RU1, RU2, Rab38, RBPJ kappa, RHAMM, stage-specific embryonic antigen-4 (SSEA-4), SCP1, SSX3, SSX4, SSX5, Tyrp-1, TAG72, thyroglobulin, human telomerase reverse transcriptase (hTERT), 5T4, tumor-associated glycoprotein (TAG72), tyrosinase, transglutaminase 5 (TGS5), TEM1, TEM7R, thyroid-stimulating hormone receptor (TSHR), Tie 2, TRP-2, TOP2A, TOP2B, uroplakin 2 (UPK2), vimentin, vascular endothelial growth factor receptor 2 (VEGFR2), Wilms tumor protein 1 (WT1), and lewis (Y) antigen.

3. The manipulated human T cell according to claim 1, wherein the artificial receptor is a chimeric antigen receptor (CAR).

4. The manipulated human T cell according to claim 1, wherein the first artificial modification is induced in a first sequence constituting 50 nucleotides comprising a sequence selected from SEQ ID NOs: 20 to 24 of the wild-type DGKA gene, thereby the engineered endogenous DGKA gene does not comprise a sequence same as the first sequence.

5. The manipulated human T cell according to claim 1, wherein the first artificial modification is induced in a first sequence constituting 50 nucleotides comprising a sequence of SEQ ID NO: 23 of the wild-type DGKA gene, thereby the engineered endogenous DGKA gene does not comprise a sequence same as the first sequence.

6. The manipulated human T cell according to claim 1, wherein the second artificial modification is induced in a second sequence constituting 50 nucleotides comprising a sequence selected from SEQ ID NOs: 109 to 113 of the wild-type DGKZ gene, thereby the engineered endogenous DGKZ gene does not comprise a sequence same as the second sequence.

7. The manipulated human T cell according to claim 1, wherein the second artificial modification is induced in a second sequence constituting 50 nucleotides comprising a sequence of SEQ ID NO: 111 of the wild-type DGKZ gene, thereby the engineered endogenous DGKZ gene does not comprise a sequence same as the second sequence.

8. The manipulated human T cell according to claim 1, wherein the second artificial modification is induced in a second sequence constituting 50 nucleotides comprising a sequence of SEQ ID NO: 113 of the wild-type DGKZ gene, thereby the engineered endogenous DGKZ gene does not comprise a sequence same as the second sequence.

9. The manipulated human T cell according to claim 1, wherein the first artificial modification is induced in a first sequence constituting 50 nucleotides comprising a sequence of SEQ ID NO: 23 of the wild-type DGKA gene, thereby the engineered endogenous DGKA gene does not comprise a sequence same as the first sequence, wherein the second artificial modification is induced in a second sequence constituting 50 nucleotides comprising a sequence selected from SEQ ID NOs: 109 to 125 of the wild-type DGKZ gene, thereby the engineered endogenous DGKZ gene does not comprise a sequence same as the second sequence.

10. The manipulated human T cell according to claim 1, wherein the first artificial modification is induced in a first sequence constituting 50 nucleotides comprising a sequence selected from SEQ ID NOs: 19 to 24 of the wild-type DGKA gene, thereby the engineered endogenous DGKA gene does not comprise a sequence same as the first sequence, wherein the second artificial modification is induced in a second sequence constituting 50 nucleotides comprising a sequence selected from SEQ ID NOs: 109 to 113, 116, 120, 121, and 123 of the wild-type DGKZ gene, thereby the engineered endogenous DGKZ gene does not comprise a sequence same as the second sequence.

11. The manipulated human T cell according to claim 1, wherein the first artificial modification is induced in a first sequence constituting 50 nucleotides comprising a sequence of SEQ ID NO: 23 of the wild-type DGKA gene, thereby the engineered endogenous DGKA gene does not comprise a sequence same as the first sequence, wherein the second artificial modification is induced in a second sequence constituting 50 nucleotides comprising a sequence of SEQ ID NO: 113 of the wild-type DGKZ gene, thereby the engineered endogenous DGKZ gene does not comprise a sequence same as the second sequence.

12. A composition for immunotherapy comprising a manipulated human T cell with an enhanced immune activity, wherein the manipulated human T cell comprises:

an engineered genome comprising an engineered endogenous DGKA gene and engineered endogenous DGKZ gene; and at least one artificial receptor and/or nucleic acid encoding the artificial receptor, wherein the engineered endogenous DGKA gene comprises a first artificial modification, wherein the first artificial modification is a first indel by CRISPR/Cas gene editing and induced in a region of exon 7 of the wild-type DGKA gene, wherein the engineered endogenous DGKA gene does not comprise any further modification other than the first artificial modification, wherein the engineered endogenous DGKZ gene comprises a second artificial modification, wherein the second artificial modification is a second indel and induced in a region of exon 3 of the wild-type DGKZ gene, wherein the engineered endogenous DGKZ gene does not comprise any further modification other than the second artificial modification, wherein the first artificial modification causes at least one of a reduced expression of engineered endogenous DGKA gene and a functional impairment of the protein expressed from the engineered endogenous DGKA gene, and the second artificial modification causes at least one of a reduced expression of engineered endogenous DGKZ gene and a functional impairment of the protein expressed from the engineered endogenous DGKZ gene, in a manner that the manipulated human T cell has the enhanced immune activity.

13. The manipulated human T cells according to claim 1, wherein the nucleic acid encoding the artificial receptor is in the engineered genome.

* * * * *

SEQUENCE LISTING

```
<160> NUMBER OF SEQ ID NOS: 289

<210> SEQ ID NO 1
<211> LENGTH: 23
<212> TYPE: DNA
<213> ORGANISM: Homo Sapiens

<400> SEQUENCE: 1

cttgtggcgc tgaaaacgaa cgg                                              23


<210> SEQ ID NO 2
<211> LENGTH: 23
<212> TYPE: DNA
<213> ORGANISM: Homo Sapiens

<400> SEQUENCE: 2

atgccacttc tcagtacatg tgg                                              23


<210> SEQ ID NO 3
<211> LENGTH: 23
<212> TYPE: DNA
<213> ORGANISM: Homo Sapiens

<400> SEQUENCE: 3

gccacttctc agtacatgtg ggg                                              23


<210> SEQ ID NO 4
<211> LENGTH: 23
<212> TYPE: DNA
<213> ORGANISM: Homo Sapiens

<400> SEQUENCE: 4

gccccacatg tactgagaag tgg                                              23


<210> SEQ ID NO 5
<211> LENGTH: 23
<212> TYPE: DNA
<213> ORGANISM: Homo Sapiens
```

<400> SEQUENCE: 5
tcagtacatg tggggcgttc agg 23

<210> SEQ ID NO 6
<211> LENGTH: 23
<212> TYPE: DNA
<213> ORGANISM: Homo Sapiens

<400> SEQUENCE: 6
gggcgttcag gacacagact tgg 23

<210> SEQ ID NO 7
<211> LENGTH: 23
<212> TYPE: DNA
<213> ORGANISM: Homo Sapiens

<400> SEQUENCE: 7
cacagacttg gtactgagga agg 23

<210> SEQ ID NO 8
<211> LENGTH: 23
<212> TYPE: DNA
<213> ORGANISM: Homo Sapiens

<400> SEQUENCE: 8
ggcgctgttc agcacgctca agg 23

<210> SEQ ID NO 9
<211> LENGTH: 23
<212> TYPE: DNA
<213> ORGANISM: Homo Sapiens

<400> SEQUENCE: 9
cacgcaactt taaattccgc tgg 23

<210> SEQ ID NO 10
<211> LENGTH: 23
<212> TYPE: DNA
<213> ORGANISM: Homo Sapiens

<400> SEQUENCE: 10
cggggctttg ctatgatact cgg 23

<210> SEQ ID NO 11
<211> LENGTH: 23
<212> TYPE: DNA
<213> ORGANISM: Homo Sapiens

<400> SEQUENCE: 11
ggcttccaca gacacaccca tgg 23

<210> SEQ ID NO 12
<211> LENGTH: 23
<212> TYPE: DNA
<213> ORGANISM: Homo Sapiens

<400> SEQUENCE: 12
tgaagtccac ttcgggccat ggg 23

<210> SEQ ID NO 13
<211> LENGTH: 23
<212> TYPE: DNA

<213> ORGANISM: Homo sapiens

<400> SEQUENCE: 13
ctgtacgaca cggacagaaa tgg 23

<210> SEQ ID NO 14
<211> LENGTH: 23
<212> TYPE: DNA
<213> ORGANISM: Homo Sapiens

<400> SEQUENCE: 14
tgtacgacac ggacagaaat ggg 23

<210> SEQ ID NO 15
<211> LENGTH: 23
<212> TYPE: DNA
<213> ORGANISM: Homo Sapiens

<400> SEQUENCE: 15
cacggacaga aatgggatcc tgg 23

<210> SEQ ID NO 16
<211> LENGTH: 23
<212> TYPE: DNA
<213> ORGANISM: Homo Sapiens

<400> SEQUENCE: 16
gatgcgagtg gctgaatacc tgg 23

<210> SEQ ID NO 17
<211> LENGTH: 23
<212> TYPE: DNA
<213> ORGANISM: Homo Sapiens

<400> SEQUENCE: 17
gagtggctga atacctggat tgg 23

<210> SEQ ID NO 18
<211> LENGTH: 23
<212> TYPE: DNA
<213> ORGANISM: Homo Sapiens

<400> SEQUENCE: 18
agtggctgaa tacctggatt ggg 23

<210> SEQ ID NO 19
<211> LENGTH: 23
<212> TYPE: DNA
<213> ORGANISM: Homo Sapiens

<400> SEQUENCE: 19
attgggatgt gtctgagctg agg 23

<210> SEQ ID NO 20
<211> LENGTH: 23
<212> TYPE: DNA
<213> ORGANISM: Homo Sapiens

<400> SEQUENCE: 20
atgaaagaga ttgactatga tgg 23

<210> SEQ ID NO 21
<211> LENGTH: 23

<212> TYPE: DNA
<213> ORGANISM: Homo Sapiens

<400> SEQUENCE: 21
ctctgtctct caagctgagt ggg 23

<210> SEQ ID NO 22
<211> LENGTH: 23
<212> TYPE: DNA
<213> ORGANISM: Homo Sapiens

<400> SEQUENCE: 22
tctctcaagc tgagtgggtc cgg 23

<210> SEQ ID NO 23
<211> LENGTH: 23
<212> TYPE: DNA
<213> ORGANISM: Homo Sapiens

<400> SEQUENCE: 23
ctctcaagct gagtgggtcc ggg 23

<210> SEQ ID NO 24
<211> LENGTH: 23
<212> TYPE: DNA
<213> ORGANISM: Homo Sapiens

<400> SEQUENCE: 24
caagctgagt gggtccgggc tgg 23

<210> SEQ ID NO 25
<211> LENGTH: 23
<212> TYPE: DNA
<213> ORGANISM: Homo Sapiens

<400> SEQUENCE: 25
ttgacatgac tggagagaag agg 23

<210> SEQ ID NO 26
<211> LENGTH: 23
<212> TYPE: DNA
<213> ORGANISM: Homo Sapiens

<400> SEQUENCE: 26
gactggagag aagaggtcgt tgg 23

<210> SEQ ID NO 27
<211> LENGTH: 23
<212> TYPE: DNA
<213> ORGANISM: Homo Sapiens

<400> SEQUENCE: 27
gagacgggag caaagctgct ggg 23

<210> SEQ ID NO 28
<211> LENGTH: 23
<212> TYPE: DNA
<213> ORGANISM: Homo Sapiens

<400> SEQUENCE: 28
agagacggga gcaaagctgc tgg 23

<210> SEQ ID NO 29

<211> LENGTH: 23
<212> TYPE: DNA
<213> ORGANISM: Homo Sapiens

<400> SEQUENCE: 29
tggtttctag gtgcagagac ggg 23

<210> SEQ ID NO 30
<211> LENGTH: 23
<212> TYPE: DNA
<213> ORGANISM: Homo Sapiens

<400> SEQUENCE: 30
taagtgaagg tctggtttct agg 23

<210> SEQ ID NO 31
<211> LENGTH: 23
<212> TYPE: DNA
<213> ORGANISM: Homo Sapiens

<400> SEQUENCE: 31
tgcccatgta agtgaaggtc tgg 23

<210> SEQ ID NO 32
<211> LENGTH: 23
<212> TYPE: DNA
<213> ORGANISM: Homo Sapiens

<400> SEQUENCE: 32
gaacttgccc atgtaagtga agg 23

<210> SEQ ID NO 33
<211> LENGTH: 23
<212> TYPE: DNA
<213> ORGANISM: Homo Sapiens

<400> SEQUENCE: 33
tccattgacc ctcagtaccc tgg 23

<210> SEQ ID NO 34
<211> LENGTH: 23
<212> TYPE: DNA
<213> ORGANISM: Homo Sapiens

<400> SEQUENCE: 34
tatgccttct gggtagcagc tgg 23

<210> SEQ ID NO 35
<211> LENGTH: 23
<212> TYPE: DNA
<213> ORGANISM: Homo Sapiens

<400> SEQUENCE: 35
tgagtgcagg catcttgcaa ggg 23

<210> SEQ ID NO 36
<211> LENGTH: 23
<212> TYPE: DNA
<213> ORGANISM: Homo Sapiens

<400> SEQUENCE: 36
gagtgcaggc atcttgcaag ggg 23

<210> SEQ ID NO 37
<211> LENGTH: 23
<212> TYPE: DNA
<213> ORGANISM: Homo Sapiens

<400> SEQUENCE: 37
gatgaggctg tggttgaagc tgg 23

<210> SEQ ID NO 38
<211> LENGTH: 23
<212> TYPE: DNA
<213> ORGANISM: Homo Sapiens

<400> SEQUENCE: 38
ccactggcca caggacccct ggg 23

<210> SEQ ID NO 39
<211> LENGTH: 23
<212> TYPE: DNA
<213> ORGANISM: Homo Sapiens

<400> SEQUENCE: 39
gggacatggt gcacacaccc agg 23

<210> SEQ ID NO 40
<211> LENGTH: 23
<212> TYPE: DNA
<213> ORGANISM: Homo Sapiens

<400> SEQUENCE: 40
gagtacaggt ggtccaggtc agg 23

<210> SEQ ID NO 41
<211> LENGTH: 23
<212> TYPE: DNA
<213> ORGANISM: Homo Sapiens

<400> SEQUENCE: 41
gcggagagta caggtggtcc agg 23

<210> SEQ ID NO 42
<211> LENGTH: 23
<212> TYPE: DNA
<213> ORGANISM: Homo Sapiens

<400> SEQUENCE: 42
gcggtggcgg agagtacagg tgg 23

<210> SEQ ID NO 43
<211> LENGTH: 23
<212> TYPE: DNA
<213> ORGANISM: Homo Sapiens

<400> SEQUENCE: 43
tctcctgcac agccagaata agg 23

<210> SEQ ID NO 44
<211> LENGTH: 23
<212> TYPE: DNA
<213> ORGANISM: Homo Sapiens

<400> SEQUENCE: 44
acgcagaagg gtcctggtag agg 23

<210> SEQ ID NO 45
<211> LENGTH: 23
<212> TYPE: DNA
<213> ORGANISM: Homo Sapiens

<400> SEQUENCE: 45
aggtggtggg taggccagag agg 23

<210> SEQ ID NO 46
<211> LENGTH: 23
<212> TYPE: DNA
<213> ORGANISM: Homo Sapiens

<400> SEQUENCE: 46
cccaagccag ccacggaccc agg 23

<210> SEQ ID NO 47
<211> LENGTH: 23
<212> TYPE: DNA
<213> ORGANISM: Homo Sapiens

<400> SEQUENCE: 47
acctgggtcc gtggctggct tgg 23

<210> SEQ ID NO 48
<211> LENGTH: 23
<212> TYPE: DNA
<213> ORGANISM: Homo Sapiens

<400> SEQUENCE: 48
aagagacctg ggtccgtggc tgg 23

<210> SEQ ID NO 49
<211> LENGTH: 23
<212> TYPE: DNA
<213> ORGANISM: Homo Sapiens

<400> SEQUENCE: 49
ggatcattgg gaagagacct ggg 23

<210> SEQ ID NO 50
<211> LENGTH: 23
<212> TYPE: DNA
<213> ORGANISM: Homo Sapiens

<400> SEQUENCE: 50
gggatcattg ggaagagacc tgg 23

<210> SEQ ID NO 51
<211> LENGTH: 23
<212> TYPE: DNA
<213> ORGANISM: Homo Sapiens

<400> SEQUENCE: 51
caggatagtc tgggatcatt ggg 23

<210> SEQ ID NO 52
<211> LENGTH: 23
<212> TYPE: DNA
<213> ORGANISM: Homo Sapiens

<400> SEQUENCE: 52
ggaaagaatc caggatagtc tgg 23

<210> SEQ ID NO 53
<211> LENGTH: 23
<212> TYPE: DNA
<213> ORGANISM: Homo Sapiens

<400> SEQUENCE: 53
cagtgccaga gagacctaca tgg 23

<210> SEQ ID NO 54
<211> LENGTH: 23
<212> TYPE: DNA
<213> ORGANISM: Homo Sapiens

<400> SEQUENCE: 54
ctgtaccatg taggtctctc tgg 23

<210> SEQ ID NO 55
<211> LENGTH: 23
<212> TYPE: DNA
<213> ORGANISM: Homo Sapiens

<400> SEQUENCE: 55
agagacctac atggtacagc tgg 23

<210> SEQ ID NO 56
<211> LENGTH: 23
<212> TYPE: DNA
<213> ORGANISM: Homo Sapiens

<400> SEQUENCE: 56
ctgggccagc tgtaccatgt agg 23

<210> SEQ ID NO 57
<211> LENGTH: 23
<212> TYPE: DNA
<213> ORGANISM: Homo Sapiens

<400> SEQUENCE: 57
agggaaaggg cttacggtct ggg 23

<210> SEQ ID NO 58
<211> LENGTH: 23
<212> TYPE: DNA
<213> ORGANISM: Homo Sapiens

<400> SEQUENCE: 58
cagggaaagg gcttacggtc tgg 23

<210> SEQ ID NO 59
<211> LENGTH: 23
<212> TYPE: DNA
<213> ORGANISM: Homo Sapiens

<400> SEQUENCE: 59
tctggagatc ttcttgcaac agg 23

<210> SEQ ID NO 60
<211> LENGTH: 23
<212> TYPE: DNA
<213> ORGANISM: Homo Sapiens

<400> SEQUENCE: 60
ctccggttca tgactttgaa agg 23

<210> SEQ ID NO 61
<211> LENGTH: 23
<212> TYPE: DNA
<213> ORGANISM: Homo Sapiens

<400> SEQUENCE: 61
gtcttccatc ttcgtctttc agg 23

<210> SEQ ID NO 62
<211> LENGTH: 23
<212> TYPE: DNA
<213> ORGANISM: Homo Sapiens

<400> SEQUENCE: 62
gaagacttcg agacccattt agg 23

<210> SEQ ID NO 63
<211> LENGTH: 23
<212> TYPE: DNA
<213> ORGANISM: Homo Sapiens

<400> SEQUENCE: 63
tcgagaccca tttaggatca cgg 23

<210> SEQ ID NO 64
<211> LENGTH: 23
<212> TYPE: DNA
<213> ORGANISM: Homo Sapiens

<400> SEQUENCE: 64
gtagcgccgt gatcctaaat ggg 23

<210> SEQ ID NO 65
<211> LENGTH: 23
<212> TYPE: DNA
<213> ORGANISM: Homo Sapiens

<400> SEQUENCE: 65
cgtagcgccg tgatcctaaa tgg 23

<210> SEQ ID NO 66
<211> LENGTH: 23
<212> TYPE: DNA
<213> ORGANISM: Homo Sapiens

<400> SEQUENCE: 66
catttaggat cacggcgcta cgg 23

<210> SEQ ID NO 67
<211> LENGTH: 23
<212> TYPE: DNA
<213> ORGANISM: Homo Sapiens

<400> SEQUENCE: 67
ggtcccaata ttgaagccca tgg 23

<210> SEQ ID NO 68
<211> LENGTH: 23
<212> TYPE: DNA

<213> ORGANISM: Homo Sapiens

<400> SEQUENCE: 68
gatccatggg cttcaatatt ggg 23

<210> SEQ ID NO 69
<211> LENGTH: 23
<212> TYPE: DNA
<213> ORGANISM: Homo Sapiens

<400> SEQUENCE: 69
agatccatgg gcttcaatat tgg 23

<210> SEQ ID NO 70
<211> LENGTH: 23
<212> TYPE: DNA
<213> ORGANISM: Homo Sapiens

<400> SEQUENCE: 70
gcttctacca taagatccat ggg 23

<210> SEQ ID NO 71
<211> LENGTH: 23
<212> TYPE: DNA
<213> ORGANISM: Homo Sapiens

<400> SEQUENCE: 71
cgcttctacc ataagatcca tgg 23

<210> SEQ ID NO 72
<211> LENGTH: 23
<212> TYPE: DNA
<213> ORGANISM: Homo Sapiens

<400> SEQUENCE: 72
gcatttgcaa aaattcgccg tgg 23

<210> SEQ ID NO 73
<211> LENGTH: 23
<212> TYPE: DNA
<213> ORGANISM: Homo Sapiens

<400> SEQUENCE: 73
atgacctgag aattaattta tgg 23

<210> SEQ ID NO 74
<211> LENGTH: 23
<212> TYPE: DNA
<213> ORGANISM: Homo Sapiens

<400> SEQUENCE: 74
ccatgcactc ccagacatcg tgg 23

<210> SEQ ID NO 75
<211> LENGTH: 23
<212> TYPE: DNA
<213> ORGANISM: Homo Sapiens

<400> SEQUENCE: 75
gcactggtgc gggtggaact cgg 23

<210> SEQ ID NO 76
<211> LENGTH: 23

<212> TYPE: DNA
<213> ORGANISM: Homo Sapiens

<400> SEQUENCE: 76
acacgttgca ctggtgcggg tgg 23

<210> SEQ ID NO 77
<211> LENGTH: 23
<212> TYPE: DNA
<213> ORGANISM: Homo Sapiens

<400> SEQUENCE: 77
cgaacacgtt gcactggtgc ggg 23

<210> SEQ ID NO 78
<211> LENGTH: 23
<212> TYPE: DNA
<213> ORGANISM: Homo Sapiens

<400> SEQUENCE: 78
acgaacacgt tgcactggtg cgg 23

<210> SEQ ID NO 79
<211> LENGTH: 23
<212> TYPE: DNA
<213> ORGANISM: Homo Sapiens

<400> SEQUENCE: 79
tgtagacgaa cacgttgcac tgg 23

<210> SEQ ID NO 80
<211> LENGTH: 23
<212> TYPE: DNA
<213> ORGANISM: Homo Sapiens

<400> SEQUENCE: 80
gcgcatgtca cacaggcgga tgg 23

<210> SEQ ID NO 81
<211> LENGTH: 23
<212> TYPE: DNA
<213> ORGANISM: Homo Sapiens

<400> SEQUENCE: 81
aggagcgcat gtcacacagg cgg 23

<210> SEQ ID NO 82
<211> LENGTH: 23
<212> TYPE: DNA
<213> ORGANISM: Homo Sapiens

<400> SEQUENCE: 82
ccgaggagcg catgtcacac agg 23

<210> SEQ ID NO 83
<211> LENGTH: 23
<212> TYPE: DNA
<213> ORGANISM: Homo Sapiens

<400> SEQUENCE: 83
cctgtgtgac atgcgctcct cgg 23

<210> SEQ ID NO 84

<211> LENGTH: 23
<212> TYPE: DNA
<213> ORGANISM: Homo Sapiens

<400> SEQUENCE: 84
cgactggcca gggcgcctgt ggg 23

<210> SEQ ID NO 85
<211> LENGTH: 23
<212> TYPE: DNA
<213> ORGANISM: Homo Sapiens

<400> SEQUENCE: 85
accgcccaga cgactggcca ggg 23

<210> SEQ ID NO 86
<211> LENGTH: 23
<212> TYPE: DNA
<213> ORGANISM: Homo Sapiens

<400> SEQUENCE: 86
caccgcccag acgactggcc agg 23

<210> SEQ ID NO 87
<211> LENGTH: 23
<212> TYPE: DNA
<213> ORGANISM: Homo Sapiens

<400> SEQUENCE: 87
gtctgggcgg tgctacaact ggg 23

<210> SEQ ID NO 88
<211> LENGTH: 23
<212> TYPE: DNA
<213> ORGANISM: Homo Sapiens

<400> SEQUENCE: 88
ctacaactgg gctggcggcc agg 23

<210> SEQ ID NO 89
<211> LENGTH: 23
<212> TYPE: DNA
<213> ORGANISM: Homo Sapiens

<400> SEQUENCE: 89
cacctaccta agaaccatcc tgg 23

<210> SEQ ID NO 90
<211> LENGTH: 23
<212> TYPE: DNA
<213> ORGANISM: Homo Sapiens

<400> SEQUENCE: 90
cggtcaccac gagcagggct ggg 23

<210> SEQ ID NO 91
<211> LENGTH: 23
<212> TYPE: DNA
<213> ORGANISM: Homo Sapiens

<400> SEQUENCE: 91
gccctgctcg tggtgaccga agg 23

<210> SEQ ID NO 92
<211> LENGTH: 23
<212> TYPE: DNA
<213> ORGANISM: Homo Sapiens

<400> SEQUENCE: 92
cggagagctt cgtgctaaac tgg 23

<210> SEQ ID NO 93
<211> LENGTH: 23
<212> TYPE: DNA
<213> ORGANISM: Homo Sapiens

<400> SEQUENCE: 93
cagcttgtcc gtctggttgc tgg 23

<210> SEQ ID NO 94
<211> LENGTH: 23
<212> TYPE: DNA
<213> ORGANISM: Homo Sapiens

<400> SEQUENCE: 94
aggcggccag cttgtccgtc tgg 23

<210> SEQ ID NO 95
<211> LENGTH: 23
<212> TYPE: DNA
<213> ORGANISM: Homo Sapiens

<400> SEQUENCE: 95
ccgggctggc tgcggtcctc ggg 23

<210> SEQ ID NO 96
<211> LENGTH: 23
<212> TYPE: DNA
<213> ORGANISM: Homo Sapiens

<400> SEQUENCE: 96
cgttgggcag ttgtgtgaca cgg 23

<210> SEQ ID NO 97
<211> LENGTH: 23
<212> TYPE: DNA
<213> ORGANISM: Homo Sapiens

<400> SEQUENCE: 97
cataaagcca tggcttgcct tgg 23

<210> SEQ ID NO 98
<211> LENGTH: 23
<212> TYPE: DNA
<213> ORGANISM: Homo Sapiens

<400> SEQUENCE: 98
ccttggattt cagcggcaca agg 23

<210> SEQ ID NO 99
<211> LENGTH: 23
<212> TYPE: DNA
<213> ORGANISM: Homo Sapiens

<400> SEQUENCE: 99
ccttgtgccg ctgaaatcca agg 23

<210> SEQ ID NO 100
<211> LENGTH: 23
<212> TYPE: DNA
<213> ORGANISM: Homo Sapiens

<400> SEQUENCE: 100
cactcacctt tgcagaagac agg 23

<210> SEQ ID NO 101
<211> LENGTH: 23
<212> TYPE: DNA
<213> ORGANISM: Homo Sapiens

<400> SEQUENCE: 101
ttccatgcta gcaatgcacg tgg 23

<210> SEQ ID NO 102
<211> LENGTH: 23
<212> TYPE: DNA
<213> ORGANISM: Homo Sapiens

<400> SEQUENCE: 102
ggccacgtgc attgctagca tgg 23

<210> SEQ ID NO 103
<211> LENGTH: 23
<212> TYPE: DNA
<213> ORGANISM: Homo Sapiens

<400> SEQUENCE: 103
ggcccagcct gctgtggtac tgg 23

<210> SEQ ID NO 104
<211> LENGTH: 23
<212> TYPE: DNA
<213> ORGANISM: Homo Sapiens

<400> SEQUENCE: 104
aggtccgggt gacagtgctt cgg 23

<210> SEQ ID NO 105
<211> LENGTH: 23
<212> TYPE: DNA
<213> ORGANISM: Homo Sapiens

<400> SEQUENCE: 105
ccgggtgaca gtgcttcggc agg 23

<210> SEQ ID NO 106
<211> LENGTH: 23
<212> TYPE: DNA
<213> ORGANISM: Homo Sapiens

<400> SEQUENCE: 106
ctgtgcggca acctacatga tgg 23

<210> SEQ ID NO 107
<211> LENGTH: 23
<212> TYPE: DNA
<213> ORGANISM: Homo Sapiens

<400> SEQUENCE: 107
caactcattc cccatcatgt agg 23

<210> SEQ ID NO 108
<211> LENGTH: 23
<212> TYPE: DNA
<213> ORGANISM: Homo Sapiens

<400> SEQUENCE: 108
ctagatgatt ccatctgcac ggg 23

<210> SEQ ID NO 109
<211> LENGTH: 23
<212> TYPE: DNA
<213> ORGANISM: Homo Sapiens

<400> SEQUENCE: 109
ggctaggagt cagcgacata tgg 23

<210> SEQ ID NO 110
<211> LENGTH: 23
<212> TYPE: DNA
<213> ORGANISM: Homo Sapiens

<400> SEQUENCE: 110
gctaggagtc agcgacatat ggg 23

<210> SEQ ID NO 111
<211> LENGTH: 23
<212> TYPE: DNA
<213> ORGANISM: Homo Sapiens

<400> SEQUENCE: 111
ctaggagtca gcgacatatg ggg 23

<210> SEQ ID NO 112
<211> LENGTH: 23
<212> TYPE: DNA
<213> ORGANISM: Homo Sapiens

<400> SEQUENCE: 112
gtactgtgta gccaggatgc tgg 23

<210> SEQ ID NO 113
<211> LENGTH: 23
<212> TYPE: DNA
<213> ORGANISM: Homo Sapiens

<400> SEQUENCE: 113
acgagcactc accagcatcc tgg 23

<210> SEQ ID NO 114
<211> LENGTH: 23
<212> TYPE: DNA
<213> ORGANISM: Homo Sapiens

<400> SEQUENCE: 114
aggctccagg aatgtccgcg agg 23

<210> SEQ ID NO 115
<211> LENGTH: 23
<212> TYPE: DNA
<213> ORGANISM: Homo Sapiens

<400> SEQUENCE: 115
acttacctcg cggacattcc tgg 23

<210> SEQ ID NO 116
<211> LENGTH: 23
<212> TYPE: DNA
<213> ORGANISM: Homo Sapiens

<400> SEQUENCE: 116
caccctgggc acttacctcg cgg 23

<210> SEQ ID NO 117
<211> LENGTH: 23
<212> TYPE: DNA
<213> ORGANISM: Homo Sapiens

<400> SEQUENCE: 117
gtgccgtaca aaggttggct ggg 23

<210> SEQ ID NO 118
<211> LENGTH: 23
<212> TYPE: DNA
<213> ORGANISM: Homo Sapiens

<400> SEQUENCE: 118
ggtgccgtac aaaggttggc tgg 23

<210> SEQ ID NO 119
<211> LENGTH: 23
<212> TYPE: DNA
<213> ORGANISM: Homo Sapiens

<400> SEQUENCE: 119
ctctcctcag taccacagca agg 23

<210> SEQ ID NO 120
<211> LENGTH: 23
<212> TYPE: DNA
<213> ORGANISM: Homo Sapiens

<400> SEQUENCE: 120
cctggggcct ccgggcgcgg agg 23

<210> SEQ ID NO 121
<211> LENGTH: 23
<212> TYPE: DNA
<213> ORGANISM: Homo Sapiens

<400> SEQUENCE: 121
agtactcacc tggggcctcc ggg 23

<210> SEQ ID NO 122
<211> LENGTH: 23
<212> TYPE: DNA
<213> ORGANISM: Homo Sapiens

<400> SEQUENCE: 122
agggtctcca gcggccctcc tgg 23

<210> SEQ ID NO 123
<211> LENGTH: 23
<212> TYPE: DNA

<213> ORGANISM: Homo Sapiens

<400> SEQUENCE: 123
gcaagtactt acgcctcctt ggg 23

<210> SEQ ID NO 124
<211> LENGTH: 23
<212> TYPE: DNA
<213> ORGANISM: Homo Sapiens

<400> SEQUENCE: 124
ttgcggtaca tctccagcct ggg 23

<210> SEQ ID NO 125
<211> LENGTH: 23
<212> TYPE: DNA
<213> ORGANISM: Homo Sapiens

<400> SEQUENCE: 125
tttgcggtac atctccagcc tgg 23

<210> SEQ ID NO 126
<211> LENGTH: 23
<212> TYPE: DNA
<213> ORGANISM: Homo Sapiens

<400> SEQUENCE: 126
gcaaaacctg tccactctta tgg 23

<210> SEQ ID NO 127
<211> LENGTH: 23
<212> TYPE: DNA
<213> ORGANISM: Homo Sapiens

<400> SEQUENCE: 127
ttggtgccat aagagtggac agg 23

<210> SEQ ID NO 128
<211> LENGTH: 23
<212> TYPE: DNA
<213> ORGANISM: Homo Sapiens

<400> SEQUENCE: 128
ggtgcaagtt tcttatatgt tgg 23

<210> SEQ ID NO 129
<211> LENGTH: 23
<212> TYPE: DNA
<213> ORGANISM: Homo Sapiens

<400> SEQUENCE: 129
acctgatgca tataataatc agg 23

<210> SEQ ID NO 130
<211> LENGTH: 23
<212> TYPE: DNA
<213> ORGANISM: Homo Sapiens

<400> SEQUENCE: 130
acctgattat tatatgcatc agg 23

<210> SEQ ID NO 131
<211> LENGTH: 23

<212> TYPE: DNA
<213> ORGANISM: Homo Sapiens

<400> SEQUENCE: 131
cagagcacca gagtgccgtc tgg 23

<210> SEQ ID NO 132
<211> LENGTH: 23
<212> TYPE: DNA
<213> ORGANISM: Homo Sapiens

<400> SEQUENCE: 132
agagcaccag agtgccgtct ggg 23

<210> SEQ ID NO 133
<211> LENGTH: 23
<212> TYPE: DNA
<213> ORGANISM: Homo Sapiens

<400> SEQUENCE: 133
agagtgccgt ctgggtctga agg 23

<210> SEQ ID NO 134
<211> LENGTH: 23
<212> TYPE: DNA
<213> ORGANISM: Homo Sapiens

<400> SEQUENCE: 134
aggaaggccg tccattctca ggg 23

<210> SEQ ID NO 135
<211> LENGTH: 23
<212> TYPE: DNA
<213> ORGANISM: Homo Sapiens

<400> SEQUENCE: 135
ggatagaacc aaccatgttg agg 23

<210> SEQ ID NO 136
<211> LENGTH: 23
<212> TYPE: DNA
<213> ORGANISM: Homo Sapiens

<400> SEQUENCE: 136
tctgttgccc tcaacatggt tgg 23

<210> SEQ ID NO 137
<211> LENGTH: 23
<212> TYPE: DNA
<213> ORGANISM: Homo Sapiens

<400> SEQUENCE: 137
ttagtctgtt gccctcaaca tgg 23

<210> SEQ ID NO 138
<211> LENGTH: 23
<212> TYPE: DNA
<213> ORGANISM: Homo Sapiens

<400> SEQUENCE: 138
gtctggcaaa tgggaggtga tgg 23

<210> SEQ ID NO 139

<211> LENGTH: 23
<212> TYPE: DNA
<213> ORGANISM: Homo Sapiens

<400> SEQUENCE: 139
cagaggttct gtctggcaaa tgg 23

<210> SEQ ID NO 140
<211> LENGTH: 23
<212> TYPE: DNA
<213> ORGANISM: Homo Sapiens

<400> SEQUENCE: 140
ttgtagccag aggttctgtc tgg 23

<210> SEQ ID NO 141
<211> LENGTH: 23
<212> TYPE: DNA
<213> ORGANISM: Homo Sapiens

<400> SEQUENCE: 141
acttctggat gagctctctc agg 23

<210> SEQ ID NO 142
<211> LENGTH: 23
<212> TYPE: DNA
<213> ORGANISM: Homo Sapiens

<400> SEQUENCE: 142
agagctcatc cagaagtaaa tgg 23

<210> SEQ ID NO 143
<211> LENGTH: 23
<212> TYPE: DNA
<213> ORGANISM: Homo Sapiens

<400> SEQUENCE: 143
ttggtgtctc catttacttc tgg 23

<210> SEQ ID NO 144
<211> LENGTH: 23
<212> TYPE: DNA
<213> ORGANISM: Homo Sapiens

<400> SEQUENCE: 144
ttctggcttc ccttcataca ggg 23

<210> SEQ ID NO 145
<211> LENGTH: 23
<212> TYPE: DNA
<213> ORGANISM: Homo Sapiens

<400> SEQUENCE: 145
caggactcac acgactattc tgg 23

<210> SEQ ID NO 146
<211> LENGTH: 23
<212> TYPE: DNA
<213> ORGANISM: Homo Sapiens

<400> SEQUENCE: 146
ctactttctt gtgtaaagtc agg 23

<210> SEQ ID NO 147
<211> LENGTH: 23
<212> TYPE: DNA
<213> ORGANISM: Homo Sapiens

<400> SEQUENCE: 147
gactttacac aagaaagtag agg 23

<210> SEQ ID NO 148
<211> LENGTH: 23
<212> TYPE: DNA
<213> ORGANISM: Homo Sapiens

<400> SEQUENCE: 148
gtctttctcc attagccttt tgg 23

<210> SEQ ID NO 149
<211> LENGTH: 23
<212> TYPE: DNA
<213> ORGANISM: Homo Sapiens

<400> SEQUENCE: 149
aatggagaaa gacgtaactt cgg 23

<210> SEQ ID NO 150
<211> LENGTH: 23
<212> TYPE: DNA
<213> ORGANISM: Homo Sapiens

<400> SEQUENCE: 150
atggagaaag acgtaacttc ggg 23

<210> SEQ ID NO 151
<211> LENGTH: 23
<212> TYPE: DNA
<213> ORGANISM: Homo Sapiens

<400> SEQUENCE: 151
tggagaaaga cgtaacttcg ggg 23

<210> SEQ ID NO 152
<211> LENGTH: 23
<212> TYPE: DNA
<213> ORGANISM: Homo Sapiens

<400> SEQUENCE: 152
tttggttgac tgctttcacc tgg 23

<210> SEQ ID NO 153
<211> LENGTH: 23
<212> TYPE: DNA
<213> ORGANISM: Homo Sapiens

<400> SEQUENCE: 153
tcactcaaat cggagacatt tgg 23

<210> SEQ ID NO 154
<211> LENGTH: 23
<212> TYPE: DNA
<213> ORGANISM: Homo Sapiens

<400> SEQUENCE: 154
atctgaagct ctggattttc agg 23

<210> SEQ ID NO 155
<211> LENGTH: 23
<212> TYPE: DNA
<213> ORGANISM: Homo Sapiens

<400> SEQUENCE: 155
gcttcagatt ctgaatgagc agg 23

<210> SEQ ID NO 156
<211> LENGTH: 23
<212> TYPE: DNA
<213> ORGANISM: Homo Sapiens

<400> SEQUENCE: 156
cagattctga atgagcagga ggg 23

<210> SEQ ID NO 157
<211> LENGTH: 23
<212> TYPE: DNA
<213> ORGANISM: Homo Sapiens

<400> SEQUENCE: 157
aaggcagtgc taatgcctaa tgg 23

<210> SEQ ID NO 158
<211> LENGTH: 23
<212> TYPE: DNA
<213> ORGANISM: Homo Sapiens

<400> SEQUENCE: 158
gcagaaactg tagcaccatt agg 23

<210> SEQ ID NO 159
<211> LENGTH: 23
<212> TYPE: DNA
<213> ORGANISM: Homo Sapiens

<400> SEQUENCE: 159
accgcaatgg aaacacaatc tgg 23

<210> SEQ ID NO 160
<211> LENGTH: 23
<212> TYPE: DNA
<213> ORGANISM: Homo Sapiens

<400> SEQUENCE: 160
tgtggttttc tgcaccgcaa tgg 23

<210> SEQ ID NO 161
<211> LENGTH: 23
<212> TYPE: DNA
<213> ORGANISM: Homo Sapiens

<400> SEQUENCE: 161
cataaatgcc attaacagtc agg 23

<210> SEQ ID NO 162
<211> LENGTH: 23
<212> TYPE: DNA
<213> ORGANISM: Homo Sapiens

<400> SEQUENCE: 162
attagtagcc tgactgttaa tgg 23

<210> SEQ ID NO 163
<211> LENGTH: 23
<212> TYPE: DNA
<213> ORGANISM: Homo Sapiens

<400> SEQUENCE: 163
cgatgggtga gtgatctcac agg 23

<210> SEQ ID NO 164
<211> LENGTH: 23
<212> TYPE: DNA
<213> ORGANISM: Homo Sapiens

<400> SEQUENCE: 164
actcacccat cgcatacctc agg 23

<210> SEQ ID NO 165
<211> LENGTH: 23
<212> TYPE: DNA
<213> ORGANISM: Homo Sapiens

<400> SEQUENCE: 165
ctcacccatc gcatacctca ggg 23

<210> SEQ ID NO 166
<211> LENGTH: 23
<212> TYPE: DNA
<213> ORGANISM: Homo Sapiens

<400> SEQUENCE: 166
agcaacagga ggagttgcag agg 23

<210> SEQ ID NO 167
<211> LENGTH: 23
<212> TYPE: DNA
<213> ORGANISM: Homo Sapiens

<400> SEQUENCE: 167
ccagtaggat cagcaacagg agg 23

<210> SEQ ID NO 168
<211> LENGTH: 23
<212> TYPE: DNA
<213> ORGANISM: Homo Sapiens

<400> SEQUENCE: 168
ctcctgttgc tgatcctact ggg 23

<210> SEQ ID NO 169
<211> LENGTH: 23
<212> TYPE: DNA
<213> ORGANISM: Homo Sapiens

<400> SEQUENCE: 169
ggcccagtag gatcagcaac agg 23

<210> SEQ ID NO 170
<211> LENGTH: 23
<212> TYPE: DNA
<213> ORGANISM: Homo Sapiens

<400> SEQUENCE: 170
ttgctgatcc tactgggccc tgg 23

<210> SEQ ID NO 171
<211> LENGTH: 23
<212> TYPE: DNA
<213> ORGANISM: Homo Sapiens

<400> SEQUENCE: 171
tggcaacagc ttgcagctgt ggg 23

<210> SEQ ID NO 172
<211> LENGTH: 23
<212> TYPE: DNA
<213> ORGANISM: Homo Sapiens

<400> SEQUENCE: 172
cttgggtccc ctgcttgccc ggg 23

<210> SEQ ID NO 173
<211> LENGTH: 23
<212> TYPE: DNA
<213> ORGANISM: Homo Sapiens

<400> SEQUENCE: 173
gtcccctgct tgcccgggac cgg 23

<210> SEQ ID NO 174
<211> LENGTH: 23
<212> TYPE: DNA
<213> ORGANISM: Homo Sapiens

<400> SEQUENCE: 174
ctccggtccc gggcaagcag ggg 23

<210> SEQ ID NO 175
<211> LENGTH: 23
<212> TYPE: DNA
<213> ORGANISM: Homo Sapiens

<400> SEQUENCE: 175
tctccggtcc cgggcaagca ggg 23

<210> SEQ ID NO 176
<211> LENGTH: 23
<212> TYPE: DNA
<213> ORGANISM: Homo Sapiens

<400> SEQUENCE: 176
gtctccggtc ccgggcaagc agg 23

<210> SEQ ID NO 177
<211> LENGTH: 23
<212> TYPE: DNA
<213> ORGANISM: Homo Sapiens

<400> SEQUENCE: 177
gcttgcccgg gaccggagac agg 23

<210> SEQ ID NO 178
<211> LENGTH: 23
<212> TYPE: DNA

<213> ORGANISM: Homo Sapiens

<400> SEQUENCE: 178
ggtggcctgt ctccggtccc ggg 23

<210> SEQ ID NO 179
<211> LENGTH: 23
<212> TYPE: DNA
<213> ORGANISM: Homo Sapiens

<400> SEQUENCE: 179
cggtggcctg tctccggtcc cgg 23

<210> SEQ ID NO 180
<211> LENGTH: 23
<212> TYPE: DNA
<213> ORGANISM: Homo Sapiens

<400> SEQUENCE: 180
catattcggt ggcctgtctc cgg 23

<210> SEQ ID NO 181
<211> LENGTH: 23
<212> TYPE: DNA
<213> ORGANISM: Homo Sapiens

<400> SEQUENCE: 181
atctaggtac tcatattcgg tgg 23

<210> SEQ ID NO 182
<211> LENGTH: 23
<212> TYPE: DNA
<213> ORGANISM: Homo Sapiens

<400> SEQUENCE: 182
ataatctagg tactcatatt cgg 23

<210> SEQ ID NO 183
<211> LENGTH: 23
<212> TYPE: DNA
<213> ORGANISM: Homo Sapiens

<400> SEQUENCE: 183
ttatgatttc ctgccagaaa cgg 23

<210> SEQ ID NO 184
<211> LENGTH: 23
<212> TYPE: DNA
<213> ORGANISM: Homo Sapiens

<400> SEQUENCE: 184
atttctggag gctccgtttc tgg 23

<210> SEQ ID NO 185
<211> LENGTH: 23
<212> TYPE: DNA
<213> ORGANISM: Homo Sapiens

<400> SEQUENCE: 185
actgacacca ctcctctgac tgg 23

<210> SEQ ID NO 186
<211> LENGTH: 23

<212> TYPE: DNA
<213> ORGANISM: Homo Sapiens

<400> SEQUENCE: 186
ctgacaccac tcctctgact ggg 23

<210> SEQ ID NO 187
<211> LENGTH: 23
<212> TYPE: DNA
<213> ORGANISM: Homo Sapiens

<400> SEQUENCE: 187
accactcctc tgactgggcc tgg 23

<210> SEQ ID NO 188
<211> LENGTH: 23
<212> TYPE: DNA
<213> ORGANISM: Homo Sapiens

<400> SEQUENCE: 188
aacccctgag tctaccactg tgg 23

<210> SEQ ID NO 189
<211> LENGTH: 23
<212> TYPE: DNA
<213> ORGANISM: Homo Sapiens

<400> SEQUENCE: 189
ctccacagtg gtagactcag ggg 23

<210> SEQ ID NO 190
<211> LENGTH: 23
<212> TYPE: DNA
<213> ORGANISM: Homo Sapiens

<400> SEQUENCE: 190
gctccacagt ggtagactca ggg 23

<210> SEQ ID NO 191
<211> LENGTH: 23
<212> TYPE: DNA
<213> ORGANISM: Homo Sapiens

<400> SEQUENCE: 191
ggctccacag tggtagactc agg 23

<210> SEQ ID NO 192
<211> LENGTH: 23
<212> TYPE: DNA
<213> ORGANISM: Homo Sapiens

<400> SEQUENCE: 192
cctgctgcaa ggcgttctac tgg 23

<210> SEQ ID NO 193
<211> LENGTH: 23
<212> TYPE: DNA
<213> ORGANISM: Homo Sapiens

<400> SEQUENCE: 193
ccagtagaac gccttgcagc agg 23

<210> SEQ ID NO 194

<211> LENGTH: 23
<212> TYPE: DNA
<213> ORGANISM: Homo Sapiens

<400> SEQUENCE: 194
cgttctactg gcctggatgc agg 23

<210> SEQ ID NO 195
<211> LENGTH: 23
<212> TYPE: DNA
<213> ORGANISM: Homo Sapiens

<400> SEQUENCE: 195
tctactggcc tggatgcagg agg 23

<210> SEQ ID NO 196
<211> LENGTH: 23
<212> TYPE: DNA
<213> ORGANISM: Homo Sapiens

<400> SEQUENCE: 196
ccacggagct ggccaacatg ggg 23

<210> SEQ ID NO 197
<211> LENGTH: 23
<212> TYPE: DNA
<213> ORGANISM: Homo Sapiens

<400> SEQUENCE: 197
cgtggacagg ttccccatgt tgg 23

<210> SEQ ID NO 198
<211> LENGTH: 23
<212> TYPE: DNA
<213> ORGANISM: Homo Sapiens

<400> SEQUENCE: 198
gtccacggat tcagcagcta tgg 23

<210> SEQ ID NO 199
<211> LENGTH: 23
<212> TYPE: DNA
<213> ORGANISM: Homo Sapiens

<400> SEQUENCE: 199
gaccactcaa ccagtgccca cgg 23

<210> SEQ ID NO 200
<211> LENGTH: 23
<212> TYPE: DNA
<213> ORGANISM: Homo Sapiens

<400> SEQUENCE: 200
ggagtggtct gtgcctccgt ggg 23

<210> SEQ ID NO 201
<211> LENGTH: 23
<212> TYPE: DNA
<213> ORGANISM: Homo Sapiens

<400> SEQUENCE: 201
ggcacagaca actcgactga cgg 23

<210> SEQ ID NO 202
<211> LENGTH: 23
<212> TYPE: DNA
<213> ORGANISM: Homo Sapiens

<400> SEQUENCE: 202
gacaactcga ctgacggcca cgg 23

<210> SEQ ID NO 203
<211> LENGTH: 23
<212> TYPE: DNA
<213> ORGANISM: Homo Sapiens

<400> SEQUENCE: 203
aactcgactg acggccacgg agg 23

<210> SEQ ID NO 204
<211> LENGTH: 23
<212> TYPE: DNA
<213> ORGANISM: Homo Sapiens

<400> SEQUENCE: 204
cacagaaccc agtgccacag agg 23

<210> SEQ ID NO 205
<211> LENGTH: 23
<212> TYPE: DNA
<213> ORGANISM: Homo Sapiens

<400> SEQUENCE: 205
ggtagtaggt tccatggaca ggg 23

<210> SEQ ID NO 206
<211> LENGTH: 23
<212> TYPE: DNA
<213> ORGANISM: Homo Sapiens

<400> SEQUENCE: 206
tggtagtagg ttccatggac agg 23

<210> SEQ ID NO 207
<211> LENGTH: 23
<212> TYPE: DNA
<213> ORGANISM: Homo Sapiens

<400> SEQUENCE: 207
tcttttggta gtaggttcca tgg 23

<210> SEQ ID NO 208
<211> LENGTH: 23
<212> TYPE: DNA
<213> ORGANISM: Homo Sapiens

<400> SEQUENCE: 208
atggaaccta ctaccaaaag agg 23

<210> SEQ ID NO 209
<211> LENGTH: 23
<212> TYPE: DNA
<213> ORGANISM: Homo Sapiens

<400> SEQUENCE: 209
aacagacctc ttttggtagt agg 23

<210> SEQ ID NO 210
<211> LENGTH: 23
<212> TYPE: DNA
<213> ORGANISM: Homo Sapiens

<400> SEQUENCE: 210
gggtatgaac agacctcttt tgg 23

<210> SEQ ID NO 211
<211> LENGTH: 23
<212> TYPE: DNA
<213> ORGANISM: Homo Sapiens

<400> SEQUENCE: 211
tgtgtcctct gttactcaca agg 23

<210> SEQ ID NO 212
<211> LENGTH: 23
<212> TYPE: DNA
<213> ORGANISM: Homo Sapiens

<400> SEQUENCE: 212
gtgtcctctg ttactcacaa ggg 23

<210> SEQ ID NO 213
<211> LENGTH: 23
<212> TYPE: DNA
<213> ORGANISM: Homo Sapiens

<400> SEQUENCE: 213
gtagttgacg gacaaattgc tgg 23

<210> SEQ ID NO 214
<211> LENGTH: 23
<212> TYPE: DNA
<213> ORGANISM: Homo Sapiens

<400> SEQUENCE: 214
tttgtccgtc aactacccag tgg 23

<210> SEQ ID NO 215
<211> LENGTH: 23
<212> TYPE: DNA
<213> ORGANISM: Homo Sapiens

<400> SEQUENCE: 215
ttgtccgtca actacccagt ggg 23

<210> SEQ ID NO 216
<211> LENGTH: 23
<212> TYPE: DNA
<213> ORGANISM: Homo Sapiens

<400> SEQUENCE: 216
tgtccgtcaa ctacccagtg ggg 23

<210> SEQ ID NO 217
<211> LENGTH: 23
<212> TYPE: DNA
<213> ORGANISM: Homo Sapiens

<400> SEQUENCE: 217
gtccgtcaac tacccagtgg ggg 23

<210> SEQ ID NO 218
<211> LENGTH: 23
<212> TYPE: DNA
<213> ORGANISM: Homo Sapiens

<400> SEQUENCE: 218
ctctgtgaag cagtgcctgc tgg 23

<210> SEQ ID NO 219
<211> LENGTH: 23
<212> TYPE: DNA
<213> ORGANISM: Homo Sapiens

<400> SEQUENCE: 219
cctgctggcc atcctaatct tgg 23

<210> SEQ ID NO 220
<211> LENGTH: 23
<212> TYPE: DNA
<213> ORGANISM: Homo Sapiens

<400> SEQUENCE: 220
ccaagattag gatggccagc agg 23

<210> SEQ ID NO 221
<211> LENGTH: 23
<212> TYPE: DNA
<213> ORGANISM: Homo Sapiens

<400> SEQUENCE: 221
ggccatccta atcttggcgc tgg 23

<210> SEQ ID NO 222
<211> LENGTH: 23
<212> TYPE: DNA
<213> ORGANISM: Homo Sapiens

<400> SEQUENCE: 222
caccagcgcc aagattagga tgg 23

<210> SEQ ID NO 223
<211> LENGTH: 23
<212> TYPE: DNA
<213> ORGANISM: Homo Sapiens

<400> SEQUENCE: 223
agtgcacacg aagaagatag tgg 23

<210> SEQ ID NO 224
<211> LENGTH: 23
<212> TYPE: DNA
<213> ORGANISM: Homo Sapiens

<400> SEQUENCE: 224
tatcttcttc gtgtgcactg tgg 23

<210> SEQ ID NO 225
<211> LENGTH: 23
<212> TYPE: DNA
<213> ORGANISM: Homo Sapiens

<400> SEQUENCE: 225
cttcgtgtgc actgtggtgc tgg 23

<210> SEQ ID NO 226
<211> LENGTH: 23
<212> TYPE: DNA
<213> ORGANISM: Homo Sapiens

<400> SEQUENCE: 226
ggcggtccgc ctctcccgca agg 23

<210> SEQ ID NO 227
<211> LENGTH: 23
<212> TYPE: DNA
<213> ORGANISM: Homo Sapiens

<400> SEQUENCE: 227
gcggtccgcc tctcccgcaa ggg 23

<210> SEQ ID NO 228
<211> LENGTH: 23
<212> TYPE: DNA
<213> ORGANISM: Homo Sapiens

<400> SEQUENCE: 228
aattacgcac ggggtacatg tgg 23

<210> SEQ ID NO 229
<211> LENGTH: 23
<212> TYPE: DNA
<213> ORGANISM: Homo Sapiens

<400> SEQUENCE: 229
tgggggagta attacgcacg ggg 23

<210> SEQ ID NO 230
<211> LENGTH: 23
<212> TYPE: DNA
<213> ORGANISM: Homo Sapiens

<400> SEQUENCE: 230
gtgggggagt aattacgcac ggg 23

<210> SEQ ID NO 231
<211> LENGTH: 23
<212> TYPE: DNA
<213> ORGANISM: Homo Sapiens

<400> SEQUENCE: 231
ggtgggggag taattacgca cgg 23

<210> SEQ ID NO 232
<211> LENGTH: 23
<212> TYPE: DNA
<213> ORGANISM: Homo Sapiens

<400> SEQUENCE: 232
taattactcc cccaccgaga tgg 23

<210> SEQ ID NO 233
<211> LENGTH: 23
<212> TYPE: DNA

<213> ORGANISM: Homo Sapiens

<400> SEQUENCE: 233
agatgcagac catctcggtg ggg 23

<210> SEQ ID NO 234
<211> LENGTH: 23
<212> TYPE: DNA
<213> ORGANISM: Homo Sapiens

<400> SEQUENCE: 234
gagatgcaga ccatctcggt ggg 23

<210> SEQ ID NO 235
<211> LENGTH: 23
<212> TYPE: DNA
<213> ORGANISM: Homo Sapiens

<400> SEQUENCE: 235
tgagatgcag accatctcgg tgg 23

<210> SEQ ID NO 236
<211> LENGTH: 23
<212> TYPE: DNA
<213> ORGANISM: Homo Sapiens

<400> SEQUENCE: 236
ggatgagatg cagaccatct cgg 23

<210> SEQ ID NO 237
<211> LENGTH: 23
<212> TYPE: DNA
<213> ORGANISM: Homo Sapiens

<400> SEQUENCE: 237
atctcatccc tgttgcctga tgg 23

<210> SEQ ID NO 238
<211> LENGTH: 23
<212> TYPE: DNA
<213> ORGANISM: Homo Sapiens

<400> SEQUENCE: 238
tcatccctgt tgcctgatgg ggg 23

<210> SEQ ID NO 239
<211> LENGTH: 23
<212> TYPE: DNA
<213> ORGANISM: Homo Sapiens

<400> SEQUENCE: 239
ctcaccccca tcaggcaaca ggg 23

<210> SEQ ID NO 240
<211> LENGTH: 23
<212> TYPE: DNA
<213> ORGANISM: Homo Sapiens

<400> SEQUENCE: 240
gagggcccct cacccccatc agg 23

<210> SEQ ID NO 241
<211> LENGTH: 23

<212> TYPE: DNA
<213> ORGANISM: Homo Sapiens

<400> SEQUENCE: 241
gggccctctg ccacagccaa tgg 23

<210> SEQ ID NO 242
<211> LENGTH: 23
<212> TYPE: DNA
<213> ORGANISM: Homo Sapiens

<400> SEQUENCE: 242
ccctctgcca cagccaatgg ggg 23

<210> SEQ ID NO 243
<211> LENGTH: 23
<212> TYPE: DNA
<213> ORGANISM: Homo Sapiens

<400> SEQUENCE: 243
cccccattgg ctgtggcaga ggg 23

<210> SEQ ID NO 244
<211> LENGTH: 23
<212> TYPE: DNA
<213> ORGANISM: Homo Sapiens

<400> SEQUENCE: 244
gcccccattg gctgtggcag agg 23

<210> SEQ ID NO 245
<211> LENGTH: 23
<212> TYPE: DNA
<213> ORGANISM: Homo Sapiens

<400> SEQUENCE: 245
ggacaggccc ccattggctg tgg 23

<210> SEQ ID NO 246
<211> LENGTH: 23
<212> TYPE: DNA
<213> ORGANISM: Homo Sapiens

<400> SEQUENCE: 246
ccgggctctt ggccttggac agg 23

<210> SEQ ID NO 247
<211> LENGTH: 23
<212> TYPE: DNA
<213> ORGANISM: Homo Sapiens

<400> SEQUENCE: 247
ctgtccaagg ccaagagccc ggg 23

<210> SEQ ID NO 248
<211> LENGTH: 23
<212> TYPE: DNA
<213> ORGANISM: Homo Sapiens

<400> SEQUENCE: 248
tggcgtcagg cccgggctct tgg 23

<210> SEQ ID NO 249

<211> LENGTH: 23
<212> TYPE: DNA
<213> ORGANISM: Homo Sapiens

<400> SEQUENCE: 249
cgggcctgac gccagagccc agg 23

<210> SEQ ID NO 250
<211> LENGTH: 23
<212> TYPE: DNA
<213> ORGANISM: Homo Sapiens

<400> SEQUENCE: 250
caacaaccat gctgggcatc tgg 23

<210> SEQ ID NO 251
<211> LENGTH: 23
<212> TYPE: DNA
<213> ORGANISM: Homo Sapiens

<400> SEQUENCE: 251
gagggtccag atgcccagca tgg 23

<210> SEQ ID NO 252
<211> LENGTH: 23
<212> TYPE: DNA
<213> ORGANISM: Homo Sapiens

<400> SEQUENCE: 252
catctggacc ctcctacctc tgg 23

<210> SEQ ID NO 253
<211> LENGTH: 23
<212> TYPE: DNA
<213> ORGANISM: Homo Sapiens

<400> SEQUENCE: 253
agggctcacc agaggtagga ggg 23

<210> SEQ ID NO 254
<211> LENGTH: 23
<212> TYPE: DNA
<213> ORGANISM: Homo Sapiens

<400> SEQUENCE: 254
ggagttgatg tcagtcactt ggg 23

<210> SEQ ID NO 255
<211> LENGTH: 23
<212> TYPE: DNA
<213> ORGANISM: Homo Sapiens

<400> SEQUENCE: 255
tggagttgat gtcagtcact tgg 23

<210> SEQ ID NO 256
<211> LENGTH: 23
<212> TYPE: DNA
<213> ORGANISM: Homo Sapiens

<400> SEQUENCE: 256
agtgactgac atcaactcca agg 23

<210> SEQ ID NO 257
<211> LENGTH: 23
<212> TYPE: DNA
<213> ORGANISM: Homo Sapiens

<400> SEQUENCE: 257
gtgactgaca tcaactccaa ggg 23

<210> SEQ ID NO 258
<211> LENGTH: 23
<212> TYPE: DNA
<213> ORGANISM: Homo Sapiens

<400> SEQUENCE: 258
actccaaggg attggaattg agg 23

<210> SEQ ID NO 259
<211> LENGTH: 23
<212> TYPE: DNA
<213> ORGANISM: Homo Sapiens

<400> SEQUENCE: 259
cttcctcaat tccaatccct tgg 23

<210> SEQ ID NO 260
<211> LENGTH: 23
<212> TYPE: DNA
<213> ORGANISM: Homo Sapiens

<400> SEQUENCE: 260
tacagttgag actcagaact tgg 23

<210> SEQ ID NO 261
<211> LENGTH: 23
<212> TYPE: DNA
<213> ORGANISM: Homo Sapiens

<400> SEQUENCE: 261
ttggaaggcc tgcatcatga tgg 23

<210> SEQ ID NO 262
<211> LENGTH: 23
<212> TYPE: DNA
<213> ORGANISM: Homo Sapiens

<400> SEQUENCE: 262
agaattggcc atcatgatgc agg 23

<210> SEQ ID NO 263
<211> LENGTH: 23
<212> TYPE: DNA
<213> ORGANISM: Homo Sapiens

<400> SEQUENCE: 263
gacagggctt atggcagaat tgg 23

<210> SEQ ID NO 264
<211> LENGTH: 23
<212> TYPE: DNA
<213> ORGANISM: Homo Sapiens

<400> SEQUENCE: 264
tgtaacatac ctggaggaca ggg 23

<210> SEQ ID NO 265
<211> LENGTH: 23
<212> TYPE: DNA
<213> ORGANISM: Homo Sapiens

<400> SEQUENCE: 265
gtgtaacata cctggaggac agg 23

<210> SEQ ID NO 266
<211> LENGTH: 23
<212> TYPE: DNA
<213> ORGANISM: Homo Sapiens

<400> SEQUENCE: 266
cgtacctgtg caactcctgt tgg 23

<210> SEQ ID NO 267
<211> LENGTH: 23
<212> TYPE: DNA
<213> ORGANISM: Homo Sapiens

<400> SEQUENCE: 267
gatctactgg aattcctaat ggg 23

<210> SEQ ID NO 268
<211> LENGTH: 23
<212> TYPE: DNA
<213> ORGANISM: Homo Sapiens

<400> SEQUENCE: 268
gagtcagctg ttggcccatt agg 23

<210> SEQ ID NO 269
<211> LENGTH: 23
<212> TYPE: DNA
<213> ORGANISM: Homo Sapiens

<400> SEQUENCE: 269
ctgcctacaa actcagtctc tgg 23

<210> SEQ ID NO 270
<211> LENGTH: 23
<212> TYPE: DNA
<213> ORGANISM: Homo Sapiens

<400> SEQUENCE: 270
gggcaggcag gacggactcc agg 23

<210> SEQ ID NO 271
<211> LENGTH: 23
<212> TYPE: DNA
<213> ORGANISM: Homo Sapiens

<400> SEQUENCE: 271
ggagtccgtc ctgcctgccc tgg 23

<210> SEQ ID NO 272
<211> LENGTH: 23
<212> TYPE: DNA
<213> ORGANISM: Homo Sapiens

<400> SEQUENCE: 272
gagtccgtcc tgcctgccct ggg 23

<210> SEQ ID NO 273
<211> LENGTH: 23
<212> TYPE: DNA
<213> ORGANISM: Homo Sapiens

<400> SEQUENCE: 273
gaaaagggtc cattggccaa agg 23

<210> SEQ ID NO 274
<211> LENGTH: 23
<212> TYPE: DNA
<213> ORGANISM: Homo Sapiens

<400> SEQUENCE: 274
gcctgcagaa aagggtccat tgg 23

<210> SEQ ID NO 275
<211> LENGTH: 23
<212> TYPE: DNA
<213> ORGANISM: Homo Sapiens

<400> SEQUENCE: 275
ttgatgtgct acagggaaca tgg 23

<210> SEQ ID NO 276
<211> LENGTH: 23
<212> TYPE: DNA
<213> ORGANISM: Homo Sapiens

<400> SEQUENCE: 276
agcgttcttg atgtgctaca ggg 23

<210> SEQ ID NO 277
<211> LENGTH: 23
<212> TYPE: DNA
<213> ORGANISM: Homo Sapiens

<400> SEQUENCE: 277
cagcgttctt gatgtgctac agg 23

<210> SEQ ID NO 278
<211> LENGTH: 23
<212> TYPE: DNA
<213> ORGANISM: Homo Sapiens

<400> SEQUENCE: 278
ctgtagcaca tcaagaacgc tgg 23

<210> SEQ ID NO 279
<211> LENGTH: 23
<212> TYPE: DNA
<213> ORGANISM: Homo Sapiens

<400> SEQUENCE: 279
tgtagcacat caagaacgct ggg 23

<210> SEQ ID NO 280
<211> LENGTH: 23
<212> TYPE: DNA
<213> ORGANISM: Homo Sapiens

<400> SEQUENCE: 280
ataggcaata atcatataac agg 23

<210> SEQ ID NO 281
<211> LENGTH: 23
<212> TYPE: DNA
<213> ORGANISM: Homo Sapiens

<400> SEQUENCE: 281
agtgcgtttc gctgcaggta agg 23

<210> SEQ ID NO 282
<211> LENGTH: 23
<212> TYPE: DNA
<213> ORGANISM: Homo Sapiens

<400> SEQUENCE: 282
gagtgagtgc gtttcgctgc agg 23

<210> SEQ ID NO 283
<211> LENGTH: 23
<212> TYPE: DNA
<213> ORGANISM: Homo Sapiens

<400> SEQUENCE: 283
gtcaggtttg tgcggttatg agg 23

<210> SEQ ID NO 284
<211> LENGTH: 23
<212> TYPE: DNA
<213> ORGANISM: Homo Sapiens

<400> SEQUENCE: 284
cgctgctggt caggtttgtg cgg 23

<210> SEQ ID NO 285
<211> LENGTH: 23
<212> TYPE: DNA
<213> ORGANISM: Homo Sapiens

<400> SEQUENCE: 285
aaacctgacc agcagcgcag agg 23

<210> SEQ ID NO 286
<211> LENGTH: 23
<212> TYPE: DNA
<213> ORGANISM: Homo Sapiens

<400> SEQUENCE: 286
ccagcagcgc agaggagccg tgg 23

<210> SEQ ID NO 287
<211> LENGTH: 23
<212> TYPE: DNA
<213> ORGANISM: Homo Sapiens

<400> SEQUENCE: 287
ccacggctcc tctgcgctgc tgg 23

<210> SEQ ID NO 288
<211> LENGTH: 23
<212> TYPE: DNA

-continued

```
<213> ORGANISM: Homo Sapiens

<400> SEQUENCE: 288

ccaactatct aactccactc agg                                    23


<210> SEQ ID NO 289
<211> LENGTH: 23
<212> TYPE: DNA
<213> ORGANISM: Homo Sapiens

<400> SEQUENCE: 289

cctgagtgga gttagatagt tgg                                    23
```